United States Patent
Nebel et al.

(10) Patent No.: US 6,274,536 B1
(45) Date of Patent: Aug. 14, 2001

(54) PYRAZOLE DERIVATIVES AS HERBICIDES

(75) Inventors: Kurt Nebel, Hochwald; Alain De Mesmaeker, Kaenerkinden, both of (CH); Jürgen Schaetzer, Rheinfelden (DE)

(73) Assignee: Syngenta Crop Protection, Inc., Greensboro, NC (US)

( * ) Notice: Subject to any disclaimer, the term of this patent is extended or adjusted under 35 U.S.C. 154(b) by 0 days.

(21) Appl. No.: 09/380,678

(22) PCT Filed: Mar. 19, 1998

(86) PCT No.: PCT/EP98/01611

§ 371 Date: Sep. 7, 1999

§ 102(e) Date: Sep. 7, 1999

(87) PCT Pub. No.: WO98/42698

PCT Pub. Date: Oct. 1, 1998

(30) Foreign Application Priority Data

Mar. 21, 1997 (CH) .......................................... 695/97

(51) Int. Cl.$^7$ ...................... A01N 43/40; C07D 401/04
(52) U.S. Cl. .................. 504/252; 504/246; 546/275.4; 546/276.1; 546/113; 546/115
(58) Field of Search ............... 546/275.4, 276.1; 504/252

(56) References Cited

U.S. PATENT DOCUMENTS

| | | |
|---|---|---|
| 2,742,476 | 4/1956 | Bernstein et al. . |
| 2,809,971 | 10/1957 | Bernstein et al. . |
| 3,047,579 | 7/1962 | Witman . |
| 4,526,895 | * 7/1985 | Jarreau et al. ........................ 514/341 |
| 5,032,165 | 7/1991 | Miura et al. ........................... 546/22 |

FOREIGN PATENT DOCUMENTS

| | | |
|---|---|---|
| 0 361 114 | 4/1990 | (EP) . |
| WO 92/02509 | 2/1992 | (WO) . |
| WO 92/06962 | 4/1992 | (WO) . |
| WO 95/33728 | 12/1995 | (WO) . |
| WO 96/01254 | 1/1996 | (WO) . |
| 97/00246 | 1/1997 | (WO) . |

OTHER PUBLICATIONS

Org. Synth. 4, 828 (1963); idem. 3, 619 (1955).
B. Iddon and H. Suschitzky in "Polychloroaromatic Compounds", Editor H. Suschitzky, Plenum Press, London 1974, p. 197.
Quart. Rev. 10, 395 (1956).
J. Am. Chem. Soc. 85, 958 (1963); idem. 73, 3681 (1951); idem. 72, 4362 (1950).
J. Am. Chem. 26, 428 (1961); idem. 35, 2517 (1970); idem. 32, 4040 (1967); idem. 19, 1633 (1954); idem. 54, 4330 (1989).
Tetrahedron 37, 187 (1981); idem. 1991, 7091.
Org. Prep. Proced. Int. 9(1), 5–8 (1977).
Tetrahedron Lett. 36(49), 8917 (1995); idem. 31(14), 1965 (1990).
Bull. Soc. Chim. Fr. 1953, 1001, in French language (the english language abstract is also enclosed).
Heterocycles 30(2), 875 (1990).
Can. J. Chem. 31, 457 (1953).
J. Chem. Soc. 1939, 1858.
J. Het. Chem. 25, 511 (1988); idem. 22, 268 (1985).
J. prakt. Chem. 330, 293 (1988); idem. 334, 119 (1992).
Chem. Ber. 62, 2732 (1929) (the english language abstract is also enclosed).
Chem. Heterocycl. Compd. (Engl. Transl.) 1988, 658.
Pharmazie 45, 731 (1990) (the english language abstract is also enclosed).

(List continued on next page.)

*Primary Examiner*—Jane Fan
(74) *Attorney, Agent, or Firm*—William A. Teoli, Jr.

(57) ABSTRACT

Compounds of the following formula I

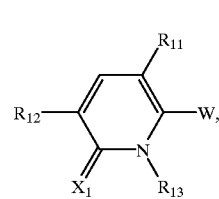

(I)

wherein

W is a group

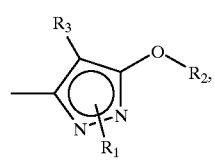

(W1)

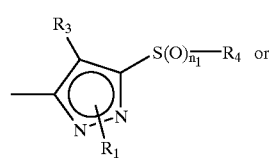

(W2)

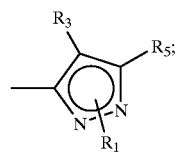

(W3)

wherein all variables are as defined in the specification and the pyrazoleN-oxides, agrochemically acceptable salts and stereisomers thereof useful as herbisdes.

6 Claims, No Drawings

OTHER PUBLICATIONS

J. Chem. Soc., Perkin Trans I 1976, 201; idem. 1987, 1159.

Liebigs Ann. Chem. 1978, 1491(english language abstract also enclosed).

Helv. Chim. Acta 73, 1679 (1990) (english language abstract also enclosed).

II Farmaco–Ed. Sc. 37, 22 (1982).

J. Chem. Res. (Miniprint) II, 3368 (1986) (english language abstract also enclosed).

"Methoden der Organischen Chemie" (Houben–Weyl), vol. E 8b, Georg Thieme Verlag Stuttgart, 1994, p. 399ff; idem. vol. E 7B, Georg Thieme Verlag Stuttgart 1992, p. 286 ff (english language abstracts of each are enclosed).

Sov. Prog. Chem. (Engl. Transl.) 42, 65 (1976).

* cited by examiner

PYRAZOLE DERIVATIVES AS HERBICIDES

This application is a 371 of PCT/EP98/01611 filed Mar. 19, 1998.

The present invention relates to novel, herbicidally active substituted pyridone derivatives, to a process for the preparation thereof, to compositions comprising those compounds, and to the use thereof in the control of weeds, especially in crops of useful plants, for example, cereals, maize, rice, cotton, soybean, rape, sorghum, sugar cane, sugar beet, sunflowers, vegetables, plantation crops and fodder plants, or in the inhibition of plant growth. Phenyl-pyrazole compounds having herbicidal activity are known and are described, for example, in EP-A-0 361 114, U.S. Pat. No. 5,032,165, WO 92,02509, WO 92,06962, WO 95/33728, WO 96/01254 and WO 97/00246.

Surprisingly, it has now been found that substituted pyridono-pyrazole derivatives have excellent herbicidal and growth-inhibiting properties.

The present invention accordingly relates to compounds of formula I

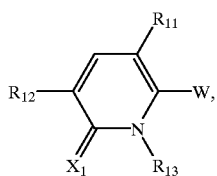
(I)

wherein

W is a group

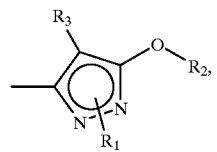
(W1)

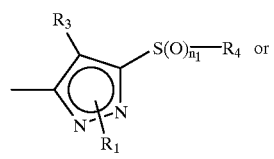
(W2)

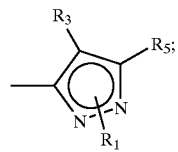
(W3)

$R_1$ is hydrogen, $C_1$–$C_4$alkyl, $C_1$–$C_4$haloalkyl, cyano-$C_1$–$C_4$alkyl, $C_3$- or $C_4$-alkenyl, $C_3$- or $C_4$-haloalkenyl, $C_3$- or $C_4$-alkynyl or $C_3$–$C_6$cycloalkyl;

$R_2$ is hydrogen, $C_1$–$C_4$alkyl, $C_1$–$C_4$haloalkyl, $C_3$–$C_6$alkenyl, $C_3$–$C_6$haloalkenyl, $C_3$–$C_6$alkynyl, $C_1$–$C_4$alkyl-$S(O)_2$— or $C_1$–$C_4$haloalkyl-$S(O)_2$—;

$R_3$ is hydrogen, $C_1$–$C_4$alkyl, $C_1$–$C_4$haloalkyl, $C_2$–$C_6$alkenyl, $C_2$–$C_6$haloalkenyl, $C_2$–$C_6$alkynyl, halogen, cyano, $NH_2C(S)$—, nitro or amino;

$n_1$ is 0, 1 or 2;

$R_4$ is hydrogen, $C_1$–$C_4$alkyl, $C_1$–$C_4$haloalkyl, $C_3$–$C_6$alkenyl, $C_3$–$C_6$haloalkenyl, $C_3$–$C_6$alkynyl or $C_3$–$C_6$cycloalkyl;

$R_5$ is hydrogen, halogen, $C_1$–$C_4$alkyl, $C_1$–$C_4$haloalkyl, cyano, nitro, amino, $NH_2C(O)$—, $NH_2C(S)$—, $C_1$–$C_4$alkylcarbonyl, $C_1$–$C_6$alkoxycarbonyl, $C_1$–$C_4$haloalkylcarbonyl, $C_2$–$C_4$alkenylcarbonyl, $C_1$–$C_3$alkyl-CH(OH)—, OHC—, HOC(O)—, ClC(O)—, HON=CH—, $C_1$–$C_4$alkoxy-N=CH—, $C_2$–$C_4$haloalkenylcarbonyl or $C_2$–$C_4$alkynylcarbonyl;

$R_{11}$ is hydrogen, fluorine, chlorine, bromine or methyl;

$R_{12}$ is hydrogen, halogen, methyl, halomethyl, nitro, amino, hydroxy, OHC—, HOC(O)—, cyano, $C_1$–$C_4$alkoxycarbonyl or halomethoxy;

$X_1$ is O, S, $R_{20}N=$ or $R_{25}ON=$;

$R_{13}$ is hydroxy, $C_1$–$C_6$alkoxy, $C_3$–$C_6$alkenyloxy, $C_3$–$C_6$alkynyloxy, $C_1$–$C_6$haloalkoxy, $C_3$–$C_6$-haloalkenyloxy, $C_1$–$C_6$alkoxy-$C_1$–$C_6$alkyl, $C_3$–$C_6$alkenyloxy-$C_1$–$C_6$alkyl, $C_3$–$C_6$alkynyloxy-$C_1$–$C_6$alkyl, $C_1$–$C_6$alkoxy-$C_1$–$C_6$alkoxy-$C_1$–$C_6$alkyl, $B_1$—$C_1$–$C_6$alkoxy, $R_{21}(R_{22})N$—, $C_1$–$C_6$alkyl, $C_3$–$C_6$alkenyl, $C_3$–$C_6$alkynyl, $C_2$–$C_6$haloalkyl, $C_3$–$C_6$haloalkenyl, $C_3$–$C_6$cycloalkyl, $C_3$–$C_6$halocycloalkyl, $B_1$—$C_1$–$C_6$alkyl, OHC—, $C_1$–$C_6$alkylcarbonyl, $C_1$–$C_6$alkylcarbonyloxy, $C_1$–$C_6$haloalkylcarbonyl, $C_2$–$C_6$alkenylcarbonyl, $C_1$–$C_6$alkoxycarbonyl, $C_1$–$C_6$alkyl-$S(O)_2$—, $C_1$–$C_6$haloalkyl-$S(O)_2$—, $(C_1$–$C_6$alkyl$)_2$N—N=CH—,

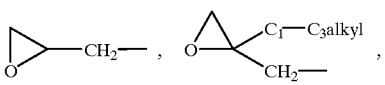

$B_1$—CH=N—, $(CH_3)_2$N—CH=N—, $(C_1$–$C_5$hydroxyalkyl)—$CH_2$—, $(B_1$—$C_1$–$C_5$hydroxyalkyl)—$CH_2$—, $(B_1$—$C_1$–$C_5$haloalkyl)—$CH_2$—, (hydroxy-$C_1$–$C_5$alkyl)—O— or $(B_1$—$C_1$–$C_5$hydroxyalkyl)—O—;

$B_1$ is cyano, OHC—, HOC(O)—, $C_1$–$C_6$alkylcarbonyl, $C_1$–$C_6$alkoxycarbonyl, $C_3$–$C_6$alkenyloxycarbonyl, $C_3$–$C_6$alkynyloxycarbonyl, benzyloxycarbonyl, benzyloxycarbonyl mono- to tri-substituted at the phenyl ring by halogen, $C_1$–$C_4$alkyl or by $C_1$–$C_4$haloalkyl, benzylthio-C(O)—, benzylthio-C(O)— mono- to tri-substituted at the phenyl ring by halogen, $C_1$–$C_4$alkyl or by $C_1$–$C_4$haloalkyl, $C_1$–$C_6$haloalkoxycarbonyl, $C_1$–$C_6$alkylthio-C(O)—, $R_{26}(R_{27})NC(O)$—, phenyl, phenyl mono- to tri-substituted by halogen, $C_1$–$C_4$alkyl or by $C_1$–$C_4$haloalkyl, $C_1$–$C_6$-alkyl-$S(O)_2$—, $C_1$–$C_6$alkyl-$S(O)$—, $C_1$–$C_6$alkylthio, $C_3$–$C_6$cycloalkyl, $C_1$–$C_6$alkoxy, $C_3$–$C_6$alkenylthio or $C_3$–$C_6$alkynylthio;

$R_{20}$ is hydrogen, $C_1$–$C_6$alkyl, $C_3$–$C_6$alkenyl, $C_3$–$C_6$alkynyl, $C_2$–$C_6$haloalkyl, cyano, $R_{23}(R_{24})N$—, $C_1$–$C_6$alkoxycarbonyl, $C_3$–$C_6$alkenyloxycarbonyl, $C_3$–$C_6$alkynyloxycarbonyl, $C_2$–$C_6$haloalkoxycarbonyl, OHC—, $C_1$–$C_6$alkylcarbonyl, $C_1$–$C_6$haloalkylcarbonyl, $C_1$–$C_6$alkyl-$S(O)_2$—, $C_1$–$C_6$haloalkyl-$S(O)_2$—, phenyl, phenyl mono- to tri-substituted by halogen, $C_1$–$C_4$alkyl or by $C_1$–$C_4$haloalkyl, phenyl-$C_1$–$C_6$alkyl, or phenyl-$C_1$–$C_6$alkyl mono- to tri-substituted at the phenyl ring by halogen, $C_1$–$C_4$alkyl or by $C_1$–$C_4$haloalkyl;

$R_{21}$ and $R_{22}$ are each independently hydrogen, $C_1$–$C_6$alkyl, $C_3$–$C_6$alkenyl, $C_3$–$C_6$alkynyl, $C_1$–$C_6$-haloalkyl, $C_3$–$C_6$haloalkenyl, $C_3$–$C_6$cycloalkyl, $C_1$–$C_6$alkoxy-$C_1$–$C_6$alkyl, OHC—, $C_1$–$C_6$alkylcarbonyl, $C_1$–$C_6$haloalkylcarbonyl, $C_1$–$C_6$alkyl-$S(O)_2$— or $C_1$–$C_6$haloalkyl-$S(O)_2$—;

$R_{23}$ and $R_{24}$ are each independently as defined for $R_{21}$;

$R_{25}$ is hydrogen, $C_1$–$C_6$alkyl, $C_3$–$C_6$alkenyl, $C_3$–$C_6$alkynyl, $C_1$–$C_6$haloalkyl, $C_3$–$C_6$haloalkenyl, $C_1$–$C_6$alkoxy- $C_1$–$C_6$alkyl, benzyl, $C_1$–$C_6$alkyl-S(O)$_2$— or $C_1$–$C_6$haloalkyl-S(O)$_2$—;

$R_{26}$ and $R_{27}$ are each independently hydrogen, $C_1$–$C_6$alkyl, $C_3$–$C_6$alkenyl, $C_3$–$C_6$alkynyl, $C_1$–$C_6$haloalkyl, $C_3$–$C_6$haloalkenyl, phenyl, phenyl mono- to tri-substituted by halogen, $C_1$–$C_4$alkyl or by $C_1$–$C_4$haloalkyl, benzyl, or benzyl mono- to tri-substituted at the phenyl ring by halogen, $C_1$–$C_4$alkyl or by $C_1$–$C_4$haloalkyl; or $X_1$ and $R_{13}$ together form a group =N—Y— wherein Y is bonded to the ring nitrogen atom;

Y is —C($R_{31}$)($R_{32}$)—CH$_2$—, —C($R_{31}$)($R_{32}$)—O—, —C($R_{31}$)($R_{32}$)—CH$_2$—CH$_2$—, —C($R_{31}$)($R_{32}$)—CH$_2$—O—, —O—CH$_2$—, —O—CH$_2$—CH$_2$—, —O—CH=CH—, —N($R_{33}$)—CH$_2$—, —N($R_{33}$)—CH$_2$—CH$_2$—, —N($R_{33}$)—CH=CH—, —N($R_{33}$)—C($X_3$)—CH$_2$—, —C($X_3$)—CH$_2$—, —C($X_3$)—CH$_2$—CH$_2$—, —C($X_3$)—CH$_2$—O—, —C($X_3$)—O—, —C($R_{34}$)=CH—, —C($R_{31}$)($R_{32}$)—CH=CH—, —C($R_{34}$) N—, —C($R_{31}$)($R_{32}$)—CH=N—, —C($R_{31}$)($R_{32}$)—N=CH—, —C($X_3$)—CH=CH—, —N=N—, —C($R_{31}$)($R_{32}$)—C(O)—, —C($R_{31}$) ($R_{32}$)—C(S)—, —C($R_{31}$)($R_{32}$)—CH$_2$—C(O)—, —C($R_{31}$)($R_{32}$)—CH$_2$—C(S)—, —N ($R_{33}$)—C(O)—, —N ($R_{33}$)—C(S)—, —N($R_{33}$)—CH$_2$—C(O)—, —N($R_{33}$)—CH$_2$—C(S)—, —O—C(O)—, —O—C(S)—, —C($R_{34}$)=CH—C(O)— or —C($R_{34}$)=CH—C(S)—, the right-hand end of the bridge members in the above definitions of Y being bonded to the ring nitrogen atom;

$R_{31}$ is hydrogen, $C_1$–$C_6$alkyl or $C_1$–$C_6$haloalkyl;

$R_{32}$ is hydrogen, $C_1$–$C_6$alkyl, $C_2$–$C_6$alkenyl, $C_2$–$C_6$alkynyl, $C_1$–$C_6$haloalkyl, $C_2$–$C_6$haloalkenyl, cyano-$C_1$–$C_6$alkyl, hydroxy-$C_1$–$C_6$alkyl, $C_1$–$C_6$alkoxy-$C_1$–$C_6$alkyl, $C_3$–$C_6$alkenyloxy-$C_1$–$C_6$alkyl, $C_3$–$C_6$alkynyloxy-$C_1$–$C_6$alkyl, $C_1$–$C_6$alkylcarbonyloxy-$C_1$–$C_6$alkyl, $C_1$–$C_6$haloalkylcarbonyloxy-$C_1$–$C_6$alkyl, carboxyl, $C_1$–$C_6$alkoxycarbonyl, $C_3$–$C_6$alkenyloxycarbonyl, $C_3$–$C_6$alkynyloxycarbonyl, $C_1$–$C_6$haloalkoxycarbonyl, $C_3$–$C_6$cycloalkoxycarbonyl, $C_1$–$C_4$alkoxy-$C_1$–$C_6$alkoxycarbonyl, $C_1$–$C_6$alkyl-NHC(O)—, ($C_1$–$C_6$alkyl)$_2$NC(O)—, $C_3$–$C_6$alkenyl-NHC(O)—, $C_1$–$C_6$alkyl-($C_3$–$C_6$-alkenyl)NC(O)—, $C_3$–$C_6$alkynyl-NHC(O)—, aminocarbonyl, $C_1$–$C_6$alkylthio-C(O)—, $C_3$–$C_6$-alkenylthio-C(O)—, $C_3$–$C_6$alkynylthio-C(O)—, benzyloxycarbonyl, benzyloxycarbonyl mono- to tri-substituted at the phenyl ring by halogen, $C_1$–$C_4$alkyl or by $C_1$–$C_4$haloalkyl, phenoxycarbonyl, $C_1$–$C_6$alkyl-S(O)$_2$NHC(O)—, $C_1$–$C_6$alkyl-S(O)$_2$($C_3$–$C_6$alkenyl)N—C(O)—, $C_1$–$C_6$haloalkyl-S(O)$_2$NHC(O)—, HON=CH—, $C_1$–$C_6$alkoxy-N=CH—, $C_3$–$C_6$alkenyloxy-N=CH—, $C_3$–$C_6$alkynyloxy-N=CH—, HOC(O)—$C_1$–$C_6$alkyl, $C_1$–$C_6$alkoxycarbonyl-$C_1$–$C_6$alkyl, $C_3$–$C_6$alkenyloxycarbonyl-$C_1$–$C_6$alkyl, $C_3$–$C_6$alkynyloxycarbonyl-$C_1$–$C_6$alkyl, $C_1$–$C_6$alkylcarbonyl, ClC(O)—, H$_2$NC(S)—, OHC—, cyano, phenyl, phenyl mono- to tri-substituted by halogen, $C_1$–$C_4$alkyl or by $C_1$–$C_4$-haloalkyl, phenyl-$C_1$–$C_6$alkyl, or phenyl-$C_1$–$C_6$alkyl mono- to tri-substituted at the phenyl ring by halogen, $C_1$–$C_4$alkyl or by $C_1$–$C_4$haloalkyl;

$X_3$ is O, S, $R_{20}$N= or $R_{25}$ON=;

$R_{33}$ is hydrogen, $C_1$–$C_6$alkyl, $C_3$–$C_6$alkenyl, $C_3$–$C_6$alkynyl, $C_1$–$C_6$haloalkyl, $C_3$–$C_6$haloalkenyl, $C_3$–$C_6$cycloalkyl, $C_1$–$C_6$alkylcarbonyl, $C_1$–$C_6$haloalkylcarbonyl, $C_1$–$C_6$alkyl-S(O)$_2$— or $B_2$–$C_1$–$C_6$-alkyl;

$B_2$ is cyano, HOC(O)—, $C_1$–$C_6$alkoxycarbonyl, $C_1$–$C_6$alkylcarbonyl or $C_1$–$C_6$alkoxy; and $R_{34}$ is as defined for $R_{32}$ or is halogen, $C_1$–$C_6$alkoxy, $C_3$–$C_6$alkenyloxy, $C_1$–$C_6$haloalkoxy, $C_1$–$C_6$alkylthio, $C_1$–$C_6$alkyl-S(O)— or $C_1$–$C_6$alkyl-S(O)$_2$—, and also to the pyrazole N-oxides, agrochemically acceptable salts and stereoisomers of those compounds of formula I.

In the above definitions, halogen is to be understood as meaning iodine or, preferably, fluorine, chlorine or bromine.

The alkyl, alkenyl and alkynyl groups in the substituent definitions may be straight-chain or branched, this applying also to the alkyl, alkenyl and alkynyl moiety of the alkylcarbonyl, hydroxyalkyl, cyanoalkyl, alkoxyalkyl, alkoxyalkoxyalkyl, alkylthio, alkylthio-C(O)—, alkylsulfonyl, alkylaminocarbonyl, dialkylaminocarbonyl, $B_1$-alkyl and HOC(O)-alkyl groups. Alkyl groups are, for example, methyl, ethyl, n-propyl, isopropyl, n-butyl, sec-butyl, isobutyl, tert-butyl and the various isomers of pentyl and hexyl. Methyl, ethyl, n-propyl, isopropyl and n-butyl are preferred.

There may be mentioned as examples of alkenyl radicals vinyl, allyl, methallyl, 1-methylvinyl, but-2-en-1-yl, pentenyl and 2-hexenyl, with preference being given to alkenyl radicals having a chain length of from 3 to S carbon atoms.

There may be mentioned as examples of alkynyl radicals ethynyl, propargyl, 1-methylpropargyl, 3-butynyl, but-2-yn-1-yl, 2-methylbutyn-2-yl, but-3-yn-2-yl, 1-pentynyl, pent-4-yn-1-yl and 2-hexynyl, with preference being given to alkynyl radicals having a chain length of from 2 to 4 carbon atoms.

Suitable haloalkyl radicals are alkyl groups that are mono- or poly-substituted, especially mono- to tri-substituted, by halogen, halogen being in particular iodine or especially fluorine, chlorine or bromine, for example fluoromethyl, difluoromethyl, trifluoromethyl, chloromethyl, dichloromethyl, trichloromethyl, 2-fluoroethyl, 2,2-difluoroethyl, 2-chloroethyl, 2,2-dichloroethyl, 2,2,2-trifluoroethyl and 2,2,2-trichloroethyl.

Suitable haloalkenyl radicals are alkenyl groups mono- or poly-substituted by halogen, halogen being in particular bromine, iodine or especially fluorine or chlorine, for example 2- or 3-fluoropropenyl, 2- or 3-chloropropenyl, 2- or 3-bromopropenyl, 2,3,3-trifluoropropenyl, 2,3,3-trichloropropenyl, 4,4,4-trifluorobut-2-en-1-yl and 4,4,4-trichlorobut-2-en-1-yl. Of the alkenyl radicals mono-, di- or tri-substituted by halogen, preference is given to those having a chain length of 3 or 4 carbon atoms. The alkenyl groups may be substituted by halogen at saturated or unsaturated carbon atoms.

Alkylsulfonyl is, for example, methylsulfonyl, ethylsulfonyl, propylsulfonyl, isopropyisulfonyl, n-butylsulfonyl, isobutylsulfonyl, sec-butylsulfonyl, tert-butylsulfonyl or an isomer of pentylsulfonyl or hexylsulfonyl; preferably methylsulfonyl or ethylsulfonyl.

Haloalkylsulfonyl is, for example, fluoromethylsulfonyl, difluoromethylsulfonyl, trifluoromethylsulfonyl, chloromethylsulfonyl, trichloromethylsulfonyl, 2-fluoroethylsulfonyl, 2,2,2-trifluoroethylsulfonyl or 2,2,2-trichloroethylsulfonyl.

Alkenylsulfonyl is, for example, allyisulfonyl, methallylsulfonyl, but-2-en-1-ylsulfonyl, pentenylsulfonyl or 2-hexenylsulfonyl.

Haloalkenylsulfonyl is, for example, 2- or 3-fluoropropenylsulfonyl, 2- or 3-chloropropenylsulfonyl, 2- or 3-bromopropenylsulfonyl, 2,3,3-trifluoropropenylsulfonyl, 2,3,3-trichloropropenylsulfonyl, 4,4,4-trifluorobut-2-en-1-ylsulfonyl or 4,4,4-trichlorobut-2-en-1-ylsulfonyl.

Cyanoalkyl is, for example, cyanomethyl, cyanoethyl, cyanoeth-1-yl or cyanopropyl. Hydroxyalkyl is, for example, hydroxymethyl, 2-hydroxyethyl or 3-hydroxypropyl.

Alkylamino is, for example, methylamino, ethylamino or an isomer of propyl- or butyl-amino.

Dialkylamino is, for example, dimethylamino, diethylamino or an isomer of dipropyl- or dibutyl-amino.

Alkenylamino is, for example, allylamino, methallylamino or but-2-en-1-ylamino.

Alkynylamino is, for example, propargylamino or 1-methyipropargylamino.

Haloalkylamino is, for example, chloroethylamino, trifluoroethylamino or 3-chloropropylamino.

Di(haloalkyl)amino is, for example, di(2-chloroethyl) amino.

Alkylcarbonyl is especially acetyl or propionyl.

Haloalkylcarbonyl is especially trifluoroacetyl, trichloroacetyl, 3,3,3-trifluoropropionyl or 3,3,3-trichloropropionyl.

Alkenylcarbonyl is especially vinylcarbonyl, allylcarbonyl, methallylcarbonyl, but-2-en-1-yl-carbonyl, pentenylcarbonyl or 2-hexenylcarbonyl.

Alkynylcarbonyl is especially acetylenecarbonyl, propargylcarbonyl, 1-methylpropargylcarbonyl, 3-butynylcarbonyl, but-2-yn-1-ylcarbonyl or pent-4-yn-1-ylcarbonyl.

Alkoxy is, for example, methoxy, ethoxy, n-propoxy, isopropoxy, n-butoxy, isobutoxy, sec-butoxy, tert-butoxy or an isomer of pentyloxy or hexyloxy.

Alkenyloxy is, for example, allyloxy, methallyloxy or but-2-en-1-yloxy.

Alkynyloxy is, for example, propargyloxy or 1-methylpropargyloxy.

Alkoxyalkyl is, for example, methoxymethyl, methoxyethyl, ethoxymethyl, ethoxyethyl, n-propoxymethyl, n-propoxyethyl, isopropoxymethyl or isopropoxyethyl.

Alkenyloxyalkyl is, for example, allyloxyalkyl, methallyloxyalkyl or but-2-en-1-yloxyalkyl.

Alkynyloxyalkyl is, for example, propargyloxyalkyl or 1-methylpropargyioxyalkyl.

Alkoxycarbonyl is, for example, methoxycarbonyl, ethoxycarbonyl, n-propoxycarbonyl, iso-propoxycarbonyl or n-butoxycarbonyl, preferably methoxycarbonyl or ethoxycarbonyl.

Alkenyloxycarbonyl is, for example, allyloxycarbonyl, methallyloxycarbonyl, but-2-en-1-yl-oxycarbonyl, pentenyloxycarbonyl or 2-hexenyloxycarbonyl.

Alkynyloxycarbonyl is, for example, propargyloxycarbonyl, 3-butynyloxycarbonyl, but-2-yn-1-yloxycarbonyl or 2-methylbutyn-2-yloxycarbonyl.

Alkoxyalkoxycarbonyl is, for example, methoxymethoxycarbonyl, ethoxymethoxycarbonyl, ethoxyethoxycarbonyl, propoxymethoxycarbonyl, propoxyethoxycarbonyl, propoxypropoxycarbonyl or butoxyethoxycarbonyl.

Haloalkoxy is, for example, fluoromethoxy, difluoromethoxy, trifluoromethoxy, 2,2,2-trifluoroethoxy, 1,1,2,2-tetrafluoroethoxy, 2-fluoroethoxy, 2-chloroethoxy or 2,2,2-trichloroethoxy.

Of the alkenyl radicals mono-, di- or tri-substituted by halogen, preference is given to those having a chain length of 3 or 4 carbon atoms. The alkenyloxy groups may be substituted by halogen at saturated or unsaturated carbon atoms.

Suitable haloalkenyloxy radicals are alkenyloxy groups mono- or poly-substituted by halogen, halogen being in particular bromine, iodine or especially fluorine or chlorine, for example 2- or 3-fluoropropenyloxy, 2- or 3-chloropropenyloxy, 2- or 3-bromopropenyloxy, 2,3,3-trifluoropropenyloxy, 2,3,3-trichloropropenyloxy, 4,4,4-trifluoro-but-2-en-1-yloxy and 4,4,4-trichlorobut-2-en-1-yloxy.

The cycloalkyl radicals suitable as substituents are, for example, cyclopropyl, cyclobutyl, cyclopentyl and cyclohexyl.

The cycloalkoxycarbonyl radicals suitable as substituents are, for example, cyclopropoxycarbonyl, cyclobutoxycarbonyl, cyclopentyloxycarbonyl and cyclohexyloxycarbonyl.

The halocycloalkyl radicals suitable as substituents are, for example, mono-, di- or up to perhalogenated cycloalkyl radicals, for example, fluorocyclopropyl, chlorocyclopropyl, bromocyclopropyl, 2,2-dichlorocyclopropyl, 2,2-difluorocyclopropyl, 2,2-dibromocyclopropyl, 2-fluoro-2-chlorocyclopropyl, 2-chloro-2-bromocyclopropyl, 2,2,3,3-tetrafluorocyclopropyl, 2,2,3,3-tetrachlorocyclopropyl, pentafluorocyclobutyl, fluorocyclobutyl, chlorocyclobutyl, 2,2-difluorocyclobutyl, 2,2,3,3-tetrafluorocyclobutyl, 2,2,3-trifluoro-3-chlorocyclobutyl, 2,2-dichloro-3,3-difluorocyclobutyl, fluorocyclopentyl, difluorocyclopentyl, chlorocyclopentyl, perfluorocyclopentyl, chlorocyclohexyl and pentachlorocyclohexyl.

Alkylthio is, for example, methylthio, ethylthio, propylthio or butylthio or a branched isomer thereof.

Phenyl or benzyl per se, or as part of a substituent, such as, for example, phenoxycarbonyl or benzyloxycarbonyl, may be unsubstituted or substituted, in which case the substituents may be in the ortho-, meta- or para-position. Substituents are, for example, $C_1$–$C_4$alkyl, $C_1$–$C_4$alkoxy, halogen or $C_1$–$C_4$haloalkyl.

Corresponding meanings may also be given to the substituents in combined definitions, such as, for example, in alkyl-S(O)—, alkoxy-N=CH—, (alkyl)$_2$N-C(O)—, (alkyl)$_2$N—N=CH—, alkenyl-NHC(O)—, alkyl(alkenyl)N—C(O)—, alkynyl-NHC(O)—, alkylcarbonyloxyalkyl, alkoxycarbonylalkyl, haloalkoxycarbonyl, haloalkylcarbonyloxyalkyl, haloalkenylcarbonyl, alkyl-S(O)$_2$—NHC(O)—, haloalkyl-S(O)$_2$NHC(O)—, B$_1$-alkoxy and B$_2$-alkyl.

In the definition of $R_{13}$, ($C_1$–$C_5$hydroxyalkyl)—CH$_2$—, (B$_1$—$C_1$–$C_5$hydroxyalkyl)—CH$_2$— and (B$_1$—$C_1$–$C_6$-haloalkyl)—CH$_2$— signify that only the $C_1$–$C_5$alkyl moiety is hydroxylated or halogenated, that is to say, the methylene group is not hydroxylated or halogenated.

In the definition of $X_1$ and $R_{13}$ together, a group =N—Y— wherein Y is bonded to the ring nitrogen atom is to be understood as meaning one of the following bicyclic ring systems of formula I:

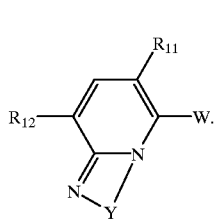

(I)

In the definition of Y, it is always the right-hand end of the bridge member that is bonded to the ring nitrogen atom, as is illustrated, for example where Y is —C(R$_{31}$)(R$_{32}$)—CH$_2$—, —C(R$_{31}$)(R$_{32}$)—O— and —C(R$_{34}$)=CH—, in the following bicyclic ring structures:

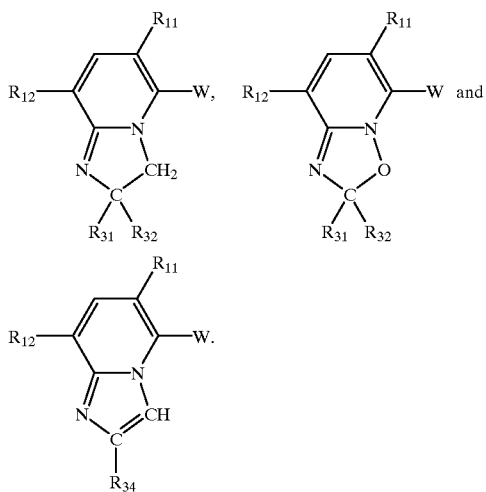

In the definitions of cyanoalkyl, alkylcarbonyl, alkenylcarbonyl, haloalkenylcarbonyl, alkynylcarbonyl, alkoxycarbonyl, alkylthiocarbonyl and haloalkylcarbonyl, the upper and lower limits of the number of carbon atoms given in each case do not include the cyano or carbonyl carbon atom, as the case may be.

The compounds of formula I may, in respect of the group W (W1 to W3), be present in the form of mixtures consisting of the isomers substituted in the 3- and 5-positions of the pyrazole ring by the pyridone group (pyridone), for example in the form of regioisomers IW1a and IW1b

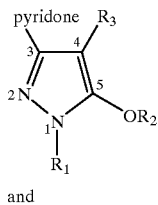
(IW1a)

and

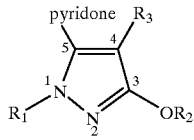
(IW1b)

for the group W1. The ratio of isomers may vary as a function of the method of synthesis.

The invention relates also to the salts that the compounds of formula I having azide hydrogen, especially the derivatives having carboxylic acid groups and sulfonamide groups (for example carboxy-substituted alkyl, alkoxy and pyridone groups ($R_{12}$) and alkyl-S(O)$_2$NH— and haloalkyl-S(O)$_2$NH— groups), are capable of forming with bases. Those salts are, for example, alkali metal salts, for example sodium and potassium salts; alkaline earth metal salts, for example calcium and magnesium salts; ammonium salts, that is to say unsubstituted ammonium salts and mono- or poly-substituted ammonium salts, for example triethylammonium and methylammonium salts; or salts with other organic bases.

Of the alkali metal and alkaline earth metal hydroxides as salt farmers, attention is drawn, for example, to the hydroxides of lithium, sodium, potassium, magnesium and calcium, but especially to the hydroxides of sodium and potassium.

Examples of amines suitable for ammonium salt formation include ammonia as well as primary, secondary and tertiary $C_1$–$C_{18}$alkylamines, $C_1$–$C_4$hydroxyalkylamines and $C_2$–$C_4$-alkoxyalkylamines, for example methylamine, ethylamine, n-propylamine, isopropylamine, the four isomers of butylamine, n-amylamine, isoamylamine, hexylamine, heptylamine, octylamine, nonylamine, decylamine, pentadecylamine, hexadecylamine, heptadecylamine, octadecylamine, methylethylamine, methylisopropylamine, methylhexylamine, methylnonylamine, methylpentadecylamine, methyloctadecylamine, ethylbutylamine, ethylheptylamine, ethyloctylamine, hexylheptylamine, hexyloctylamine, dimethylamine, diethylamine, di-n-propylamine, diisopropylamine, di-n-butylamine, di-n-amylamine, diisoamylamine, dihexylamine, diheptylamine, dioctylamine, ethanolamine, n-propanolamine, isopropanolamine, N,N-diethanolamine, N-ethylpropanolamine, N-butylethanolamine, allylamine, n-butenyl-2-amine, n-pentenyl-2-amine, 2,3-dimethylbutenyl-2-amine, dibutenyl-2-amine, n-hexenyl-2-amine, propylenediamine, trimethylamine, triethylamine, tri-n-propylamine, triisopropylamine, tri-n-butylamine, triisobutylamine, tri-sec-butylamine, tri-n-amylamine, methoxyethylamine and ethoxyethylamine; heterocyclic amines, for example pyridine, quinoline, isoquinoline, morpholine, thiomorpholine, piperidine, pyrrolidine, indoline, quinuclidine and azepine; primary arylamines, for example anilines, methoxyanilines, ethoxyanilines, o-, m- and p-toluidines, phenylenediamines, benzidines, naphthylamines and o-, m- and p-chloroanilines; especially triethylamine, isopropylamine and diisopropylamine.

The salts of compounds of formula I having basic groups, especially having basic pyrazolyl rings, or of derivatives having amino groups, for example alkylamino and dialkylamino groups, in the definition of $R_3$, $R_5$ or $R_{13}$ are, for example, salts with inorganic or organic acids, for example hydrohalic acids, such as hydrofluoric acid, hydrochloric acid, hydrobromic acid or hydriodic acid, and also sulfuric acid, phosphoric acid, nitric acid, and organic acids, such as acetic acid, trifluoroacetic acid, trichloroacetic acid, propionic acid, glycolic acid, thiocyanic acid, citric acid, benzoic acid, oxalic acid, formic acid, benzenesulfonic acid, p-toluenesulfonic acid and methanesulfonic acid.

The possible presence of at least one asymmetrical carbon atom in the compounds of formula I, for example in the substituent $R_{13}$, where $R_{13}$ is a branched alkyl, alkenyl, haloalkyl or alkoxyalkyl group or where $R_{13}$ is ($B_1$—$C_1$–$C_6$hydroxyalkyl)—$CH_2$— wherein, for example, $B_1$ is $C_1$–$C_6$alkyl-S(O)—, means that the compounds may occur in the form of optically active single isomers or in the form of racemic mixtures. In the present invention, "compounds of formula I" is to be understood as including both the pure optical antipodes and the racemates or diastereoisomers. When an aliphatic C=C or C=N—O double bond (syn/anti) is present, geometric isomerism may occur. The invention relates to those isomers also.

Preferred compounds of formula I correspond to formula Ia

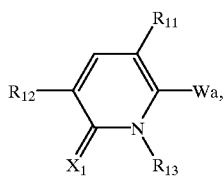
(Ia)

wherein

Wa is a group

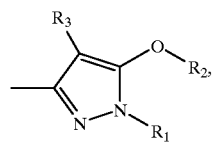
(W1a)

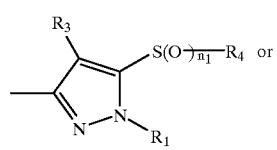  or
(W2a)

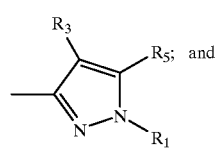  and
(W3a)

$R_1$, $R_2$, $R_3$, $R_4$, $R_5$, $R_{11}$, $R_{12}$, $R_{13}$, $X_1$ and $n_1$ are as defined for formula I. Of the compounds of formula Ia, preference is given to those wherein in the group Wa $R_3$ is $C_1$–$C_4$alkyl or halogen; and $R_1$ is methyl or ethyl.

Special preference is given to compounds of formula Ia wherein $R_3$ is methyl, halomethyl, chlorine or bromine. Of those, the compounds wherein Wa is a group W1a or W2a are especially important.

Also especially important are compounds of formula 1a wherein Wa is the group W3a; and $R_5$ is $C_1$- or $C_2$-halomethyl, cyano or $H_2NC(S)$—.

Also particularly important are compounds of formula 1a wherein Wa is the group W1a; $R_1$ is $C_1$–$C_6$alkyl; $R_2$ is $C_1$- or $C_2$-haloalkyl; $R_3$ is chlorine, bromine, methyl or halomethyl; $R_1$ is fluorine, chlorine or bromine; and $R_{12}$ is halogen, methyl or halomethyl. Of those, compounds in which $R_1$ is methyl or ethyl; and $R_2$ is difluoromethyl are more especially important.

Special preference is given also to compounds of formula 1a wherein Wa is the group W2a; $R_1$ is $C_1$–$C_4$alkyl; $R_4$ is methyl or ethyl; $R_3$ is chlorine, bromine or methyl; $R_1$, is fluorine, chlorine or bromine; and $R_{12}$ is halogen, methyl or halomethyl. Of those compounds, those wherein $R_1$ is methyl or ethyl; and $R_4$ is methyl are more especially preferred. Particularly important compounds of formula 1a are those wherein Wa is the group W3a; $R_1$ is $C_1$–$C_4$alkyl; $R_5$ is $C_1$- or $C_2$-haloalkyl, cyano, $H_2NC(S)$— or $CH_3C(O)$—; $R_3$ is chlorine, bromine, methyl or halomethyl; $R_{11}$ is fluorine, chlorine or bromine; and $R_{12}$ is halogen, methyl or halomethyl. Of those, especially compounds wherein $R_1$ is methyl or ethyl; and $R_5$ is halomethyl or cyano are more especially important.

The process according to the invention for the preparation of a compound of formula I

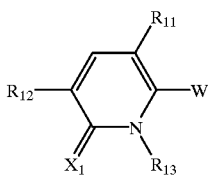
(I)

wherein $R_{11}$, $R_{12}$ and W are as defined for formula I; $X_1$ is O or S; $R_{13}$ is $C_1$–$C_6$alkoxy-$C_1$–$C_6$alkyl, $C_1$–$C_6$alkoxy-$C_1$–$C_6$alkoxy-$C_1$–$C_6$alkyl, $C_1$–$C_6$alkyl, $C_3$–$C_6$alkenyl, $C_3$–$C_6$alkynyl, $C_2$–$C_6$haloalkyl, $C_3$–$C_6$haloalkenyl, $C_3$–$C_6$cycloalkyl, $C_3$–$C_6$halocycloalkyl, $B_1$–$C_1$–$C_6$alkyl,

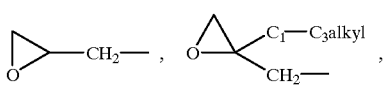

$(C_1$–$C_5$hydroxyalkyl)—$CH_2$—, $(B_1$—$C_1$–$C_5$hydroxyalkyl)—$CH_2$— or $(B_1$—$C_1$–$C_5$haloalkyl)—$CH_2$—; and $B_1$ is as defined for formula I, is carried out analogously to known processes and comprises oxidising a compound of formula III

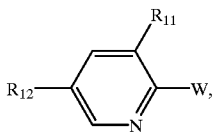
(III)

for example with hydrogen peroxide-urea adduct in the presence of carboxylic acids and/or carboxylic acid anhydrides, organic peracids or persulfonic acid (Caro's acid) in a suitable solvent, to form a compound of formula V

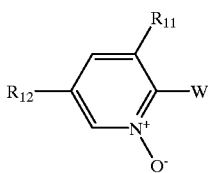
(V)

and subsequently rearranging that compound in an inert solvent in the presence of an anhydride or in the presence of antimony pentachloride to yield, after aqueous working up, a compound of formula II

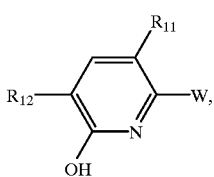
(II)

the radicals $R_{11}$, $R_{12}$ and W in the compounds of formulae II, II and V being as defined above, and then alkylating that compound in the presence of an inert solvent and a base with a compound of formula VI

 (VI), wherein $R_{13}$ is as defined above and L is a leaving group, preferably chlorine, bromine, iodine, $CH_3SO_2O-$ or

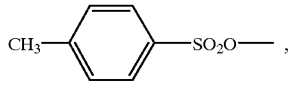

to form the isomeric compounds of formulae I and IV

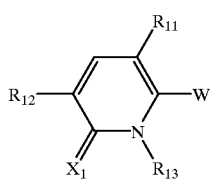 (I)

and

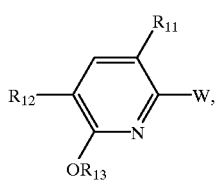 (IV)

wherein $R_{11}$, $R_{12}$, $R_{13}$ and W are as defined above and $X_1$ is O, and subsequently, where appropriate after separating off the compound of formula I, functionalising the pyridone group thereof according to the definition of $X_1$ and $R_{13}$, if desired, for example, converting it with the aid of a suitable sulfur reagent into the corresponding pyridinethione derivative ($X_1$=S) (Reaction Scheme 1).

The process according to the invention for the preparation of a compound of formula I

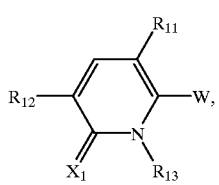 (I)

wherein $R_{11}$, $R_{12}$ and W are as defined for formula I; $X_1$ is S; $R_{13}$ is hydroxy, $C_1$–$C_6$alkoxy, $C_3$–$C_6$alkenyloxy, $C_3$–$C_6$alkynyloxy, $C_1$–$C_6$haloalkoxy, $C_3$–$C_6$haloalkenyloxy, $B_1$—$C_1$–$C_6$alkoxy, $C_1$–$C_6$alkylcarbonyl, $C_1$–$C_6$alkylcarbonyloxy, $C_1$–$C_6$haloalkylcarbonyl, $C_2$–$C_6$alkenylcarbonyl or $C_1$–$C_6$alkoxycarbonyl; and $B_1$ is as defined for formula I, is carried out analogously to known processes and comprises first of all oxidising a compound of formula III

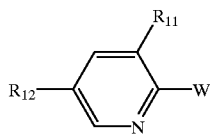 (III)

to yield a compound of formula V

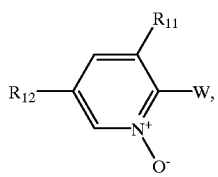 (V)

chlorinating or brominating that compound to form a compound of formula VIII

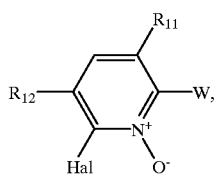 (VIII)

the radicals $R_{11}$, $R_{12}$ and W in the compounds of formulae III, V and VIII being as defined above and Hal in the compound of formula VIII being chlorine or bromine, subsequently converting the compound of formula VIII with a suitable sulfur reagent, for example thiourea, sodium hydrogen sulfide (NaSH) or phosphorus pentasulfide ($P_2S_5$), in the presence of a solvent into a compound of formula Ic

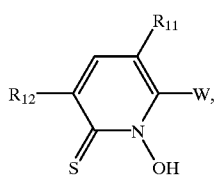 (Ic)

and reacting that compound in the presence of a solvent and a base with a compound of formula XI

 (XI), wherein $R_{14}$ is $C_1$–$C_6$alkyl, $C_3$–$C_6$alkenyl, $C_3$–$C_6$alkynyl, $C_1$–$C_6$haloalkyl, $C_3$–$C_6$haloalkenyl, $B_1$—$C_1$–$C_6$alkyl or $C_1$–$C_6$alkylcarbonyl; $B_1$ is as defined above; and L is a leaving group (Reaction Scheme 2).

The process according to the invention for the preparation of a compound of formula I

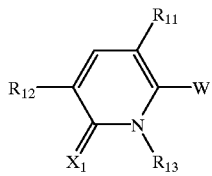

(I)

wherein $R_{11}$, $R_{12}$, $R_{13}$ and W are as defined for formula I and XI is S is carried out analogously to known processes and comprises treating a compound of formula I

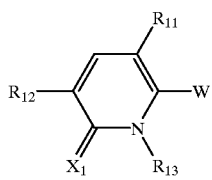

(I)

wherein $R_{11}$, $R_{12}$, $R_{13}$ and W are as defined above and $X_1$ is O, with a sulfur reagent in an inert solvent.

The preparation of compounds of formula I wherein $X_1$ is O or S; and $R_{13}$ is $C_1$–$C_6$alkoxy-$C_1$–$C_6$alkyl, $C_1$–$C_6$alkoxy-$C_1$–$C_6$alkoxy-$C_1$–$C_6$alkyl, $C_1$–$C_6$alkyl, $C_3$–$C_6$alkenyl, $C_3$–$C_6$alkynyl, $C_2$–$C_6$haloalkyl, $C_3$–$C_6$haloalkenyl, $C_3$–$C_6$cycloalkyl, $C_3$–$C_6$halocycloalkyl, $B_1$—$C_1$–$C_6$alkyl,

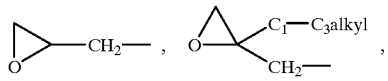

($C_1$–$C_5$hydroxyalkyl)—$CH_2$—, ($B_1$—$C_1$–$C_5$hydroxyalkyl)—$CH_2$— or ($B_1$—$C_1$–$C_5$haloalkyl)—$CH_2$—; and $B_1$ is as defined for formula I is illustrated in the following Reaction Scheme 1.

Reaction Scheme 1

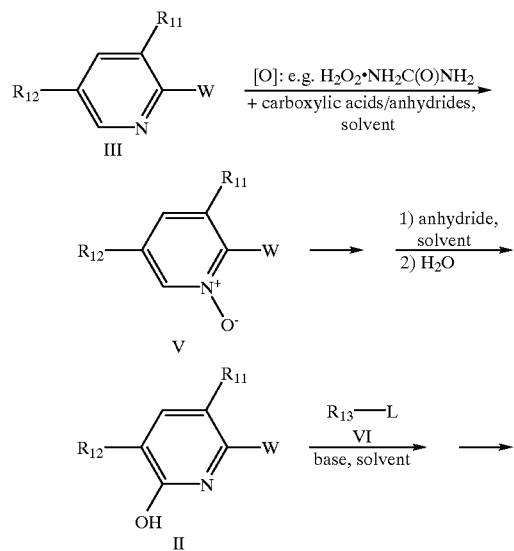

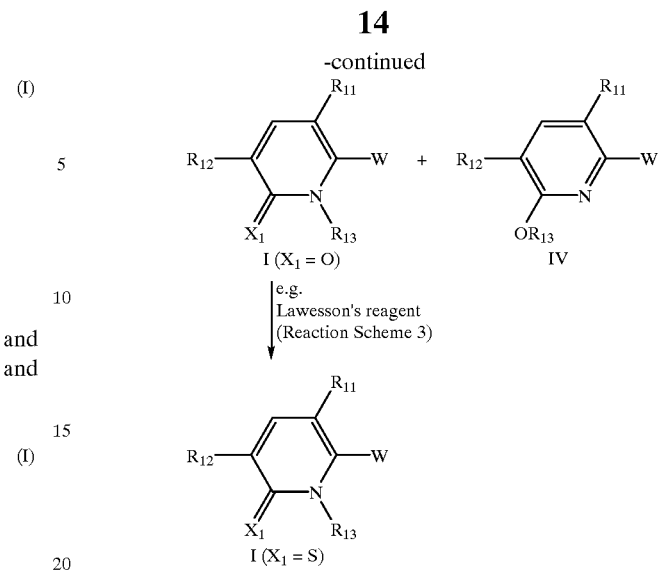

The pyridine N-oxides of formula V (Reaction Scheme 1) can be prepared according to known methods (e.g. Org. Synth. 4, 828 (1963); ibid. 3, 619 (1955); U.S. Pat. No. 3,047,579; and B. Iddon and H. Suschitzky in "Polychloroaromatic Compounds", Editor H. Suschitzky, Plenum Press, London 1974, page 197), advantageously by reaction of a pyridine derivative of formula III with an oxidising agent, such as, for example, an organic peracid, for example m-chloroperbenzoic acid (MCPBA), peracetic acid or pertrifluoroacetic acid, or aqueous hydrogen peroxide solution or hydrogen peroxide-urea adduct together with a carboxylic acid and/or a carboxylic acid anhydride, or an inorganic peracid, for example pertungstic acid. Solvents suitable for that reaction are, for example, water, organic acids, for example acetic acid and trifluoroacetic acid, halogenated hydrocarbons, for example dichloromethane and 1,2-dichloroethane, esters, for example ethyl acetate, ethers, for example tetrahydrofuran and dioxane, or mixtures of those solvents. The reaction temperatures are generally in the range from −20° C. to 100° C., depending on the solvent or mixture of solvents used.

The 6-hydroxypyridine derivatives of formula II can be prepared according to known methods (e.g. Quart. Rev. 10, 395 (1956); J. Am. Chem. Soc. 85, 958 (1963); and J. Org. Chem. 26, 428 (1961)), advantageously by rearrangement of the pyridine N-oxides of formula V in the presence of an anhydride, for example acetic anhydride, trifluoroacetic anhydride or methanesulfonic anhydride, in a suitable inert solvent, such as, for example, a halogenated hydrocarbon, for example dichloromethane or 1,2-dichloroethane, an amide, for example N,N-dimethylformamide or 1-methyl-2-pyrrolidone (NMP), and, where appropriate, in the presence of sodium acetate. The reaction temperatures are generally in the range from −30° C. to 80° C.

The 6-O-acyl- or 6-O-sulfonyl-pyridines formed first can readily be hydrolysed, by aqueous working up of the reaction mixture, to form the desired 6-hydroxypyridines of formula II. Analogously to Tetrahedron 37, 187 (1981), as a further variant it is possible to use antimony pentachloride in the above rearrangement reaction.

The subsequent alkylation may be carried out according to known methods (e.g. Org. Prep. Proced. Int. 9, 5 (1977); J. Org. Chem. 35, 2517 (1970); ibid. 32, 4040 (1967); and Tetrahedron Lett. 36, 8917 (1995) as well as Preparation Examples P20 and P21), advantageously using an alkylation reagent of formula VI. The alkylation usually results in an isomeric mixture consisting of the compounds of formulae I (N-alkylation) and IV (O-alkylation).

Suitable solvents are, for example, alcohols, for example methanol, ethanol and isopropanol, amides, for example N,N-dimethylformamide (DMF) and 1-methyl-2-pyrrolidone (NMP), sulfoxides, for example dimethyl sulfoxide (DMSO), and sulfones, for example sulfolan, or mixtures of the above solvents with water, ethers, for example diethyl ether, tert-butyl methyl ether, dimethoxyethane (DME), dioxane and tetrahydrofuran (THF), esters, for example ethyl acetate, ketones, for example acetone and methyl ethyl ketone, and hydrocarbons, for example n-hexane, toluene and xylenes.

Suitable bases are organic and inorganic bases, for example alkali metal alcoholates, for example sodium methanolate, sodium ethanolate and potassium tert-butanolate, trialkylammonium hydroxides, trialkylammonium halides, for example triethylammonium iodide, alkali metal and alkaline earth metal hydrides, for example sodium hydride together with lithium bromide (2 equivalents), alkali metal carbonates, for example potassium carbonate, alkali metal hydroxides, for example sodium and potassium hydroxide, and also caesium fluoride.

The reaction temperatures for the alkylation are in the range from −20° C. to the reflux temperature of the solvent used, preferably from 0° C. to 50° C. The isomers of formulae I and IV can readily be separated by means of silica gel chromatography or fractional crystallisation.

Optionally, the desired pyridone derivative of formula I separated from the secondary product of formula IV can readily be converted into the corresponding pyridinethione derivative ($X_1$=S) according to known methods (e.g. Bull. Soc. Chim. Fr. 1953, 1001; and J. Am. Chem. Soc. 73, 3681 (1951)), for example with the aid of a suitable sulfur reagent, for example Lawesson's reagent or phosphorus pentasulfide in an inert solvent, such as, for example, a xylene, pyridine or sulfolan. The reaction temperatures are generally in the range from 20° C. to the boiling temperature of the solvent used.

The preparation of compounds of formula I wherein $X_1$ is S; and $R_{13}$ is hydroxy, $C_1$–$C_6$alkoxy, $C_3$–$C_6$alkenyloxy, $C_3$–$C_6$alkynyloxy, $C_1$–$C_6$haloalkoxy, $C_3$–$C_6$haloalkenyloxy, $B_1$—$C_1$–$C_6$alkoxy, $C_1$–$C_6$alkylcarbonyl, $C_1$–$C_6$alkylcarbonyloxy, $C_1$–$C_6$haloalkylcarbonyl, $C_2$–$C_6$alkenylcarbonyl or $C_1$–$C_6$alkoxycarbonyl; and $B_1$ is as defined for formula I is illustrated in the following Reaction Scheme 2.

Reaction Scheme 2

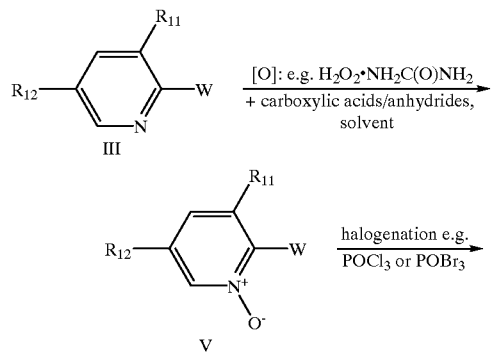

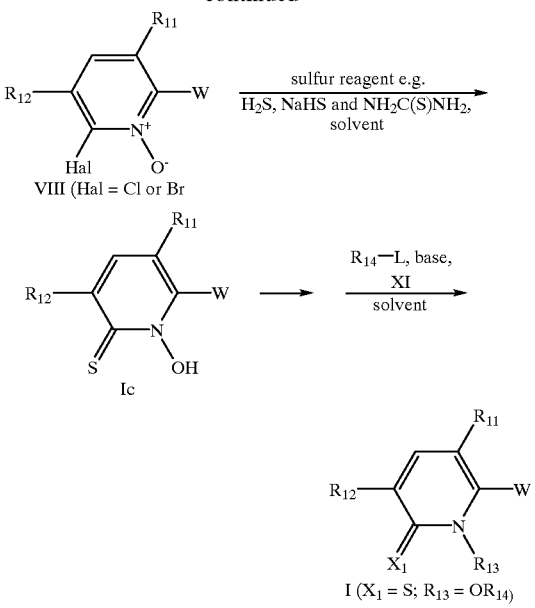

The procedure for the preparation of pyridine N-oxides of formula V (Reaction Scheme 2) is analogous to that indicated under Reaction Scheme 1.

The pyridine N-oxides of formula V can be converted into the corresponding 6-chloro- or 6-bromo-pyridine derivatives of formula VIII analogously to known processes (e.g. Heterocycles 30, 875 (1990); Can. J. Chem. 31, 457 (1953); and J. Org. Chem. 19, 1633 (1954)), advantageously using a halogenating agent, for example phosphorus oxychloride, phosphorus oxybromide, sulfuryl chloride, thionyl chloride or phosphorus pentachloride in phosphorus oxychloride. The halogenation can generally be carried out at temperatures of from 20° C. to 100° C.

The reaction of the halopyridine N-oxides of formula VII to form the compound of formula Ic can be effected analogously to known processes (e.g. U.S. Pat. No. 2,742,476, U.S. Pat. No. 2,809,971, J. Am. Chem. Soc. 72, 4362 (1950) and J. Chem. Soc. 1939, 1858), advantageously using a suitable sulfur reagent, such as, for example, hydrogen sulfide, sodium hydrogen sulfide or thiourea, in a solvent, such as, for example, water, an alcohol, for example ethanol, or a water/alcohol mixture, or an amide, for example N,N-dimethylformamide (DMF) or NMP. The reaction is generally carried out at temperatures of from −10° C. to 100° C.

The reaction of the compound of formula Ic with the reactive reagent of formula XI, wherein L is a leaving group, such as, for example, halogen, for example chlorine, bromine or iodine,

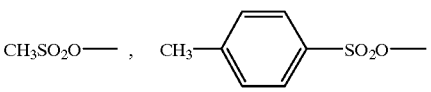

or, in the case where $R_{14}$ is $C_1$–$C_6$alkylcarbonyl and there is used as reactive reagent of formula XI the corresponding acid anhydride, $C_1$–$C_6$alkylcarbonyloxy, can be carried out analogously to known processes (e.g. Tetrahedron Lett. 31, 1965 (1990); Tetrahedron 1991, 7091; and J. Org. Chem. 54, 4330 (1989)). Advantageously, equimolar amounts of compound of formula Ic and reactive reagent of formula XI are reacted at temperatures of from 0° C. to 100° C. in the presence of a solvent and a base.

Suitable solvents include the familiar inert organic solvents, such as, for example, chlorinated hydrocarbons, for example dichloromethane, aromatic hydrocarbons, for example benzene, toluene and pyridine, ethers, for example dioxane and DME, amides, for example N,N-dimethylformamide and NMP, and sulfoxides, for example DMSO. Suitable bases include the known inorganic and organic bases, such as, for example, alkali metal and trialkylammonium hydroxides, for example sodium or potassium hydroxide and triethylammonium hydroxide, respectively, carbonates, for example sodium and potassium carbonate, and alcoholates, for example sodium ethanolate or potassium isopropanolate. The reaction may also, where appropriate, be carried out under phase transfer conditions. There may be used as phase transfer catalysts the customary quaternary ammonium salts, such as, for example tetraoctylammonium bromide and benzyltriethylammonium chloride. Under those conditions, a suitable organic solvent is any inert non-polar solvent, such as, for example, benzene or toluene.

The preparation of compounds of formula I wherein $X_1$ is S; and $R_{13}$ is $C_1$–$C_6$alkoxy-$C_1$–$C_6$-alkyl, $C_1$–$C_6$alkoxy-$C_1$–$C_6$alkoxy-$C_1$–$C_6$alkyl, $C_1$–$C_6$alkyl, $C_3$–$C_6$alkenyl, $C_3$–$C_6$alkynyl, $C_2$–$C_6$haloalkyl, $C_3$–$C_6$haloalkenyl, $C_3$–$C_6$cycloalkyl, $C_3$–$C_6$halocycloalkyl, $B_1$—$C_1$–$C_6$alkyl,

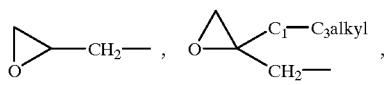

($C_1$-$C_5$hydroxyalkyl)—$CH_2$—, ($B_1$— $C_1$-$C_5$hydroxyalkyl)—$CH_2$— or ($B_1$— $C_1$–$C_6$haloalkyl)— $CH_2$—; and $B_1$ is as defined for formula I is illustrated in the following Reaction Scheme 3.

Reaction Scheme 3

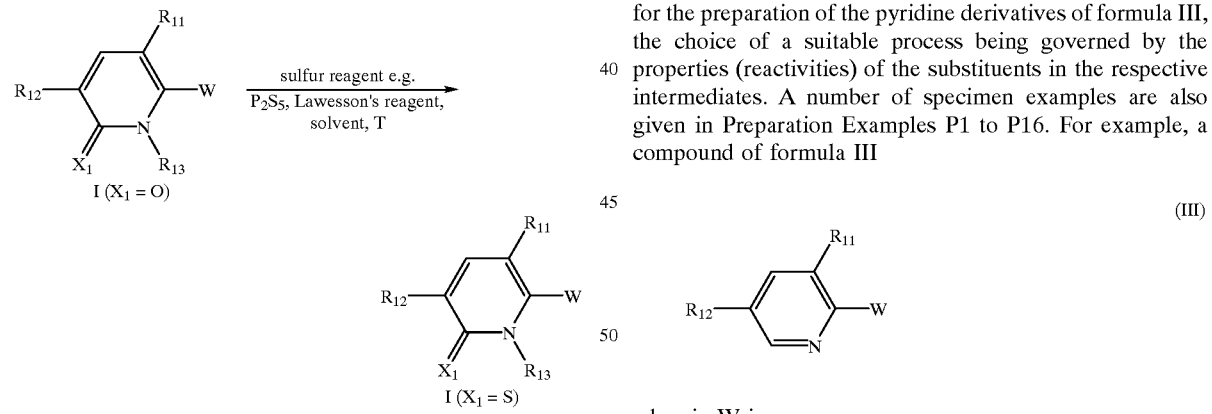

The conversion of the pyridone derivatives of formula I wherein $R_{11}$, $R_{12}$, $R_{13}$ and W are as defined for formula I and $X_1$ is O into the corresponding pyridinethione derivatives of formula I wherein $X_1$ is S (Reaction Scheme 3) can be carried out analogously to known processes (e.g. J. Het. Chem. 25, 511 (1988); ibid. 22, 265 (1985); Bull. Soc. Chim. Fr. 1953, 1001; J. Prakt. Chem. 1988, 293; Chem. Ber. 62, 2732 (1929); Chem. Heterocycl. Compd. (Engl. Transl.) 1988, 658; Pharmazie 45, 731 (1990); and J. Prakt. Chem./Chem-Ztg 334, 119 (1992)), advantageously with the aid of a sulfur reagent, such as, for example, $P_2S_5$ or Lawesson's reagent, in an organic solvent, such as, for example, an aromatic hydrocarbon, for example benzene, toluene, a xylene or pyridine, a halogenated aromatic hydrocarbon, for example dichlorobenzene, or an amide, for example DMF or NMP. The reaction temperatures are generally in the range from 20° C. to 200° C. depending on the solvent used.

The compounds lying within the scope of formula I wherein $X_1$ and $R_{13}$ together form a group =N—Y— and Y is, for example, a bridge member —C($R_{31}$)($R_{32}$)—$CH_2$— can be prepared analogously to known processes, as described, for example, in Sov, Prog. Chem. (Engl. Transl.) 42, 65 (1976); J. Chem. Soc., Perkin Trans 1 1976, 201; Justus Liebigs Ann. 1978, 1491; and Helv. Chim. Acta 73, 1679 (1990).

The compounds lying within the scope of formula I wherein $X_1$ and $R_{13}$ together form a group =N—Y— and Y is, for example, a bridge member —C($R_{34}$)=CH— can be prepared analogously to known processes, as described, for example, in Farmaco Ed. Sci. 37, 22 (1982); J. Chem. Res. (Miniprint) II, 3368 (1986); and J. Chem. Soc., Perkin Trans 1 1987, 1159.

Taking into consideration the chemical properties of the pyridyl or pyridonyl moiety, as the case may be, all other compounds within the scope of formula I can readily be prepared, in terms of the construction of the pyrazole rings, in a manner analogous to that described in Preparation Examples P1 to P21, or as described, for example, in "Methoden der Organ-ischen Chemie" (Houben-Weyl), Volume E 8b, Georg Thieme Verlag Stuttgart, 1994, page 399 ff.; or in "Pyrazoles, Pyrazolines, Pyrazolidines, Indazoles and Condensed Rings", Editor R. H. Wiley, Interscience Publishers, John Wiley & Sons, New York, 1967, page 1 ff.; or as described in the patent specifications WO 96/01254 and WO 97/00246.

A large number of known standard processes are available for the preparation of the pyridine derivatives of formula III, the choice of a suitable process being governed by the properties (reactivities) of the substituents in the respective intermediates. A number of specimen examples are also given in Preparation Examples P1 to P16. For example, a compound of formula III $$R_{12}\diagdown\diagup R_{11} \diagdown W \diagdown N \qquad (III)$$

wherein W is a group

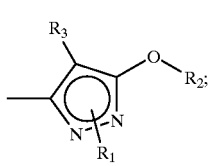

(W1)

$R_1$, $R_2$, $R_{11}$ and $R_{12}$ are as defined for formula I; and $R_3$ is hydrogen, halogen, $C_1$–$C_4$alkyl or $C_1$–$C_4$haloalkyl, can be prepared starting from, for example, a compound of formula XII

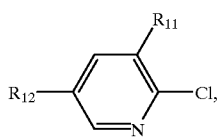
(XII)

wherein $R_{11}$ and $R_{12}$ are as defined above, which is reacted in an alcohol of formula XIII $$R_8\text{—OH} \quad (XIII),$$

wherein $R_8$ is $C_1$–$C_4$alkyl, in the presence of a suitable palladium or nickel catalyst, such as, for example, palladium bis(triphenylphosphine) dichloride ($PdCl_2(PPh_3)_2$) and a base, such as, for example, triethylamine, under carbon monoxide excess pressure, to form a compound of formula XIV

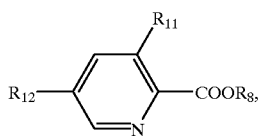
(XIV)

wherein $R_8$, $R_{11}$ and $R_{12}$ are as defined above, which is subjected to acid or basic hydrolysis to form the corresponding carboxylic acid of formula XV

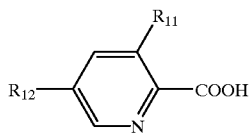
(XV)

and converted with a carboxylic acid halogenating reagent, such as, for example, thionyl chloride, phosphorus pentachloride or oxalyl chloride, into the corresponding carboxylic acid halide of formula XVI

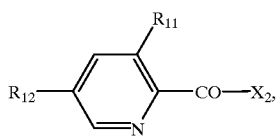
(XVI)

wherein $R_{11}$ and $R_{12}$ are as defined above and $X_2$ is halogen, preferably chlorine, and that compound is reacted in a solvent, such as, for example, acetonitrile in the presence of an alkaline earth metal salt, preferably magnesium chloride, and a base, such as, for example, triethylamine, with the malonic acid mono ester salt of formula XVII

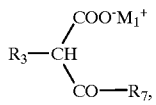
(XVII)

wherein $R_3$ is hydrogen, $C_1$–$C_4$alkyl or $C_1$–$C_4$haloalkyl; $M_1^+$ is an alkali metal ion, preferably a potassium ion; and $R_7$ is $C_1$–$C_4$alkoxy, to yield the keto ester of formula XIX

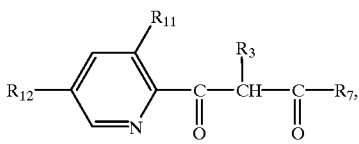
(XIX)

wherein $R_3$, $R_7$, $R_{11}$ and $R_{12}$ are as defined above, and that compound is cyclised in a solvent, such as, for example, glacial acetic acid, with a compound of formula XX $$NH_2NH\text{—}R_1 \quad (XX),$$

wherein $R_1$ is as defined for formula I, to yield a compound of formula XXI

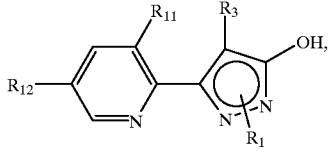
(XXI)

wherein $R_1$, $R_3$, $R_{11}$ and $R_{12}$ are as defined above, and subsequently in accordance with standard methods the hydroxyl group is functionalised, especially freonised (Example P13), according to the definition of $R_2$, and the pyrazole ring is optionally halogenated ($R_3$ is halogen; Example P14) or oxidised to the corresponding pyridine N-oxide (Example P17). The compounds of formula XXII

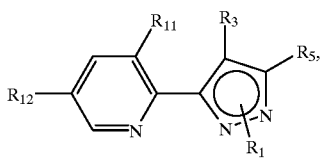
(XXII)

wherein $R_1$, $R_3$, $R_5$, $R_{11}$ and $R_{12}$ are as defined for formula I, are important intermediates for the preparation of compounds of formula III, especially compounds of formula III wherein W is a group W3; $R_5$ is haloalkyl (Example P11); and $R_1$, $R_3$, $R_{11}$ and $R_{12}$ are as defined for formula I.

The compounds of formula XXII are prepared according to EP-A-0 361 114, U.S. Pat. No. 5,032,165, WO 92/02509, WO 92/06962, WO 95/33728 and WO 96/01254.

The compounds of formula XIX

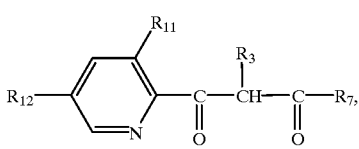
(XIX)

wherein $R_{11}$ and $R_{12}$ are as defined for formula I; $R_3$ is hydrogen, $C_1$–$C_4$alkyl or $C_1$–$C_4$-haloalkyl; and $R_7$ is $C_1$–$C_4$alkoxy, $C_1$- or $C_2$-haloalkyl or $C_1$–$C_4$alkoxycarbonyl, are important intermediates for the preparation of compounds of formula I, especially compounds of formula I wherein W is a group

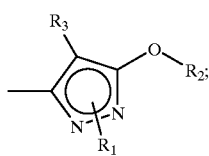
(W1)

$R_1$, $R_2$, $R_{11}$ and $R_{12}$ are as defined for formula I; and $R_3$ is hydrogen, halogen, $C_1$–$C_4$alkyl or $C_1$–$C_4$haloalkyl. The compounds of formula XXIII

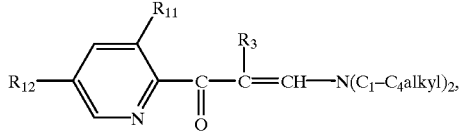
(XXIII)

wherein $R_{11}$ and $R_{12}$ are as defined for formula I; and $R_3$ is hydrogen, halogen, $C_1$–$C_4$alkyl or $C_1$–$C_4$haloalkyl, are important intermediates for the preparation of compounds of formula 1a wherein Wa is a group W3a; $R_5$ is hydrogen; and $R_1$, $R_3$, $R_1$, and $R_{12}$ are as defined for formula I (Example 8).

The compounds of formula XXIII are prepared according to EP-A-0 361 114, U.S. Pat. No. 5,032,165, WO 92/02509, WO 92/06962, WO 95/33728 and WO 96/01254.

The compounds of formula XXIV

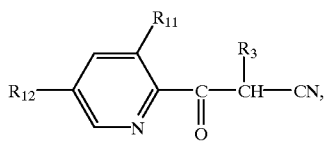
(XXIV)

wherein $R_{11}$ and $R_{12}$ are as defined for formula I; and $R_3$ is hydrogen, $C_1$–$C_4$alkyl or $C_1$–$C_4$-haloalkyl, are important intermediates for the preparation of compounds of formula I wherein W is a group

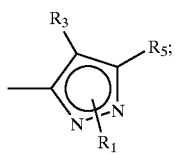
(W3)

$R_3$ is hydrogen, $C_1$–$C_4$alkyl or $C_1$–$C_4$haloalkyl; $R_5$ is amino; and $R_1$, $R_{11}$ and $R_{12}$ are as defined for formula I.

The compounds of formula XXIV are prepared according to EP-A-0 361 114, U.S. Pat. No. 5,032,165, WO 92/02509, WO 92/06962, WO 95/33728 and WO 96/01254.

A large number of known standard processes are available for the preparation of the pyridonylpyrazoles of formula I substituted at the pyridone ring, the choice of a suitable preparation process being governed by the properties (reactivities) of the substituents in the respective intermediates.

A number of specimen examples are also given in Preparation Examples P19 to P24. The compound of formula XII, and the starting compounds 2,5-dichloro-3-fluoropyridine, 2,3-dichloro-5-trifluoromethylpyridine and 3,5-dichloro-2-acetylpyridine used in Preparation Examples P1, P2 and P9, are either known or can be prepared analogously to published processes.

The reagents of formulae VI and XI used in the Reaction Schemes 1, 2 and 3 are either known or can be prepared analogously to published processes.

All other compounds within the scope of formula I can readily be prepared, taking into consideration the respective chemical reactivities, analogously to the processes according to Preparation Examples P1 to P25, or analogously to the methods described in "Methoden der Organischen Chemie" (Houben-Weyl), volume E 8b, Georg Thieme Verlag Stuttgart, 1994, page 399 ff.; ibid, volume E7B, Georg Thieme Verlag Stuttgart, 1992, page 286 ff.; in "Pyrazoles, Pyrazolines, Pyrazolidines, Indazoles and Condensed Rings", Editor R. H. Wiley, Interscience Publishers, John Wiley & Sons, New York, 1967, page 1 ff.; or in "Comprehensive Heterocyclic Chemistry", Editors A. R. Katritzky and C. W. Rees, Pergamon Press, Oxford, 1987, or by derivatisation according to known standard methods as described, for example, in "Advanced Organic Chemistry, Third Edition, Editor J. March, John Wiley & Sons, New York, 1985; in "Comprehensive Organic Transformations", Editor R. C. Larock, VCH Publishers, Inc., New York, 1989; or in "Comprehensive Organic Functional Group Transformations", Editors A. R. Katritzky, 0. Meth-Cohn, C. W. Rees, Pergamon Press, Oxford, 1995, or as described in the Patent Specifications EP-A-0 361 114, U.S. Pat. No. 5,032,165, WO 92/02509, WO 92/06962, WO 95/33728 and WO 96/01254.

The end products of formula I can be isolated in conventional manner by concentration or evaporation of the solvent and purified by recrystallisation or trituration of the solid residue in solvents in which they are not readily soluble, such as ethers, aromatic hydrocarbons or chlorinated hydrocarbons, by distillation or by means of column chromatography and a suitable eluant. The sequence in which it is advantageous for certain reactions to be carried out so as to avoid possible secondary reactions will also be familiar to the person skilled in the art. Unless the synthesis is specifically aimed at the isolation of pure isomers, the product may be obtained in the form of a mixture of two or more isomers. The isomers can be separated according to methods known per se.

For the use according to the invention of the compounds of formula I or of compositions comprising them, there come into consideration all methods of application customary in agriculture, for example pre-emergence application, post-emergence application and seed dressing, and also various methods and techniques such as, for example, the controlled release of active ingredient. For that purpose a solution of the active ingredient is applied to mineral granule carriers or polymerised granules (urea/formaidehyde) and dried. If required, it is also possible to apply a coating (coated granules), which allows the active ingredient to be released in metered amounts over a specific period of time.

The compounds of formula I may be used in unmodified form, that is to say as obtained in the synthesising process, but they are preferably formulated in customary manner together with the adjuvants conventionally employed in formulation technology, for example into emulsifiable concentrates, directly sprayable or dilutable solutions, dilute emulsions, wettable powders, soluble powders, dusts, granules or microcapsules. Such formulations are described, for example, in WO 97/34485, pages 9 to 13. As with the nature of the compositions, the methods of application, such as spraying, atomising, dusting, wetting, scattering or pouring, are chosen in accordance with the intended objectives and the prevailing circumstances.

The formulations, that is to say the compositions, preparations or mixtures comprising the compound (active ingredient) of formula I or at least one compound of formula I and, usually, one or more solid or liquid formulation adjuvants, are prepared in known manner, e.g. by homogeneously mixing and/or grinding the active ingredients with the formulation adjuvants, for example solvents or solid carriers. Surface-active compounds (surfactants) may also be used in addition in the preparation of the formulations. Examples of solvents and solid carriers are given, for example, in WO 97/34485, page 6.

Depending on the nature of the compound of formula I to be formulated, suitable surface-active compounds are non-ionic, cationic and/or anionic surfactants and surfactant mixtures having good emulsifying, dispersing and wetting properties. Examples of suitable anionic, non-ionic and cationic surfactants are listed, for example, in WO 97/34485, pages 7 and 8. In addition, the surfactants conventionally employed in formulation technology, which are described in, inter alia, uMcCutcheon's Detergents and Emulsifiers Annual" MC Publishing Corp., Ridgewood New Jersey, 1981, Stache, H., "Tensid-Taschenbuch", Carl Hanser Verlag, Munich/Vienna 1981, and M. and J. Ash, "Encyclopedia of Surfactants", Vol. I–III, Chemical Publishing Co., New York, 1980–81, are also suitable for the preparation of the herbicidal compositions according to the invention.

The herbicidal formulations generally contain from 0.1 to 99% by weight, especially from 0.1 to 95% by weight, of herbicide, from 1 to 99.9% by weight, especially from 5 to 99.8% by weight, of a solid or liquid formulation adjuvant, and from 0 to 25% by weight, especially from 0.1 to 25% by weight, of a surfactant. Whereas commercial products will preferably be formulated as concentrates, the end user will normally employ dilute formulations. The compositions may also comprise further ingredients, such as stabilisers, for example vegetable oils or epoxidised vegetable oils (epoxidised coconut oil, rape oil or soybean oil), anti-foams, for example silicone oil, preservatives, viscosity regulators, binders, tackifiers, and also fertilisers or other active ingredients.

The compounds of formula I can be used successfully either in the form of a mixture comprising the isomers IW1a and IW1b or in the form of pure isomer IW1a or IW1b, generally on plants or the locus thereof, at rates of application of from 0.001 to 4 kg/ha, especially from 0.005 to 2 kg/ha. The concentration required to achieve the desired effect can be determined by experiment. It is dependent on the nature of the action, the stage of development of the cultivated plant and of the weed and on the application (place, time, method) and may vary within wide limits as a function of those parameters.

The compounds of formula I and, generally, the isomers of formula 1a especially, are distinguished by herbicidal and growth-inhibiting properties, allowing them to be used in crops of useful plants, especially cereals, cotton, soybeans, sugar beet, sugar cane, plantation crops, rape, maize and rice, and also for non-selective weed control.

"Crops" is to be understood as meaning also crops that have been made tolerant to herbicides or classes of herbicides as a result of conventional methods of breeding or genetic techniques. The weeds to be controlled may be either monocotyledonous or dicotyledonous weeds, such as, for example, Stellaria, Nasturtium, Agrostis, Digitaria, Avena, Setaria, Sinapis, Lolium, Solanum, Phaseolus, Echinochloa, Scirpus, Monochoria, Sagittaria, Bromus, Alopecurus, *Sorghum halepense,* Rottboellia, Cyperus, Abutilon, Sida, Xanthium, Amaranthus, Chenopodium, Ipomoea, Chrysanthemum, Galium, Viola and Veronica.

The following Examples further illustrate but do not limit the invention.

PREPARATION EXAMPLES

Example P1

3-Fluoro-5-chloro-2-pyridinecarboxylic Acid Ethyl Ester

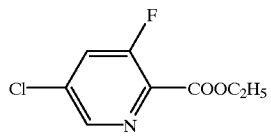

An autoclave is charged with 31.4 g of 2,5-dichloro-3-fluoropyridine, 400 ml of dry ethanol, 27.8 ml of triethylamine and 3.5 g of palladium bis(triphenylphosphine) dichloride (PdCl$_2$(PPh$_3$)$_2$) and then a pressure of 180 bars is applied with carbon monoxide. The mixture is maintained at 90° C. for 4 days. After cooling and releasing the pressure, a further 3.5 g of PdCl$_2$(PPh$_3$)$_2$ are added, a pressure of 130 bars is applied with carbon monoxide, and the mixture is maintained at 90° C. for 3 days, after which it is cooled to 25° C., the pressure is released and the mixture is discharged. After concentration in vacuo, absorption from ethyl acetate onto silica gel is carried out. The silica gel is applied to a flash chromatography column (silica gel) and then eluted with n-hexanelethyl acetate 3/1. 24.3 g of the desired target compound having a melting point of 48–50° C. are obtained.

Example P2

3-Chloro-5-trifluoromethyl-2-pyridinecarboxylic Acid Ethyl Ester

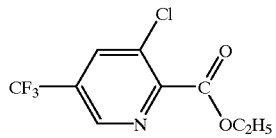

An autoclave is charged with 200 g of 2,3-dichloro-5-trifluoromethylpyridine, 1.85 liters of ethanol, 260 ml of triethylamine and 6.5 g of palladium bis (triphenylphosphine) dichloride (PdCl$_2$(PPh$_3$)$_2$). At 25° C. a pressure of 110 bars is then applied with carbon monoxide and the mixture is maintained at 110° C. for 24 hours. After cooling to 25° C., the crude mixture is concentrated to a thick slurry, which is then partitioned between dilute sodium chloride solution and ethyl acetate. After extraction by shaking, and separation of the phases, the ethyl acetate phase is washed with water, dried over sodium sulfate and concentrated to dryness. The crude product is distilled under a high vacuum of 0.035 mbar. 200 g of the desired product are obtained in the form of a yellow oil having a boiling point of 67–70° C./0.035 mbar (yield 85% of the theoretical yield).

Example P3

3-Chloro-5-trifluoromethyl-2-pyridinecarboxylic Acid

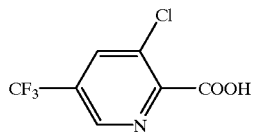

423 g of 3-chloro-5-trifluoromethyl-2-pyridinecarboxylic acid ethyl ester (Example P2) is placed in a mixture of 800 ml of water and 160 ml of ethanol. 800 ml of a 2N sodium hydroxide solution are added dropwise at below 35° C. After 3 hours, the mixture is washed twice with dichloromethane and then rendered acidic with excess concentrated hydrochloric acid while cooling with an ice-bath. The resulting slurry is filtered, washed with water and dried in vacuo. 318 g of the desired product are obtained in the form of a white solid having a melting point of 135° C. (decomposition).

Example P4

3-Fluoro-5-chlorotyridine-2-carboxylic Acid

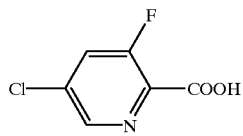

70 g of 3-fluoro-5-chloro-2-pyridinecarboxylic acid ethyl ester (Example P1) are placed in 105 ml of dimethyl sulfoxide (DMSO). 230 ml of a 2N sodium hydroxide solution are added dropwise at 40° C. over a period of 30 minutes. The resulting yellow suspension is introduced into a mixture of 2 liters of ice-water and 400 ml of 2N hydrochloric acid. After subsequently stirring for 20 minutes, the mixture is filtered and the filtration residue is washed twice with water. 56.4 g of the desired target compound are obtained in the form of a white solid.

$^1$H-NMR (DMSO-D$_6$): 13.79 ppm (broad signal, 1H); 8.60 ppm (d, 1H); 8.27 ppm (dxd, 1H).

Example P5

3-Chloro-5-trifluoromethyl-2-pyridinecarboxylic Acid Chloride

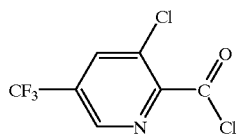

89.3 g of 3-chloro-5-trifluoromethyl-2-pyridinecarboxylic acid (Example P3) are slowly heated to reflux with 60 ml of thionyl chloride and the mixture is then stirred at that temperature for 4 hours, after which it is cooled to 25° C. and concentrated to dryness in vacuo. Twice, toluene is added and the mixture is again concentrated to dryness. 94.0 g of the desired product are obtained in the form of a yellow residue.

$^1$H-NMR (CDCl$_3$): 8.91 ppm (d, 1H); 8.13 ppm (d, 1H).

Example P6

3-Fluoro-5-chloro-2-pyridinecarboxylic Acid Chloride

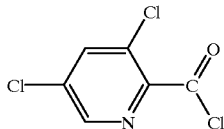

71.38 g of 3-fluoro-5-chloro-2-pyridinecarboxylic acid (Example P4) are placed in a round-bottomed flask and heated to 90° C. 59 ml of thionyl chloride are added dropwise from a dropping funnel over a period of 30 minutes, and the gas formed is introduced into sodium hydroxide solution. Stirring is then carried out for 5 hours at 100° C., after which the thionyl chloride is distilled off at normal pressure. After the addition of 50 ml of dry toluene, 20 ml thereof are distilled off. The resulting solution is poured into 200 ml of n-hexane and stirred overnight. After cooling in an ice-bath, the mixture is filtered and the filtration residue is washed twice with n-hexane. 68.7 g of the desired compound are obtained in the form of a brown solid.

$^1$H-NMR (CDCl$_3$): 8.60 ppm (d, 1H); 7.69 ppm (dxd, 1H).

Example P7

5-Chloro-3-fluoro-2-pyridinecarbaldehyde

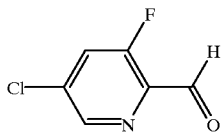

110 g of 5-chloro-3-fluoro-2-pyridinecarboxylic acid ethyl ester (Example P1) are dissolved in 180 ml of tert-butanol. 27.4 g of sodium borohydride (NaBH$_4$, 97%) are added to the slightly brown solution, in the course of which a weak exothermic reaction is observed. By cooling occasionally with an ice-bath, the internal temperature is maintained below 30° C. The exothermic reaction has subsided after 1½ hours. The reaction mixture is then stirred overnight at 22° C. and subsequently cold water is added slowly, while stirring well. Extraction is carried out with diethyl ether, and the combined ethereal phases are washed with dilute sodium hydrogen carbonate solution and brine, dried over sodium sulfate, filtered and concentrated in vacuo. 58 g of a tacky solid are isolated. After digestion with n-hexane/-diethyl ether 50/1 and drying in vacuo, 48.6 g of a yellow solid are obtained having an R$_f$ value on silica gel 60 F$_{254}$ (eluant: n-hexane/ethyl acetate 1/1 (v/v)) of 0.40.

160.7 g of active manganese(IV) oxide (90%) are added to 22.4 g of the alcohol obtained as intermediate in 300 ml of methylene chloride, and a slight exothermic reaction can be detected. After stirring for 3 hours, the mixture is filtered over Hyflo and the filtrate is concentrated in vacuo. The residue (20 g) is purified by means of flash chromatography (silica gel; eluant: n-hexane/ethyl acetate 4/1 (v/v)). In that manner 11.0 g of the desired target compound are obtained in the form of a white solid having a melting point of 70–72° C. The R$_f$ value of the product on silica gel 60 F$_{254}$ (eluant: n-hexane/ethyl acetate 3/1 (v/v)) is 0.61.

Example P8

3-Chloro-5-trifluoromethyl-2-acetylpyridine

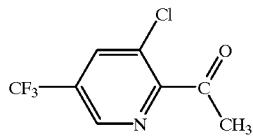

55.3 ml of malonic acid dimethyl ester are stirred with 129 ml of triethylamine and 24.9 g of anhydrous magnesium chloride for 2 hours in 250 ml of dry toluene. With the exothermic reaction, the reaction temperature rises to 45° C. At 25° C. 94.0 g of 3-chloro-5-trifluoromethyl-2-pyridinecarboxylic acid chloride (Example P5) in 150 ml of toluene are added dropwise thereto and the reaction mixture is further stirred overnight. An excess of concentrated hydrochloric acid is then added dropwise, and the mixture is diluted with water and extracted with ethyl acetate. The organic phase is washed with brine, dried over sodium sulfate, filtered and concentrated to yield 142 g of a red oil which is slowly introduced into a mixture of 20 ml of water and 400 ml of dimethyl sulfoxide, which is under gentle reflux by means of an oil bath of a temperature of 150° C. When the evolution of gas can no longer be detected, water is added and extraction is carried out with ether. The combined ethereal phases are washed with water, dried over sodium sulfate, filtered and concentrated. The residue is purified by means of column chromatography (silica gel; eluant: n-hexane/ethyl acetate 15/1 (v/v)), yielding 61 g of the desired product in the form of a yellow oil (70% of the theoretical yield).

$^1$H-NMR (CDCl$_3$): 8.81 ppm (d, 1H); 8.05 ppm (d, 1H); 2.72 ppm (s, 3H).

Example P9

1-(3-Chloro-5-trifluoromethyl-2-pyridyl)-3-dimethylamino-2-propen-1-one

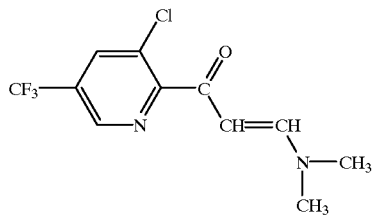

5.0 g of 3-chloro-5-trifluoromethyl-2-acetylpyridine (Example P8) are introduced into 30 ml of toluene and 3.60 ml of N,N-dimethylformamide-dimethylacetal are added. The resulting yellow solution is stirred overnight at 100° C. After cooling to 25° C., the mixture is concentrated to dryness in vacuo, yielding 6.17 g of the desired target compound in the form of a dark-yellow oil which later solidifies.

$^1$H-NMR (CDCl$_3$): 8.74 ppm (d, 1H); 7.98 ppm (d, 1H); 7.92 ppm (broad signal, 1H); 5.54 ppm (broad d, 1H); 3.17 ppm (broad signal, 3H); 2.94 ppm (broad signal, 3H).

Example P10

3-(3.5-Dichloro-2-pyridyl)-5-trifluoromethyl-[1H]-pyrazole

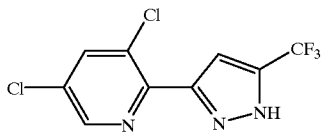

15.8 g of 3,5-dichloro-2-acetylpyridine are introduced together with 12.0 ml of trifluoroethyl acetate into 125 ml of absolute ether. With stirring, the mixture is cooled using an ice-bath and 46.6 ml of, a 21% sodium ethanolate solution in ethanol are added dropwise. The ice-bath is then removed and the mixture is subsequently stirred overnight at 25° C. After cooling the reaction mixture in an ice-bath and adding dropwise 7.5 ml of glacial acetic acid, the mixture is concentrated in vacuo. 39.0 g of 1-(3,5-dichloro-2-pyridyl)-3-trifluoromethylpropane-1,3-dione are obtained, which can be used directly for the following cyclisation step.

39.0 g of 1-(3,5-dichloro-2-pyridyl)-3-trifluoromethylpropane-1,3-dione

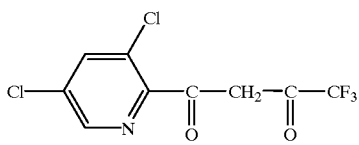

are introduced into ethanol and 4.85 ml of hydrazine hydrate are slowly added. The reaction mixture is then heated at reflux with stirring. After one hour, the mixture is concentrated to dryness in vacuo and the residue is partitioned between dilute sodium hydrogen carbonate solution and ethyl acetate. After extraction by shaking, and separation of the phases, the organic phase is washed with brine, dried over sodium sulfate, filtered and concentrated to dryness. 22.25 g of a yellow oil are obtained, which is purified by means of flash chromatgraphy (silica gel; eluant: n-hexane/ethyl acetate 4/1 (v/v)) to yield 15.0 g of the desired product in the form of a yellow solid.

$^1$H-NMR (DMSO-D$_6$): 8.81 ppm (m, 1H); 8.64 ppm (m, 1H); 8.26 ppm (m, 1H); 7.45 ppm (broad signal, 1H).

Example P11

3-(3,5-Dichloro-2-pyridyl)-5-trifluoromethyl-1-methyl-[1H]-pyrazole and 5-(3,5-dichloro-2-pyridyl)-3-trifluoromethyl-1-methyl-[1H]-pyrazole

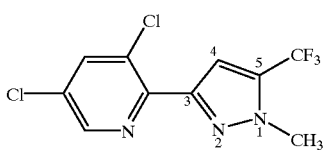

and

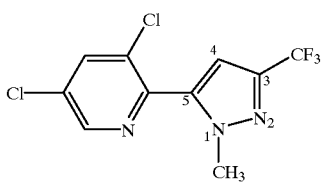

8.88 g of 3-(3,5-dichloro-2-pyridyl)-5-trifluoromethyl-[1H]-pyrazole (Example P10) are introduced into 35 ml of N-methylpyrrolidone. After the addition of 13.0 g of potassium carbonate, the mixture is stirred and heated to 55° C. 2.36 ml of methyl iodide in 5.0 ml of N-methylpyrrolidone are then slowly added dropwise. After subsequently stirring for 2 hours, diethyl ether and water are added, the mixture is extracted by shaking and the organic phase is separated off. The separated ethereal phase is washed with brine, dried over sodium sulfate, filtered and concentrated. The crude product is purified by means of flash chromatography (silica gel; eluant: toluene/ethyl acetate 100/1). First of all 3.96 g of the 5-pyridylpyrazole isomer (yield 42%) are isolated in the form of a yellow oil and then 1.96 g of the 3-pyridylpyrazole (yield 21%) are isolated in the form of a yellow solid. The $R_f$ values of the 3- and 5-pyridylpyrazole isomers on silica gel 60 $F_{254}$ using toluene/ethyl acetate 30/1 as eluant (UV) are:

$R_f$ value of 5-pyridylpyrazole: 0.50
$R_f$ value of 3-pyridylpyrazole: 0.35

Example P12

3-(3,5-Dichloro-2-pyridyl)-4-chloro-5-trifluoromethyl-1-methyl-[1H]-pyrazole

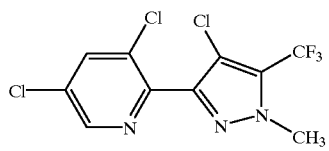

2.0 g of 3-(3,5-dichloro-2-pyridyl)-5-trifluoromethyl-1-methyl-[1H]-pyrazole (Example P11) are introduced into glacial acetic acid at 40° C. and, with stirring, chlorine gas is slowly passed over the solution. The reaction can be monitored analytically by means of thin-layer chromatography (silica gel 60 $F_{254}$, eluant: n-hexane/ethyl acetate 4/1, UV). Once starting material can no longer be detected, glacial acetic acid is removed in vacuo and the residue is partitioned between dilute aqueous sodium hydroxide solution and ethyl acetate. After extraction by shaking, the separated organic phase is washed with brine, dried over sodium sulfate, filtered and concentrated. The yellow oil is purified by means of flash chromatography (silica gel; eluant: n-hexane/ethyl acetate 5/1). 1.6 g of of the desired compound are obtained in the form of a yellow oil (70% of the theoretical yield).

$^1$H-NMR (DMSO-D$_6$): 8.80 ppm (d, 1H); 8.48 ppm (d, 1H); 4.11 ppm (s, 3H).

The 5-pyridylpyrazole isomer is obtained in an analogous manner in a 90% yield (crude). $^1$H-NMR (CDCl$_3$): 8.66 ppm (d, 1H); 7.95 ppm (d, 1H); 3.83 ppm (s, 3H).

Example P13

3-(3-Fluoro-5-chloro-2-pyridyl)-5-hydroxy-1-methyl-[1H]-pyrazole

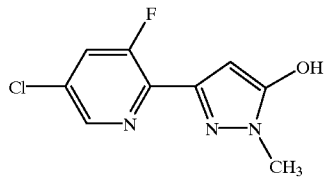

110.6 g of malonic acid monomethyl ester·potassium salt are introduced into 500 ml of absolute acetonitrile. With stirring, the mixture is cooled in an ice-bath and 109 ml of triethylamine are added dropwise. 84.3 g of anhydrous magnesium chloride are then added. A slight exothermic reaction is observed. After removal of the ice-bath, the mixture is stirred for 2 hours at 25° C. After cooling again in an ice-bath, 68.7 g of 3-fluoro-5-chloro-2-pyridinecarboxylic acid chloride (Example P6) are added in several portions and 300 ml of absolute acetonitrile are added. A thick slurry gradually forms. The cooling bath is removed and the slurry is then stirred for 5 hours. The reaction mixture is subsequently poured into 3 liters of ice-water and 200 ml of concentrated hydrochloric acid, and then stirred for 15 minutes and extracted with ethyl acetate. The organic phase is washed with water and brine, dried over sodium sulfate, filtered and concentrated to dryness in vacuo. 110 g of a brown oil are obtained, which is used directly for the next reaction step.

For that reaction step, the brown oil obtained above is introduced at 25° C. into a solution of 20.5 ml of methyl hydrazine in 300 ml of glacial acetic acid and then stirred for 2 hours at 85° C. After the resulting brown suspension has been cooled to 25° C. it is introduced in portions into 2.5 liters of ice-water, stirred for 1 hour, filtered and washed with water and n-hexane. After drying at 60° C. in vacuo, 65.8 g of the desired title compound having a melting point of 195–199° C. are obtained.

Example P14

3-(3-Fluoro-5-chloro-2-pyridyl)-5-difluoromethoxy-1-methyl-[1H]-pyrazole

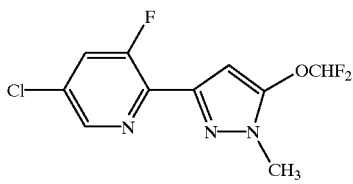

46.0 g of 3-(3-fluoro-5-chloro-2-pyridyl)-5-hydroxy-1-methyl-[1H]-pyrazole (Example P13) and 84 g of potassium carbonate are introduced into 250 ml of dry dimethylformamide and heated to 85° C. While stirring well, Freon 22 (chlorodifluoromethane) is then introduced for a period of 2 hours. TLC analysis of a worked-up sample (silica gel 60 F2s; eluant: n-hexane/ethyl acetate/glacial acetic acid 20/20/1, UV) shows that there is no starting material present. The reaction mixture is partitioned between water and diethyl ether (foaming occurs on the addition of water). After extraction by shaking, and separation of the phases, the ethereal phase is washed twice with water and once with brine. After drying the organic phase over sodium sulfate and filtration, concentration in vacuo is carried out and the residue is purified by means of flash chromatography (silica gel; eluant: n-hexane/ethyl acetate 2/1 (v/v)). 22.0 g of the desired title compound are obtained in the form of a light-yellow solid.

$^1$H-NMR (CDCl$_3$): 8.51 ppm (broad signal, 1H); 7.56 ppm (dxd, 1H); 6.61 ppm (t, 1H); 6.53 ppm (d, 1H); 3.89 ppm (s, 3H).

Example P15
3-(3-Fluoro-5-chloro-2-pyridyl)-4-chloro-5-difluorometho)-1-methyl-[1H]-pyrazole

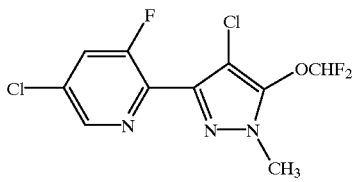

17.92 g of 3-(3-fluoro-5-chloro-2-pyridyl)-5-difluoromethoxy-1-methyl-[1H]-pyrazole (Example P14) are introduced into 60 ml of glacial acetic acid together with 10.6 g of sodium acetate. With stirring, the mixture is heated to 60° C. and a saturated solution of chlorine in glacial acetic acid is added until TLC analysis of a worked-up sample shows that the reaction is complete (silica gel 60 $F_{254}$; eluant: n-hexane/ethyl acetate 2/1; UV, $R_1$ value of the starting material 0.34; $R_1$ value of the product 0.48). The mixture is then concentrated to dryness in vacuo and the residue obtained is partitioned between sodium hydrogen carbonate solution and ethyl acetate. The organic phase is washed with brine, dried over sodium sulfate, filtered and concentrated to dryness by evaporation in vacuo. 19.8 g of the desired target compound (pure according to TLC) having a melting point of 95–96° C. are obtained.

Example P16
3-(3-Fluoro-5-chloro-2-pyridyl)-4-formyl-5-difluoromethoxy-1-methyl-[1H]-pyrazole

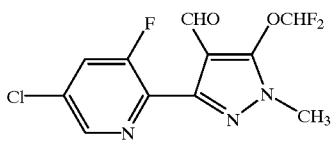

With cooling in an ice-bath, 2.41 ml of phosphorus oxychloride are introduced into 5 ml of N,N-dimethylformamide and the mixture is then stirred for 2 hours at 25° C. The mixture is then added dropwise at 80° C. to 5.0 g of 3-(3-fluoro-5-chloro-2-pyridyl)-5-hydroxy-1-methyl-[1H]-pyrazole (Example P13) in 15 ml of N,N-dimethylformamide over a period of 30 minutes. After subsequently stirring for 1.5 hours at 80° C., the mixture is cooled to 25° C. and ice and then water are added and extraction is carried out with diethyl ether. The organic phase is washed with water and dried over sodium sulfate to yield 1.1 g of a yellow solid as intermediate. The solid is introduced together with 1.72 g of pulverised anhydrous potassium carbonate into 10 ml of dry N,N-dimethylformamide. While stirring well, the mixture is heated to 75° C. and freon 22 ($CHClF_2$) is slowly introduced for a period of 7 hours. The mixture is then cooled to 25° C. and taken up in diethyl ether. The ethereal phase is washed with water and then with brine, dried over sodium sulfate, filtered and concentrated. 1.50 g of crude product are obtained in the form of a brown solid, which is purified using a flash chromatography column (silica gel; eluant: n-hexane/ethyl acetate 4/1 (v/v)). In that manner 0.14 g of the desired target compound is obtained in the form of a yellow solid having a melting point of 111–116° C.

Example P17
3-(3-Fluoro-5-chloro-2-pyridyl)-4-difluoromethyl-5-difluoromethoxy-1-methyl-[1H]-pyrazole

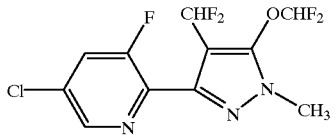

0.13 g of 3-(3-fluoro-5-chloro-2-pyridyl)-4-formyl-5-difluoromethoxy-1-methyl-[1H]-pyrazole (Example P16) is introduced into 3.0 ml of dry 1,2-dichlorethane. With stirring, 0.11 ml of diethylamino-sulfur trifluoride (DAST) is added dropwise using a syringe, the reaction mixture taking on a dark colour. The mixture is then stirred for 1 hour at 50° C. The reaction solution is cooled to 25° C. and applied directly to a flash chromatography column (silica gel) and eluted with n-hexane/ethyl acetate 5/1 (v/v). 0.07 g of the desired compound is obtained in the form of a light-yellow oil having a melting point of 79–81° C.

Example P18
3-(3-Fluoro-5-chloro-2-pyridyl)-5-bromo-1-methyl-[1H]-pyrazole

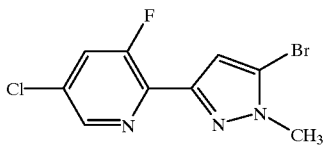

20.0 g of 3-(3-fluoro-5-chloro-2-pyridyl)-5-hydroxy-1-methyl-[1H]-pyrazole (Example P13) are introduced into 80 ml of tetrachloroethane. A total of 25.2 g of phosphorus oxybromide ($POBr_3$) is added in portions to the brown suspension. The mixture is then stirred for 2 hours at an internal temperature of 130° C., after which it is cooled and, with cooling with an ice-bath, 150 ml of a 2M sodium hydroxide solution are added dropwise. After the addition of diethyl ether and separation of the phases, the organic phase is washed in succession with water, dilute hydrochloric acid and brine, dried over sodium sulfate, filtered and concentrated to dryness in vacuo. 19.94 g of a brown solid (crude product) are obtained, which is purified by means of digestion with 50 ml of n-hexane. 12.65 g of the desired compound are obtained in the form of a brown solid having a melting point of 110–111° C.

Example P19
5-(5-Chloro-3-fluoro-2-pyridyl)-2-methyl-[2H]-pyrazole-3-carboxylic Acid Ethyl Ester

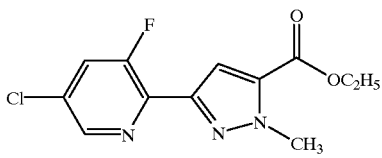

5.0 g of 3-(3-fluoro-5-chloro-2-pyridyl)-5-bromo-1-methyl-[1H]-pyrazole (Example P18) are introduced into an autoclave together with 7.2 ml of triethylamine, 0.48 g of bis-triphenylphosphinepalladium dichloride ($PdCl_2(PPh_3)_2$) and 70 ml of absolute ethanol. At 22° C. a pressure of 100

Example P20
5-(5-Chloro-3-fluoro-2-pyridyl)-4-chloro-2-methyl-[2H]-pyrazole-3-carboxylic Acid Ethyl Ester

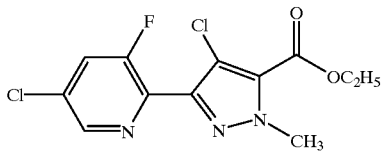

22.9 g of 5-(5-chloro-3-fluoro-2-pyridyl)-2-methyl-[2H]-pyrazole-3-carboxylic acid ethyl ester (Example P19) are introduced together with 19.9 g of sodium acetate into 300 ml of glacial acetic acid at a temperature of 65° C. With stirring, 6.3 g of chlorine gas are passed over the solution at that temperature in the course of 1 hour. The reaction mixture is then poured into 2.5 liters of ice-water and subsequently stirred for 20 minutes. The resulting precipitate is filtered off, washed with ice-water and then dried in vacuo at 50° C. 24.4 g of the desired title compound are obtained in the form of a yellow solid having a melting point of 77–79° C.

Example P21
5-(5-Chloro-3-fluoro-2-pyridyl)-4-chloro-2-methyl-[2H]-pyrazole-3-carboxylic Acid

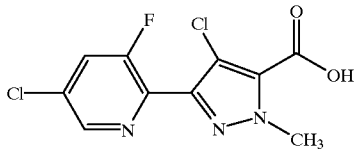

11.0 g of 5-(5-chloro-3-fluoro-2-pyridyl)-4-chloro-2-methyl-[2H]-pyrazole-3-carboxylic acid ethyl ester (Example P20) are introduced into 60 ml of dimethyl sulfoxide at 22° C. With stirring, 25.9 ml of a 2N aqueous sodium hydroxide solution are added dropwise, in the course of which an exothermic reaction can be detected. After subsequently stirring for one hour, TLC analysis of a sample shows that all the starting material has reacted. The reaction mixture is introduced into 2 liters of ice-cold dilute hydrochloric acid, then stirred for 15 minutes and filtered over a paper filter. The filtration residue is washed with cold water and, after drying overnight at 60° C. in vacuo, 8.7 g of the desired title compound having a melting point of 230° C. (decomposition) are obtained.

The $R_f$ value of the starting material on silica gel 60 $F_{254}$ (eluant: n-hexane/ethyl acetate 1/1 (v/v)) is 0.75; and the $R_f$ value of the desired title compound is 0.36.

Example P22
3-(3-Fluoro-5-chloro-2-pyridyl)-4-chloro-5-trifluoromethyl-1-methyl-[1H]-pyrazole

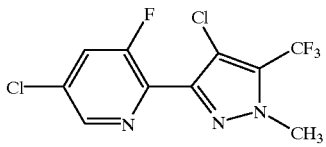

8.63 g of 5-(5-chloro-3-fluoro-2-pyridyl)-4-chloro-2-methyl-[2H]-pyrazole-3-carboxylic acid (Example P21) are introduced into a fluorination unit with 27 g of hydrogen fluoride (HF), 16.2 g of sulfur tetrafluoride ($SF_4$) and 270 ml of methylene chloride. The mixture is maintained at 80° C. for 5 hours. It is then cooled to 22° C. and the $SF_4$ is removed by way of a gas destroying unit (argon stream) and the HF is removed using a water-jet vacuum. After the addition of methylene chloride, the reaction mixture is extracted three times with ice-water, and the organic phase is dried over sodium sulfate and then concentrated to dryness in vacuo together with 40 g of silica gel. After applying the silica gel to a flash chromatography column, elution is carried out with an n-hexane/ethyl acetate 5/1 (v/v) mixture. 5.48 g of the desired title compound are obtained in the form of a beige solid having a melting point of 76–78° C.

Example P23
3-(5,6-Dichloro-2-pyridyl)- and 3-(4,5-dichloro-2-pyridyl)-4-chloro-5-trifluoromethyl-1-methyl-[1H]-pyrazole (isomers A and B)

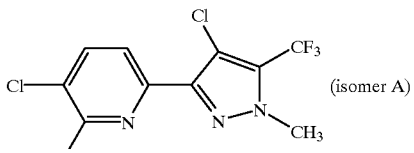

(isomer A)

and

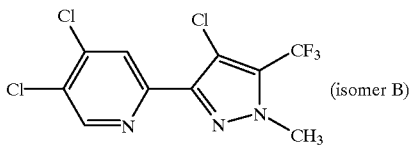

(isomer B)

20 ml of phosphorus oxychloride are heated to 90° C. With stirring, 10.37 g of 3-(5-chloro-2-pyridyl-N-oxide)-4-chloro-5-trifluoromethyl-1-methyl-[1H]-pyrazole (Example P25) are introduced in several portions at that temperature and the mixture is then stirred for 1 hour at 90° C. The phosphorus oxychloride is then evaporated off in vacuo, the residue is taken up in diethyl ether and the ethereal phase is subsequently washed in succession with water, 0.5M sodium hydroxide solution and brine. After drying over sodium sulfate and filtering, concentration in vacuo is carried out and the residue obtained (8.93 g) is purified by column chromatography (silica gel; eluant: n-hexane/ethyl acetate 10/1). First 0.57 g of isomer B and then 5.11 g of isomer A are isolated in the form of a white solid.

On silica gel 60 $F_{254}$ using the eluant n-hexane/ethyl acetate 4/1 (v/v), the $R_f$ value of isomer A is 0.31 and the $R_f$ value of isomer B is 0.41.

The treatment of 6.3 g of 3-(5-chloro-2-pyridyl-N-oxide)-4-chloro-5-trifluoromethyl-1-methyl-[1H]-pyrazole (Example P25) for 1 hour at 90° C. with 6.3 g of phosphorus pentachloride in 20 ml of phosphorus oxychloride yields, after working up as above, 4.36 g of isomer A and 1.01 g of isomer B.

Example P24

3-(3-Fluoro-5,6-dichloro-2-pyridyl-N-oxide)-4-chloro-5-difluoromethoxy-1-methyl-[1H]-pyrazole

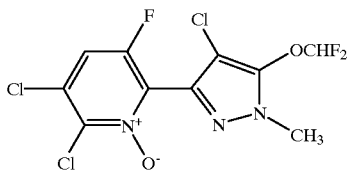

1.5 g of 3-(3-fluoro-5,6-dichloro-2-pyridyl)-4-chloro-5-difluoromethoxy-1-methyl-[1H]-pyrazole are dissolved in 10 ml of 1,2-dichloroethane and 0.5 g of hydrogen peroxide/urea adduct is added. With cooling in an ice-bath, 0.66 ml of trifluoroacetic anhydride is then metered in using a syringe and the mixture is stirred at 22° C. for 3 hours. According to TLC analysis there is only partial reaction of the starting material. Consequently, 0.5 g of hydrogen peroxide/urea adduct and 0.66 ml of trifluoroacetic anhydride are added to the reaction mixture one after the other, in the manner described above, four times, followed each time by stirring for 3 hours at 22° C., in the course of which a yellow suspension is formed which is taken up in ethyl acetate. The organic phase is washed in succession with 1 N sodium hydroxide solution, water and brine, dried over sodium sulfate, filtered and concentrated in vacuo. The crude product is purified by means of flash chromatography (silica gel; eluant: hexane/ethyl acetate 3/2). 0.25 g of the desired product is obtained in the form of yellow crystals having a melting point of 114–118° C.

Example P25

3-(5-Chloro-2-pyridyl-N-oxide)-4-chloro-5-trifluoromethyl-1-methyl-[1H]-pyrazole

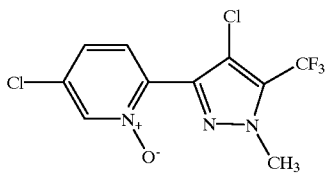

6.82 g of 3-(5-chloro-2-pyridyl)-4-chloro-5-trifluoromethyl-1-methyl-[1H]-pyrazole are introduced into 30 ml of methylene chloride at 25° C. With stirring, 7.23 g of m-chloroperbenzoic acid are added. After 48 hours a further 2.50 g of m-chloroperbenzoic acid are added. After a further 24 hours the reaction mixture is taken up in ethyl acetate and extracted twice with dilute sodium hydroxide solution, then washed with brine, dried over sodium sulfate and concentrated. Chromatography is then carried out (silica gel; eluant: n-hexane/ethyl acetate 1/1 (v/v)). 6.31 g of the desired compound are isolated in the form of a white solid.

$^1$H-NMR (DMSO-D$_6$): 8.75 ppm (d, 1H); 7.66 ppm (d, 1H); 7.59 ppm (dxd, 1H); 4.08 ppm (s, 3H).

Starting from the S-(5-chloro-2-pyridyl)-4-chloro-3-trifluoromethyl-1-methyl-[1H]-pyrazole isomer, the 5-(5-chloro-2-pyridyl-N-oxide)-4-chloro-3-trifluoromethyl-1-methyl-[1H]-pyrazole isomer can be obtained in a yield of 70%.

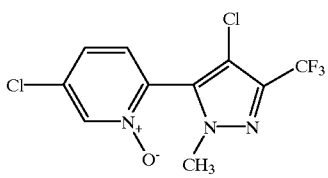

Example P26

3-(3-Fluoro-5-chloro-2-pyridyl-N-oxide)-4-chloro-S-difluoromethoxy-1-methyl-[1H]-pyrazole

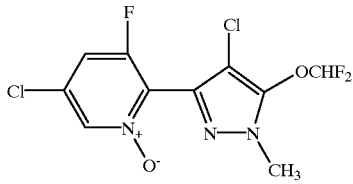

0.57 g of 3- (3-fluoro-5-chloro-2-pyridyl)-4-chloro-5-difluoromethoxy-1-methyl-[1H]-pyrazole (Example P15) is introduced into 5 ml of methylene chloride and 0.63 g of a 55% m-chloro- perbenzoic acid is added. After stirring for 4 days at 25° C., the crude mixture is taken up in ethyl acetate and washed in succession with sodium hydrogen carbonate solution, water and brine. After drying over sodium sulfate and filtering, concentration is carried out and the residue is purified by means of flash chromatography. 0.45 g of the desired target compound is obtained in the form of a white solid having a melting point of 115–120° C.

Example P27

3-Chloro-6-(4-chloro-5-difluoromethoxy-1-methyl-[1H]-pyrazol-3-yl)-5-fluoropyridin-2-ol

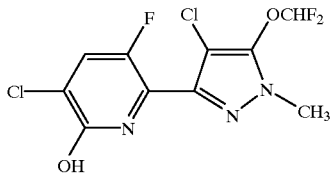

1.0 g of 3-(3-fluoro-5-chloro-2-pyridyl-N-oxide)-4-chloro-5-difluoromethoxy-1-methyl-[1H]-pyrazole (Example P26) is introduced into 12 ml of dry N,N-dimethylformamide. With stirring and cooling with an ice-bath, 4.2 ml of trifluoroacetic anhydride are added dropwise from a syringe and the mixture is subsequently stirred overnight at 25° C. The mixture is then concentrated by evaporation in vacuo and the residue is partitioned between diethyl ether and water. After extraction by shaking, and separation of the phases, the ethereal phase is washed with dilute aqueous sodium hydrogen carbonate solution and brine, dried over sodium sulfate, filtered and concentrated. 1.23 g of a yellow oil are obtained, which is purified using a flash chromatography column (silica gel; eluant: n-hexane/ethyl acetate 2/3 (v/v) and 1% glacial acetic acid). 0.59 g of the desired compound is obtained in the form of a yellow solid having a melting point of 126–128° C.

Example P28
5-(5-Chloro-3-fluoropyridin-2-yl)-2,4-dimethyl-[2H]-pyrazole-3-carboxylic Acid

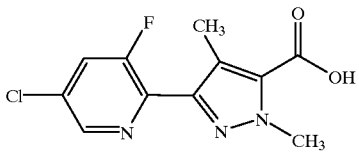

6.75 g of 5-(5-chloro-3-fluoropyridin-2-yl)-2,4-dimethyl-[2H]-pyrazole-3-carboxylic acid ethyl ester are suspended in 40 ml of dimethyl sulfoxide. With occasional cooling in an ice-bath (internal temperature <30° C.), 14.3 ml of a 2N sodium hydroxide solution are added dropwise. The thick, yellowish-brown suspension is stirred at 22° C. for 2 hours. The suspension is then introduced into ice-water and adjusted to pH 1 with 2N hydrochloric acid. The resulting slurry is filtered, washed well with cold water and then dried in vacuo at 60° C. 5.97 g of the desired title compound are obtained in the form of a beige solid having a melting point of 194–196° C.

Example P29
5-(5-Chloro-3-fluoropyridin-2dl)-2,4-dimethyl-[2H]-pyrazole-3-carboxylic Acid Amide

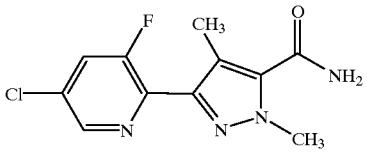

3.0 g of 5-(5-chloro-3-fluoropyridin-2-yl)-2,4-dimethyl-[2H]-pyrazole-3-carboxylic acid (Example P28) are introduced into 25 ml of 1,2-dichloroethane and, at 80° C., a total of 1.21 ml of thionyl chloride is added and the mixture is subsequently stirred for 5 hours at 80° C. The mixture is concentrated in vacuo, 20 ml of carbon tetrachloride are added three times and each time the mixture is concentrated to dryness by evaporation. The resulting acid chloride is introduced into 35 ml of tetrahydrofuran. With cooling in an ice-bath, ammonia gas is introduced. A brown precipitate forms. Stirring is carried out overnight at 22° C. The resulting suspension is introduced into five times its volume of ice-water. After then stirring briefly, filtration is carried out and the filtration residue is subsequently washed with cold water and dried in vacuo at 60° C. 2.0 g of the desired title compound are obtained in the form of a brown solid having a melting point of 201–204° C.

Example P30
5-Chloro-3-fluoropyridin-2-yl)-2,4-dimethyl-[2H]-pyrazole-3-carbonitrile

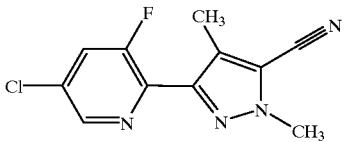

1.82 g of 5-(5-chloro-3-fluoropyridin-2-yl)-2,4-dimethyl-[2H]-pyrazole-3-carboxylic acid amide (Example P29) are suspended in 20 ml of dioxane. With cooling with an ice-bath, first 1.65 ml of pyridine and then 1.44 ml of trifluoroacetic anhydride are added. After 5 minutes the cooling bath is removed and the mixture is subsequently stirred for 1 hour at 22° C. The brownish-red solution is diluted with diethyl ether and washed with 1 N hydrochloric acid and then with brine. The mixture is dried over sodium sulfate and filtered and then directly concentrated with twice the amount of silica gel. After application of the silica gel to a flash chromatography column, elution is carried out with n-hexane/ethyl acetate 4/1 (v/v). 1.60 g of the desired title compound are obtained in the form of a beige solid having a melting point of 144–146° C.

Example P31
3-(3-Fluoro-5-methyl-2-pyridyl)-4-chloro-5-difluoromethoxy-1-methyl-[1H]-pyrazole

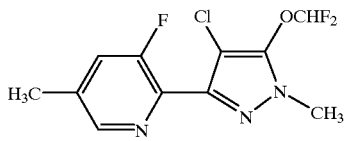

2.0 g of 3-(3-fluoro-5-chloro-2-pyridyl)-4-chloro-5-difluoromethoxy-1-methyl-[1H]-pyrazole (Example P15) are introduced into 6 ml of absolute dioxane. In order to remove the oxygen, gentle evacuation is carried out three times (water-jet pump) and the mixture is gassed with argon. 6.4 ml of a 2M solution of trimethylaiuminium in toluene and 0.10 g of tetrakistriphenylphosphinepalladium (Pd(PPh$_3$)$_4$) are added thereto. The mixture is heated to 90° C., with stirring, in an argon atmosphere. The next day the mixture is cooled to 22° C., a further 0.10 g of Pd(PPh$_3$)$_4$ and 6.4 ml of a 2M solution of trimethylaluminium in toluene are added and the mixture is stirred at 110° C. After 4 hours, TLC analysis of a worked-up sample shows that all the starting material has reacted. The reaction mixture is introduced carefully into cold, dilute hydrochloric acid and is then extracted with ethyl acetate. The combined organic phases are washed with brine, dried over sodium sulfate, filtered and concentrated by evaporation in vacuo. The crude product obtained is purified over a flash chromatography column (silica gel; eluant: n-hexane/ethyl acetate 1/1 (v/v)). 1.36 g of the desired compound are obtained in the form of a yellow oil, which slowly crystallises; melting point 41–42° C.

The R$_f$ value of the starting material on silica gel 60 F$_{254}$ (eluant: n-hexane/ethyl acetate 2/1 (v/v)) is 0.37 and the R$_1$ value of the title compound is 0.15.

Example P32
3-Chloro-6-(4-chloro-5-difluoromethoxy-1-methyl-[1H]-pyrazol-3-yl)-5-fluoro-1-hydroxy-[1H]-2-pyridin-2-one (Compd. No. 1.397)

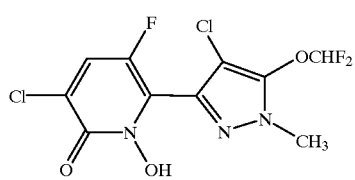

0.50 g of 3-chloro-6-(4-chloro-5-difluoromethoxy-1-methyl-[11]-pyrazol-3-yl)-5-fluoropyridin-2-ol (Example P27) is introduced into 4 ml of 1,2-dichloroethane, and 0.15 g of hydrogen peroxide/urea adduct (30%) and 0.22 ml of trifluoroacetic anhydride are added. The mixture is stirred overnight at 22° C. and then a further 0.15 g of hydrogen peroxide/urea adduct is added together with 0.22 ml of trifluoroacetic anhydride. The mixture is subsequently stirred for 5 hours and then partitioned between ethyl acetate and dilute hydrochloric acid. The separated organic phase is washed with brine, dried over sodium sulfate, filtered and concentrated to dryness. 0.55 g of the desired compound is obtained in the form of a yellow resinous precipitate (crude product).

$^1$H-NMR (CDCl$_3$): 7.65 ppm (d, 1H); 6.74 ppm (t, 1H); 3.90 ppm (s, 3H).

Example P33
3-Chloro-6-(4-chloro-5-difluoromethoxy-1-methyl-[1H]-pyrazol-3-yl)-5-fluoro-1-methoxy-[1H]-pyridin-2-one (Compd. No. 1.400)

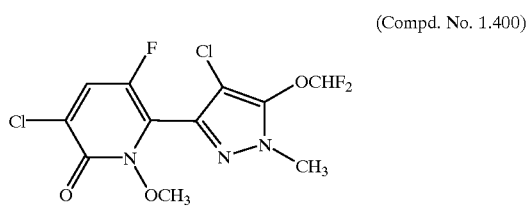

0.20 g of 3-chloro-6-(4-chloro-5-difluoromethoxy-1-methyl-[1H]-pyrazol-3-yl)-5-fluoro-1-hydroxy-[1H]-pyridin-2-one (Example P32) is introduced into 2 ml of N-methylpyrrolidone (NMP) at 22° C. and 0.16 g of anhydrous potassium carbonate is added. With stirring, 0.10 g of methyl iodide in 0.5 ml of NMP is then added dropwise. The reaction mixture is stirred for 2 hours at 22° C. and then partitioned between 20 ml of water and diethyl ether. The separated ethereal phase is washed with brine, dried over sodium sulfate, filtered and concentrated to dryness by evaporation in vacuo. 0.13 g of the desired crude product is obtained in the form of a yellow oil which, after purification by means of flash chromatography (silica gel; eluant: n-hexane/ethyl acetate 1/1 (v/v)), yields 0.08 g of pure product in the form of a colourless oil.

$^1$H-NMR (CDCl$_3$): 7.62 ppm (d, 1H); 6.74 ppm (t, 1H); 4.00 ppm (s, 3H); 3.90 ppm (s, 3H).

Example P34
3-(5-Chloro-3-fluoropyridin-2-yl)-2-methyl-3-oxopropionic Acid Tert-Butyl Ester

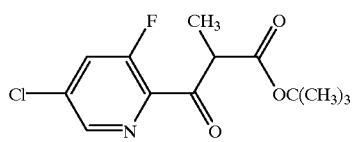

32.3 g of diisopropylamine are introduced into 200 ml of tetrahydrofuran and, with cooling with a CO$_2$/acetone cooling bath, 200 ml of a 1.6M solution of n-butyllithium in hexane are added dropwise. 49.2 ml of propionic acid tert-butyl ester are then added dropwise at approximately −75° C. and the mixture is stirred at that temperature for 45 minutes. At approximately −75° C. a solution of 32.6 g of 3-fluoro-5-chloro-2-pyridinecarboxylic acid ethyl ester (Example P1) in 40 ml of tetrahydrofuran (THF) is then added dropwise and the mixture is stirred at that temperature for 1 hour, after which it is diluted with 250 ml of tert-butyl methyl ether. A mixture of 100 ml of water and 200 ml of glacial acetic acid is added, the phases are separated, the aqueous phase is extracted again, and the combined organic phases are washed with water. After drying over magnesium sulfate, filtration and concentration to dryness in vacuo are carried out. 51 g of the desired compound are obtained in the form of an oil (crude product).

The R$_f$ value of the starting material on silica gel 60 F$_{254}$ (eluant: n-hexane/ethyl acetate 3/1 (v/v)) is 0.46, and the R$_f$ value of the product is 0.63.

Example P35
3-(5-Chloro-3-fluoropyridin-2-yl)-2-methyl-3-oxopropionic acid

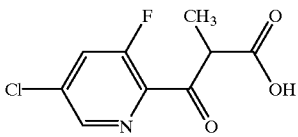

25.5 g of 3- (5-chloro-3-fluoropyridin-2-yl)-2-methyl-3-oxopropionic acid tert-but yl ester (Example P34) are added dropwise to 30 ml of a 33% solution of hydrogen bromide (HBr) in glacial acetic acid to form a suspension. The mixture is subsequently stirred for 90 minutes and then introduced into 300 ml of ice-water. The resulting precipitate is filtered off, washed with water and dried. 15.9 g of the desired title compound are obtained in the form of a solid having a melting point of 101–102° C.

Example P36
2-Chloro-1-(5-chloro-3-fluoropyridin-2-yl)- propan-1-one

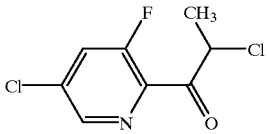

20.8 g of 3-(5-chloro-3-fluoropyridin-2-yl)-2-methyl-3-oxopropionic acid (Example P35) are introduced into 125 ml of glacial acetic acid. 6.3 g of chlorine gas are introduced into the solution in the course of 1 hour . The mixture is then poured into 700 ml of water and extracted with tert-butyl methyl ether. The combined ethereal phases a rewashed with water and dried over magnesium sulfate, filtered and concentrated by evaporation in vacuo. The crude product is dissolved in 180 ml of tert-butyl methyl ether, 45 g of silica gel are added and the mixture is stirred for 30 minutes, in the course of which the evolution of gas observed initially comes to a halt. The silica gel is then filtered off and subsequently washed and the combined ethereal phases are concentrated to dryness in vacuo. 20.1 g of an oily crude product are obtained, which is purified over a flash chromatography column (silica gel; eluant: n-hexane/ethyl acetate 411 (v/v)). 17.0 g of the desired title compound are obtained in the form of a solid having a melting point of 29–32° C.

Example P37
5-(5-Chloro-3-fluoropyridin-2-yl)-3,6-dimethyl-3,6-dihydro-[1,3,4]-thiadiazine-2-thione

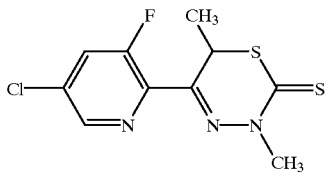

19.1 ml of a 4N sodium hydroxide solution and 3.5 g of methyl hydrazine are introduced into 76 ml of ethanol. At an internal temperature of <5° C., 4.5 ml of carbon disulfide are added dropwise with stirring, and the mixture is then stirred for 30 minutes. 17.0 g of 2-chloro-1-(5-chloro-3-fluoropyridin-2-yl)-propan-1-one (Example P36) are subsequently added in the course of 15 minutes at an internal temperature of <5° C. The temperature is then allowed to rise to 22° C. and the mixture is subsequently stirred for 30 minutes. TLC analysis (silica gel 60 $F_{254}$; eluant: n-hexane/ethyl acetate, UV) of a worked-up sample shows that starting material is no longer present. 2.5 ml of a concentrated hydrochloric acid solution are then added dropwise to form a yellow precipitate. Stirring is carried out for 1 hour and the mixture is then poured into water and extracted with tert-butyl methyl ether. The combined ethereal phases are washed with water, dried over magnesium sulfate, filtered and concentrated to dryness in vacuo. 20.3 g of the desired title compound are obtained in the form of a solid having a melting point of 107–112° C.

Example P38
5-Chloro-2-(1,4-dimethyl-5-methylsulfanyl-[1H]-pyrazol-3-yl)-3-fluoropyridine

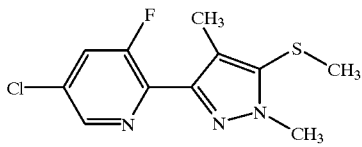

21.6 g of crude 5-(5-chloro-3-fluoropyridin-2-yl)-3,6-dimethyl-3,6-dihydro-[1.3.4]-thiadiazine-2-thione (Example P37) are introduced into 70 ml of tert-butanol, 19.1 g of triphenylphosphine are added and the mixture is stirred at an internal temperature of 65° C. for approximately 15 minutes, a clear solution forming. After cooling to 22° C., a suspension again forms, to which 8.2 g of potassium tert-butanolate are added in portions at an internal temperature of <40° C. (cooling with an ice-bath). The mixture is then stirred overnight, subsequently poured into 600 ml of water, stirred, filtered and washed, and the aqueous phase is extracted thoroughly with tert-butyl methyl ether. The aqueous phase is rendered strongly acidic with concentrated hydrochloric acid and extracted with tert-butyl methyl ether. The combined ethereal phases are washed with water, dried over magnesium sulfate, filtered and concentrated to dryness in vacuo. 6.8 g of a crude intermediate are obtained.

1.9 g of the intermediate are dissolved in 10 ml of dimethylformamide (DMF) and 2.2 g of potassium carbonate are added. 0.5 ml of methyl iodide in 2 ml of DMF is then added dropwise. The mixture is subsequently stirred at 22° C. for 5 hours, poured into 120 ml of ice-water, and extracted with diethyl ether. The combined ethereal phases are washed with water, dried over magnesium sulfate, filtered and concentrated in vacuo. 1.8 g of an oil are obtained, which is purified over a flash chromatography column (silica gel; eluant: n-hexane/ethyl acetate 2/1 (v/v)). 1.3 g of the desired title compound are obtained in the form of a solid having a melting point of 61–64° C.

Example P39
5-Chloro-2-(1,4-dimethyl-5-methylsulfanyl-[1H]-pyrazol-3-yl)-3-fluororyridine

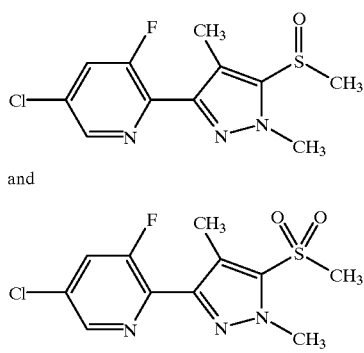

and 2.1 g of 5chloro-2-(1,4-dimethyl-5-methylsulfanyl-[1H]-pyrazol-3-yl)-3-fluoropyridine (Example P38) are dissolved in 40 ml of methylene chloride, and 2.84 g of 70% meta-chloroperbenzoic acid are added in portions. The mixture is then stirred for 4 hours at 22° C. and subsequently stirred with 1N sodium hydrogen carbonate solution for 30 minutes. The organic phase is separated off, washed with water, dried over magnesium sulfate, filtered and concentrated in vacuo. 1.7 g of a solid are obtained, which is purified over a flash chromatography column (silica gel; eluant: n-hexane/ethyl acetate 1/1 (v/v)). 0.80 g of the desired sulfone having a melting point of 145–147° C. and 0.70 g of the sulfoxide having a melting point of 112–114° C. are obtained.

Example P40
5-Chloro-3-fluoro-2-(5-methanesulfonyl-1.4-dimethyl-[1H]-pyrazol-3-yl)-pyridine-1-oxide

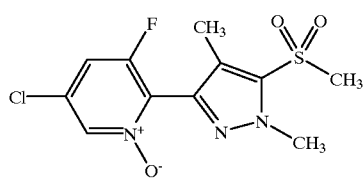

5.3 g of 5-chloro-2-(1,4-dimethyl-5-methylsulfanyl-[1H]-pyrazol-3-yl)-3-fluoropyridine (Example P39) are dissolved in 50 ml of methylene chloride. With stirring, 19.2 g of 70% m-chloroperbenzoic acid (MCPBA) are introduced in portions at 22° C. with exothermic reaction. The mixture is then stirred overnight at 22° C. The next day, a further 4.9 g of MCPBA are added and the mixture is stirred overnight. The mixture is subsequently extracted with dilute sodium hydrogen carbonate solution and then with sodium thiosulfate solution. The extract is dried over magnesium sulfate and then filtered and concentrated to dryness in vacuo. The crude product (6 g) is purified over silica gel using ethyl acetate as eluant. 3.6 g of the desired title compound having a melting point of 174–176° C. are obtained.

Example P41

3-Chloro-5-fluoro-6-(5-methanesulfonyl-1,4-dimethyl-[1H]-pyrazol-3-yl)-[1H]-pyridin-2-one

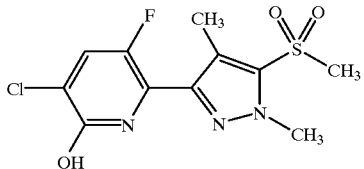

2.6 go 5-chloro-3-fluoro-2-(5-methanesulfonyl-1,4-dimethyl-[1H]-pyrazol-3-yl)-pyridine-1-oxide (Example P40) are introduced into 35 ml of dry dimethylformamide. At a temperature of 10° C., 16.8 g of trifluoroacetic anhydride are added dropwise and the mixture is then stirred overnight at 22° C., subsequently poured into 2 liters of ice-water and extracted with tert-butyl methyl ether. After drying over magnesium sulfate, filtering and concentrating to dryness by evaporation in vacuo, 1.8 g of the desired compound are obtained as crude product, which can be used directly in the next step.

Example P42

3-Chloro-5-fluoro-6-(5-methanesulfonyl-1,4-dimethyl-[1H]-pyrazol-3-yl)-1-propyn-2-yl-[1H]-pyridin-2-one (Compd. No. 28.100)

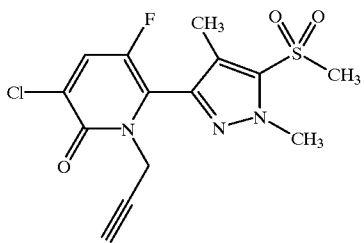

1.8 g of 3-chloro-5-fluoro-6-(5-methanesulfonyl-1,4-dimethyl-[1H]-pyrazol-3-yl)-[1H]-pyridin-2-one (Example P41) are dissolved in 10 ml of dimethyl sulfoxide and 3.0 ml of a 2N aqueous sodium hydroxide solution are added (slightly exothermic reaction). After subsequently stirring for 30 minutes at 22° C., 0.46 ml of propargyl bromide is added dropwise and the mixture is further stirred overnight at 22° C. The reaction mixture is then introduced into 120 ml of ice-water, filtered, and washed with water. It is taken up in ethyl acetate, dried over magnesium sulfate, filtered and concentrated to dryness by evaporation in vacuo. The crude product is purified by means of silica gel chromatography (eluant: n-hexane/ethyl acetate 1/1 (v/v)). 0.74 g of the desired title compound, which still contains 20% of the isomeric 0-propargyl derivative, is obtained; m.p. 189–192° C.

The $R_f$ value of the title compound on silica gel 60 $F_{254}$ (eluant: n-hexane/ethyl acetate 1/1 (v/v)) is 0.28, the $R_f$ value of the O-propargyl isomer is 0.55, and the $R_f$ value of the starting compound is 0.05.

Example P43

5-(5-Chloro-3-fluoro-1-methyl-6-oxo-1,6-dihydropyridin-2-yl)-2,4-dimethyl-[2H]-pyrazole-3-carbonitrile (Compd. No. 22.100)

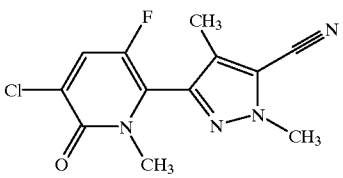

1.54 g of 3-chloro-6-(1,4-dimethyl-5-cyano-[1H]-pyrazol-3-yl)-5-fluoropyridin-2-ol are introduced into a mixture of 20 ml of absolute 1,2-dimethoxyethane and 5 ml of absolute dimethylformamide at 22° C. With stirring, first 1.20 g of lithium bromide are added and then, 10 minutes later, in portions, 0.28 g of a 60% sodium hydride dispersion in oil. After a further 10 minutes, 0.86 ml of methyl iodide is added, after which the mixture is stirred overnight at 90° C. The mixture is then cooled to 22° C., carefully poured into dilute hydrochloric acid, and extracted with diethyl ether. The combined ethereal phases are washed with brine, dried over sodium sulfate, filtered and concentrated in vacuo together with 4 g of silica gel. The silica gel is applied to a flash chromatography column and fractionated by means of gradient elution using n-hexane/ethyl acetate 3/1 to 1/1 (v/v). 0.68 g of the desired compound is obtained in the form of a white solid having a melting point of 190–191° C.

Example P44

1-Allyl-3-chloro-6-(4-chloro-5-difluoromethoxy-1-methyl-[1H]-pyrazol-3-yl)-5-fluoro-[1H]-pyridin-2-one (Compd. No. 1.080)

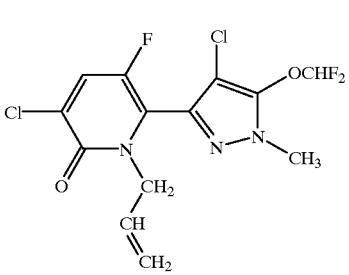

1.50 g of 3-(3-fluoro-5-chloro-6-hydroxy-2-pyridyl)-4-chloro-5-difluoromethoxy-1-methyl-[1H]-pyrazole (Example P27) are suspended in a dry mixture of 16 ml of dimethoxyethane and 4 ml of N,N-dimethylformamide (DMF). With stirring, a total of 0.20 g of a 55% sodium hydride dispersion is added, in portions, at 25° C. The suspension is subsequently stirred for ten minutes, 0.79 g of anhydrous lithium bromide is then added and, after a further fifteen minutes' stirring, 0.77 ml of allyl bromide is added dropwise. The mixture is subsequently stirred overnight at 65° C. The next day, TLC analysis of a worked-up sample shows that starting material is no longer present. The reaction mixture is cooled to 2500 and partitioned between dilute hydrochloric acid and tert-butyl methyl ether. After extraction by shaking, and separation of the phases, the ethereal phase is washed with brine, dried over sodium sulfate, filtered, and concentrated in vacuo together with 5 g of silica gel. The silica gel is applied to a flash chromatography column and chromatography is carried out (silica gel; eluant: n-hexane/ethyl acetate 2/1 (v/v)). 0.95 g of the target com-

Example P45
1-Ethyl-3-chloro-6-(4-chloro-5-difluoromethoxy-1-methyl-[1H]-pyrazol-3-yl)-5-fluoro-[1H]-pyridin-2-one (Compd. No. 1.004)

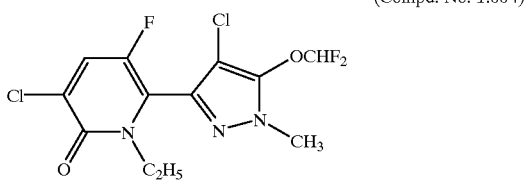

1.5 g of 3-(3-fluoro-5-chloro-6-hydroxy-2-pyridyl)-4-chloro-5-difluoromethoxy-1-methyl-[1H]-pyrazole (Example P27) are introduced into 6 ml of dimethyl sulfoxide (DMSO). 2.5 ml of a 2N aqueous sodium hydroxide solution are added thereto. 0.78 g of ethyl iodide in 2 ml of DMSO is then added dropwise, with stirring, and the mixture is further stirred overnight at 70° C. The next day, the reaction mixture is partitioned between dilute hydrochloric acid and diethyl ether. After extraction by shaking, and separation of the phases, the ethereal phase is washed with brine, dried over sodium sulfate, filtered and concentrated in vacuo. Finally, the residue is purified over a flash chromatography column (silica gel; elution gradient: n-hexane/ethyl acetate 4/1 to 1/1 (v/v)). 0.54 g of the desired target compound is obtained in the form of a yellow oil having an $R_f$ value of 0.17 on silica gel 60 $F_{254}$ (eluant: n-hexane/-ethyl acetate 2/1 (v/v)).

Example P46
3-(3-Chloro-6-(4-chloro-5-difluoromethoxy-1-methyl-[1H]-pyrazol-3-yl)-5-fluoro-2-oxo-[2H]-pyridin-1-yl)-acetic acid benzyl ester (Compd. No. 1.195)

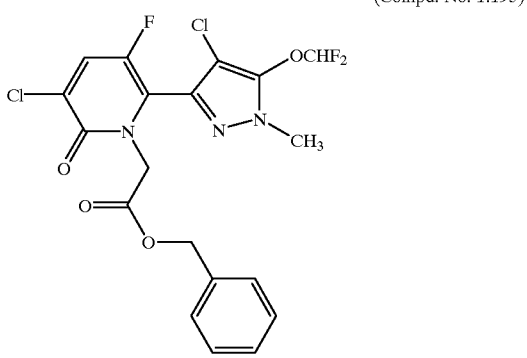

10.0 g of 3-chloro-6-(4-chloro-5-difluoromethoxy-1-methyl-[1H]-pyrazol-3-yl)-5-fluoropyridin-2-ol (Example P27) are introduced into a mixture of 100 ml of dimethoxyethane and 25 ml of dimethylformamide at 22° C. 1.22 g of sodium hydride (60%, moistened in oil) are then added in portions, evolution of gas being observed. After subsequently stirring for 15 minutes at 22° C., 5.3 g of dry lithium bromide are added (slightly exothermic reaction) and, after 10 minutes, 9.6 ml of bromoacetic acid benzyl ester are added. The mixture is then stirred for 5 hours at 75° C. After cooling to 22° C., the mixture is taken up in ethyl acetate, washed with dilute hydrochloric acid and then with brine, subsequently dried over sodium sulfate, filtered, and concentrated to dryness in vacuo. 24.3 g of a yellow oil are obtained, which is purified by means of flash chromatography (silica gel; eluant: n-hexane/-ethyl acetate 2/1 (v/v)). 7.67 g of the desired compound are obtained in the form of a yellow oil which crystallises on being left to stand; m.p. 83–85° C.

The $R_f$ value of the starting material on silica gel 60 $F_{254}$ (eluant: n-hexane/ethyl acetate/-glacial acetic acid 20/20/1 (v/v/v)) is 0.45, and the $R_f$ value of the title compound is 0.60. The isomeric O-alkyl derivative is isolated as secondary product.

Example P47
3-(3-Chloro-6-(4-chloro-5-difluoromethoxy-1-methyl-[1H]-pyrazol-3-yl)-5-fluoro-2-oxo-[2H]-pyridin-1-yl)-acetic acid (Compd. No. 1.177)

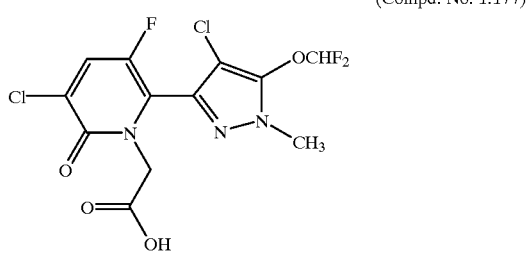

6.0 g of 3-(3-chloro-6-(4-chloro-5-difluoromethoxy-1-methyl-[1H]-pyrazol-3-yl)-5-fluoro-2-oxo-[2H]-pyridin-1-yl)-acetic acid benzyl ester (Example P46) are hydrogenated at normal pressure and 22° C. with 0.35 g of 5% palladium-on-active carbon in 90 ml of tetrahydrofuran (THF). After 2.5 hours, the reaction mixture is filtered over Hyflo and washed with THF. 5.11 g of the desired title compound are obtained in the form of a colourless resin, which solidifies on being left to stand.

$^1$H-NMR (CDCl$_3$): 7.58 ppm (d, 1H); 6.66 ppm (t, 1H); 4.73 ppm (s, 2H); 3.77 ppm (s, 3H).

Example P48
3-(3-Chloro-6-(4-chloro-5-difluoromethoxy-1-methyl-[1H]-pyrazol-3-yl)-5-fluoro-2-oxo-[2H]-pyridin-1-yl)-acetic acid imidazolide

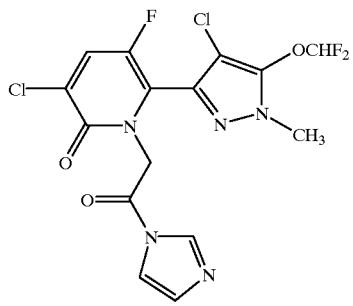

2.0 g of 3-(3-chloro-6-(4-chloro-5-difluoromethoxy-1-methyl-[1H]-pyrazol-3-yl)-5-fluoro-2-oxo-[2H]-pyridin-1-yl)-acetic acid (Example P47) are suspended in 20 ml of 1,2-dichloroethane. With stirring, 0.92 g of 1,1'-carbonyldiimidazole is added at 22° C. The mixture is stirred overnight and the resulting solution is concentrated to dryness by evaporation in vacuo. 2.40 g of the desired title compound are obtained in the form of a beige solid, which contains 20% by weight imidazole.

¹H-NMR (DMSO-D₆): 8.51 ppm (s, 1H); 8.41 ppm (d, 1H); 7.77 ppm (m, 1H); 7.33 ppm (t, 1H); 7.13 ppm (m, 1H); 5.46 ppm (s, 2H); 3.60 ppm (s, 3H).

Example P49
3-(3-Chloro-6-(4-chloro-5-difluoromethoxy-1-methyl-[1H]-pyrazol-3-yl)-5-fluoro-2-oxo-[2H]-pyridin-1-yl)-acetic Acid Diethylamide

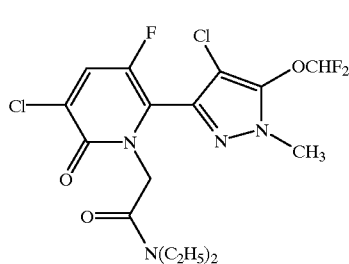

(Compd. No. 1.234)

1.0 g of 3-(3-chloro-6-(4-chloro-5-difluoromethoxy-1-methyl-[1H]-pyrazol-3-yl)-5-fluoro-2-oxo-[2H]-pyridin-1-yl)-acetic acid (Example P47) is introduced into 8 ml of 1,2-dichloroethane. 0.50 g of carbonyidiimidazole is added to the white suspension and the mixture is stirred for one hour at 22° C., in the course of which all undissolved components dissolve. 0.39 ml of diethylamine is then added and the mixture is stirred overnight at 22° C. The next day, the reaction mixture is taken up in ethyl acetate and washed in succession with dilute sodium hydrogen carbonate solution, dilute hydrochloric acid and brine. After drying over sodium sulfate, filtration is carried out and the residue is concentrated to dryness in vacuo. 1.20 g of a yellow oil is obtained which is purified over a flash chromatography column (silica gel;

eluant: ethyl acetate). 1.27 g of the desired title compound are obtained in the form of a colourless resin.

¹H-NMR (CDCl₃): 7.61 ppm (d, 1H); 6.72 ppm (t, 1H); 4.99 ppm (s, 2H); 3.82 ppm (s, 3H); 3.27 ppm (m, 4H); 1.13 ppm (t, 3H); 1.04 ppm (t, 3H).

Example P50
3-(3-Chloro-6-(4-chloro-5-difluoromethoxy-1-methyl-[1H]-pyrazol-3-yl)-5-fluoro-2-oxo-[2H]-pyridin-1-yl-acetic Acid Allylamide

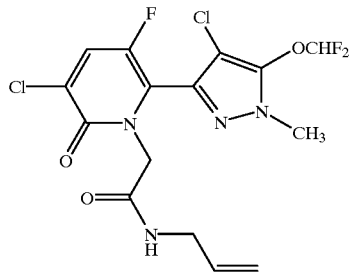

(Compd. No. 1.244)

1.0 g of 3-(3-chloro-6-(4-chloro-5-difluoromethoxy-1-methyl-[1H]-pyrazol-3-yl)-5-fluoro-2-oxo-[2H]-pyridin-1-yl)-acetic acid imidazolide (crude product) (Example P48) is introduced into 6 ml of 1,2-dichloroethane at 22° C. After the addition of 0.21 ml of allylamine, the mixture is stirred overnight and then taken up in ethyl acetate and washed in succession with dilute sodium hydroxide solution, brine, dilute hydrochloric acid and brine. Drying over sodium sulfate, filtration and concentration by evaporation in vacuo yield 0.77 g of the desired compound in the form of a white solid having a melting point of 146–148° C.

Example P51
3-Chloro-6-(4-chloro-5-difluoromethoxy-1-methyl-[1H]-pyrazol-3-yl)-5-fluoro-1-methanesulfanylmethyl)-[1H]-pyridin-2-one

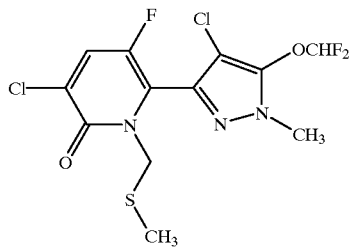

(Compd. No. 1.147)

4.0 g of 3-chloro-6-(4-chloro-5-difluoromethoxy-1-methyl-[1H]-pyrazol-3-yl)-5-fluoropyridin-2-ol (Example P27) are introduced into a mixture of 40 ml of dry dimethoxyethane and 10 ml of dry dimethylformamide at 22° C., and 0.49 g of a 60% sodium hydride (NaH) dispersion in hexane is added. After 15 minutes' stirring, 2.12 g of lithium bromide are added and the mixture is subsequently stirred for 10 minutes. 2.0 ml of chlorodimethyl sulfide are then added and the mixture is further stirred overnight at 70° C. After cooling to 22° C., a sample is removed and analysed in a thin-layer chromatogram (TLC). Since starting material is still present, a further 0.30 g of sodium hydride dispersion (60%) and 0.60 ml of chlorodimethyl sulfide are added and the mixture is then again stirred overnight at 70° C. After cooling to 22° C., the mixture is taken up in ethyl acetate, and dilute hydrochloric acid is added carefully. After extraction by shaking, and separation of the phases, the ethyl acetate phase is washed with brine, dried over sodium sulfate, filtered and concentrated to dryness in vacuo. The crude product is purified over silica gel (eluant: n-hexane/ethyl acetate 2/1 (v/v)). First 0.51 g of the 0-alkyl isomer is eluted and then 3.04 g of the desired title compound in the form of a yellow oil, which slowly crystallises out.

The $R_f$ value of the title compound on silica gel 60 $F_{254}$ (eluant: n-hexane/ethyl acetate/glacial acetic acid 20/20/1 (v/v/v)) is 0.37, the $R_f$ value of the 0-alkyl isomer is 0.70 and the $R_f$ value of the starting material is 0.31.

Example P52
3-Chloro-6-(4-chloro-5-difluoromethoxy-1-methyl-[1H]-pyrazol-3-yl)-5-fluoro-1-methanesulfonylmethyl)-[1H]-pyridin-2-one

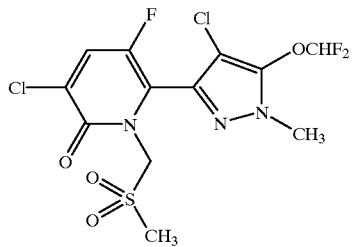

(Compd. No. 1.153)

1.97 g of 3-chloro-6-(4-chloro-5-difluoromethoxy-1-methyl-[1H]-pyrazol-3-yl)-5-fluoro-1- methanesulfanylmethyl)-[1H]-pyridin-2-one (Example P51) are introduced into 25 ml of dichloroethane at 22° C. 3.75 g of m-chloroperbenzoic acid (70%) are added to the yellow solution with a slight exothermic reaction. The mixture is stirred overnight at 22° C. The next day, the reaction mixture is taken up in ethyl acetate and washed with dilute sodium hydroxide solution and then with brine. After drying over sodium sulfate, filtration is carried out followed by concentration to dryness in vacuo. 2.05 g of the desired title compound are obtained in the form of a white solid having a melting point of 171–172° C.

Example P53
3-Chloro-6-(4-chloro-5-difluoromethoxy-1-methyl-[1H]-pyrazol-3-yl)-5-fluoro-1-methanesulfinylethyl)-[1H]-pyridin-2-one (Compd. No. 1.161)

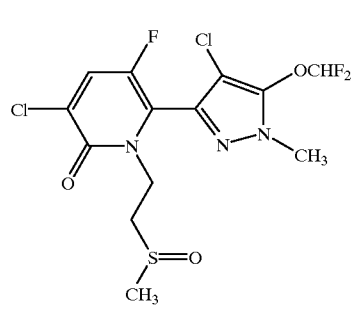

1.18 g o 3-chloro-6-(4-chloro-5-difluoromethoxy-1-methyl-[1H]-pyrazol-3-yl)-5-fluoro-1-methanesulfanylethyl)-[1H]-pyridin-2-one are introduced into 7 ml of glacial acetic acid. After the addition of 0.27 g of hydrogen peroxide/urea adduct, the mixture is stirred overnight at 22° C. The next day, the reaction mixture is taken up in ethyl acetate and washed in succession with dilute sodium hydroxide solution, dilute hydrochloric acid and brine. After drying over sodium sulfate, the mixture is filtered and concentrated to dryness in vacuo. The residue (1.12 g of a yellow solid) is stirred with 10 ml of diethyl ether, and then filtered and washed with n-hexane. 1.05 g of the desired compound are obtained in the form of a white solid having a melting point of 143–145° C.

Example P54
1-Benzyl-3-chloro-6-(4-chloro-5-difluoromethoxy-1-methyl-[1H]-pyrazol-3-yl)-5-fluoro-[1H]-pyridine-2-thione (Compd. No. 1.494)

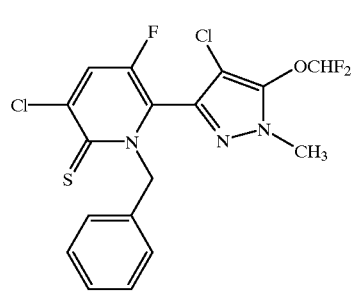

0.50 g of 1-benzyl-3-chloro-6-(4-chloro-5-difluoromethoxy-1-methyl-[1H]-pyrazol-3-yl)-5-fluoro-[1H]-pyridin-2-one is introduced into 5 ml of toluene, 0.63 g of Lawesson's reagent is added and the resulting yellow suspension is stirred overnight at 120° C. The next day, the mixture is cooled to 22° C., diluted with methylene chloride and, after the addition of 3 g of silica gel, concentrated to dryness in vacuo. The silica gel is applied to a flash chromatography column and eluted first with toluene/ethyl acetate 30/1 (v/v) and then with n-hexane/ethyl acetate 2/1 (v/v). 0.32 g of the desired title compound is obtained in the form of a yellow solid having a melting point of 135–138° C.

The $R_f$ value of the starting material on silica gel 60 $F_{254}$ (eluant: toluenelethyl acetate 30/1 (v/v)) is 0.02 and the $R_f$ value of the title compound is 0.18.

Example P55
3-(3-Chloro-6-(4-chloro-5-difluoromethoxy-1-methyl-[1H]-pyrazol-3-yl)-5-fluoro-2-oxo-[2H]-pyridin-1-yl)-propionaldehyde (Compd. No. 1.294)

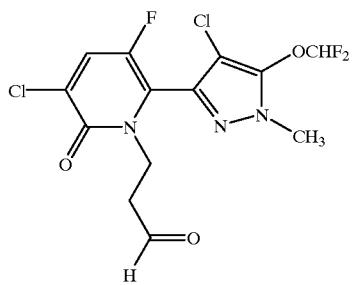

0.40 g of 3-chloro-6-(4-chloro-5-difluoromethoxy-1-methyl-[1H]-pyrazol-3-yl)-1-(2-[1.3]-dioxolan-2-ylethyl)-5-fluoro-[1H]-pyridin-2-one is stirred overnight at 22° C. in a mixture of 6 ml of 2N hydrochloric acid and 6 ml of diethyl ether. The next day, the same amount of the mixture together with 2 ml of tetrahydrofuran are added and the mixture is again stirred overnight. The mixture is subsequently diluted with diethyl ether and washed three times with brine, dried over sodium sulfate, filtered and concentrated to dryness in vacuo. 0.23 g of the desired compound (crude) is obtained in the form of a yellow oil.

$^1$H-NMR (CDCl$_3$): 9.73 ppm (s, 1H); 7.61 ppm (d, 1H); 6.73 ppm (t, 1H); 4.15 ppm (broad signal, 2H); 3.85 ppm (s, 3H); 2.98 ppm (t, 2H).

Example P56
2-(3-Chloro-6-(4-chloro-5-difluoromethoxy-1-methyl-[1H]-pyrazol-3-yl)-5-fluoropyridin-2-yloxy)-acetamide

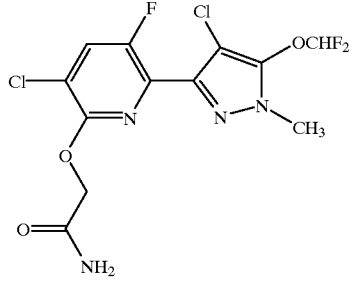

20.0 g of 3-chloro-6-(4-chloro-5-difluoromethoxy-1-methyl-[1H]-pyrazol-3-yl)-5-fluoropyridin-2-ol (Example P27) are placed together with 18.9 g of potassium carbonate and 6.4 g of chloroacetamide at 22° C. and the mixture is stirred overnight at 50° C. The next day, the mixture is cooled to 22° C. and then introduced into 2 liters of ice-water. After subsequently stirring for 10 minutes at 22° C., the resulting slurry is filtered. The filtration residue is washed with cold water and then dried in vacuo at 60° C. 20.2 g of the desired title compound are obtained in the form of a white solid having a melting point of 178–180° C.

Example P57
3-Chloro-6-(4-chloro-5-difluoromethoxy-1-methyl-[1H]-pyrazol-3-yl)-5-fluoropyridin-2-ylamine

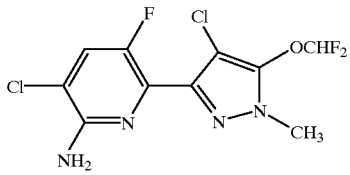

7.1 g of potassium carbonate are introduced into 200 ml of dry N-methylpyrrolidone (NMP) and the mixture is heated to a temperature of 150° C. With stirring, 19.6 g of 2-(3-chloro-6-(4-chloro-5-difluoromethoxy-1-methyl-[1H]-pyrazol-3-yl)-5-fluoropyridin-2-yloxy)-acetamide (Example P56) are introduced in portions in the course of 2 hours and then the mixture is stirred for 10 hours at 150° C., subsequently cooled to 22° C. and partitioned between diethyl ether and water. After extraction by shaking, and separation of the phases, the ethereal phase is washed with brine, dried over sodium sulfate, filtered and concentrated together with twice the amount of silica gel. The silica gel is applied to a flash chromatography column and then elution is carried out with a n-hexane/ethyl acetate 111 (v/v) mixture. 9.3 g of the desired title compound having a melting point of 100–101° C. are obtained.

The $R_f$ value of the starting material on silica gel 60 $F_{254}$ (eluant: n-hexane/ethyl acetate 1/1 (v/v)) is 0.14 and the $R_f$ value of the target compound is 0.43.

Example P58
8-Chloro-5-(4-chloro-5-difluoromethoxy-1-methyl-[1H]-pyrazol-3-yl)-6-fluoro-imidazo[1,2-a]pyridine-2-carboxylic Acid Ethyl Ester (Compd. No. 72.133)

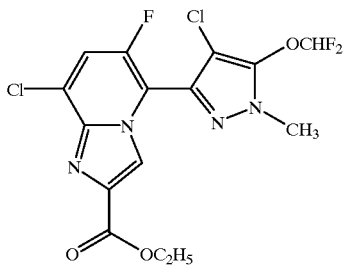

1.96 g of 3-chloro-6-(4-chloro-5-difluoromethoxy-1-methyl-[1H]-pyrazol-3-yl)-S-fluoropyridin-2-ylamine (Example P57) are placed together with 1.25 ml of bromopyruvic acid ethyl ester (90%) in 20 ml of absolute ethanol. The mixture is stirred for 6 hours at 90° C. and cooled to 22° C. and concentrated to dryness in vacuo. The residue is crystallised by the addition of diethyl ether and stirred, and n-hexane is added until precipitation is complete. The crystal fraction is filtered off, washed with n-hexane and dried in vacuo. 2.52 g of a yellowish-brown solid are obtained, which is dissolved in ethyl acetate and washed with dilute sodium hydrogen carbonate solution and then with brine. The organic phase is dried over sodium sulfate and then filtered and concentrated to dryness in vacuo. The residue obtained is digested in n-hexane, filtered, washed and dried. 1.88 g of the title compound are obtained in the form of a beige solid having a melting point of 140–143° C.

Example P59
8-Chloro-5-(4-chloro-5-difluoromethoxy-1-methyl-[1H]-pyrazol-3-yl)-6fluoro-imidazo[1,2-a]pyridine-2-carboxylic Acid (Compd. No. 72.113)

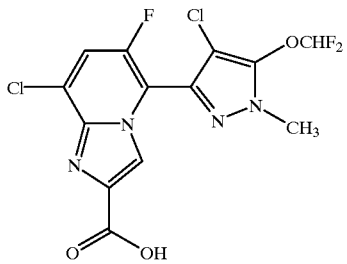

0.51 g of 8-chloro-5-(4-chloro-5-difluoromethoxy-1-methyl-[1H]-pyrazol-3-yl)-6-fluoro-imidazo[1,2-a]pyridine-2-carboxylic acid ethyl ester (Example P58) is dissolved in 3 ml of dimethyl sulfoxide and, with cooling in an ice-bath, 0.63 ml of a 2N aqueous sodium hydroxide solution is added. The mixture is then stirred for 1 hour at 22° C. Because the TLC analysis of a worked-up sample indicates that starting material is still present, a further 0.1 ml of 2N sodium hydroxide solution is added. After subsequently stirring for 30 minutes, the mixture is rendered strongly acidic with dilute hydrochloric acid, the resulting slurry is filtered, and the filtration residue is subsequently washed with cold water and dried in vacuo at 50° C. 0.35 g of the desired title compound is obtained in the form of a white solid (crude product).

Example P60
8-Chloro-5-(4-chloro-5-difluoromethoxy-1-methyl-[1H]-pyrazol-3-yl)-6-fluoro-imidazo[1,2-a]pyridin-2-yl)methanol (Compd. No. 72.083)

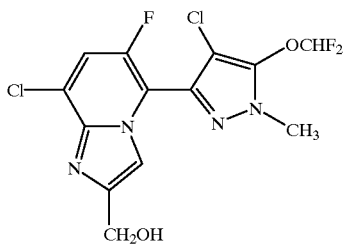

0.56 g of 8-chloro-5-(4-chloro-5-difluoromethoxy-1-methyl-[1H]-pyrazol-3-yl)-6-fluoro- imidazo[1,2-a]pyridine-2-carboxylic acid ethyl ester (Example P58) is introduced at 22° C. into 5 ml of diethyl ether and then treated with a total of 0.18 g of lithium aluminium hydride in portions with stirring. The resulting reddish-brown suspension is subsequently stirred for 1 hour and then first an excess of ethyl acetate and then dilute hydrochloric acid are added dropwise. The separated organic phase is washed with brine, filtered and concentrated to dryness in vacuo. 0.14 g of a yellowish-brown oil is obtained, which is purified over silica gel using ethyl acetate as eluant. 0.40 g of the desired compound is obtained in the form of a beige solid having a melting point of 152–153° C.

The preferred compounds listed in the following Tables can also be prepared in an analogous manner, and according to methods such as are illustrated in the general Reaction Schemes 1–3 and in the references quoted.

Table 1:

A preferred group of compounds of formula I corresponds to the general formula

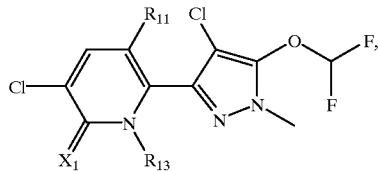

(I₁)

in which the sets of correlated substituents $R_{11}$, $X_1$ and $R_{13}$ are given in Table A, thus disclosing 654 specific compounds of formula $I_1$.

Table 2:

Another preferred group of compounds of formula I corresponds to the general formula

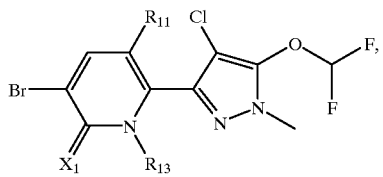

(I₂)

in which the sets of correlated substituents $R_{11}$, $X_1$ and $R_{13}$ are given in Table A, thus disclosing 654 specific compounds of formula $I_2$.

Table 3:

Another preferred group of compounds of formula I corresponds to the general formula

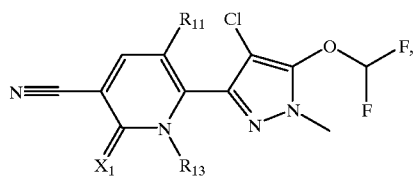

(I₃)

in which the sets of correlated substituents $R_{11}$, $X_1$ and $R_{13}$ are given in Table A, thus disclosing 654 specific compounds of formula $I_3$.

Table 4:

Another preferred group of compounds of formula I corresponds to the general formula

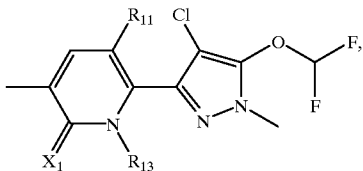

(I₄)

in which the sets of correlated substituents $R_{11}$, $X_1$ and $R_{13}$ are given in Table A, thus disclosing 654 specific compounds of formula $I_4$.

Table 5:

Another preferred group of compounds of formula I corresponds to the general formula

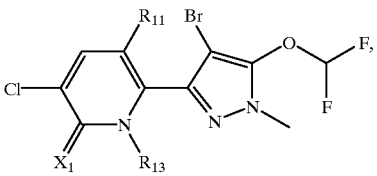

(I₅)

in which the sets of correlated substituents $R_{11}$, $X_1$ and $R_{13}$ are given in Table A, thus disclosing 654 specific compounds of formula $I_5$.

Table 6:

Another preferred group of compounds of formula I corresponds to the general formula

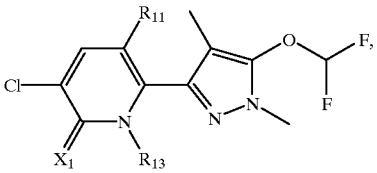

(I₆)

in which the sets of correlated substituents $R_{11}$, $X_1$ and $R_{13}$ are given in Table A, thus disclosing 654 specific compounds of formula $I_6$.

Table 7:

Another preferred group of compounds of formula I corresponds to the general formula

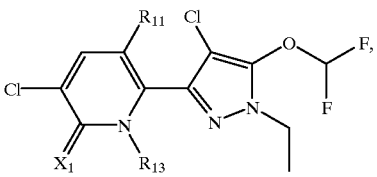

(I₇)

in which the sets of correlated substituents $R_{11}$, $X_1$ and $R_{13}$ are given in Table A, thus disclosing 654 specific compounds of formula $I_7$.

Table 8:

Another preferred group of compounds of formula I corresponds to the general formula

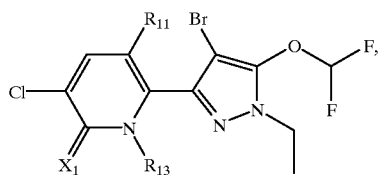

(I$_8$)

in which the sets of correlated substituents $R_{11}$, $X_1$ and $R_{13}$ are given in Table A, thus disclosing 654 specific compounds of formula $I_8$.

Table 9:

Another preferred group of compounds of formula I corresponds to the general formula

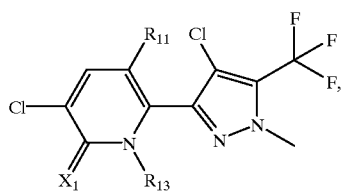

(I$_9$)

in which the sets of correlated substituents $R_{11}$, $X_1$ and $R_{13}$ are given in Table A, thus disclosing 654 specific compounds of formula $I_9$.

Table 10:

Another preferred group of compounds of formula I corresponds to the general formula

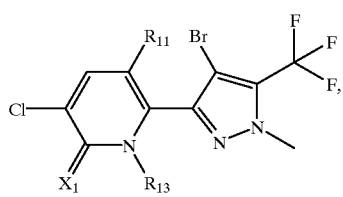

(I$_{10}$)

in which the sets of correlated substituents $R_{11}$, $X_1$ and $R_{13}$ are given in Table A, thus disclosing 654 specific compounds of formula $I_{10}$.

Table 11:

Another preferred group of compounds of formula I corresponds to the general formula

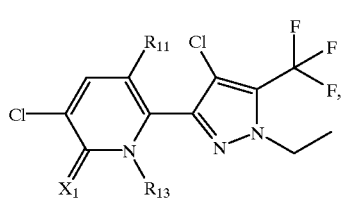

(I$_{11}$)

in which the sets of correlated substituents $R_{11}$, $X_1$ and $R_{13}$ are given in Table A, thus disclosing 654 specific compounds of formula $I_{11}$.

Table 12:

Another preferred group of compounds of formula I corresponds to the general formula

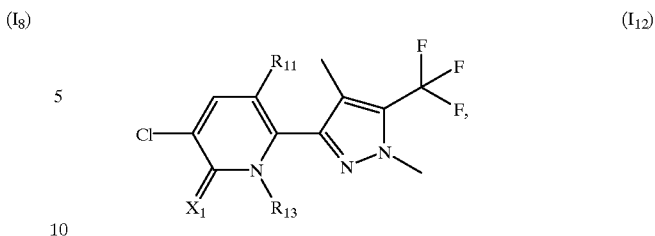

(I$_{12}$)

in which the sets of correlated substituents $R_{11}$, $X_1$ and $R_{13}$ are given in Table A, thus disclosing 654 specific compounds of formula $I_{12}$.

Table 13:

Another preferred group of compounds of formula I corresponds to the general formula

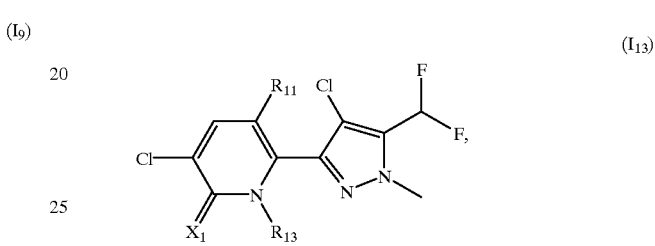

(I$_{13}$)

in which the sets of correlated substituents $R_{11}$, $X_1$ and $R_{13}$ are given in Table A, thus disclosing 654 specific compounds of formula $I_{13}$.

Table 14:

Another preferred group of compounds of formula I corresponds to the general formula

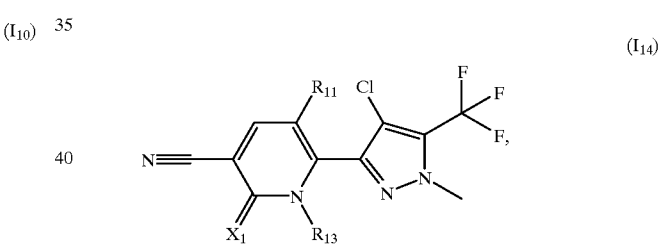

(I$_{14}$)

in which the sets of correlated substituents $R_{11}$, $X_1$ and $R_{13}$ are given in Table A, thus disclosing 654 specific compounds of formula $I_{14}$.

Table 15:

Another preferred group of compounds of formula I corresponds to the general formula

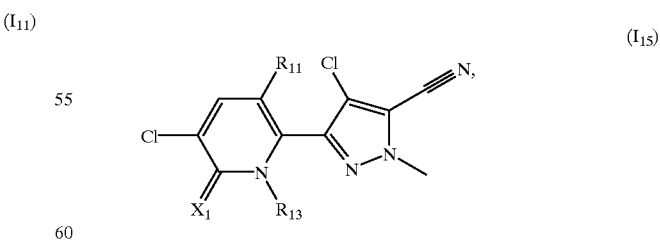

(I$_{15}$)

in which the sets of correlated substituents $R_{11}$, $X_1$ and $R_{13}$ are given in Table A, thus disclosing 654 specific compounds of formula $I_{15}$.

Table 16:

Another preferred group of compounds of formula I corresponds to the general formula

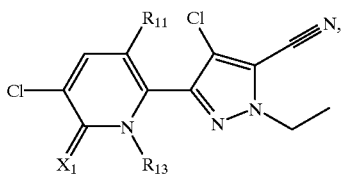
(I₁₆)

in which the sets of correlated substituents $R_{11}$, $X_1$ and $R_{13}$ are given in Table A, thus disclosing 654 specific compounds of formula $I_{16}$.

Table 17:
Another preferred group of compounds of formula I corresponds to the general formula

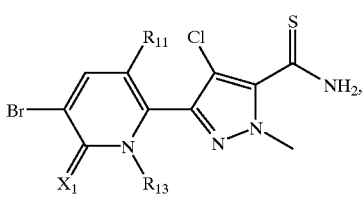
(I₁₇)

in which the sets of correlated substituents $R_{11}$, $X_1$ and $R_{13}$ are given in Table A, thus disclosing 654 specific compounds of formula $I_{17}$.

Table 18:
Another preferred group of compounds of formula I corresponds to the general formula

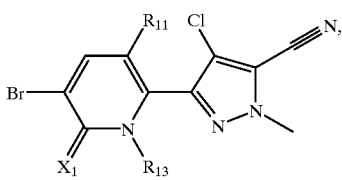
(I₁₈)

in which the sets of correlated substituents $R_{11}$, $X_1$ and $R_{13}$ are given in Table A, thus disclosing 654 specific compounds of formula $I_{18}$.

Table 19:
Another preferred group of compounds of formula I corresponds to the general formula

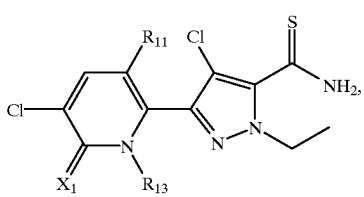
(I₁₉)

in which the sets of correlated substituents $R_{11}$, $X_1$ and $R_{13}$ are given in Table A, thus disclosing 654 specific compounds of formula $I_{19}$.

Table 20:
Another preferred group of compounds of formula I corresponds to the general formula

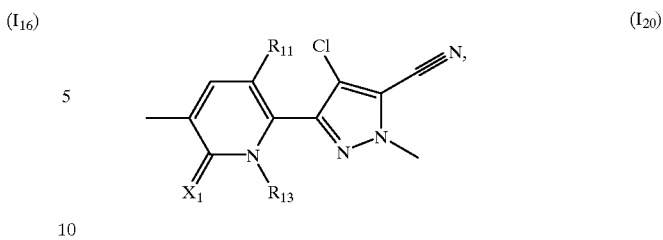
(I₂₀)

in which the sets of correlated substituents $R_{11}$, $X_1$ and $R_{13}$ are given in Table A, thus disclosing 654 specific compounds of formula $I_{20}$.

Table 21:
Another preferred group of compounds of formula I corresponds to the general formula

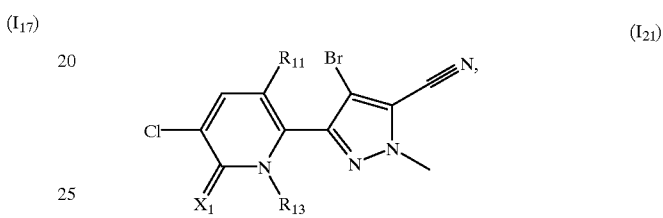
(I₂₁)

in which the sets of correlated substituents $R_{11}$, $X_1$ and $R_{13}$ are given in Table A, thus disclosing 654 specific compounds of formula $I_{21}$.

Table 22:
Another preferred group of compounds of formula I corresponds to the general formula

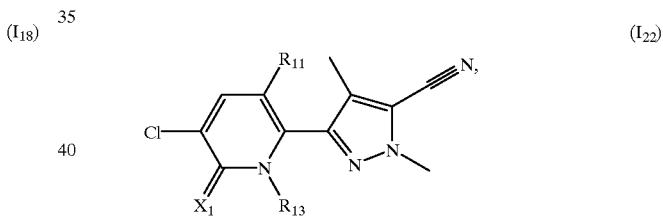
(I₂₂)

in which the sets of correlated substituents $R_{11}$, $X_1$ and $R_{13}$ are given in Table A, thus disclosing 654 specific compounds of formula $I_{22}$.

Table 23:
Another preferred group of compounds of formula I corresponds to the general formula

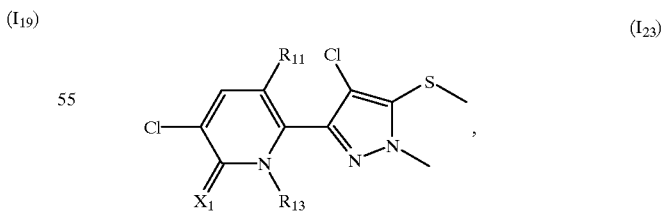
(I₂₃)

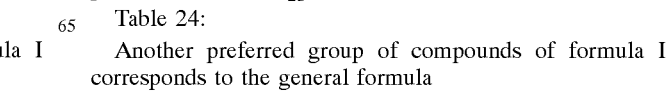

in which the sets of correlated substituents $R_{11}$, $X_1$ and $R_{13}$ are given in Table A, thus disclosing 654 specific compounds of formula $I_{23}$.

Table 24:
Another preferred group of compounds of formula I corresponds to the general formula

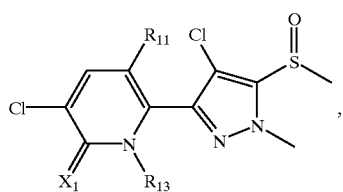

(I$_{24}$)

in which the sets of correlated substituents $R_{11}$, $X_1$ and $R_{13}$ are given in Table A, thus disclosing 654 specific compounds of formula $I_{24}$.

Table 25:

Another preferred group of compounds of formula I corresponds to the general

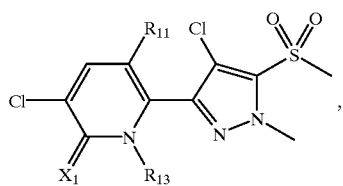

(I$_{25}$)

in which the sets of correlated substituents $R_{11}$, $X_1$ and $R_13$ are given in Table A, thus disclosing 654 specific compounds of formula $I_{25}$.

Table 26:

Another preferred group of compounds of formula I corresponds to the general

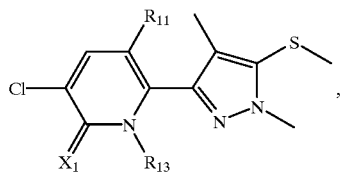

(I$_{26}$)

in which the sets of correlated substituents $R_{11}$, $X_1$ and $R_{13}$ are given in Table Ax thus disclosing 654 specific compounds of formula $I_{26}$.

Table 27:

Another preferred group of compounds of formula i corresponds to the general formula

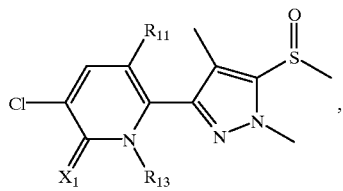

(I$_{27}$)

in which the sets of correlated substituents $R_{11}$, $X_1$ and $R_{13}$ are given in Table A, thus disclosing 654 specific compounds of formula $I_{27}$.

Table 28:

Another preferred group of compounds of formula I corresponds to the general formula

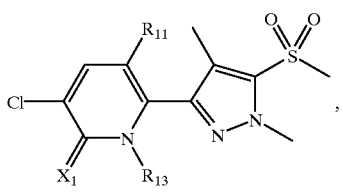

(I$_{28}$)

in which the sets of correlated substituents $R_{11}$, $X_1$ and $R_{13}$ are given in Table A, thus disclosing 654 specific compounds of formula $I_{28}$.

Table 29:

Another preferred group of compounds of formula I corresponds to the general formula

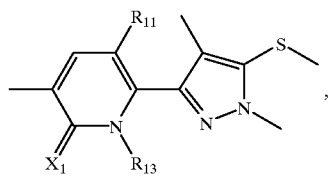

(I$_{29}$)

in which the sets of correlated substituents $R_{11}$, $X_1$ and $R_{13}$ are given in Table A, thus disclosing 654 specific compounds of formula $I_{29}$.

Table 30:

Another preferred group of compounds of formula I corresponds to the general formula

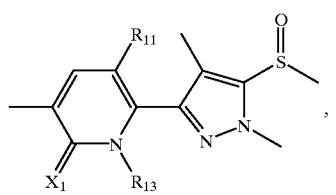

(I$_{30}$)

in which the sets of correlated substituents $R_{11}$, $X_1$ and $R_{13}$ are given in Table A, thus disclosing 654 specific compounds of formula $I_{30}$.

Table 31:

Another preferred group of compounds of formula I corresponds to the general formula

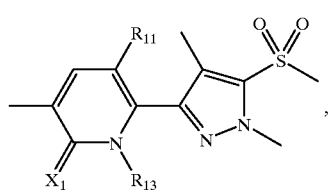

(I$_{31}$)

in which the sets of correlated substituents $R_{11}$, $X_1$ and $R_{13}$ are given in Table A, thus disclosing 654 specific compounds of formula $I_{31}$.

Table 32:

Another preferred group of compounds of formula I corresponds to the general formula

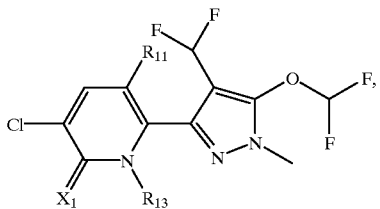

(I₃₂)

in which the sets of correlated substituents $R_{11}$, $X_1$ and $R_{13}$ are given in Table A, thus disclosing 654 specific compounds of formula $I_{32}$.

Table 33:
Another preferred group of compounds of formula I corresponds to the general formula

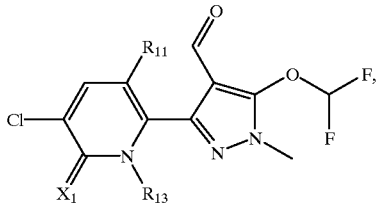

(I₃₃)

in which the sets of correlated substituents $R_{11}$, $X_1$ and $R_{13}$ are given in Table A, thus disclosing 654 specific compounds of formula $I_{33}$.

Table 34:
Another preferred group of compounds of formula I corresponds to the general formula

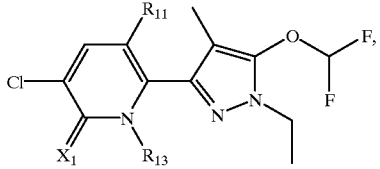

(I₃₄)

in which the sets of correlated substituents $R_{11}$, $X_1$ and $R_{13}$ are given in Table A, thus disclosing 654 specific compounds of formula $I_{34}$.

Table 35: Another preferred group of compounds of formula I corresponds to the general formula

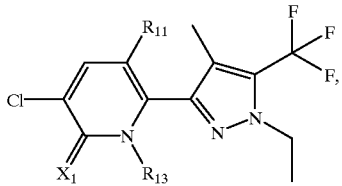

(I₃₅)

in which the sets of correlated substituents $R_{11}$, $X_1$ and $R_{13}$ are given in Table A, thus disclosing 654 specific compounds of formula $I_{35}$.

Table 36: Another preferred group of compounds of formula I corresponds to the general formula

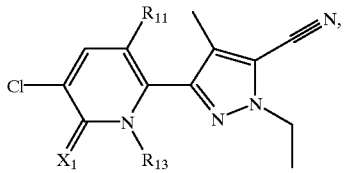

(I₃₆)

in which the sets of correlated substituents $R_{11}$, $X_1$ and $R_{13}$ are given in Table A, thus disclosing 654 specific compounds of formula $I_{36}$.

Table 37:
Another preferred group of compounds of formula I corresponds to the general formula

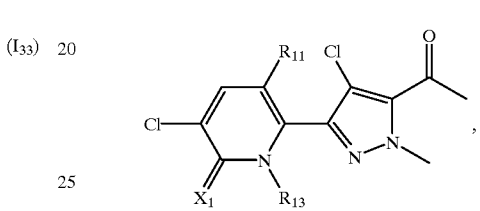

(I₃₇)

in which the sets of correlated substituents $R_{11}$, $X_1$ and $R_{13}$ are given in Table A, thus disclosing 654 specific compounds of formula $I_{37}$.

TABLE A

| Compd. No. | $R_{11}$ | $X_1$ | $R_{13}$ |
|---|---|---|---|
| .001 | H | O | $CH_3$ |
| .002 | F | O | $CH_3$ |
| .003 | Cl | O | $CH_3$ |
| .004 | F | O | $CH_2CH_3$ |
| .005 | Cl | O | $CH_2CH_3$ |
| .006 | H | O | $CH_2CH_3$ |
| .007 | F | O | $CH_2CH_2CH_3$ |
| .008 | Cl | O | $CH_2CH_2CH_3$ |
| .009 | H | O | $CH_2CH_2CH_3$ |
| .010 | F | O | $CH_2CH_2CH_2CH_3$ |
| .011 | Cl | O | $CH_2CH_2CH_2CH_3$ |
| .012 | F | O | $CH_2CH_2CH_2CH_2CH_3$ |
| .013 | Cl | O | $CH_2CH_2CH_2CH_2CH_3$ |
| .014 | F | O | $CH_2CH_2CH_2CH_2CH_2CH_3$ |
| .015 | F | O | $CH_2CH_2CH(CH_3)_2$ |
| .016 | Cl | O | $CH_2CH_2CH(CH_3)_2$ |
| .017 | H | O | $CH_2CH_2CH(CH_3)_2$ |
| .018 | F | O | $CH_2CH(CH_3)CH_2CH_3$ |
| .019 | Cl | O | $CH_2CH(CH_3)CH_2CH_3$ |
| .020 | H | O | $CH_2CH(CH_3)CH_2CH_3$ |
| .021 | F | O | $CH_2CH(CH_3)CH_2CH_2CH_3$ |
| .022 | F | O | $CH_2CH_2CH(CH_3)CH_2CH_3$ |
| .023 | F | O | $CH_2CH_2CH_2CH(CH_3)_2$ |
| .024 | F | O | $CH(CH_3)CH_2CH_2CH_2CH_3$ |
| .025 | Cl | O | $CH(CH_3)CH_2CH_2CH_2CH_3$ |
| .026 | H | O | $CH(CH_3)CH_2CH_2CH_2CH_3$ |
| .027 | F | O | $CH_2C(CH_3)_3$ |
| .028 | Cl | O | $CH_2C(CH_3)_3$ |
| .029 | H | O | $CH_2CH(CH_3)_2$ |
| .030 | Cl | O | $CH_2CH(CH_3)_2$ |
| .031 | F | O | $CH_2CH(CH_3)_2$ |
| .032 | F | O | $CH_2C(CH_3)_2CH_2CH_3$ |
| .033 | Cl | O | $CH_2C(CH_3)_2CH_2CH_3$ |
| .034 | H | O | $CH_2C(CH_3)_2CH_2CH_3$ |
| .035 | F | O | $CH_2CH_2C(CH_3)_3$ |
| .036 | Cl | O | $CH_2CH_2C(CH_3)_3$ |
| .037 | F | O | $CH_2CH_2CHCH_2$ |
| .038 | Cl | O | $CH_2CH_2CHCH_2$ |

TABLE A-continued

| Compd. No. | $R_{11}$ | $X_1$ | $R_{13}$ |
|---|---|---|---|
| .039 | H | O | $CH_2CH_2CHCH_2$ |
| .040 | F | O | $CH_2CH_2CH_2CHCH_2$ |
| .041 | Cl | O | $CH_2CH_2CH_2CHCH_2$ |
| .042 | H | O | $CH_2CH_2CH_2CHCH_2$ |
| .043 | F | O | $CH_2CH_2CH_2CH_3$ |
| .044 | F | O | $CH(CH_3)_2$ |
| .045 | F | O | $CH_2CF_3$ |
| .046 | Cl | O | $CH_2CF_3$ |
| .047 | H | O | $CH_2CF_3$ |
| .048 | F | O | $CH_2CHF_2$ |
| .049 | Cl | O | $CH_2CHF_2$ |
| .050 | F | O | $CH_2CH_2CF_3$ |
| .051 | Cl | O | $CH_2CH_2CF_3$ |
| .052 | F | O | $CH_2CCl_3$ |
| .053 | F | O | $CH_2CH_2CF_3$ |
| .054 | Cl | O | $CH_2CH_2CF_3$ |
| .055 | F | O | $CH_2CH_2CHF_2$ |
| .056 | Cl | O | $CH_2CH_2CHF_2$ |
| .057 | H | O | $CH_2CH_2CHF_2$ |
| .058 | F | O | $CH_2CH(OH)CH_3$ |
| .059 | F | O | $CH_2CH(OH)CH_2CH_3$ |
| .060 | Cl | O | $CH_2CH(OH)CH_2CH_3$ |
| .061 | F | Cl | $CH_2CH(OH)CH_3$ |
| .062 | H | O | $CH_2CH_2CHClCH_3$ |
| .063 | Cl | O | $CH_2CH_2CHClCH_3$ |
| .064 | F | O | $CH_2CH_2CHClCH_3$ |
| .065 | F | O | $CH_2CH_2CHFCH_3$ |
| .066 | F | O | $CH_2CHFCH_2CH_3$ |
| .067 | Cl | O | $CH_2CHFCH_2CH_3$ |
| .068 | H | O | $CH_2CHFCH_2CH_3$ |
| .069 | F | O | $CH_2CHClCH_2CH_3$ |
| .070 | F | O | $CH_2CH_2F$ |
| .071 | Cl | O | $CH_2CH_2F$ |
| .072 | F | O | $CH_2CH_2Cl$ |
| .073 | F | O | $CH_2CH_2Br$ |
| .074 | Cl | O | $CH_2CH_2Cl$ |
| .075 | H | O | $CH_2CH_2Cl$ |
| .076 | F | O | $CH_2CHF_2$ |
| .077 | F | O | $CH_2CHBr_2$ |
| .078 | H | O | $CH_2CHCH_2$ |
| .079 | Cl | O | $CH_2CHCH_2$ |
| .080 | F | O | $CH_2CHCH_2$ |
| .081 | F | O | $CH_2CH(CH_3)CH_2$ |
| .082 | F | O | $CH_2CHCH(CH_3)$ |
| .083 | F | O | $CH_2CHCH(Cl)$ (E-form) |
| .084 | Cl | O | $CH_2CHCH(Cl)$ (E-form) |
| .085 | H | O | $CH_2CHCH(Cl)$ (E-form) |
| .086 | F | O | $CH_2CHCH(Cl)$ (Z-form) |
| .087 | Cl | O | $CH_2CHCH(Cl)$ (Z-form) |
| .088 | H | O | $CH_2CH_2OH$ |
| .089 | Cl | O | $CH_2CH_2OH$ |
| .090 | F | O | $CH_2CH_2OH$ |
| .091 | F | O | $CH_2CH_2CH_2OH$ |
| .092 | Cl | O | $CH_2CH_2CH_2OH$ |
| .093 | F | O | $CH_2CH(OH)CH_3$ |
| .094 | Cl | O | $CH_2CH(OH)CH_3$ |
| .095 | F | O | $CH_2CHCHCl$ |
| .096 | Cl | O | $CH_2CHCHCl$ |
| .097 | H | O | $CH_2CHCHCl$ |
| .098 | H | O | $CH_2CCH$ |
| .099 | Cl | O | $CH_2CCH$ |
| .100 | F | O | $CH_2CCH$ |
| .101 | F | O | $CH_2CH(CH_3)CCH$ |
| .102 | Cl | O | $CH_2CH_2CCH$ |
| .103 | F | O | $CH_2CH_2CCH$ |
| .104 | Cl | O | $CH_2CH_2C_6H_5$ |
| .105 | F | O | $CH_2CH_2C_6H_5$ |
| .106 | F | O | $CH_2CH_2CH_2C_6H_5$ |
| .107 | F | O | $CH_2CH_2CH(CH_3)C_6H_5$ |
| .108 | F | O | $CH_2CH_2CH_2CH_2(p\text{-}F\text{—}C_6H_4)$ |
| .109 | H | O | $CH_2C_6H_5$ |
| .110 | Cl | O | $CH_2C_6H_5$ |
| .111 | F | O | $CH_2C_6H_5$ |
| .112 | F | O | $CH_2(o\text{-}F\text{—}C_6H_4)$ |
| .113 | H | O | $CH_2(p\text{-}Cl\text{—}C_6H_4)$ |
| .114 | F | O | $CH_2(m\text{-}CF_3\text{—}C_6H_4)$ |
| .115 | F | O | $CH_2(3,4\text{-di-}Cl\text{—}C_6H_3)$ |
| .116 | F | O | $CH_2(3,5\text{-di-}CH_3\text{—}C_6H_3)$ |
| .117 | F | O | $CH_2CH_2(2,6\text{-di-}F\text{—}C_6H_3)$ |
| .118 | Cl | O | $CH_2CH_2(2,6\text{-di-}F\text{—}C_6H_3)$ |
| .119 | H | O | $CH_2CH_2(2,6\text{-di-}F\text{—}C_6H_3)$ |
| .120 | F | O | $CH_2CH_2CH_2(4\text{-}F\text{—}C_6H_4)$ |
| .121 | Cl | O | $CH_2CH_2CH_2(4\text{-}F\text{—}C_6H_4)$ |
| .122 | F | O | $CH_2CH_2CH(CH_3)(4\text{-}CH_3\text{—}C_6H_4)$ |
| .123 | Cl | O | $CH_2CH_2CH(CH_3)(4\text{-}CH_3\text{—}C_6H_4)$ |
| .124 | H | O | $CH_2CN$ |
| .125 | Cl | O | $CH_2CN$ |
| .126 | F | O | $CH_2CN$ |
| .127 | F | O | $CH_2CHFCN$ |
| .128 | F | O | cyclopropyl |
| .129 | F | O | cyclopentyl |
| .130 | F | O | $CH_2$-cyclopentyl |
| .131 | F | O | $CH_2$-cyclopropyl |
| .132 | F | O | $CH_2CH_2Cl$ |
| .133 | F | O | $CH_2CHCl_2$ |
| .134 | H | O | $CH_2OCH_3$ |
| .135 | Cl | O | $CH_2OCH_3$ |
| .136 | F | O | $CH_2OCH_3$ |
| .137 | F | O | $CH_2CH_2OCH_3$ |
| .138 | Cl | O | $CH_2CH_2OCH_3$ |
| .139 | H | O | $CH_2CH_2OCH_3$ |
| .140 | F | O | $CH_2CH_2OCH_2CH_3$ |
| .141 | F | O | $CH_2CH(CH_3)OCH_3$ |
| .142 | H | O | $CH_2CH_2OCH_2CH_2OCH_3$ |
| .143 | Cl | O | $CH_2CH_2OCH_2CH_2OCH_3$ |
| .144 | F | O | $CH_2CH_2OCH_2CH_2OCH_3$ |
| .145 | H | O | $CH_2SCH_3$ |
| .146 | Cl | O | $CH_2SCH_3$ |
| .147 | F | O | $CH_2SCH_3$ |
| .148 | H | O | $CH_2S(O)CH_3$ |
| .149 | Cl | O | $CH_2S(O)CH_3$ |
| .150 | F | O | $CH_2S(O)CH_3$ |
| .151 | H | O | $CH_2S(O)_2CH_3$ |
| .152 | Cl | O | $CH_2S(O)_2CH_3$ |
| .153 | F | O | $CH_2S(O)_2CH_3$ |
| .154 | F | O | $CH_2SCH_2CH_3$ |
| .155 | F | O | $CH_2CH_2SCH_3$ |
| .156 | F | O | $CH_2CH_2SCH_2CH_3$ |
| .157 | Cl | O | $CH_2CH_2SCH_2CH_3$ |
| .158 | H | O | $CH_2CH_2SCH_2CH_3$ |
| .159 | Cl | O | $CH_2CH_2SCH_3$ |
| .160 | H | O | $CH_2CH_2SCH_3$ |
| .161 | F | O | $CH_2CH_2S(O)CH_3$ |
| .162 | F | O | $CH_2CH_2S(O)_2CH_3$ |
| .163 | Cl | O | $CH_2CH_2S(O)CH_3$ |
| .164 | Cl | O | $CH_2CH_2S(O)_2CH_3$ |
| .165 | F | O | $CH_2CH_2S(O)CH_2CH_3$ |
| .166 | Cl | O | $CH_2CH_2S(O)CH_2CH_3$ |
| .167 | H | O | $CH_2CH_2S(O)CH_2CH_3$ |
| .168 | F | O | $CH_2CH_2S(O)_2CH_2CH_3$ |
| .169 | Cl | O | $CH_2CH_2S(O)_2CH_2CH_3$ |
| .170 | H | O | $CH_2CH_2S(O)_2CH_2CH_3$ |
| .171 | F | O | $CH_2CH_2CH_2SCH_3$ |
| .172 | F | O | $CH_2CH_2CH_2S(O)CH_3$ |
| .173 | F | O | $CH_2CH_2CH_2S(O)_2CH_3$ |
| .174 | F | O | $CH_2CH(CH_3)SCH_3$ |
| .175 | H | O | $CH_2COOH$ |
| .176 | Cl | O | $CH_2COOH$ |
| .177 | F | O | $CH_2COOH$ |
| .178 | F | O | $CH_2COOCH_3$ |
| .179 | H | O | $CH_2COOCH_2CH_3$ |
| .180 | Cl | O | $CH_2COOCH_2CH_3$ |
| .181 | F | O | $CH_2COOCH_2CH_3$ |
| .182 | F | O | $CH_2COOCH(CH_3)_2$ |
| .183 | Cl | O | $CH_2COOCH(CH_3)_2$ |
| .184 | H | O | $CH_2COOCH(CH_3)_2$ |
| .185 | F | O | $CH_2COOCH(CH_3)_2$ |
| .186 | Cl | O | $CH_2CCOCH(CH_3)CH_2CH_3$ |
| .187 | F | O | $CH_2COOCH_2CH_3$ |
| .188 | F | O | $CH_2COOCH_2CH_2CH_3$ |
| .189 | F | O | $CH_2COOCH_2CH(CH_3)_2$ |
| .190 | F | O | $CH_2COOC(CH_3)_3$ |

TABLE A-continued

| Compd. No. | $R_{11}$ | $X_1$ | $R_{13}$ |
|---|---|---|---|
| .191 | F | O | $CH_2COOCH_2CHCH_2$ |
| .192 | F | O | $CH_2COOCH_2CCH$ |
| .193 | Cl | O | $CH_2COOCH_2CCH$ |
| .194 | H | O | $CH_2COOCH_2CCH$ |
| .195 | F | O | $CH_2COOCH_2C_6H_5$ |
| .196 | F | O | $CH_2COOCH_2(o\text{-}F\text{—}C_6H_4)$ |
| .197 | F | O | $CH_2COOCH_2(p\text{-}Cl\text{—}C_6H_4)$ |
| .198 | F | O | $CH_2COOCH_2(m\text{-}CH_3\text{—}C_6H_4)$ |
| .199 | F | O | $CH_2COOCH_2(2,4\text{-}di\text{-}CH_3\text{—}C_6H_3)$ |
| .200 | Cl | O | $CH_2COOCH_2(2,4\text{-}di\text{-}CH_3\text{—}C_6H_3)$ |
| .201 | F | O | $CH_2CH_2COOCH_2(3,4\text{-}di\text{-}Cl\text{—}C_6H_3)$ |
| .202 | F | O | $CH_2CH_2CH_2COOH$ |
| .203 | Cl | O | $CH_2CH_2CH_2COOH$ |
| .204 | F | O | $CH_2CH_2CH_2CCOCH_3$ |
| .205 | F | O | $CH_2CH_2CH_2COOCH_2CH_3$ |
| .206 | Cl | O | $CH_2CH_2CH_2COOCH_2CH_3$ |
| .207 | F | O | $CH_2CH_2CH_2CH_2COOH$ |
| .208 | F | O | $CH_2CH_2CH_2CH_2COOCH_3$ |
| .209 | Cl | O | $CH_2CH_2CH_2CH_2COOCH_3$ |
| .210 | H | O | $CH_2CH_2CH_2CH_2COOCH_3$ |
| .211 | H | O | $CH_2CHO$ |
| .212 | Cl | O | $CH_2CHO$ |
| .213 | F | O | $CH_2CHO$ |
| .214 | H | O | $CH_2C(O)CH_3$ |
| .215 | Cl | O | $CH_2C(O)CH_3$ |
| .216 | F | O | $CH_2C(O)CH_3$ |
| .217 | F | O | $CH_2C(O)SCH_3$ |
| .218 | Cl | O | $CH_2C(O)SCH_3$ |
| .219 | F | O | $CH_2C(O)SCH_2CH_2CH_3$ |
| .220 | Cl | O | $CH_2C(O)SCH_2CH_2CH_3$ |
| .221 | F | O | $CH_2C(O)SCH_2CHCH_2$ |
| .222 | Cl | O | $CH_2C(O)SCH_2CHCH_2$ |
| .223 | F | O | $CH_2COSCH_2CH_3$ |
| .224 | H | O | $CH_2COSCH(CH_3)_2$ |
| .225 | Cl | O | $CH_2COSCH(CH_3)_2$ |
| .226 | F | O | $CH_2COSCH(CH_3)_2$ |
| .227 | F | O | $CH_2COSCH_2C_6H_5$ |
| .228 | Cl | O | $CH_2COSCH_2C_6H_5$ |
| .229 | H | O | $CH_2COSCH_2C_6H_5$ |
| .230 | F | O | $CH_2CONH_2$ |
| .231 | F | O | $CH_2CONH(CH_3)$ |
| .232 | F | O | $CH_2CON(CH_3)_2$ |
| .233 | Cl | O | $CH_2CON(CH_3)_2$ |
| .234 | F | O | $CH_2CON(CH_2CH_3)_2$ |
| .235 | Cl | O | $CH_2CON(CH_2CH_3)_2$ |
| .236 | H | O | $CH_2CON(CH_2CH_3)_2$ |
| .237 | F | O | $CH_2CON(CH_2CH_3)(CH_3)$ |
| .238 | F | O | $CH_2CON(CH_2CH_2CH_3)_2$ |
| .239 | Cl | O | $CH_2CON(CH_2CH_2CH_3)_2$ |
| .240 | H | O | $CH_2CONH(CH_2CH_3)$ |
| .241 | F | O | $CH_2CONH(CH_2CH_3)$ |
| .242 | H | O | $CH_2CONHCH_2CHCH_2$ |
| .243 | Cl | O | $CH_2CONHCH_2CHCH_2$ |
| .244 | F | O | $CH_2CONHCH_2CHCH_2$ |
| .245 | H | O | $CH_2CONHCH_2CCH$ |
| .246 | Cl | O | $CH_2CONHCH_2CCH$ |
| .247 | F | O | $CH_2CONHCH_2CCH$ |
| .248 | F | O | $CH_2CONHC_6H_5$ |
| .249 | Cl | O | $CH_2CONHC_6H_5$ |
| .250 | F | O | $CH_2CONH(3,4\text{-}di\text{-}Cl\text{—}C_6H_3)$ |
| .251 | F | O | $CH_2CON(CH_3)(C_6H_5)$ |
| .252 | Cl | O | $CH_2CON(CH_3)(C_6H_5)$ |
| .253 | F | O | $CH_2CONH(o\text{-}F\text{—}C_6H_4)$ |
| .254 | F | O | $CH_2CONHCH_2(C_6H_6)$ |
| .255 | Cl | O | $CH_2CONHCH_2(C_6H_5)$ |
| .256 | H | O | $CH_2CONHCH_2(C_6H_5)$ |
| .257 | F | O | $CH_2CON(CH_3)CH_2(C_6H_5)$ |
| .258 | F | O | $CH_2CONH(3,4\text{-}di\text{-}Cl\text{—}C_6H_3)$ |
| .259 | Cl | O | $CH_2CONH(3,4\text{-}di\text{-}Cl\text{—}C_6H_3)$ |
| .260 | F | O | $CH_2CONHCH_2(4\text{-}Cl\text{—}C_5H_4)$ |
| .261 | Cl | O | $CH_2CONHCH_2(4\text{-}Cl\text{—}C_6H_4)$ |
| .262 | F | O | $CH_2CON(CH_3)CH_2(4\text{-}Cl\text{—}C_6H_4)$ |
| .263 | F | O | $CH_2CON(CH_2CH_3)CH_2(4\text{-}Cl\text{—}C_6H_4)$ |
| .264 | Cl | O | $CH_2CON(CH_2CH_3)CH_2(4\text{-}Cl\text{—}C_6H_4)$ |
| .265 | F | O | $CH_2CON(CH_2CHCH_2)CH_2(4\text{-}Cl\text{—}C_6H_4)$ |
| .266 | Cl | O | $CH_2CON(CH_2CHCH_2)CH_2(4\text{-}Cl\text{—}C_6H_4)$ |
| .267 | H | O | $CH_2CH_2COOH$ |
| .268 | Cl | O | $CH_2CH_2COOH$ |
| .269 | F | O | $CH_2CH_2COOH$ |
| .270 | F | O | $CH_2CH_2COOCH_2CH_3$ |
| .271 | Cl | O | $CH_2CH_2COOCH_2CH_3$ |
| .272 | H | O | $CH_2CH_2COOCH_2CH_3$ |
| .273 | F | O | $CH_2CH_2COOCH_2CHCH_2$ |
| .274 | Cl | O | $CH_2CH_2COOCH_2CHCH_2$ |
| .275 | F | O | $CH_2CH_2COOCH_2(C_6H_5)$ |
| .276 | F | O | $CH_2CH_2COOCH(CH_3)_2$ |
| .277 | Cl | O | $CH_2CH_2COOCH(CH_3)_2$ |
| .278 | H | O | $CH_2CH_2CN$ |
| .279 | Cl | O | $CH_2CH_2CN$ |
| .280 | F | O | $CH_2CH_2CN$ |
| .281 | F | O | $CH_2CH(CH_3)CN$ |
| .282 | Cl | O | $CH_2CH(CH_3)CN$ |
| .283 | H | O | $CH_2CH(CH_3)CN$ |
| .284 | F | O | $CH_2CH(Cl)CN$ |
| .285 | Cl | O | $CH_2CH(Cl)CN$ |
| .286 | F | O | $CH_2CH_2CH_2CN$ |
| .287 | Cl | O | $CH_2CH_2CH_2CN$ |
| .288 | F | O | $CH_2CH_2CH(CH_3)CN$ |
| .289 | F | O | $CH_2CH(CH_3)CH_2CN$ |
| .290 | Cl | O | $CH_2CH(CH_3)CHO$ |
| .291 | Cl | O | $CH(CH_3)CH_2CN$ |
| .292 | H | O | $CH_2CH_2CHO$ |
| .293 | Cl | O | $CH_2CH_2CHO$ |
| .294 | F | O | $CH_2CH_2CHO$ |
| .295 | F | O | $CH_2CH(Cl)CHO$ |
| .296 | Cl | O | $CH_2CH(Cl)CHO$ |
| .297 | F | O | $CH_2CH(CH_3)CHO$ |
| .298 | Cl | O | $CH_2CH(CH_3)CHO$ |
| .299 | H | O | $CH_2CH(CH_3)CHO$ |
| .300 | F | O | $CH_2CH_2C(O)CH_3$ |
| .301 | Cl | O | $CH_2CH_2C(O)CH_3$ |
| .302 | F | O | $CH_2COCH_2CH_3$ |
| .303 | Cl | O | $CH_2COCH_2CH_3$ |
| .304 | H | O | $CH_2COCH_2CH_3$ |
| .305 | F | O | $CH_2COCH_2CH_2CH_3$ |
| .306 | F | O | $CH_2CH_2COCH_2CH_3$ |
| .307 | F | O | $CH_2CH_2COCH_2CH_3$ |
| .308 | F | O | $CH_2CH(CH_3)COOH$ |
| .309 | Cl | O | $CH_2CH(CH_3)COOH$ |
| .310 | H | O | $CH_2CH(CH_3)COOH$ |
| .311 | F | O | $CH_2CH(CH_3)COOCH_3$ |
| .312 | F | O | $CH_2CH(CH_3)COOCH_2CH_3$ |
| .313 | Cl | O | $CH_2CH(CH_3)COOCH_2CH_3$ |
| .314 | F | O | $CH_2CH_2CH_2COOH$ |
| .315 | Cl | O | $CH_2CH_2CH_2COOH$ |
| .316 | Cl | O | $CH_2CH_2CH_2COOCH_3$ |
| .317 | F | O | $CH_2CH_2CH_2COOCH_3$ |
| .318 | F | O | $CH_2CH_2CH_2COSCH_2CH_3$ |
| .319 | F | O | $CH_2CH_2CH_2CONHCH_2CCH$ |
| .320 | F | O | $CH_2CH_2CH_2CON(CH_3)(CH_2CCH)$ |
| .321 | F | O | $CH_2CH_2CH_2CON(CH_3)_2$ |
| .322 | F | O | $CH_2CH_2CH(CH_3)COOCH_2CH_3$ |
| .323 | H | O | $CH_2CH(OH)COOH$ |
| .324 | Cl | O | $CH_2CH(OH)COOH$ |
| .325 | F | O | $CH_2CH(OH)COOH$ |
| .326 | H | O | $CH_2CH(Cl)COOH$ |
| .327 | Cl | O | $CH_2CH(Cl)COOH$ |
| .328 | F | O | $CH_2CH(Cl)COOH$ |
| .329 | Cl | O | $CH_2CH(Cl)COOCH_2CH_3$ |
| .330 | F | O | $CH_2CH(Cl)COOCH_2CH_3$ |
| .331 | F | O | $CH_2CH(Cl)COOCH_2(4\text{-}Cl\text{—}C_6H_4)$ |
| .332 | F | O | $CH_2CH(Cl)COOCH_2CHCH_2$ |
| .333 | Cl | O | $CH_2CH(Cl)COOCH_2CHCH_2$ |
| .334 | F | O | $CH_2CH(Cl)COOC(CH_3)_3$ |
| .335 | Cl | O | $CH_2CH(Cl)COOC(CH_3)_3$ |
| .336 | F | O | $CH_2CH(Cl)COOCH_2CH_2CH_3$ |
| .337 | F | O | $CH_2C(CH_3)(Cl)COOH$ |
| .338 | Cl | O | $CH_2C(CH_3)(Cl)COOH$ |
| .339 | H | O | $CH_2C(CH_3)(Cl)COOH$ |
| .340 | F | O | $CH_2CH(Cl)COOCH_2CHCH_2$ |
| .341 | Cl | O | $CH_2CH(Cl)COOCH_2CHCH_2$ |
| .342 | H | O | $CH_2CH(Cl)COOCH_2CHCH_2$ |

TABLE A-continued

| Compd. No. | $R_{11}$ | $X_1$ | $R_{13}$ |
|---|---|---|---|
| .343 | F | O | $CH_2CH(Cl)COOCH_2CCH$ |
| .344 | F | O | $CH_2CH(Cl)COOCH_2C_6H_5$ |
| .345 | F | O | $CH_2CH(Br)COOH$ |
| .346 | Cl | O | $CH_2CH(Br)COOH$ |
| .347 | H | O | $CH_2CH(Br)COOH$ |
| .348 | F | O | $CH_2CH(Br)COOCH_3$ |
| .349 | Cl | O | $CH_2CH(Br)COOCH_3$ |
| .350 | F | O | $CH_2CH(Br)COOCH_2CH_3$ |
| .351 | F | O | $CH_2CH(Br)COOCH_2CHCH_2$ |
| .352 | Cl | O | $CH_2CH(Br)COOCH_2CHCH_2$ |
| .353 | F | O | $CH_2CH(Br)COOCH_2CCH$ |
| .354 | Cl | O | $CH_2CH(Br)COOCH_2CCH$ |
| .355 | F | O | $CH_2CHBrCOOC(CH_3)_3$ |
| .356 | Cl | O | $CH_2CHBrCOOC(CH_3)_3$ |
| .357 | F | O | $CH_2CH(Cl)C(O)SCH(CH_3)_2$ |
| .358 | F | O | $CH_2CH(Cl)C(O)NH_2$ |
| .359 | Cl | O | $CH_2CH(Cl)C(O)NH_2$ |
| .360 | F | O | $CH_2CH(Cl)C(O)NH(CH_2CCH)$ |
| .361 | Cl | O | $CH_2CH(Cl)C(O)NH(CH_2CCH)$ |
| .362 | F | O | $CH_2CH(Cl)C(O)NH(CH_2CHCH_2)$ |
| .363 | F | O | $CH_2CH(Cl)C(O)N(CH_2CH_3)(CH_2CHCH_2)$ |
| .364 | Cl | O | $CH_2CH(Cl)C(O)N(CH_2CH_3)(CH_2CHCH_2)$ |
| .365 | F | O | $CH_2CH(CH_3)C(O)N(CH_3)(CH_2CHCH_2)$ |
| .366 | F | O | $CH_2COOCH_2CH_2Cl$ |
| .367 | F | O | $CH_2COOCH_2CF_3$ |
| .368 | Cl | O | $CH_2COOCH_2CF_3$ |
| .369 | H | O | $CH_2COOCH_2CF_3$ |
| .370 | F | O | $CH_2COOCH_2CH_2F$ |
| .371 | Cl | O | $CH_2COOCH_2CH_2F$ |
| .372 | F | O | $CH_2COOCH_2CH_2Cl$ |
| .373 | Cl | O | $CH_2COOCH_2CH_2Cl$ |
| .374 | F | O | $CH_2COOCH_2CH_2CH_2Cl$ |
| .375 | F | O | $CH_2COOCH_2CH(Cl)CH_3$ |
| .376 | Cl | O | $CH_2COOCH_2CH(Cl)CH_3$ |
| .377 | F | C | $CH_2COOCH_2CH(F)CH_3$ |
| .378 | Cl | O | $CH_2COOCH_2CH(F)CH_3$ |
| .379 | H | O | 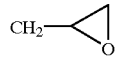 |
| .380 | H | O | 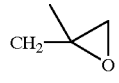 |
| .381 | Cl | O | 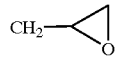 |
| .382 | Cl | O | 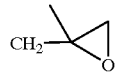 |
| .383 | F | O | 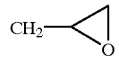 |
| .384 | F | O | 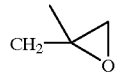 |
| .385 | F | O | $S(O)_2CH_3$ |
| .386 | F | O | $S(O)_2CH_2CH_3$ |
| .387 | Cl | O | $S(O)_2CF_3$ |
| .388 | Cl | O | $S(O)_2CH_2CH_3$ |
| .389 | F | O | $S(O)_2CH(CH_3)_2$ |
| .390 | H | O | $C(O)CH_3$ |
| .391 | Cl | O | $C(O)CH_3$ |
| .392 | F | O | $C(O)CH_3$ |
| .393 | F | O | $C(O)CF_3$ |
| .394 | F | O | $C(O)CH_2CH_3$ |
| .395 | H | O | OH |
| .396 | Cl | O | OH |
| .397 | F | O | OH |
| .398 | H | O | $OCH_3$ |
| .399 | Cl | O | $OCH_3$ |
| .400 | F | O | $OCH_3$ |
| .401 | H | O | $OCH_2CH_3$ |
| .402 | Cl | O | $OCH_2CH_3$ |
| .403 | F | O | $OCH_2CH_3$ |
| .404 | F | O | $OCH_2CH(CH_3)_2$ |
| .405 | F | O | $OCH_2C(CH_3)_3$ |
| .406 | F | O | $OCF_3$ |
| .407 | F | O | $OCHF_2$ |
| .408 | F | O | $OCH_2CHCH_2$ |
| .409 | F | O | $OCH_2C(CH_3)CH_2$ |
| .410 | F | O | $OCH_2CHCHCl$ |
| .411 | H | O | $OCH_2OCH_3$ |
| .412 | Cl | O | $OCH_2OCH_3$ |
| .413 | F | O | $OCH_2OCH_3$ |
| .414 | H | O | $OCH_2SCH_3$ |
| .415 | Cl | O | $OCH_2SCH_3$ |
| .416 | F | O | $OCH_2SCH_3$ |
| .417 | F | O | $OCH_2CCH$ |
| .418 | H | O | $OCH_2COOH$ |
| .419 | Cl | O | $OCH_2COOH$ |
| .420 | F | O | $OCH_2COOH$ |
| .421 | F | O | $OCH_2COOCH_3$ |
| .422 | F | O | $OCH_2COOCH_2CH_3$ |
| .423 | F | O | $OCH_2COOCH(CH_3)_2$ |
| .424 | H | O | $OCH(CH_3)COOH$ |
| .425 | Cl | O | $OCH(CH_3)COOH$ |
| .426 | F | O | $OCH(CH_3)COOH$ |
| .427 | F | O | $OCH(CH_3)COOCH_2CH_3$ |
| .428 | F | O | $OCH(CH_3)COOCH_2CCH$ |
| .429 | F | O | $OCH(CH_3)COOCH_2CHCH_2$ |
| .430 | F | O | $OCH_2COSCH_2CH_3$ |
| .431 | H | O | $OCH_2COSCH(CH_3)_2$ |
| .432 | Cl | O | $OCH_2COSCH(CH_3)_2$ |
| .433 | F | O | $OCH_2COSCH(CH_3)_2$ |
| .434 | F | O | $OCH_2COSCH_2C_6H_5$ |
| .435 | F | O | $OCH_2CONH_2$ |
| .436 | F | O | $OCH_2CON(CH_3)_2$ |
| .437 | H | O | $OCH_2CONHCH_2CCH$ |
| .438 | Cl | O | $OCH_2CONHCH_2CCH$ |
| .439 | F | O | $OCH_2CONHCH_2CCH$ |
| .440 | F | O | $OCH_2C_6H_5$ |
| .441 | F | O | $OCH_2(p-CH_3O-C_6H_4)$ |
| .442 | F | O | $OCH_2(o-F-C_6H_4)$ |
| .443 | Cl | O | $OCH_2(m-CF_3-C_6H_4)$ |
| .444 | F | O | $OCH_2CH_2C_6H_5$ |
| .445 | H | O | $OCH_2CN$ |
| .446 | H | O | $OCH_2CH_2Cl$ |
| .447 | Cl | O | $OCH_2CN$ |
| .448 | Cl | O | $OCH_2CH_2Cl$ |
| .449 | F | O | $OCH_2CN$ |
| .450 | F | O | $OCH_2CH_2Cl$ |
| .451 | F | O | $OCH_2CH_2CF_3$ |
| .452 | H | O | $OCH_2CH_2OH$ |
| .453 | Cl | O | $OCH_2CH_2OH$ |
| .454 | F | O | $OCH_2CH_2OH$ |
| .455 | H | O | $OCH_2CH_2CN$ |
| .456 | Cl | O | $OCH_2CH_2CN$ |
| .457 | F | O | $OCH_2CH_2CN$ |
| .458 | F | O | $OCH_2CH(OH)(C_6H_5)$ |
| .459 | F | O | $OCH_2CH(OH)(CH_3)$ |
| .460 | Cl | O | $OCH_2CH(OCH_3)(CH_3)$ |
| .461 | F | O | $OCH_2CH(OCH_3)(CH_3)$ |
| .462 | H | O | $OC(O)CH_3$ |
| .463 | Cl | O | $OC(O)CH_3$ |
| .464 | F | O | $OC(O)CH_3$ |
| .465 | H | S | $CH_3$ |
| .466 | Cl | S | $CH_3$ |
| .467 | F | S | $CH_3$ |
| .468 | H | S | $CH_2CH_3$ |
| .469 | Cl | S | $CH_2CH_3$ |
| .470 | F | S | $CH_2CH_3$ |
| .471 | F | S | $CH_2CH_2CH_3$ |

TABLE A-continued

| Compd. No. | $R_{11}$ | $X_1$ | $R_{13}$ |
|---|---|---|---|
| .472 | F | S | $CH_2CH(CH_3)_2$ |
| .473 | F | S | $CH_2CH_2CF_3$ |
| .474 | F | S | $CH(CH_3)_2$ |
| .475 | F | S | $CH_2CH(CH_3)_2$ |
| .476 | F | S | $CH_2CH(Cl)CH_3$ |
| .477 | F | S | $CH_2CH_2CH(Cl)CH_3$ |
| .478 | F | S | $CH_2CH_2CH(OH)CH_3$ |
| .479 | H | S | $CH_2CHCH_2$ |
| .480 | Cl | S | $CH_2CHCH_2$ |
| .481 | F | S | $CH_2CHCH_2$ |
| .482 | F | S | $CH_2C(CH_3)CH_2$ |
| .483 | H | S | $CH_2CCH$ |
| .484 | Cl | S | $CH_2CCH$ |
| .485 | F | S | $CH_2CCH$ |
| .486 | F | S | $CH_2CH_2CCH$ |
| .487 | F | S | $CH(CH_3)CCH$ |
| .488 | H | S | $CH_2CH_2OH$ |
| .489 | Cl | S | $CH_2CH_2OH$ |
| .490 | F | S | $CH_2CH_2OH$ |
| .491 | F | S | $CH_2CH(OH)CH_3$ |
| .492 | H | S | $CH_2C_6H_5$ |
| .493 | Cl | S | $CH_2C_6H_5$ |
| .494 | F | S | $CH_2C_6H_5$ |
| .495 | Cl | S | $CH_2(o\text{-}F\text{—}C_6H_4)$ |
| .496 | F | S | $CH_2(o\text{-}F\text{—}C_6H_5)$ |
| .497 | F | S | $CH_2(m\text{-}CF_3\text{—}C_6H_5)$ |
| .498 | F | S | $CH_2(p\text{-}CH_3\text{—}C_6H_4)$ |
| .499 | F | S | $CH_2(2,4\text{-}di\text{-}F\text{—}C_6H_3)$ |
| .500 | F | S | $CH_2CH_2CH(CH_3)C_6H_5$ |
| .501 | F | S | $CH_2CH_2CH_2CH_2(p\text{-}F\text{—}C_6H_4)$ |
| .502 | Cl | S | $CH_2CN$ |
| .503 | F | S | $CH_2CN$ |
| .504 | F | S | cyclopropyl |
| .505 | Cl | S | $CH_2$-cyclopropyl |
| .506 | F | S | $CH_2$-cyclopropyl |
| .507 | F | S | $CH_2Cl$ |
| .508 | H | S | $CH_2OCH_3$ |
| .509 | Cl | S | $CH_2OCH_3$ |
| .510 | F | S | $CH_2OCH_3$ |
| .511 | F | S | $CH_2OCH_2CHCH_2$ |
| .512 | F | S | $CH_2CH_2OCH_3$ |
| .513 | F | S | $CH_2CH(OCH_3)CH_3$ |
| .514 | F | S | $CH_2CH(OCH_2CCH)CH_3$ |
| .515 | H | S | $CH_2CH_2OCH_2CH_2OCH_3$ |
| .516 | Cl | S | $CH_2CH_2OCH_2CH_2OCH_3$ |
| .517 | F | S | $CH_2CH_2OCH_2CH_2OCH_3$ |
| .518 | H | S | $CH_2SCH_3$ |
| .519 | Cl | S | $CH_2SCH_3$ |
| .520 | F | S | $CH_2SCH_3$ |
| .521 | F | S | $CH_2SCH_2CHCH_2$ |
| .522 | F | S | $CH_2SCH_2CCH$ |
| .523 | F | S | $CH_2CH_2SCH_3$ |
| .524 | F | S | $CH_2CH_2S(O)CH_3$ |
| .525 | F | S | $CH_2CH_2S(O)_2CH_3$ |
| .526 | H | S | $CH_2COOH$ |
| .527 | Cl | S | $CH_2COOH$ |
| .528 | F | S | $CH_2COOH$ |
| .529 | F | S | $CH_2COOCH_3$ |
| .530 | F | S | $CH_2COOCH_2CH_3$ |
| .531 | F | S | $CH_2COOC(CH_3)_3$ |
| .532 | F | S | $CH_2COOCH_2C_6H_5$ |
| .533 | F | S | $CH_2COOCH_2(p\text{-}Cl\text{—}C_6H_4)$ |
| .534 | F | S | $CH_2C(O)SCH_3$ |
| .535 | H | S | $CH_2C(O)SCH(CH_3)_2$ |
| .536 | Cl | S | $CH_2C(O)SCH(CH_3)_2$ |
| .537 | F | S | $CH_2C(O)SCH(CH_3)_2$ |
| .538 | F | S | $CH_2C(O)SCH_2C_6H_5$ |
| .539 | F | S | $CH_2C(O)NH_2$ |
| .540 | F | S | $CH_2C(O)NH(CH_3)$ |
| .541 | Cl | S | $CH_2C(O)NH(CH_2CCH)$ |
| .542 | F | S | $CH_2C(O)NH(CH_2CCH)$ |
| .543 | F | S | $CH_2C(O)N(CH_2CH_3)_2$ |
| .544 | H | S | $CH_2CHO$ |
| .545 | Cl | S | $CH_2CHO$ |
| .546 | F | S | $CH_2CHO$ |
| .547 | F | S | $CH_2C(O)CH_3$ |
| .548 | H | S | $CH_2CH_2COOH$ |
| .549 | Cl | S | $CH_2CH_2COOH$ |
| .550 | F | S | $CH_2CH_2COOH$ |
| .551 | H | S | $CH_2CH_2CN$ |
| .552 | Cl | S | $CH_2CH_2CN$ |
| .553 | F | S | $CH_2CH_2CN$ |
| .554 | F | S | $CH_2CH_2COOCH_3$ |
| .555 | F | S | $CH_2CH_2COOCH_2C_6H_5$ |
| .556 | Cl | S | $CH_2CH_2C(O)SCH_2CH_3$ |
| .557 | F | S | $CH_2CH_2C(O)SCH_2CH_3$ |
| .558 | H | S | $CH_2CH(OH)COOH$ |
| .559 | Cl | S | $CH_2CH(OH)COOH$ |
| .560 | F | S | $CH_2CH(OH)COOH$ |
| .561 | H | S | $CH_2CH(Cl)COOH$ |
| .562 | Cl | S | $CH_2CH(Cl)COOH$ |
| .563 | F | S | $CH_2CH(Cl)COOH$ |
| .564 | Cl | S | $CH_2CH(Cl)COOCH_2CH_3$ |
| .565 | F | S | $CH_2CH(Cl)COOCH_2CH_3$ |
| .566 | F | S | $CH_2CH(Cl)COOH$ |
| .567 | F | S | $CH_2C(CH_3)(Cl)COOH$ |
| .568 | F | S | $CH_2CH(Cl)COOCH_2CHCH_2$ |
| .569 | Cl | S | $CH_2CH(Cl)COOCH_2CCH$ |
| .570 | F | S | $CH_2CH(Cl)COOCH_2CCH$ |
| .571 | F | S | $CH_2CH(Cl)COOCH_2C_6H_5$ |
| .572 | Cl | S | $CH_2CH(Br)COOH$ |
| .573 | F | S | $CH_2CH(Br)COOH$ |
| .574 | Cl | S | $CH_2CH(Cl)C(O)SCH(CH_3)_2$ |
| .575 | F | S | $CH_2CH(Cl)C(O)SCH(CH_3)_2$ |
| .576 | F | S | $CH_2CH(Cl)C(C)NH(CH_2CCH)$ |
| .577 | F | S | $CH_2CH(CH_3)C(O)N(CH_3)(CH_2CHCH_2)$ |
| .578 | F | S | $CH_2CH_2C(O)NH(CH_2CCH)$ |
| .579 | H | S |  |
| .580 | Cl | S |  |
| .581 | F | S |  |
| .582 | H | S |  |
| .583 | Cl | S |  |
| .584 | F | S |  |
| .585 | H | S | OH |
| .586 | Cl | S | OH |
| .587 | F | S | OH |
| .588 | H | S | $OCH_3$ |
| .589 | Cl | S | $OCH_3$ |
| .590 | F | S | $OCH_3$ |
| .591 | F | S | $OCH_2CH_3$ |
| .592 | Cl | S | $OCH_2CH(CH_3)_2$ |
| .593 | F | S | $OCH_2CH(CH_3)_2$ |
| .594 | F | S | $OCH(CH_3)_2$ |
| .595 | F | S | $OCF_3$ |
| .596 | H | S | $OCH_2OCH_3$ |
| .597 | Cl | S | $OCH_2OCH_3$ |
| .598 | F | S | $OCH_2OCH_3$ |
| .599 | H | S | $OCH_2SCH_3$ |
| .600 | Cl | S | $OCH_2SCH_3$ |

TABLE A-continued

| Compd. No. | $R_{11}$ | $X_1$ | $R_{13}$ |
|---|---|---|---|
| .601 | F | S | $OCH_2SCH_3$ |
| .602 | Cl | S | $OCH_2CHCH_2$ |
| .603 | F | S | $OCH_2CHCH_2$ |
| .604 | H | S | $OCH_2CCH$ |
| .605 | Cl | S | $OCH_2CCH$ |
| .606 | F | S | $OCH_2CCH$ |
| .607 | F | S | $OCH(CH_3)CHCH_2$ |
| .608 | F | S | $OCH(CH_3)CCH$ |
| .609 | F | S | $OCH_2CH_2Cl$ |
| .610 | F | S | $OCH_2CH_2CF_3$ |
| .611 | F | S | $OCH_2CHCH(Cl)$ |
| .612 | H | S | $OCH_2CHO$ |
| .613 | H | S | $OCH_2CHO$ |
| .614 | H | S | $OCH_2CHO$ |
| .615 | H | S | $OCH_2COOH$ |
| .616 | Cl | S | $OCH_2COOH$ |
| .617 | F | S | $OCH_2COOH$ |
| .618 | H | S | $OCH_2COOCH_2CH_3$ |
| .619 | Cl | S | $OCH_2COOCH_2CH_3$ |
| .620 | F | S | $OCH_2COOCH_2CH_3$ |
| .621 | F | S | $OCH(CH_3)COOH$ |
| .622 | F | S | $OCH(CH_3)COOCH_2CH_3$ |
| .623 | F | S | $OCH(CH_3)COOCH_2CCH$ |
| .624 | F | S | $OCH_2C(O)NH_2$ |
| .625 | F | S | $OCH_2C(O)NH(CH_3)$ |
| .626 | F | S | $OCH_2C(O)N(CH_2CH_3)_2$ |
| .627 | F | S | $OCH_2C(O)NH(CH_2CCH)$ |
| .628 | Cl | S | $OCH_2C(O)N(CH_3)_2$ |
| .629 | F | S | $OCH_2C(O)N(CH_3)_2$ |
| .630 | F | S | $OCH_2C(O)N(CH_3)(CH_2(o\text{-}F\text{—}C_6H_4))$ |
| .631 | Cl | S | $OCH_2C(O)SCH_3$ |
| .632 | F | S | $OCH_2C(O)SCH_3$ |
| .633 | F | S | $OCH_2(O)SCH_2CH_3$ |
| .634 | H | S | $OCH_2C(O)SCH(CH_3)_2$ |
| .635 | Cl | S | $OCH_2C(O)SCH(CH_3)_2$ |
| .636 | F | S | $OCH_2C(O)SCH(CH_3)_2$ |
| .637 | Cl | S | $OCH_2C(O)SCH_2C_6H_5$ |
| .638 | F | S | $OCH(CH_3)C(O)SCH_2C_8H_5$ |
| .639 | H | S | $OCH_2CH_2OH$ |
| .640 | Cl | S | $OCH_2CH_2OH$ |
| .641 | F | S | $OCH_2CH_2OH$ |
| .642 | H | S | $OCH_2CH(CH_3)OH$ |
| .643 | Cl | S | $OCH_2CH(CH_3)OH$ |
| .644 | F | S | $OCH_2CH(CH_3)OH$ |
| .645 | F | S | $OCH_2CH_2Cl$ |
| .646 | F | S | $OCH_2CF_3$ |
| .647 | Cl | S | $OCH_2CN$ |
| .648 | F | S | $OCH_2CN$ |
| .649 | H | S | $OCH_2CH_2CN$ |
| .650 | Cl | S | $OCH_2CH_2CN$ |
| .651 | F | S | $OCH_2CH_2CN$ |
| .652 | Cl | S | $OCH_2CH_2CF_3$ |
| .653 | F | S | $OCH_2CH_2CF_3$ |
| .654 | F | S | $OCH_2CH(OH)(C_6H_5)$ |

Table 38:

A preferred group of compounds of formula I corresponds to the general formula

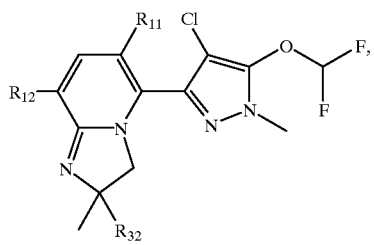

($I_{38}$)

in which the sets of correlated substituents $R_{11}$, $R_{12}$ and $R_{32}$ are given in Table B, thus disclosing 264 specific compounds of formula $I_{38}$.

Table 39:

Another preferred group of compounds of formula I corresponds to the general formula

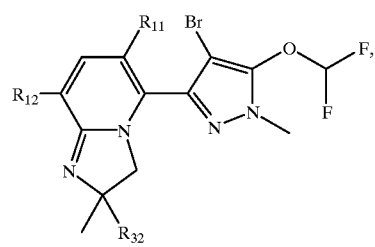

($I_{39}$)

in which the sets of correlated substituents $R_{11}$, $R_{12}$ and $R_{32}$ are given in Table B, thus disclosing 264 specific compounds of formula $I_{39}$.

Table 40:

Another preferred group of compounds of formula I corresponds to the general formula

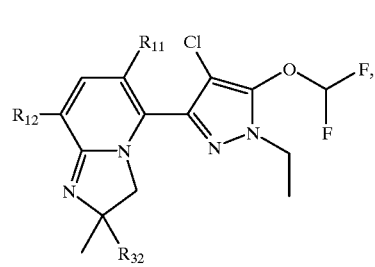

($I_{40}$)

in which the sets of correlated substituents $R_{11}$, $R_{12}$ and $R_{32}$ are given in Table B, thus disclosing 264 specific compounds of formula $I_{40}$.

Table 41:

Another preferred group of compounds of formula I corresponds to the general formula

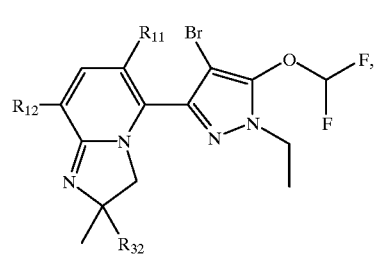

($I_{41}$)

in which the sets of correlated substituents $R_{11}$, $R_{12}$ and $R_{32}$ are given in Table B, thus disclosing 264 specific compounds of formula $I_{41}$.

Table 42

Another preferred group of compounds of formula I corresponds to the general formula

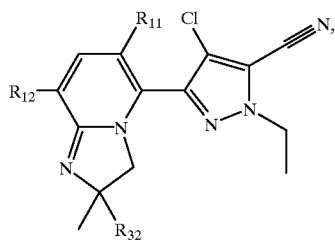
(I₄₂)

in which the sets of correlated substituents $R_{11}$, $R_{12}$ and $R_{32}$ are given in Table B, thus disclosing 264 specific compounds of formula $I_{42}$.

Table 43:

Another preferred group of compounds of formula I corresponds to the general formula

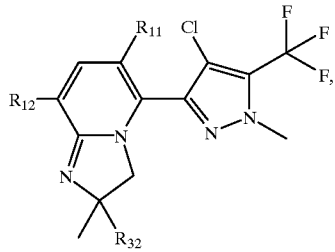
(I₄₃)

in which the sets of correlated substituents $R_{11}$, $R_{12}$ and $R_{32}$ are given in Table B, thus disclosing 264 specific compounds of formula $I_{43}$.

Table 44:

Another preferred group of compounds of formula I corresponds to the general formula

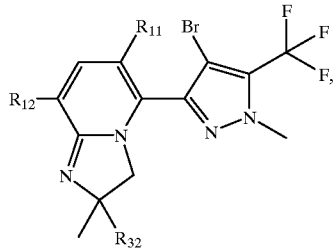
(I₄₄)

in which the sets of correlated substituents $R_{11}$, $R_{12}$ and $R_{32}$ are given in Table B, thus disclosing 264 specific compounds of formula $I_{44}$.

Table 45:

Another preferred group of compounds of formula I corresponds to the general formula

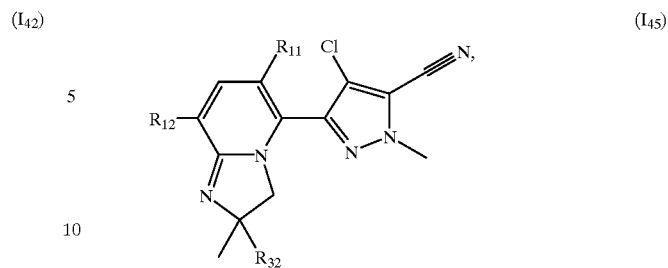
(I₄₅)

in which the sets of correlated substituents $R_{11}$, $R_{12}$ and $R_{32}$ are given in Table B. thus disclosing 264 specific compounds of formula $I_{45}$.

Table 46:

Another preferred group of compounds of formula I corresponds to the general formula

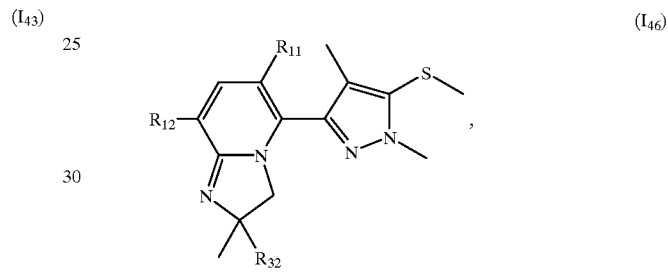
(I₄₆)

in which the sets of correlated substituents $R_{11}$, $R_{12}$ and $R_{32}$ are given in Table B, thus disclosing 264 specific compounds of formula $I_{46}$.

Table 47:

Another preferred group of compounds of formula I corresponds to the general formula

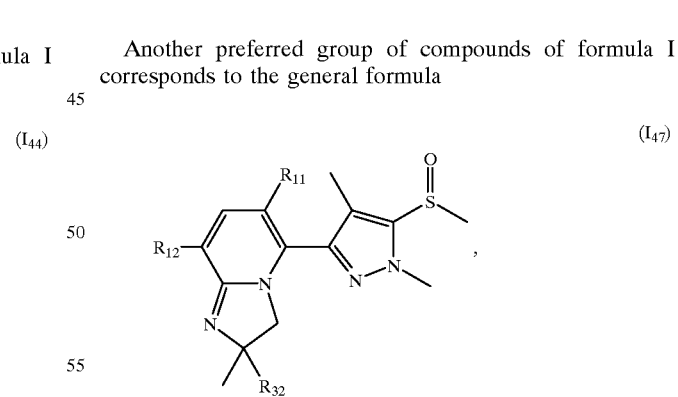
(I₄₇)

in which the sets of correlated substituents $R_{11}$, $R_{12}$ and $R_{32}$ are given in Table B, thus disclosing 264 specific compounds of formula $I_{47}$.

Table 48:

Another preferred group of compounds of formula I corresponds to the general formula

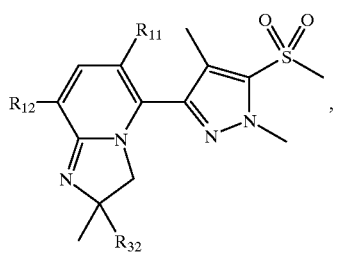

($I_{48}$)

in which the sets of correlated substituents $R_{11}$, $R_{12}$ and $R_{32}$ are given in Table B, thus disclosing 264 specific compounds of formula $I_{48}$.

Table 49:

Another preferred group of compounds of formula I corresponds to the general formula

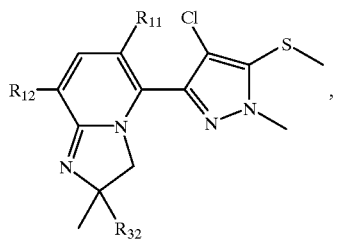

($I_{49}$)

in which the sets of correlated substituents $R_{11}$, $R_{12}$ and $R_{32}$ are given in Table B, thus disclosing 264 specific compounds of formula $I_{49}$.

Table 50:

Another preferred group of compounds of formula I corresponds to the general formula

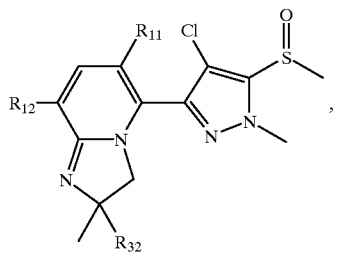

($I_{50}$)

in which the sets of correlated substituents $R_{11}$, $R_{12}$ and $R_{32}$ are given in Table B, thus disclosing 264 specific compounds of formula $I_{50}$.

Table 51:

Another preferred group of compounds of formula I corresponds to the general formula

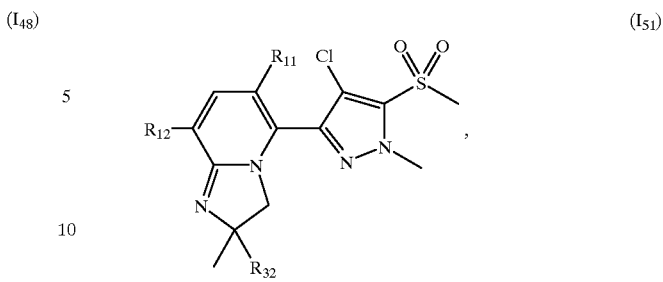

($I_{51}$)

in which the sets of correlated substituents $R_{11}$, $R_{12}$ and $R_{32}$ are given in Table B, thus disclosing 264 specific compounds of formula $I_{51}$.

Table 52:

Another preferred group of compounds of formula I corresponds to the general formula

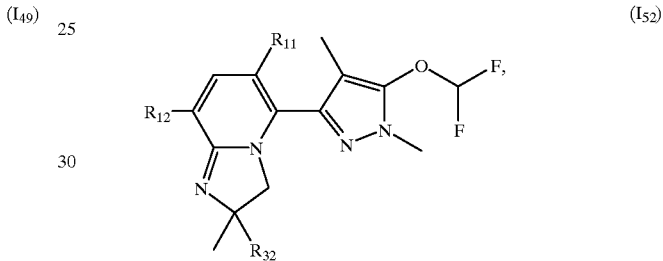

($I_{52}$)

in which the sets of correlated substituents $R_{11}$, $R_{12}$ and $R_{32}$ are given in Table B, thus disclosing 264 specific compounds of formula $I_{52}$.

Table 53:

Another preferred group of compounds of formula I corresponds to the general formula

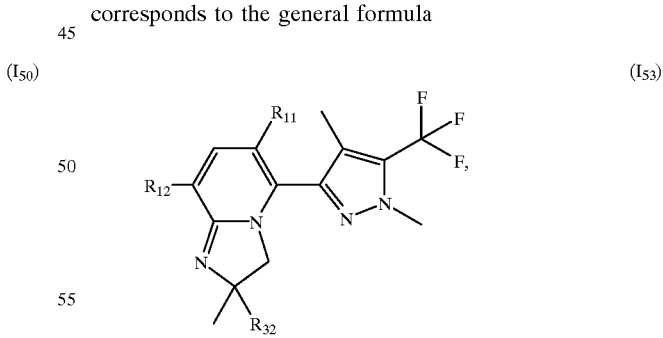

($I_{53}$)

in which the sets of correlated substituents $R_{11}$, $R_{12}$ and $R_{32}$ are given in Table B, thus disclosing 264 specific compounds of formula $I_{53}$.

Table 54:

Another preferred group of compounds of formula I corresponds to the general formula

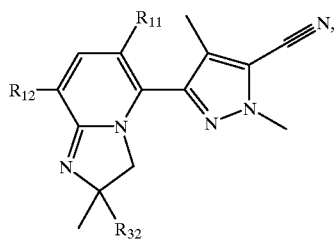

(I$_{54}$)

in which the sets of correlated substituents $R_{11}$, $R_{12}$ and $R_{32}$ are given in Table B, thus disclosing 264 specific compounds of formula I$_{54}$.

Table 55:

Another preferred group of compounds of formula I corresponds to the general formula

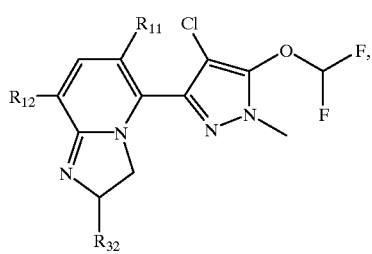

(I$_{55}$)

in which the sets of correlated substituents $R_{11}$, $R_{12}$ and $R_{32}$ are given in Table B, thus disclosing 264 specific compounds of formula I$_{55}$.

Table 56:

Another preferred group of compounds of formula I corresponds to the general formula

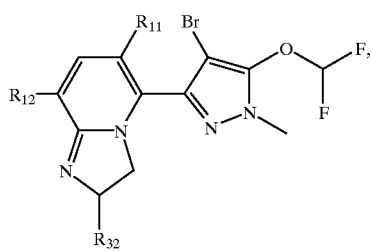

(I$_{56}$)

in which the sets of correlated substituents $R_{11}$, $R_{12}$ and $R_{32}$ are given in Table e, thus disclosing 264 specific compounds of formula I$_{56}$.

Table 57:

Another preferred group of compounds of formula I corresponds to the general formula

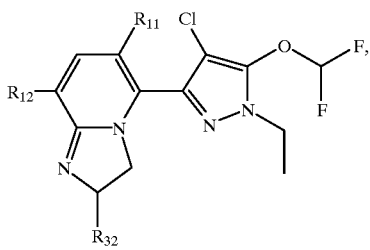

(I$_{57}$)

in which the sets of correlated substituents $R_{11}$, $R_{12}$ and $R_{32}$ are given in Table B, thus disclosing 264 specific compounds of formula I$_{57}$.

Table 58:

Another preferred group of compounds of formula I corresponds to the general formula

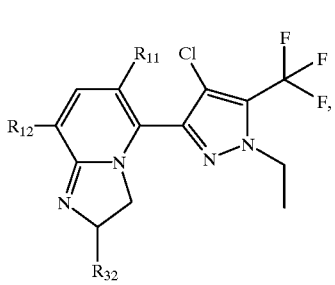

(I$_{58}$)

in which the sets of correlated substituents $R_{11}$, $R_{12}$ and $R_{32}$ are given in Table B, thus disclosing 264 specific compounds of formula I$_{58}$.

Table 59:

Another preferred group of compounds of formula I corresponds to the general formula

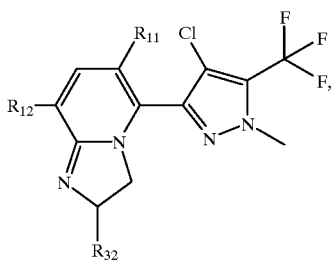

(I$_{59}$)

in which the sets of correlated substituents $R_{11}$, $R_{12}$ and $R_{32}$ are given in Table B, thus disclosing 264 specific compounds of formula I$_{59}$.

Table 60:

Another preferred group of compounds of formula I corresponds to the general formula

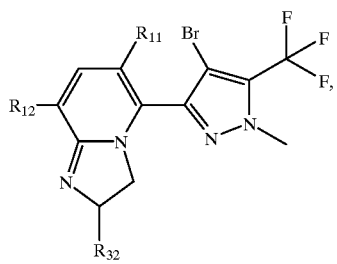

(I$_{60}$)

in which the sets of correlated substituents R$_{11}$, R$_{12}$ and R$_{32}$ are given in Table B, thus disclosing 264 specific compounds of formula I$_{60}$.

Table 61:

Another preferred group of compounds of formula I corresponds to the general formula

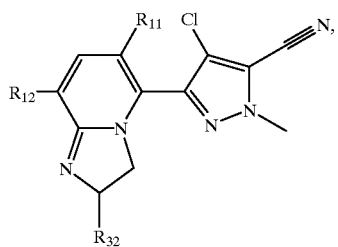

(I$_{61}$)

in which the sets of correlated substituents R$_{11}$, R$_{12}$ and R$_{32}$ are given in Table B, thus disclosing 264 specific compounds of formula I$_{81}$.

Table 62:

Another preferred group of compounds of formula I corresponds to the general formula

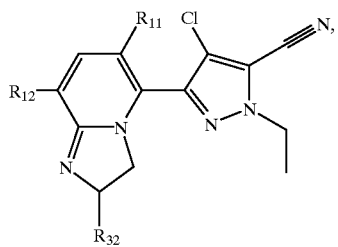

(I$_{62}$)

in which the sets of correlated substituents R$_{11}$, R$_{12}$ and R$_{32}$ are given in Table B, thus disclosing 264 specific compounds of formula I$_{62}$.

Table 63:

Another preferred group of compounds of formula I corresponds to the general formula

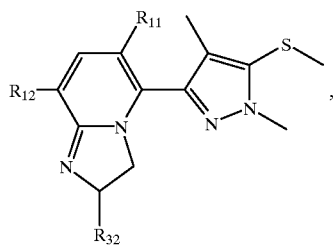

(I$_{63}$)

in which the sets of correlated substituents R$_{11}$, R$_{12}$ and R$_{32}$ are given in Table B, thus disclosing 264 specific compounds of formula I$_{63}$.

Table 64:

Another preferred group of compounds of formula I corresponds to the general formula

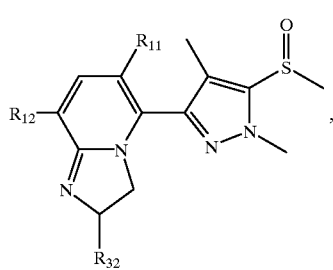

(I$_{64}$)

in which the sets of correlated substituents R$_{11}$, R$_{12}$ and R$_{32}$ are given in Table B, thus disclosing 264 specific compounds of formula I$_{64}$.

Table 65:

Another preferred group of compounds of formula I corresponds to the general formula

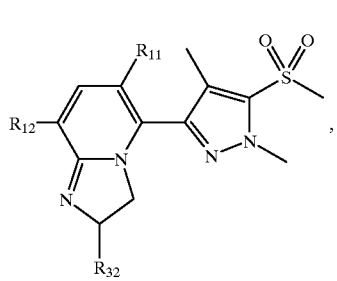

(I$_{65}$)

in which the sets of correlated substituents R$_{11}$, R$_{12}$ and R$_{32}$ are given in Table B, thus disclosing 264 specific compounds of formula I$_{65}$.

Table 66:

Another preferred group of compounds of formula I corresponds to the general formula

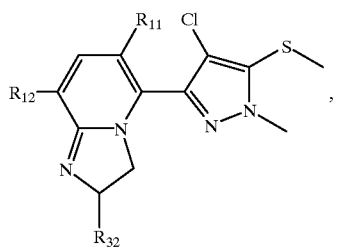

(I₆₆)

in which the sets of correlated substituents $R_{11}$, $R_{12}$ and $R_{32}$ are given in Table B, thus disclosing 264 specific compounds of formula $I_{66}$.

Table 67:

Another preferred group of compounds of formula I corresponds to the general formula

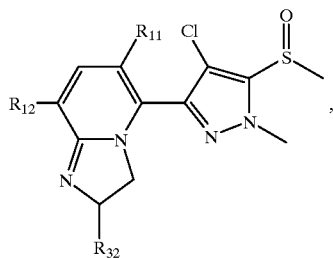

(I₆₇)

in which the sets of correlated substituents $R_{11}$, $R_{12}$ and $R_{32}$ are given in Table B, thus disclosing 264 specific compounds of formula $I_{67}$.

Table 68

Another preferred group of compounds of formula I corresponds to the general formula

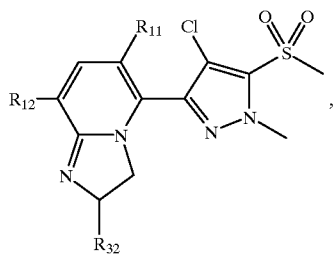

(I₆₈)

in which the sets of correlated substituents $R_{11}$, $R_{12}$ and $R_{32}$ are given in Table B, thus disclosing 264 specific compounds of formula $I_{68}$.

Table 69:

Another preferred group of compounds of formula I corresponds to the general formula

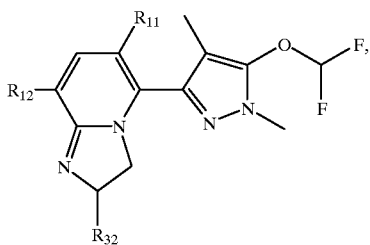

(I₆₉)

in which the sets of correlated substituents $R_{11}$, $R_{12}$ and $R_{32}$ are given in Table B, thus disclosing 264 specific compounds of formula $I_{69}$.

Table 70:

Another preferred group of compounds of formula I corresponds to the general formula

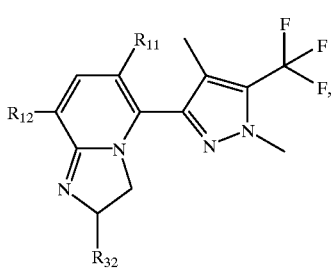

(I₇₀)

in which the sets of correlated substituents $R_{11}$, $R_{12}$ and $R_{32}$ are given in Table B, thus disclosing 264 specific compounds of formula $I_{70}$.

Table 71:

Another preferred group of compounds of formula I corresponds to the general formula

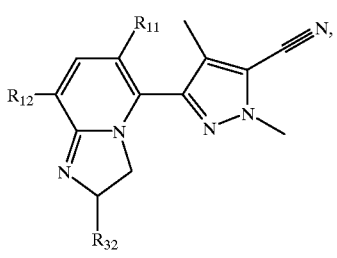

(I₇₁)

in which the sets of correlated substituents $R_{11}$, $R_{12}$ and $R_{32}$ are given in Table B, thus disclosing 264 specific compounds of formula $I_{71}$.

Table 72:

Another preferred group of compounds of formula I corresponds to the general formula

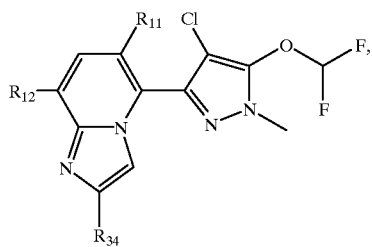

(I$_{72}$)

in which the sets of correlated substituents $R_{11}$, $R_{12}$ and $R_{32}$ are given in Table B. thus disclosing 264 specific compounds of formula I$_{72}$.

Table 73:

Another preferred group of compounds of formula I corresponds to the general formula

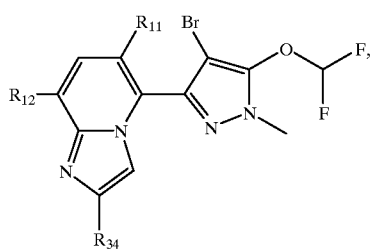

(I$_{73}$)

in which the sets of correlated substituents $R_{11}$, $R_{12}$ and $R_{32}$ are given in Table B, thus disclosing 264 specific compounds of formula I$_{73}$.

Table 74:

Another preferred group of compounds of formula I corresponds to the general formula

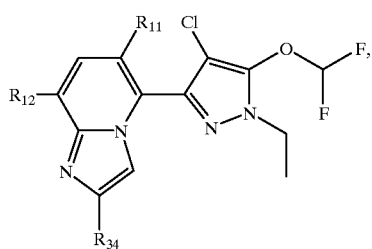

(I$_{74}$)

in which the sets of correlated substituents $R_{11}$, $R_{12}$ and $R_{32}$ are given in Table B, thus disclosing 264 specific compounds of formula I$_{74}$.

Table 75:

Another preferred group of compounds of formula I corresponds to the general formula

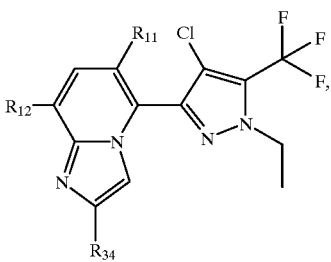

(I$_{75}$)

in which the sets of correlated substituents $R_{11}$, $R_{12}$ and $R_{32}$ are given in Table B, thus disclosing 264 specific compounds of formula I$_{75}$.

Table 76:

Another preferred group of compounds of formula I corresponds to the general formula

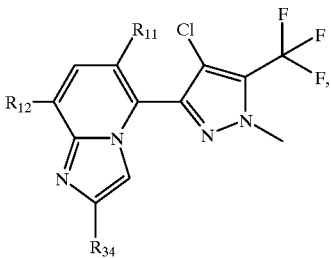

(I$_{76}$)

in which the sets of correlated substituents $R_{11}$, $R_{12}$ and $R_{32}$ are given in Table B, thus disclosing 264 specific compounds of formula I$_{76}$.

Table 77:

Another preferred group of compounds of formula I corresponds to the general formula

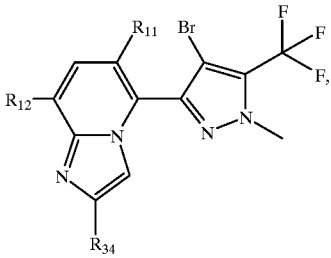

(I$_{77}$)

in which the sets of correlated substituents $R_{11}$, $R_{12}$ and $R_{32}$ are given in Table B, thus disclosing 264 specific compounds of formula I$_{77}$.

Table 78:

Another preferred group of compounds of formula I corresponds to the general formula

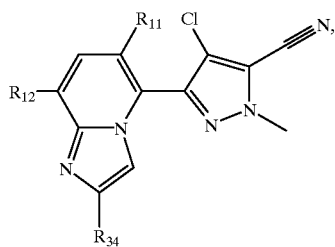

(I₇₈)

in which the sets of correlated substituents $R_{11}$, $R_{12}$ and $R_{32}$ are given in Table B, thus disclosing 254 specific compounds of formula $I_{78}$.

Table 79:

Another preferred group of compounds of formula I corresponds to the general formula

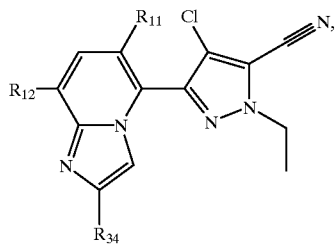

(I₇₉)

in which the sets of correlated substituents $R_{11}$, $R_{12}$ and $R_{32}$ are given in Table B. thus disclosing 264 specific compounds of formula $I_{79}$.

Table 80:

Another preferred group of compounds of formula I corresponds to the general formula

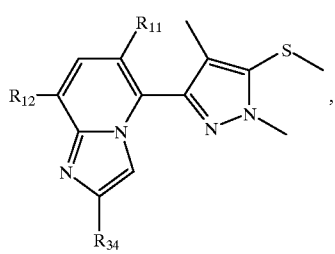

(I₈₀)

in which the sets of correlated substituents $R_{11}$, $R_{12}$ and $R_{32}$ are given in Table B, thus disclosing 264 specific compounds of formula $I_{80}$.

Table 81:

Another preferred group of compounds of formula I corresponds to the general formula

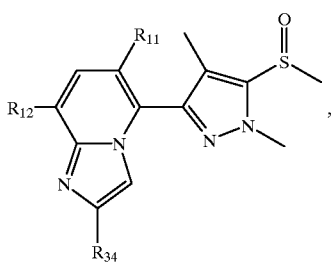

(I₈₁)

in which the sets of correlated substituents $R_{11}$, $R_{12}$ and $R_{32}$ are given in Table B, thus disclosing 264 specific compounds of formula $I_{81}$.

Table 82:

Another preferred group of compounds of formula I corresponds to the general formula

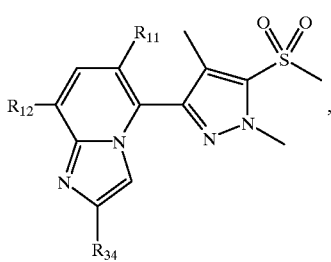

(I₈₂)

in which the sets of correlated substituents $R_{11}$, $R_{12}$ and $R_{32}$ are given in Table B, thus disclosing 264 specific compounds of formula $I_{82}$.

Table 83:

Another preferred group of compounds of formula I corresponds to the general formula

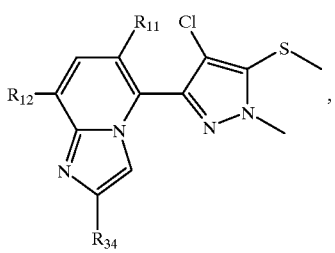

(I₈₃)

in which the sets of correlated substituents $R_{11}$, $R_{12}$ and $R_{32}$ are given in Table B. thus disclosing 264 specific compounds of formula $I_{83}$.

Table 84:

Another preferred group of compounds of formula I corresponds to the general formula

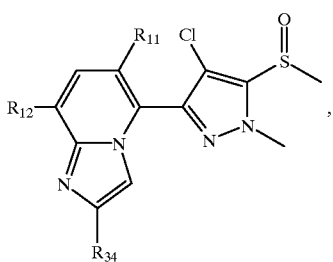

(I₈₄)

in which the sets of correlated substituents $R_{11}$, $R_{12}$ and $R_{32}$ are given in Table B. thus disclosing 264 specific compounds of formula $I_{84}$.

Table 85:

Another preferred group of compounds of formula I corresponds to the general formula

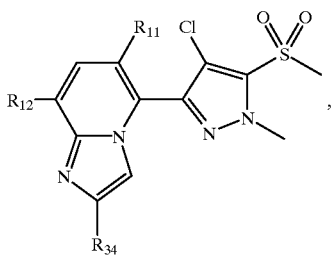

(I₈₅)

in which the sets of correlated substituents $R_{11}$, $R_{12}$ and $R_{32}$ are given in Table B, thus disclosing 264 specific compounds of formula $I_{85}$.

Table 86:

Another preferred group of compounds of formula I corresponds to the general formula

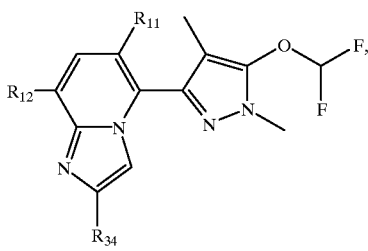

(I₈₆)

in which the sets of correlated substituents $R_{11}$, $R_{12}$ and $R_{32}$ are given in Table B, thus disclosing 264 specific compounds of formula $I_{86}$.

Table 87:

Another preferred group of compounds of formula I corresponds to the general formula

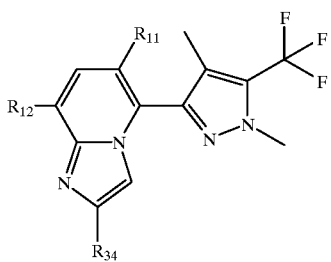

(I₈₇)

in which the sets of correlated substituents $R_{11}$, $R_{12}$ and $R_{32}$ are given in Table B. thus disclosing 264 specific compounds of formula $I_{87}$.

Table 88:

Another preferred group of compounds of formula I corresponds to the general formula

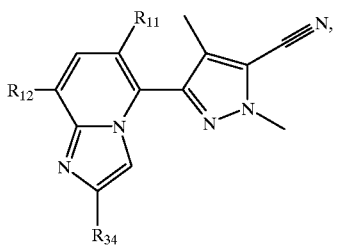

(I₈₈)

in which the sets of correlated substituents $R_{11}$, $R_{12}$ and $R_{32}$ are given in Table B, thus disclosing 264 specific compounds of formula $I_{88}$.

TABLE B

| Compd. No. | $R_{11}$ | $R_{12}$ | $R_{32}$ or $R_{34}$ |
|---|---|---|---|
| .001 | H | Cl | H |
| .002 | Cl | Cl | H |
| .003 | F | Cl | H |
| .004 | H | Br | H |
| .005 | Cl | Br | H |
| .006 | F | Br | H |
| .007 | Cl | $CF_3$ | H |
| .008 | F | $CF_3$ | H |
| .009 | F | $CH_3$ | H |
| .010 | F | $OCF_3$ | H |
| .011 | H | Cl | $CH_3$ |
| .012 | Cl | Cl | $CH_3$ |
| .013 | F | Cl | $CH_3$ |
| .014 | H | Br | $CH_3$ |
| .015 | Cl | Br | $CH_3$ |
| .016 | F | Br | $CH_3$ |
| .017 | Cl | $CF_3$ | $CH_3$ |
| .018 | F | $CF_3$ | $CH_3$ |
| .019 | F | $CH_3$ | $CH_3$ |
| .020 | F | $OCF_3$ | $CH_3$ |
| .021 | H | Cl | $CH_2CHCH_2$ |
| .022 | Cl | Cl | $CH_2CHCH_2$ |
| .023 | F | Cl | $CH_2CHCH_2$ |
| .024 | H | Br | $CH_2CHCH_2$ |
| .025 | Cl | Br | $CH_2CHCH_2$ |
| .026 | F | Br | $CH_2CHCH_2$ |
| .027 | Cl | $CF_3$ | $CH_2CHCH_2$ |
| .028 | F | $CF_3$ | $CH_2CHCH_2$ |
| .029 | F | $CH_3$ | $CH_2CHCH_2$ |
| .030 | F | $OCF_3$ | $CH_2CHCH_2$ |
| .031 | H | Cl | $CH_2CH(CH_3)_2$ |

TABLE B-continued

| Compd. No. | $R_{11}$ | $R_{12}$ | $R_{32}$ or $R_{34}$ |
|---|---|---|---|
| .032 | Cl | Cl | $CH_2CH(CH_3)_2$ |
| .033 | F | Cl | $CH_2CH(CH_3)_2$ |
| .034 | H | Br | $CH_2CH(CH_3)_2$ |
| .035 | Cl | Br | $CH_2CH(CH_3)_2$ |
| .036 | F | Br | $CH_2CH(CH_3)_2$ |
| .037 | Cl | $CF_3$ | $CH_2CH(CH_3)_2$ |
| .038 | F | $CF_3$ | $CH_2CH(CH_3)_2$ |
| .039 | F | $CH_3$ | $CH_2CH(CH_3)_2$ |
| .040 | F | $OCF_3$ | $CH_2CH(CH_3)_2$ |
| .041 | H | Cl | $CH_2CCH$ |
| .042 | Cl | Cl | $CH_2CCH$ |
| .043 | F | Cl | $CH_2CCH$ |
| .044 | H | Br | $CH_2CCH$ |
| .045 | Cl | Br | $CH_2CCH$ |
| .046 | F | Br | $CH_2CCH$ |
| .047 | Cl | $CF_3$ | $CH_2CCH$ |
| .048 | F | $CF_3$ | $CH_2CCH$ |
| .049 | F | $CH_3$ | $CH_2CCH$ |
| .050 | F | $OCF_3$ | $CH_2CCH$ |
| .051 | H | Cl | $CF_3$ |
| .052 | Cl | Cl | $CF_3$ |
| .053 | F | Cl | $CF_3$ |
| .054 | H | Br | $CF_3$ |
| .055 | Cl | Br | $CF_3$ |
| .056 | F | Br | $CF_3$ |
| .057 | Cl | $CF_3$ | $CF_3$ |
| .058 | F | $CF_3$ | $CF_3$ |
| .059 | F | $CH_3$ | $CF_3$ |
| .060 | F | $OCF_3$ | $CF_3$ |
| .061 | H | Cl | $CH_2Cl$ |
| .062 | Cl | Cl | $CH_2Cl$ |
| .063 | F | Cl | $CH_2Cl$ |
| 064 | H | Br | $CH_2Cl$ |
| .065 | Cl | Br | $CH_2Cl$ |
| .066 | F | Br | $CH_2Cl$ |
| .067 | Cl | $CF_3$ | $CH_2Cl$ |
| .068 | F | $CF_3$ | $CH_2Cl$ |
| .069 | F | $CH_3$ | $CH_2Cl$ |
| .070 | F | $OCF_3$ | $CH_2Cl$ |
| .071 | H | Cl | $CH_2CN$ |
| .072 | Cl | Cl | $CH_2CN$ |
| .073 | F | Cl | $CH_2CN$ |
| .074 | H | Br | $CH_2CN$ |
| .075 | Cl | Br | $CH_2CN$ |
| .076 | F | Br | $CH_2CN$ |
| .077 | Cl | $CF_3$ | $CH_2CN$ |
| .078 | F | $CF_3$ | $CH_2CN$ |
| .079 | F | $CH_3$ | $CH_2CN$ |
| .080 | F | $OCF_3$ | $CH_2CN$ |
| .081 | H | Cl | $CH_2OH$ |
| .082 | Cl | Cl | $CH_2OH$ |
| .083 | F | Cl | $CH_2OH$ |
| .084 | H | Br | $CH_2OH$ |
| .085 | Cl | Br | $CH_2OH$ |
| .086 | F | Br | $CH_2OH$ |
| .087 | Cl | $CF_3$ | $CH_2OH$ |
| .088 | F | $CF_3$ | $CH_2OH$ |
| .089 | F | $CH_3$ | $CH_2OH$ |
| .090 | F | $OCF_3$ | $CH_2OH$ |
| .091 | H | Cl | $CH_2OC(O)CH_3$ |
| .092 | Cl | Cl | $CH_2OC(O)CH_3$ |
| .093 | F | Cl | $CH_2OC(O)CH_3$ |
| .094 | H | Br | $CH_2OC(O)CH_3$ |
| .095 | Cl | Br | $CH_2OC(O)CH_3$ |
| .096 | F | Br | $CH_2OC(O)CH_3$ |
| .097 | Cl | $CF_3$ | $CH_2OC(O)CH_3$ |
| .098 | F | $CF_3$ | $CH_2OC(O)CH_3$ |
| .099 | F | $CH_3$ | $CH_2OC(O)CH_3$ |
| .100 | F | $OCF_3$ | $CH_2OC(O)CH_3$ |
| .101 | H | Cl | $CH_2OCH_2CHCH_2$ |
| .102 | Cl | Cl | $CH_2OCH_2CHCH_2$ |
| .103 | F | Cl | $CH_2OCH_2CHCH_2$ |
| .104 | H | Br | $CH_2OCH_2CHCH_2$ |
| .105 | Cl | Br | $CH_2OCH_2CHCH_2$ |
| .106 | F | Br | $CH_2OCH_2CHCH_2$ |
| .107 | Cl | $CF_3$ | $CH_2OCH_2CHCH_2$ |
| .108 | F | $CF_3$ | $CH_2OCH_2CHCH_2$ |
| .109 | F | $CH_3$ | $CH_2OCH_2CHCH_2$ |
| .110 | F | $OCF_3$ | $CH_2OCH_2CHCH_2$ |
| .111 | H | Cl | COOH |
| .112 | Cl | Cl | COOH |
| .113 | F | Cl | COOH |
| .114 | H | Br | COOH |
| .115 | Cl | Br | COOH |
| .116 | F | Br | COOH |
| .117 | Cl | $CF_3$ | COOH |
| .118 | F | $CF_3$ | COOH |
| .119 | F | $CH_3$ | COOH |
| .120 | F | $OCF_3$ | COOH |
| .121 | H | Cl | $COOCH_3$ |
| .122 | Cl | Cl | $COOCH_3$ |
| .123 | F | Cl | $COOCH_3$ |
| .124 | H | Br | $COOCH_3$ |
| .125 | Cl | Br | $COOCH_3$ |
| .126 | F | Br | $COOCH_3$ |
| .127 | Cl | $CF_3$ | $COOCH_3$ |
| .128 | F | $CF_3$ | $COOCH_3$ |
| .129 | F | $CH_3$ | $COOCH_3$ |
| .130 | F | $OCF_3$ | $COOCH_3$ |
| .131 | H | Cl | $COOCH_2CH_3$ |
| .132 | Cl | Cl | $COOCH_2CH_3$ |
| .133 | F | Cl | $COOCH_2CH_3$ |
| .134 | H | Br | $COOCH_2CH_3$ |
| .135 | Cl | Br | $COOCH_2CH_3$ |
| .136 | F | Br | $COOCH_2CH_3$ |
| .137 | Cl | $CF_3$ | $COOCH_2CH_3$ |
| .138 | F | $CF_3$ | $COOCH_2CH_3$ |
| .139 | F | $CH_3$ | $COOCH_2CH_3$ |
| .140 | F | $OCF_3$ | $COOCH_2CH_3$ |
| .141 | Cl | Cl | $COOCH(CH_3)_2$ |
| .142 | F | Cl | $COOCH(CH_3)_2$ |
| .143 | H | Br | $COOCH(CH_3)_2$ |
| .144 | Cl | Br | $COOCH(CH_3)_2$ |
| .145 | F | Br | $COOCH(CH_3)_2$ |
| .146 | Cl | $CF_3$ | $COOCH(CH_3)_2$ |
| .147 | F | $CF_3$ | $COOCH(CH_3)_2$ |
| .148 | F | $CH_3$ | $COOCH(CH_3)_2$ |
| .149 | F | $OCF_3$ | $COOCH(CH_3)_2$ |
| .150 | F | Cl | $COOCH_2CHCH_2$ |
| .151 | F | Cl | $COOCH_2CCH$ |
| .152 | F | Cl | $COOCH_2(o\text{-}F\text{-}C_6H_5)$ |
| .153 | H | Cl | $COOCH_2C_6H_5$ |
| .154 | Cl | Cl | $COOCH_2C_6H_5$ |
| .155 | F | Cl | $COOCH_2C_6H_5$ |
| .156 | H | Br | $COOCH_2C_6H_5$ |
| .157 | Cl | Br | $COOCH_2C_6H_5$ |
| .158 | F | Br | $COOCH_2C_6H_5$ |
| .159 | Cl | $CF_3$ | $COOCH_2C_6H_5$ |
| .160 | F | $CF_3$ | $COOCH_2C_6H_5$ |
| .161 | F | $CH_3$ | $COOCH_2C_6H_5$ |
| .162 | F | $OCF_3$ | $COOCH_2C_6H_5$ |
| .163 | F | Cl | $COOCH_2CH_2Cl$ |
| .164 | H | Cl | $COSCH(CH_3)_2$ |
| .165 | Cl | Cl | $COSCH(CH_3)_2$ |
| .166 | F | Cl | $COSCH(CH_3)_2$ |
| .167 | H | Br | $COSCH(CH_3)_2$ |
| .168 | Cl | Br | $COSCH(CH_3)_2$ |
| .169 | F | Br | $COSCH(CH_3)_2$ |
| .170 | Cl | $CF_3$ | $COSCH(CH_3)_2$ |
| .171 | F | $CF_3$ | $COSCH(CH_3)_2$ |
| .172 | F | $CH_3$ | $COSCH(CH_3)_2$ |
| .173 | F | $OCF_3$ | $COSCH(CH_3)_2$ |
| 174 | H | Cl | $CONHCH_2CCH$ |
| .175 | Cl | Cl | $CONHCH_2CCH$ |
| .176 | F | Cl | $CONHCH_2CCH$ |
| .177 | H | Br | $CONHCH_2CCH$ |
| .178 | Cl | Br | $CONHCH_2CCH$ |
| .179 | F | Br | $CONHCH_2CCH$ |
| .180 | Cl | $CF_3$ | $CONHCH_2CCH$ |
| .181 | F | $CF_3$ | $CONHCH_2CCH$ |
| .182 | F | $CH_3$ | $CONHCH_2CCH$ |
| .183 | F | $OCF_3$ | $CONHCH_2CCH$ |

TABLE B-continued

| Compd. No. | $R_{11}$ | $R_{12}$ | $R_{32}$ or $R_{34}$ |
|---|---|---|---|
| .184 | H | Cl | $CON(CH_2CH_3)_2$ |
| .185 | Cl | Cl | $CON(CH_2CH_3)_2$ |
| .186 | F | Cl | $CON(CH_2CH_3)_2$ |
| .187 | H | Br | $CON(CH_2CH_3)_2$ |
| .188 | Cl | Br | $CON(CH_2CH_3)_2$ |
| .189 | F | Br | $CON(CH_2CH_3)_2$ |
| .190 | Cl | $CF_3$ | $CON(CH_2CH_3)_2$ |
| .191 | F | $CF_3$ | $CON(CH_2CH_3)_2$ |
| .192 | F | $CH_3$ | $CON(CH_2CH_3)_2$ |
| .193 | F | $OCF_3$ | $CON(CH_2CH_3)_2$ |
| .194 | F | Cl | $CON(CH_2CHCH_2)_2$ |
| .195 | F | Cl | $CON(CH_2CH_3)CH_2CHCH_2$ |
| .196 | F | Cl | $CONHCH_2CH(CH_3)_2$ |
| .197 | F | Cl | $CONH(SO_2CH_3)$ |
| .198 | H | Cl | CHO |
| .199 | Cl | Cl | CHO |
| .200 | F | Cl | CHO |
| .201 | H | Br | CHO |
| .202 | Cl | Br | CHO |
| .203 | F | Br | CHO |
| .204 | Cl | $CF_3$ | CHO |
| .205 | F | $CF_3$ | CHO |
| .206 | F | $CH_3$ | CHO |
| .207 | F | $OCF_3$ | CHO |
| .208 | H | Cl | CHNOH |
| .209 | Cl | Cl | CHNOH |
| .210 | F | Cl | CHNOH |
| .211 | H | Br | CHNOH |
| .212 | Cl | Br | CHNOH |
| .213 | F | Br | CHNOH |
| .214 | Cl | $CF_3$ | CHNOH |
| .215 | F | $CF_3$ | CHNOH |
| .216 | F | $CH_3$ | CHNOH |
| .217 | F | $OCF_3$ | CHNOH |
| .218 | H | Cl | $CHNOCH_2CCH$ |
| .219 | Cl | Cl | $CHNOCH_2CCH$ |
| .220 | F | Cl | $CHNOCH_2CCH$ |
| .221 | H | Br | $CHNCCH_2CCH$ |
| .222 | Cl | Br | $CHNOCH_2CCH$ |
| .223 | F | Br | $CHNOCH_2CCH$ |
| .224 | Cl | $CF_3$ | $CHNOCH_2CCH$ |
| .225 | F | $CF_3$ | $CHNOCH_2CCH$ |
| .226 | F | $CH_3$ | $CHNOCH_2CCH$ |
| .227 | F | $OCF_3$ | $CHNOCH_2CCH$ |
| .228 | F | Cl | $CHNOCH_3$ |
| .229 | F | Cl | $CHNOCH_2CHCH_2$ |
| .230 | H | Cl | $CH_2COOH$ |
| .231 | Cl | Cl | $CH_2COOH$ |
| .232 | F | Cl | $CH_2COOH$ |
| .233 | H | Br | $CH_2COOH$ |
| .234 | Cl | Br | $CH_2COOH$ |
| .235 | F | Br | $CH_2COOH$ |
| .236 | Cl | $CF_3$ | $CH_2COOH$ |
| .237 | F | $CF_3$ | $CH_2COOH$ |
| .238 | F | $CH_3$ | $CH_2COOH$ |
| .239 | F | $OCF_3$ | $CH_2COOH$ |
| .240 | F | Cl | $CH_2COOCH_3$ |
| .241 | F | Cl | $CH_2COOCH(CH_3)_2$ |
| .242 | F | Cl | $CH_2COOCH_2CHCH_2$ |
| .243 | H | Cl | $CH_2CH_2COOH$ |
| .244 | Cl | Cl | $CH_2CH_2COOH$ |
| .245 | F | Cl | $CH_2CH_2COOH$ |
| .246 | H | Br | $CH_2CH_2COOH$ |
| .247 | Cl | Br | $CH_2CH_2COOH$ |
| .248 | F | Br | $CH_2CH_2COOH$ |
| .249 | Cl | $CF_3$ | $CH_2CH_2COOH$ |
| .250 | F | $CF_3$ | $CH_2CH_2COOH$ |
| .251 | F | $CH_3$ | $CH_2CH_2COOH$ |
| .252 | F | $OCF_3$ | $CH_2CH_2COOH$ |
| .253 | F | Cl | $CH_2CH_2COOCH_2CH_3$ |
| .254 | F | Cl | $CH_2CH_2COOCH(CH_3)_2$ |
| .255 | F | Cl | $CH_2CH_2COOCH_2CHCH_2$ |
| .256 | F | Cl | $CH_2CH_2COOCH_2C(CH_3)CH_2$ |
| .257 | F | Cl | $CH_2CH_2COOCH_2CCH$ |
| .258 | F | Cl | $CH_2CH_2COOCH(CH_3)CCH$ |
| .259 | F | Cl | $CH(OH)CH_3$ |

TABLE B-continued

| Compd. No. | $R_{11}$ | $R_{12}$ | $R_{32}$ or $R_{34}$ |
|---|---|---|---|
| .260 | F | Cl | $C(O)CH_3$ |
| .261 | F | Cl | CN |
| .262 | Cl | $CF_3$ | CN |
| .263 | F | Cl | $C(S)NH_2$ |
| .264 | Cl | $CF_3$ | $C(S)NH_2$ |

Table 89:

A preferred group of compounds of formula I corresponds to the general formula

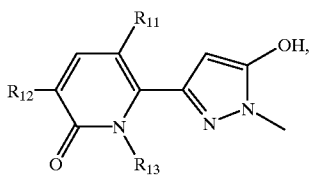

(I_{89})

in which the sets of correlated substituents $R_{11}$, $R_{12}$ and $R_{13}$ are given in Table C, thus disclosing 627 specific compounds of formula $I_{89}$.

Table 90:

Another preferred group of compounds of formula I corresponds to the general formula

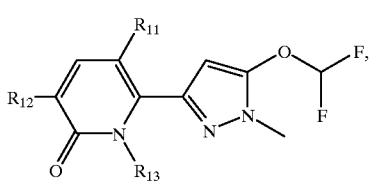

(I_{90})

in which the sets of correlated substituents $R_{11}$, $R_{12}$ and $R_{13}$ are given in Table C, thus disclosing 627 specific compounds of formula $I_{90}$.

Table 91:

Another preferred group of compounds of formula I corresponds to the general formula

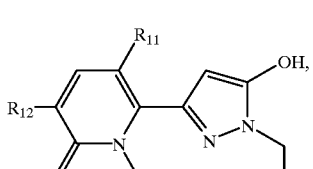

(I_{91})

in which the sets of correlated substituents $R_{11}$, $R_{12}$ and $R_{13}$ are given in Table C, thus disclosing 627 specific compounds of formula $I_{91}$.

Table 92:

Another preferred group of compounds of formula I corresponds to the general formula (I₉₂)

in which the sets of correlated substituents $R_{11}$, $R_{12}$ and $R_{13}$ are given in Table C, thus disclosing 627 specific compounds of formula $I_{92}$.

Table 93:
Another preferred group of compounds of formula I corresponds to the general formula (I₉₃)

in which the sets of correlated substituents $R_{11}$, $R_{12}$ and $R_{13}$ are given in Table C, thus disclosing 627 specific compounds of formula $I_{93}$.

Table 94:
Another preferred group of compounds of formula I corresponds to the general formula (I₉₄)

in which the sets of correlated substituents $R_{11}$, $R_{12}$ and $R_{13}$ are given in Table C, thus do sing 627 specific compounds of formula $I_{94}$.

Table 95:
Another preferred group of compounds of formula I corresponds to the general formula (I₉₅)

in which the sets of correlated substituents $R_{11}$, $R_{12}$ and $R_{13}$ are given in Table C, thus disclosing 627 specific compounds of formula $I_{95}$.

Table 96:
Another preferred group of compounds of formula I corresponds to the general formula (I₉₆)

in which the sets of correlated substituents $R_{11}$, $R_{12}$ and $R_{13}$ are given in Table C, thus disclosing 627 specific compounds of formula $I_{96}$.

Table 97:
Another preferred group of compounds of formula I corresponds to the general formula (I₉₇)

in which the sets of correlated substituents $R_{11}$, $R_{12}$ and $R_{13}$ are given in Table C, thus disclosing 627 specific compounds of formula $I_{97}$.

Table 98:
Another preferred group of compounds of formula I corresponds to the general formula (I₉₈)

in which the sets of correlated substituents $R_{11}$, $R_{12}$ and $R_{13}$ are given in Table C, thus disclosing 627 specific compounds of formula $I_{98}$.

Table 99:
Another preferred group of compounds of formula I corresponds to the general formula (I₉₉)

in which the sets of correlated substituents $R_{11}$, $R_{12}$ and $R_{13}$ are given in Table C, thus disclosing 627 specific compounds of formula $I_{99}$.

Table 100:
Another preferred group of compounds of formula I corresponds to the general formula

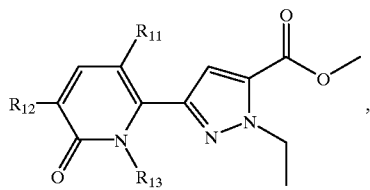

(I₁₀₀)

in which the sets of correlated substituents $R_{11}$, $R_{12}$ and $R_{13}$ are given in Table C, thus disclosing 627 specific compounds of formula $I_{100}$.

Table 101:
Another preferred group of compounds of formula I corresponds to the general formula

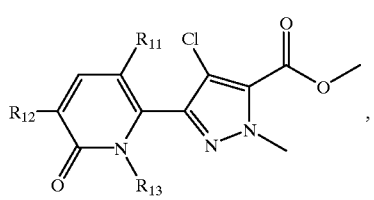

(I₁₀₁)

in which the sets of correlated substituents $R_{11}$, $R_{12}$ and $R_{13}$ are given in Table C, thus disclosing 627 specific compounds of formula $I_{102}$.

Table 102:
Another preferred group of compounds of formula I corresponds to the general formula

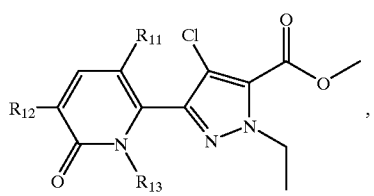

(I₁₀₂)

in which the sets of correlated substituents $R_{11}$, $R_{12}$ and $R_{13}$ are given in Table C, thus disclosing 627 specific compounds of formula $I_{102}$.

Table 103:
Another preferred group of compounds of formula I corresponds to the general formula

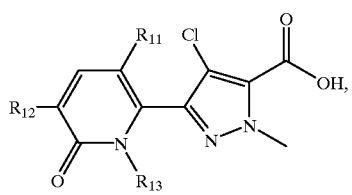

(I₁₀₃)

in which tire sets of correlated substituents $R_{11}$, $R_{12}$ and $R_{13}$ are given in Table C, thus disclosing 627 specific compounds of formula $I_{103}$.

Table 104:
Another preferred group of compounds of formula I corresponds to the general formula

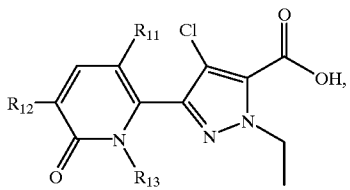

(I₁₀₄)

in which the sets of correlated substituents $R_{11}$, $R_{12}$ and $R_{13}$ are given in Table C, thus disclosing 627 specific compounds of formula $I_{104}$.

Table 105:
Another preferred group of compounds of formula I corresponds to the general formula

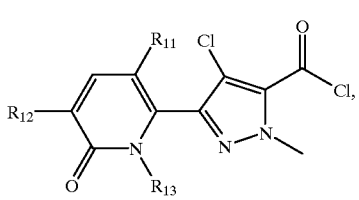

(I₁₀₅)

in which the sets of correlated substituents $R_{11}$, $R_{12}$ and $R_{13}$ are given in Table C, thus disclosing 627 specific compounds of formula $I_{105}$.

Table 106:
Another preferred group of compounds of formula I corresponds to the general formula

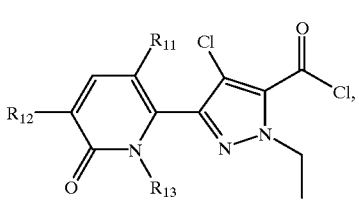

(I₁₀₆)

in which the sets of correlated substituents $R_{11}$, $R_{12}$ and $R_{13}$ are given in Table C, thus disclosing 627 specific compounds of formula $I_{106}$.

Table 107:
Another preferred group of compounds of formula I corresponds to the general formula

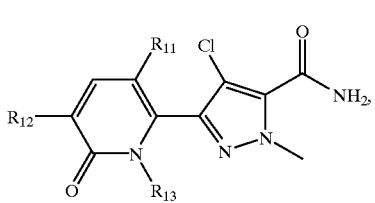

(I₁₀₇)

in which the sets of correlated substituents $R_{11}$, $R_{12}$ and $R_{13}$ are given in Table C, thus disclosing 627 specific compounds of formula $I_{107}$.

Table 108:
Another preferred group of compounds of formula I corresponds to the general formula ($I_{108}$)

in which the sets of correlated substituents $R_{11}$, $R_{12}$ and $R_{13}$ are given in Table C, thus disclosing 627 specific compounds of formula $I_{108}$.

Table 109:
Another preferred group of compounds of formula I corresponds to the general formula ($I_{109}$)

in which the sets of correlated substituents $R_{11}$, $R_{12}$ and $R_{13}$ are given in Table C, thus disclosing 627 specific compounds of formula $I_{109}$.

Table 110:
Another preferred group of compounds of formula I corresponds to the general formula ($I_{110}$)

in which the sets of correlated substituents $R_{11}$, $R_{12}$ and $R_{13}$ are given in Table C, thus disclosing 627 specific compounds of formula $I_{110}$.

Table 111:
Another preferred group of compounds of formula I corresponds to the general formula ($I_{111}$)

in which the sets of correlated substituents $R_{11}$, $R_{12}$ and $R_{13}$ are given in Table C, thus disclosing 627 specific compounds of formula $I_{111}$.

Table 112:
Another preferred group of compounds of formula I corresponds to the general formula ($I_{112}$)

in which the sets of correlated substituents $R_{11}$, $R_{12}$ and $R_{13}$ are given in Table C, thus disclosing 627 specific compounds of formula $I_{112}$.

Table 113:
Another preferred group of compounds of formula I corresponds to the general formula ($I_{113}$)

in which the sets of correlated substituents $R_{11}$, $R_{12}$ and $R_{13}$ are given in Table C, thus disclosing 627 specific compounds of formula $I_{113}$.

Table 114:
Another preferred group of compounds of formula I corresponds to the general formula ($I_{114}$)

in which the sets of correlated substituents $R_{11}$, $R_{12}$ and $R_{13}$ are given in Table C, thus disclosing 627 specific compounds of formula $I_{114}$.

Table 115:
Another preferred group of compounds of formula I corresponds to the general formula ($I_{115}$)

in which the sets of correlated substituents $R_{11}$, $R_{12}$ and $R_{13}$ are given in Table C, thus disclosing 627 specific compounds of formula $I_{115}$.

Table 116:
Another preferred group of compounds of formula I corresponds to the general formula

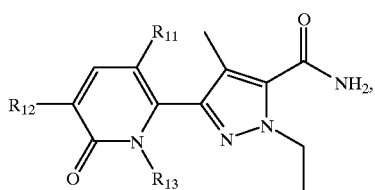
($I_{116}$)

in which the sets of correlated substituents $R_{11}$, $R_{12}$ and $R_{13}$ are given in Table C, thus disclosing 627 specific compounds of formula $I_{116}$.

Table 117:
Another preferred group of compounds of formula I corresponds to the general formula

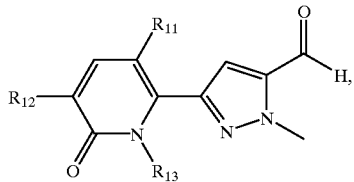
($I_{117}$)

in which the sets of correlated substituents $R_{11}$, $R_{12}$ and $R_{13}$ are given in Table C, thus disclosing 627 specific compounds of formula $I_{117}$.

Table 118:
Another preferred group of compounds of formula I corresponds to the general formula

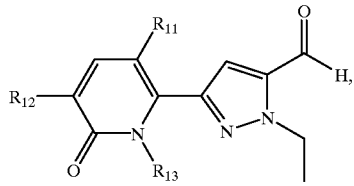
($I_{118}$)

in which the sets of correlated substituents $R_{11}$, $R_{12}$ and $R_{13}$ are given in Table C, thus disclosing 627 specific compounds of formula $I_{118}$.

Table 119:
Another preferred group of compounds of formula I corresponds to the general formula

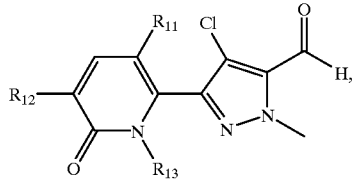
($I_{119}$)

in which the sets of correlated substituents $R_{11}$, $R_{12}$ and $R_{13}$ are given in Table C, thus disclosing 627 specific compounds of formula $I_{119}$.

Table 120:
Another preferred group of compounds of formula I corresponds to the general formula

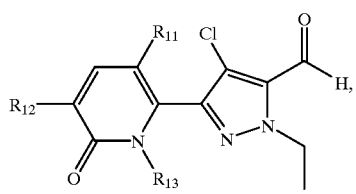
($I_{120}$)

in which the sets of correlated substituents $R_{11}$, $R_{12}$ and $R_{13}$ are given in Table C, thus disclosing 627 specific compounds of formula $I_{120}$.

Table 121:
Another preferred group of compounds of formula I corresponds to the general formula

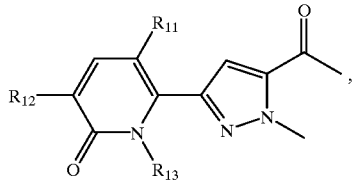
($I_{121}$)

in which the sets of correlated substituents $R_{11}$, $R_{12}$ and $R_{13}$ are given in Table C, thus disclosing 627 specific compounds of formula $I_{121}$.

Table 122:
Another preferred group of compounds of formula I corresponds to the general formula

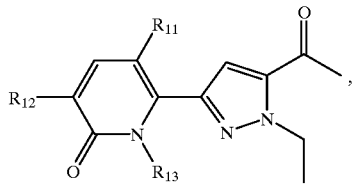
($I_{122}$)

in which the sets of correlated substituents $R_{11}$, $R_{12}$ and $R_{13}$ are given in Table C, thus disclosing 627 specific compounds of formula $I_{122}$.

Table 123:
Another preferred group of compounds of formula I corresponds to the general formula

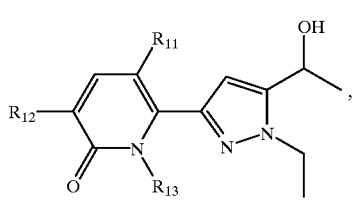
($I_{123}$)

in which the sets of correlated substituents $R_{11}$, $R_{12}$ and $R_{13}$ are given in Table C, thus disclosing 627 specific compounds of formula $I_{123}$.

Table 124:
Another preferred group of compounds of formula I corresponds to the general formula

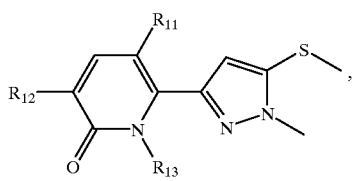

(I$_{124}$)

in which the sets of correlated substituents $R_{11}$, $R_{12}$ and $R_{13}$ are given in Table C, thus disclosing 627 specific compounds of formula I$_{124}$.

Table 125:

Another preferred group of compounds of formula I corresponds to the general formula

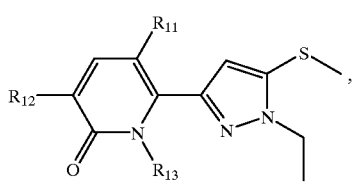

(I$_{125}$)

in which the sets of correlated substituents $R_{11}$, $R_{12}$ and $R_{13}$ are given in Table C, thus disclosing 627 specific compounds of formula I$_{125}$.

Table 126:

Another preferred group of compounds of formula I corresponds to the general formula

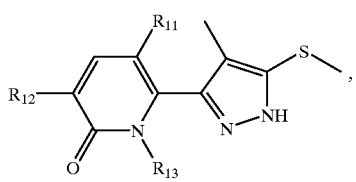

(I$_{126}$)

in which the sets of correlated substituents $R_{11}$, $R_{12}$ and $R_{13}$ are given in Table C, thus disclosing 627 specific compounds of formula I$_{126}$.

Table 127:

Another preferred group of compounds of formula I corresponds to the general formula

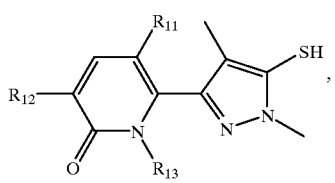

(I$_{127}$)

in which the sets of correlated substituents $R_{11}$, $R_{12}$ and $R_{13}$ are given in Table C, thus disclosing 627 specific compounds of formula I$_{127}$.

Table 128:

Another preferred group of compounds of formula I corresponds to the genera; formula

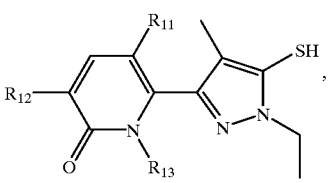

(I$_{128}$)

in which the sets of correlated substituents $R_{11}$, $R_{12}$ and $R_{13}$ are given in Table C, thus disclosing 627 specific compounds of formula I$_{128}$.

Table 129:

Another preferred group of compounds of formula I corresponds to the general formula

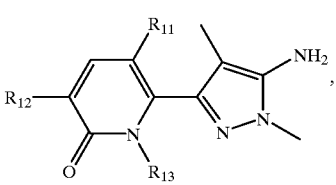

(I$_{129}$)

in which the sets of correlated substituents $R_{11}$, $R_{12}$ and $R_{13}$ are given in Table C, thus disclosing 627 specific compounds of formula I$_{129}$.

Table 130:

Another preferred group of compounds of formula I corresponds to the general formula

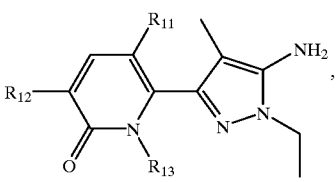

(I$_{130}$)

in which the sets of correlated substituents $R_{11}$, $R_{12}$ and $R_{13}$ are given in Table C, thus disclosing 627 specific compounds of formula I$_{130}$.

Table 131:

Another preferred group of compounds of formula I corresponds to the general formula

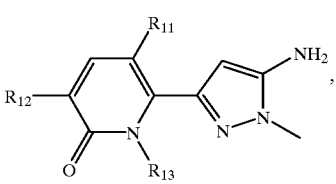

(I$_{131}$)

in which the sets of correlated substituents $R_{11}$, $R_{12}$ and $R_{13}$ are given in Table C, thus disclosing 627 specific compounds of formula I$_{131}$.

Table 132:

Another preferred group of compounds of formula I corresponds to the general formula

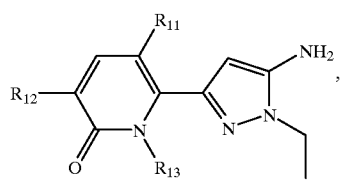

(I₁₃₂)

in which the sets of correlated substituents $R_{11}$, $R_{12}$ and $R_{13}$ are given in Table C, thus disclosing 627 specific compounds of formula $I_{132}$.

Table 133:

Another preferred group of compounds of formula I corresponds to the general formula

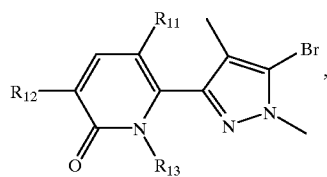

(I₁₃₃)

in which the sets of correlated substituents $R_{11}$, $R_{12}$ and $R_{13}$ are given in Table C, thus disclosing 627 specific compounds of formula $I_{133}$.

Table 134:

Another preferred group of compounds of formula I corresponds to the general formula

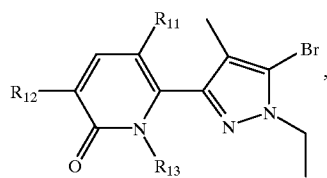

(I₁₃₄)

in which the sets of correlated substituents $R_{11}$, $R_{12}$ and $R_{13}$ are given in Table C. thus disclosing 627 specific compounds of formula $I_{134}$.

Table 135:

Another preferred group of compounds of formula I corresponds to the general formula

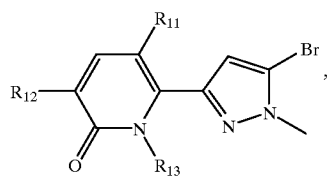

(I₁₃₅)

in which the sets of correlated substituents $R_{11}$, $R_{12}$ and $R_{13}$ are given in Table C, thus disclosing 627 specific compounds of formula $I_{135}$.

Table 136:

Another preferred group of compounds of formula I corresponds to the general formula

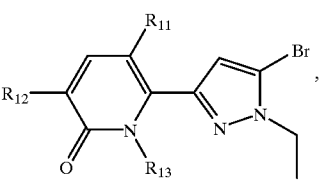

(I₁₃₆)

in which the sets of correlated substituents $R_{11}$, $R_{12}$ and $R_{13}$ are given in Table C, thus disclosing 627 specific compounds of formula $I_{136}$.

Table 137:

Another preferred group of compounds of formula I corresponds to the general formula

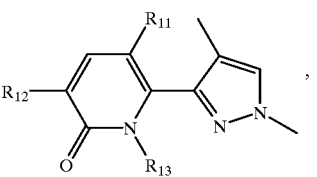

(I₁₃₇)

in which the sets of correlated substituents $R_{11}$, $R_{12}$ and $R_{13}$ are given in Table C, thus disclosing 627 specific compounds of formula $I_{137}$.

Table 138:

Another preferred group of compounds of formula I corresponds to the general formula

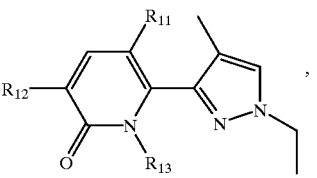

(I₁₃₈)

in which the sets of correlated substituents $R_{11}$, $R_{12}$ and $R_{13}$ are given in Table C, thus disclosing 627 specific compounds of formula $I_{138}$.

Table 139:

Another preferred group of compounds of formula I corresponds to the general formula

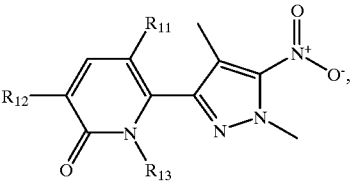

(I₁₃₉)

in which the sets of correlated substituents $R_{11}$, $R_{12}$ and $R_{13}$ are given in Table C, thus disclosing 627 specific compounds of formula $I_{139}$.

Table 140:

Another preferred group of compounds of formula I corresponds to the general formula

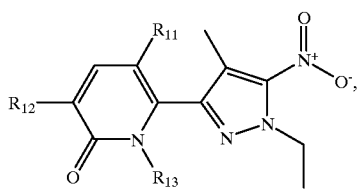

(I$_{140}$)

in which the sets of correlated substituents R$_{11}$, R$_{12}$ and R$_{13}$ are given in Table C, thus disclosing 627 specific compounds of formula I$_{140}$.

Table 141:

Another preferred group of compounds of formula I corresponds to the general formula

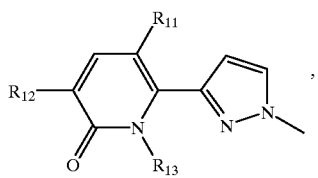

(I$_{141}$)

in which the sets of correlated substituents R$_{11}$, R$_{12}$ and R$_{13}$ are given in Table C, thus disclosing 627 specific compounds of formula I$_{141}$.

Table 142:

Another preferred group of compounds of formula I corresponds to the general formula

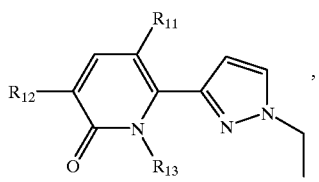

(I$_{142}$)

in which the sets of correlated substituents R$_{11}$, R$_{12}$ and R$_{13}$ are given in Table C, thus disclosing 627 specific compounds of formula I$_{142}$.

TABLE C

| Compd. No. | R$_{11}$ | R$_{12}$ | R$_{13}$ |
|---|---|---|---|
| .001 | H | Cl | CH$_2$CHCH$_2$ |
| .002 | Cl | Cl | CH$_2$CHCH$_2$ |
| .003 | F | Cl | CH$_2$CHCH$_2$ |
| .004 | H | Br | CH$_2$CHCH$_2$ |
| .005 | Cl | Br | CH$_2$CHCH$_2$ |
| .006 | F | Br | CH$_2$CHCH$_2$ |
| .007 | H | I | CH$_2$CHCH$_2$ |
| .008 | Cl | I | CH$_2$CHCH$_2$ |
| .009 | F | I | CH$_2$CHCH$_2$ |
| .010 | H | CH$_3$ | CH$_2$CHCH$_2$ |
| .011 | Cl | CH$_3$ | CH$_2$CHCH$_2$ |
| .012 | F | CH$_3$ | CH$_2$CHCH$_2$ |
| .013 | H | OH | CH$_2$CHCH$_2$ |
| .014 | Cl | OH | CH$_2$CHCH$_2$ |
| .015 | F | OH | CH$_2$CHCH$_2$ |
| .016 | H | OCF$_3$ | CH$_2$CHCH$_2$ |
| .017 | Cl | OCF$_3$ | CH$_2$CHCH$_2$ |
| .018 | F | OCF$_3$ | CH$_2$CHCH$_2$ |

TABLE C-continued

| Compd. No. | R$_{11}$ | R$_{12}$ | R$_{13}$ |
|---|---|---|---|
| .019 | H | CHO | CH$_2$CHCH$_2$ |
| .020 | Cl | CHO | CH$_2$CHCH$_2$ |
| .021 | F | CHO | CH$_2$CHCH$_2$ |
| .022 | H | CHF$_2$ | CH$_2$CHCH$_2$ |
| .023 | Cl | CHF$_2$ | CH$_2$CHCH$_2$ |
| .024 | F | CHF$_2$ | CH$_2$CHCH$_2$ |
| .025 | H | COOH | CH$_2$CHCH$_2$ |
| .026 | Cl | COOH | CH$_2$CHCH$_2$ |
| .027 | F | COOH | CH$_2$CHCH$_2$ |
| .028 | H | COOCH$_2$CH$_3$ | CH$_2$CHCH$_2$ |
| .029 | Cl | COOCH$_2$CH$_3$ | CH$_2$CHCH$_2$ |
| .030 | F | COOCH$_2$CH$_3$ | CH$_2$CHCH$_2$ |
| .031 | H | CN | CH$_2$CHCH$_2$ |
| .032 | Cl | CN | CH$_2$CHCH$_2$ |
| .033 | F | CN | CH$_2$CHCH$_2$ |
| .034 | H | Cl | CH$_2$C$_6$H$_5$ |
| .035 | Cl | Cl | CH$_2$C$_6$H$_5$ |
| .036 | F | Cl | CH$_2$C$_6$H$_5$ |
| .037 | H | Br | CH$_2$C$_6$H$_5$ |
| .038 | Cl | Br | CH$_2$C$_6$H$_5$ |
| .039 | F | Br | CH$_2$C$_6$H$_5$ |
| .040 | H | I | CH$_2$C$_6$H$_5$ |
| .041 | Cl | I | CH$_2$C$_6$H$_5$ |
| .042 | F | I | CH$_2$C$_6$H$_5$ |
| .043 | H | CH$_3$ | CH$_2$C$_6$H$_5$ |
| .044 | Cl | CH$_3$ | CH$_2$C$_6$H$_5$ |
| .045 | F | CH$_3$ | CH$_2$C$_6$H$_5$ |
| .046 | H | OH | CH$_2$C$_6$H$_5$ |
| .047 | Cl | OH | CH$_2$C$_6$H$_5$ |
| .048 | F | OH | CH$_2$C$_6$H$_5$ |
| .049 | H | OCF$_3$ | CH$_2$C$_6$H$_5$ |
| .050 | Cl | OCF$_3$ | CH$_2$C$_6$H$_5$ |
| .051 | F | OCF$_3$ | CH$_2$C$_6$H$_5$ |
| .052 | H | CHO | CH$_2$C$_6$H$_5$ |
| .053 | Cl | CHO | CH$_2$C$_6$H$_5$ |
| .054 | F | CHO | CH$_2$C$_6$H$_5$ |
| .055 | H | CHF$_2$ | CH$_2$C$_6$H$_5$ |
| .056 | Cl | CHF$_2$ | CH$_2$C$_6$H$_5$ |
| .057 | F | CHF$_2$ | CH$_2$C$_6$H$_5$ |
| .058 | H | COOH | CH$_2$C$_6$H$_5$ |
| .059 | Cl | COOH | CH$_2$C$_6$H$_5$ |
| .060 | F | COOH | CH$_2$C$_6$H$_5$ |
| .061 | H | COOCH$_2$CH$_3$ | CH$_2$C$_6$H$_5$ |
| .062 | Cl | COOCH$_2$CH$_3$ | CH$_2$C$_6$H$_5$ |
| .063 | F | COOCH$_2$CH$_3$ | CH$_2$C$_6$H$_5$ |
| .064 | H | CN | CH$_2$C$_6$H$_5$ |
| .065 | Cl | CN | CH$_2$C$_6$H$_5$ |
| .066 | F | CN | CH$_2$C$_6$H$_5$ |
| .067 | H | Cl | CH$_2$CCH |
| .068 | Cl | Cl | CH$_2$CCH |
| .069 | F | Cl | CH$_2$CCH |
| .070 | H | Br | CH$_2$CCH |
| .071 | Cl | Br | CH$_2$CCH |
| .072 | F | Br | CH$_2$CCH |
| .073 | H | I | CH$_2$CCH |
| .074 | Cl | I | CH$_2$CCH |
| .075 | F | I | CH$_2$CCH |
| .076 | H | CH$_3$ | CH$_2$CCH |
| .077 | Cl | CH$_3$ | CH$_2$CCH |
| .078 | F | CH$_3$ | CH$_2$CCH |
| .079 | H | OH | CH$_2$CCH |
| .080 | Cl | OH | CH$_2$CCH |
| .081 | F | OH | CH$_2$CCH |
| .082 | H | OCF$_3$ | CH$_2$CCH |
| .083 | Cl | OCF$_3$ | CH$_2$CCH |
| .084 | F | OCF$_3$ | CH$_2$CCH |
| .085 | H | CHO | CH$_2$CCH |
| .086 | Cl | CHO | CH$_2$CCH |
| .087 | F | CHO | CH$_2$CCH |
| .088 | H | CHF$_2$ | CH$_2$CCH |
| .089 | Cl | CHF$_2$ | CH$_2$CCH |
| .090 | F | CHF$_2$ | CH$_2$CCH |
| .091 | H | COOH | CH$_2$CCH |
| .092 | Cl | COOH | CH$_2$CCH |
| .093 | F | COOH | CH$_2$CCH |
| .094 | H | COOCH$_2$CH$_3$ | CH$_2$CCH |
| .095 | Cl | COOCH$_2$CH$_3$ | CH$_2$CCH |

TABLE C-continued

| Compd. No. | $R_{11}$ | $R_{12}$ | $R_{13}$ |
|---|---|---|---|
| .096 | F | COOCH$_2$CH$_3$ | CH$_2$CCH |
| .097 | H | CN | CH$_2$CCH |
| .098 | Cl | CN | CH$_2$CCH |
| .099 | F | CN | CH$_2$CCH |
| .100 | H | Cl | CH$_2$COOH |
| .101 | Cl | Cl | CH$_2$COOH |
| .102 | F | Cl | CH$_2$COOH |
| .103 | H | Br | CH$_2$COOH |
| .104 | Cl | Br | CH$_2$COOH |
| .105 | F | Br | CH$_2$COOH |
| .106 | H | I | CH$_2$COOH |
| .107 | Cl | I | CH$_2$COOH |
| .108 | F | I | CH$_2$COOH |
| .109 | H | CH$_3$ | CH$_2$COOH |
| .110 | Cl | CH$_3$ | CH$_2$COOH |
| .111 | F | CH$_3$ | CH$_2$COOH |
| .112 | H | OH | CH$_2$COOH |
| .113 | Cl | OH | CH$_2$COOH |
| .114 | F | OH | CH$_2$COOH |
| .115 | H | OCF$_3$ | CH$_2$COOH |
| .116 | Cl | OCF$_3$ | CH$_2$COOH |
| .117 | F | OCF$_3$ | CH$_2$COOH |
| .118 | H | CHO | CH$_2$COOH |
| .119 | Cl | CHO | CH$_2$COOH |
| .120 | F | CHO | CH$_2$COOH |
| .121 | H | CHF$_2$ | CH$_2$COOH |
| .122 | Cl | CHF$_2$ | CH$_2$COOH |
| .123 | F | CHF$_2$ | CH$_2$COOH |
| .124 | H | COOH | CH$_2$COOH |
| .125 | Cl | COOH | CH$_2$COOH |
| .126 | F | COOH | CH$_2$COOH |
| .127 | H | COOCH$_2$CH$_3$ | CH$_2$COOH |
| .128 | Cl | COOCH$_2$CH$_3$ | CH$_2$COOH |
| .129 | F | COOCH$_2$CH$_3$ | CH$_2$COOH |
| .130 | H | CN | CH$_2$COOH |
| .131 | Cl | CN | CH$_2$COOH |
| .132 | F | CN | CH$_2$COOH |
| .133 | H | Cl | CH$_2$COOCH$_3$ |
| .134 | Cl | Cl | CH$_2$COOCH$_3$ |
| .135 | F | Cl | CH$_2$COOCH$_3$ |
| .136 | H | Br | CH$_2$COOCH$_3$ |
| .137 | Cl | Br | CH$_2$COOCH$_3$ |
| .138 | F | Br | CH$_2$COOCH$_3$ |
| .139 | H | I | CH$_2$COOCH$_3$ |
| .140 | Cl | I | CH$_2$COOCH$_3$ |
| .141 | F | I | CH$_2$COOCH$_3$ |
| .142 | H | CH$_3$ | CH$_2$COOCH$_3$ |
| .143 | Cl | CH$_3$ | CH$_2$COOCH$_3$ |
| .144 | F | CH$_3$ | CH$_2$COOCH$_3$ |
| .145 | H | OH | CH$_2$COOCH$_3$ |
| .146 | Cl | OH | CH$_2$COOCH$_3$ |
| .147 | F | OH | CH$_2$COOCH$_3$ |
| .148 | H | OCF$_3$ | CH$_2$COOCH$_3$ |
| .149 | Cl | OCF$_3$ | CH$_2$COOCH$_3$ |
| .150 | F | OCF$_3$ | CH$_2$COOCH$_3$ |
| .151 | H | CHO | CH$_2$COOCH$_3$ |
| .152 | Cl | CHO | CH$_2$COOCH$_3$ |
| .153 | F | CHO | CH$_2$COOCH$_3$ |
| .154 | H | CHF$_2$ | CH$_2$COOCH$_3$ |
| .155 | Cl | CHF$_2$ | CH$_2$COOCH$_3$ |
| .156 | F | CHF$_2$ | CH$_2$COOCH$_3$ |
| .157 | H | COOH | CH$_2$COOCH$_3$ |
| .158 | Cl | COOH | CH$_2$COOCH$_3$ |
| .159 | F | COOH | CH$_2$COOCH$_3$ |
| .160 | H | COOCH$_2$CH$_3$ | CH$_2$COOCH$_3$ |
| .161 | Cl | COOCH$_2$CH$_3$ | CH$_2$COOCH$_3$ |
| .162 | F | COOCH$_2$CH$_3$ | CH$_2$COOCH$_3$ |
| .163 | H | CN | CH$_2$COOCH$_3$ |
| .164 | Cl | CN | CH$_2$COOCH$_3$ |
| .165 | F | CN | CH$_2$COOCH$_3$ |
| .166 | H | Cl | OH |
| .167 | Cl | Cl | OH |
| .168 | F | Cl | OH |
| .169 | H | Br | OH |
| .170 | Cl | Br | OH |
| .171 | F | Br | OH |
| .172 | H | I | OH |
| .173 | Cl | I | OH |
| .174 | F | I | OH |
| .175 | H | CH$_3$ | OH |
| .176 | Cl | CH$_3$ | OH |
| .177 | F | CH$_3$ | OH |
| .178 | H | OH | OH |
| .179 | Cl | OH | OH |
| .180 | F | OH | OH |
| .181 | H | OCF$_3$ | OH |
| .182 | Cl | OCF$_3$ | OH |
| .183 | F | OCF$_3$ | OH |
| .184 | H | CHO | OH |
| .185 | Cl | CHO | OH |
| .186 | F | CHO | OH |
| .187 | H | CHF$_2$ | OH |
| .188 | Cl | CHF$_2$ | OH |
| .189 | F | CHF$_2$ | OH |
| .190 | H | COOH | OH |
| .191 | Cl | COOH | OH |
| .192 | F | COOH | OH |
| .193 | H | COOCH$_2$CH$_3$ | OH |
| .194 | Cl | COOCH$_2$CH$_3$ | OH |
| .195 | F | COCCH$_2$CH$_3$ | OH |
| .196 | H | CN | OH |
| .197 | Cl | CN | OH |
| .198 | F | CN | OH |
| .199 | H | Cl | OCH$_2$CHCH$_2$ |
| .200 | Cl | Cl | OCH$_2$CHCH$_2$ |
| .201 | F | Cl | OCH$_2$CHCH$_2$ |
| .202 | H | Br | OCH$_2$CHCH$_2$ |
| .203 | Cl | Br | OCH$_2$CHCH$_2$ |
| .204 | F | Br | OCH$_2$CHCH$_2$ |
| .205 | H | I | OCH$_2$CHCH$_2$ |
| .206 | Cl | I | OCH$_2$CHCH$_2$ |
| .207 | F | I | OCH$_2$CHCH$_2$ |
| .208 | H | CH$_3$ | OCH$_2$CHCH$_2$ |
| .209 | Cl | CH$_3$ | OCH$_2$CHCH$_2$ |
| .210 | F | CH$_3$ | OCH$_2$CHCH$_2$ |
| .211 | H | OH | OCH$_2$CHCH$_2$ |
| .212 | Cl | OH | OCH$_2$CHCH$_2$ |
| .213 | F | OH | OCH$_2$CHCH$_2$ |
| .214 | H | OCF$_3$ | OCH$_2$CHCH$_2$ |
| .215 | Cl | OCF$_3$ | OCH$_2$CHCH$_2$ |
| .216 | F | OCF$_3$ | OCH$_2$CHCH$_2$ |
| .217 | H | CHO | OCH$_2$CHCH$_2$ |
| .218 | Cl | CHO | OCH$_2$CHCH$_2$ |
| .219 | F | CHO | OCH$_2$CHCH$_2$ |
| .220 | H | CHF$_2$ | OCH$_2$CHCH$_2$ |
| .221 | Cl | CHF$_2$ | OCH$_2$CHCH$_2$ |
| .222 | F | CHF$_2$ | OCH$_2$CHCH$_2$ |
| .223 | H | COOH | OCH$_2$CHCH$_2$ |
| .224 | Cl | COOH | OCH$_2$CHCH$_2$ |
| .225 | F | COOH | OCH$_2$CHCH$_2$ |
| .226 | H | COOCH$_2$CH$_3$ | OCH$_2$CHCH$_2$ |
| .227 | Cl | COOCH$_2$CH$_3$ | OCH$_2$CHCH$_2$ |
| .228 | F | COOCH$_2$CH$_3$ | OCH$_2$CHCH$_2$ |
| .229 | H | CN | OCH$_2$CHCH$_2$ |
| .230 | Cl | CN | OCH$_2$CHCH$_2$ |
| .231 | F | CN | OCH$_2$CHCH$_2$ |
| .232 | H | Cl | OCH$_2$C$_6$H$_5$ |
| .233 | Cl | Cl | OCH$_2$C$_6$H$_5$ |
| .234 | F | Cl | OCH$_2$C$_6$H$_5$ |
| .235 | H | Br | OCH$_2$C$_6$H$_5$ |
| .236 | Cl | Br | OCH$_2$C$_6$H$_5$ |
| .237 | F | Br | OCH$_2$C$_6$H$_5$ |
| .238 | H | I | OCH$_2$C$_6$H$_5$ |
| .239 | Cl | I | OCH$_2$C$_6$H$_5$ |
| .240 | F | I | OCH$_2$C$_6$H$_5$ |
| .241 | H | CH$_3$ | OCH$_2$C$_6$H$_5$ |
| .242 | Cl | CH$_3$ | OCH$_2$C$_6$H$_5$ |
| .243 | F | CH$_3$ | OCH$_2$C$_6$H$_5$ |
| .244 | H | OH | OCH$_2$C$_6$H$_5$ |
| .245 | Cl | OH | OCH$_2$C$_6$H$_5$ |
| .246 | F | OH | OCH$_2$C$_6$H$_5$ |
| .247 | H | OCF$_3$ | OCH$_2$C$_6$H$_5$ |
| .248 | Cl | OCF$_3$ | OCH$_2$C$_6$H$_5$ |
| .249 | F | OCF$_3$ | OCH$_2$C$_6$H$_5$ |

TABLE C-continued

| Compd. No. | $R_{11}$ | $R_{12}$ | $R_{13}$ |
|---|---|---|---|
| .250 | H | CHO | $OCH_2C_6H_5$ |
| .251 | Cl | CHO | $OCH_2C_6H_5$ |
| .252 | F | CHO | $OCH_2C_6H_5$ |
| .253 | H | $CHF_2$ | $OCH_2C_6H_5$ |
| .254 | Cl | $CHF_2$ | $OCH_2C_6H_5$ |
| .255 | F | $CHF_2$ | $OCH_2C_6H_5$ |
| .256 | H | COOH | $OCH_2C_6H_5$ |
| .257 | Cl | COOH | $OCH_2C_6H_5$ |
| .258 | F | COOH | $OCH_2C_6H_5$ |
| .259 | H | $COOCH_2CH_3$ | $OCH_2C_6H_5$ |
| .260 | Cl | $COOCH_2CH_3$ | $OCH_2C_6H_5$ |
| .261 | F | $COOCH_2CH_3$ | $OCH_2C_6H_5$ |
| .262 | H | CN | $OCH_2C_6H_5$ |
| .263 | Cl | CN | $OCH_2C_6H_5$ |
| .264 | F | CN | $OCH_2C_6H_5$ |
| .265 | H | Cl | $OCH_2COOH$ |
| .266 | Cl | Cl | $OCH_2COOH$ |
| .267 | F | Cl | $OCH_2COOH$ |
| .268 | H | Br | $OCH_2COOH$ |
| .269 | Cl | Br | $OCH_2COOH$ |
| .270 | F | Br | $OCH_2COOH$ |
| .271 | H | I | $OCH_2COOH$ |
| .272 | Cl | I | $OCH_2COOH$ |
| .273 | F | I | $OCH_2COOH$ |
| .274 | H | $CH_3$ | $OCH_2COOH$ |
| .275 | Cl | $CH_3$ | $OCH_2COOH$ |
| .276 | F | $CH_3$ | $OCH_2COOH$ |
| .277 | H | OH | $OCH_2COOH$ |
| .278 | Cl | OH | $OCH_2COOH$ |
| .279 | F | OH | $OCH_2COOH$ |
| .280 | H | $OCF_3$ | $OCH_2COOH$ |
| .281 | Cl | $OCF_3$ | $OCH_2COOH$ |
| .282 | F | $OCF_3$ | $OCH_2COOH$ |
| .283 | H | CHO | $OCH_2COOH$ |
| .284 | Cl | CHO | $OCH_2COOH$ |
| .285 | F | CHO | $OCH_2COOH$ |
| .286 | H | $CHF_2$ | $OCH_2COOH$ |
| .287 | Cl | $CHF_2$ | $OCH_2COOH$ |
| .288 | F | $CHF_2$ | $OCH_2COOH$ |
| .289 | H | COOH | $OCH_2COOH$ |
| .290 | Cl | COOH | $OCH_2COOH$ |
| .291 | F | COOH | $OCH_2COOH$ |
| .292 | H | $COOCH_2CH_3$ | $OCH_2COOH$ |
| .293 | Cl | $COOCH_2CH_3$ | $OCH_2COOH$ |
| .294 | F | $COOCH_2CH_3$ | $OCH_2COOH$ |
| .295 | H | CN | $OCH_2COOH$ |
| .296 | Cl | CN | $OCH_2COOH$ |
| .297 | F | CN | $OCH_2COOH$ |
| .298 | H | Cl | $OCH_2COOCH_3$ |
| .299 | Cl | Cl | $OCH_2COOCH_3$ |
| .300 | F | Cl | $OCH_2COOCH_3$ |
| .301 | H | Br | $OCH_2COOCH_3$ |
| .302 | Cl | Br | $OCH_2COOCH_3$ |
| .303 | F | Br | $OCH_2COQCH_3$ |
| .304 | H | I | $OCH_2COOCH_3$ |
| .305 | Cl | I | $OCH_2COOCH_3$ |
| .306 | F | I | $OCH_2COOCH_3$ |
| .307 | H | $CH_3$ | $OCH_2COOCH_3$ |
| .308 | Cl | $CH_3$ | $OCH_2COOCH_3$ |
| .309 | F | $CH_3$ | $OCH_2COOCH_3$ |
| .310 | H | OH | $OCH_2COOCH_3$ |
| .311 | Cl | OH | $OCH_2COOCH_3$ |
| .312 | F | OH | $OCH_2COOCH_3$ |
| .313 | H | $OCF_3$ | $OCH_2COOCH_3$ |
| .314 | Cl | $OCF_3$ | $OCH_2COOCH_3$ |
| .315 | F | $OCF_3$ | $OCH_2COOCH_3$ |
| .316 | H | CHO | $OCH_2COOCH_3$ |
| .317 | Cl | CHO | $OCH_2COOCH_3$ |
| .318 | F | CHO | $OCH_2COOCH_3$ |
| .319 | H | $CHF_2$ | $OCH_2COOCH_3$ |
| .320 | Cl | $CHF_2$ | $OCH_2COOCH_3$ |
| .321 | F | $CHF_2$ | $OCH_2COOCH_3$ |
| .322 | H | COOH | $OCH_2COOCH_3$ |
| .323 | Cl | COOH | $OCH_2COOCH_3$ |
| .324 | F | COOH | $OCH_2COOCH_3$ |
| .325 | H | $COOCH_2CH_3$ | $OCH_2COOCH_3$ |
| .326 | Cl | $COOCH_2CH_3$ | $OCH_2COOCH_3$ |
| .327 | F | $COOCH_2CH_3$ | $OCH_2COOCH_3$ |
| .328 | H | CN | $OCH_2COOCH_3$ |
| .329 | Cl | CN | $OCH_2COOCH_3$ |
| .330 | F | CN | $QCH_2COOCH_3$ |
| .331 | H | Cl | $CH_2CHO$ |
| .332 | Cl | Cl | $CH_2CHO$ |
| .333 | F | Cl | $CH_2CHO$ |
| .334 | H | Br | $CH_2CHO$ |
| .335 | Cl | Br | $CH_2CHO$ |
| .336 | F | Br | $CH_2CHO$ |
| .337 | H | I | $CH_2CHO$ |
| .338 | Cl | I | $CH_2CHO$ |
| .339 | F | I | $CH_2CHO$ |
| .340 | H | $CH_3$ | $CH_2CHO$ |
| .341 | Cl | $CH_3$ | $CH_2CHO$ |
| .342 | F | $CH_3$ | $CH_2CHO$ |
| .343 | H | OH | $CH_2CHO$ |
| .344 | Cl | OH | $CH_2CHO$ |
| .345 | F | OH | $CH_2CHO$ |
| .346 | H | $OCF_3$ | $CH_2CHO$ |
| .347 | Cl | $OCF_3$ | $CH_2CHO$ |
| .348 | F | $OCF_3$ | $CH_2CHO$ |
| .349 | H | CHO | $CH_2CHO$ |
| .350 | Cl | CHO | $CH_2CHO$ |
| .351 | F | CHO | $CH_2CHO$ |
| .352 | H | $CHF_2$ | $CH_2CHO$ |
| .353 | Cl | $CHF_2$ | $CH_2CHO$ |
| .354 | F | $CHF_2$ | $CH_2CHO$ |
| .355 | H | COOH | $CH_2CHO$ |
| .356 | Cl | COOH | $CH_2CHO$ |
| .357 | F | COOH | $CH_2CHO$ |
| .358 | H | $COOCH_2CH_3$ | $CH_2CHO$ |
| .359 | Cl | $COOCH_2CH_3$ | $CH_2CHO$ |
| .360 | F | $COOCH_2CH_3$ | $CH_2CHO$ |
| .361 | H | CN | $CH_2CHO$ |
| .362 | Cl | CN | $CH_2CHO$ |
| .363 | F | CN | $CH_2CHO$ |
| .364 | H | Cl | $OCH_2CHO$ |
| .365 | Cl | Cl | $OCH_2CHO$ |
| .366 | F | Cl | $OCH_2CHO$ |
| .367 | H | Br | $OCH_2CHO$ |
| .368 | Cl | Br | $OCH_2CHO$ |
| .369 | F | Br | $OCH_2CHO$ |
| .370 | H | I | $OCH_2CHO$ |
| .371 | Cl | I | $OCH_2CHO$ |
| .372 | F | I | $OCH_2CHO$ |
| .373 | H | $CH_3$ | $OCH_2CHO$ |
| .374 | Cl | $CH_3$ | $OCH_2CHO$ |
| .375 | F | $CH_3$ | $OCH_2CHO$ |
| .376 | H | OH | $OCH_2CHO$ |
| .377 | Cl | OH | $OCH_2CHO$ |
| .378 | F | OH | $OCH_2CHO$ |
| .379 | H | $OCF_3$ | $OCH_2CHO$ |
| .380 | Cl | $OCF_3$ | $OCH_2CHO$ |
| .381 | F | $OCF_3$ | $OCH_2CHO$ |
| .382 | H | CHO | $OCH_2CHO$ |
| .383 | Cl | CHO | $OCH_2CHO$ |
| .384 | F | CHO | $OCH_2CHO$ |
| .385 | H | $CHF_2$ | $OCH_2CHO$ |
| .386 | Cl | $CHF_2$ | $OCH_2CHO$ |
| .387 | F | $CHF_2$ | $OCH_2CHO$ |
| .388 | H | COOH | $OCH_2CHO$ |
| .389 | Cl | COOH | $OCH_2CHO$ |
| .390 | F | COOH | $OCH_2CHO$ |
| .391 | H | $COOCH_2CH_3$ | $OCH_2CHO$ |
| .392 | Cl | $COOCH_2CH_3$ | $OCH_2CHO$ |
| .393 | F | $COOCH_2CH_3$ | $OCH_2CHO$ |
| .394 | H | CN | $OCH_2CHO$ |
| .395 | Cl | CN | $OCH_2CHO$ |
| .396 | F | CN | $OCH_2CHO$ |
| .397 | H | Cl | $OCH_3$ |
| .398 | Cl | Cl | $OCH_3$ |
| .399 | F | Cl | $OCH_3$ |
| .400 | H | Br | $OCH_3$ |
| .401 | Cl | Br | $OCH_3$ |
| .402 | F | Br | $OCH_3$ |
| .403 | H | I | $OCH_3$ |

TABLE C-continued

| Compd. No. | $R_{11}$ | $R_{12}$ | $R_{13}$ |
|---|---|---|---|
| .404 | Cl | I | $OCH_3$ |
| .405 | F | I | $OCH_3$ |
| .406 | H | $CH_3$ | $OCH_3$ |
| .407 | Cl | $CH_3$ | $OCH_3$ |
| .408 | F | $CH_3$ | $OCH_3$ |
| .409 | H | OH | $OCH_3$ |
| .410 | Cl | OH | $OCH_3$ |
| .411 | F | OH | $OCH_3$ |
| .412 | H | $OCF_3$ | $OCH_3$ |
| .413 | Cl | $OCF_3$ | $OCH_3$ |
| .414 | F | $OCF_3$ | $OCH_3$ |
| .415 | H | CHO | $OCH_3$ |
| .416 | Cl | CHO | $OCH_3$ |
| .417 | F | CHO | $OCH_3$ |
| .418 | H | $CHF_2$ | $OCH_3$ |
| .419 | Cl | $CHF_2$ | $OCH_3$ |
| .420 | F | $CHF_2$ | $OCH_3$ |
| .421 | H | COOH | $OCH_3$ |
| .422 | Cl | COOH | $OCH_3$ |
| .423 | F | COOH | $OCH_3$ |
| .424 | H | $COOCH_2CH_3$ | $OCH_3$ |
| .425 | Cl | $COOCH_2CH_3$ | $OCH_3$ |
| .426 | F | $COOCH_2CH_3$ | $OCH_3$ |
| .427 | H | CN | $OCH_3$ |
| .428 | Cl | CN | $OCH_3$ |
| .429 | F | CN | $OCH_3$ |
| .430 | H | Cl | $CH_2OCH_3$ |
| .431 | Cl | Cl | $CH_2OCH_3$ |
| .432 | F | Cl | $CH_2OCH_3$ |
| .433 | H | Br | $CH_2OCH_3$ |
| .434 | Cl | Br | $CH_2OCH_3$ |
| .435 | F | Br | $CH_2OCH_3$ |
| .436 | H | I | $CH_2OCH_3$ |
| .437 | Cl | I | $CH_2OCH_3$ |
| .438 | F | I | $CH_2OCH_3$ |
| .439 | H | $CH_3$ | $CH_2OCH_3$ |
| .440 | Cl | $CH_3$ | $CH_2OCH_3$ |
| .441 | F | $CH_3$ | $CH_2OCH_3$ |
| .442 | H | OH | $CH_2OCH_3$ |
| .443 | Cl | OH | $CH_2OCH_3$ |
| .444 | F | OH | $CH_2OCH_3$ |
| .445 | H | $OCF_3$ | $CH_2OCH_3$ |
| .446 | Cl | $OCF_3$ | $CH_2OCH_3$ |
| .447 | F | $OCF_3$ | $CH_2OCH_3$ |
| .448 | H | CHO | $CH_2OCH_3$ |
| .449 | Cl | CHO | $CH_2OCH_3$ |
| .450 | F | CHO | $CH_2OCH_3$ |
| .451 | H | $CHF_2$ | $CH_2OCH_3$ |
| .452 | Cl | $CHF_2$ | $CH_2OCH_3$ |
| .453 | F | $CHF_2$ | $CH_2OCH_3$ |
| .454 | H | COOH | $CH_2OCH_3$ |
| .455 | Cl | COOH | $CH_2OCH_3$ |
| .456 | F | COOH | $CH_2OCH_3$ |
| .457 | H | $COOCH_2CH_3$ | $CH_2OCH_3$ |
| .458 | Cl | $COOCH_2CH_3$ | $CH_2OCH_3$ |
| .459 | F | $COOCH_2CH_3$ | $CH_2OCH_3$ |
| .460 | H | CN | $CH_2OCH_3$ |
| .461 | Cl | CN | $CH_2OCH_3$ |
| .462 | F | CN | $CH_2OCH_3$ |
| .463 | H | Cl | $CH_2SCH_3$ |
| .464 | Cl | Cl | $CH_2SCH_3$ |
| .465 | F | Cl | $CH_2SCH_3$ |
| .466 | H | Br | $CH_2SCH_3$ |
| .467 | Cl | Br | $CH_2SCH_3$ |
| .468 | F | Br | $CH_2SCH_3$ |
| .469 | H | I | $CH_2SCH_3$ |
| .470 | Cl | I | $CH_2SCH_3$ |
| .471 | F | I | $CH_2SCH_3$ |
| .472 | H | $CH_3$ | $CH_2SCH_3$ |
| .473 | Cl | $CH_3$ | $CH_2SCH_3$ |
| .474 | F | $CH_3$ | $CH_2SCH_3$ |
| .475 | H | OH | $CH_2SCH_3$ |
| .476 | Cl | OH | $CH_2SCH_3$ |
| .477 | F | OH | $CH_2SCH_3$ |
| .478 | H | $OCF_3$ | $CH_2SCH_3$ |
| .479 | Cl | $OCF_3$ | $CH_2SCH_3$ |
| .480 | F | $OCF_3$ | $CH_2SCH_3$ |
| .481 | H | CHO | $CH_2SCH_3$ |
| .482 | Cl | CHO | $CH_2SCH_3$ |
| .483 | F | CHO | $CH_2SCH_3$ |
| .484 | H | $CHF_2$ | $CH_2SCH_3$ |
| .485 | Cl | $CHF_2$ | $CH_2SCH_3$ |
| .486 | F | $CHF_2$ | $CH_2SCH_3$ |
| .487 | H | COOH | $CH_2SCH_3$ |
| .488 | Cl | COOH | $CH_2SCH_3$ |
| .489 | F | COOH | $CH_2SCH_3$ |
| .490 | H | $COOCH_2CH_3$ | $CH_2SCH_3$ |
| .491 | Cl | $COOCH_2CH_3$ | $CH_2SCH_3$ |
| .492 | F | $COOCH_2CH_3$ | $CH_2SCH_3$ |
| .493 | H | CN | $CH_2SCH_3$ |
| .494 | Cl | CN | $CH_2SCH_3$ |
| .495 | F | CN | $CH_2SCH_3$ |
| .496 | H | Cl | $OCH_2OCH_3$ |
| .497 | Cl | Cl | $OCH_2OCH_3$ |
| .498 | F | Cl | $OCH_2OCH_3$ |
| .499 | H | Br | $OCH_2OCH_3$ |
| .500 | Cl | Br | $OCH_2OCH_3$ |
| .501 | F | Br | $OCH_2OCH_3$ |
| .502 | H | I | $OCH_2OCH_3$ |
| .503 | Cl | I | $OCH_2OCH_3$ |
| .504 | F | I | $OCH_2OCH_3$ |
| .505 | H | $CH_3$ | $OCH_2OCH_3$ |
| .506 | Cl | $CH_3$ | $OCH_2OCH_3$ |
| .507 | F | $CH_3$ | $OCH_2OCH_3$ |
| .508 | H | OH | $OCH_2OCH_3$ |
| .509 | Cl | OH | $OCH_2OCH_3$ |
| .510 | F | OH | $OCH_2OCH_3$ |
| .511 | H | $OCF_3$ | $OCH_2OCH_3$ |
| .512 | Cl | $OCF_3$ | $OCH_2OCH_3$ |
| .513 | F | $OCF_3$ | $OCH_2OCH_3$ |
| .514 | H | CHO | $OCH_2OCH_3$ |
| .515 | Cl | CHO | $OCH_2OCH_3$ |
| .516 | F | CHO | $OCH_2OCH_3$ |
| .517 | H | $CHF_2$ | $OCH_2OCH_3$ |
| .518 | Cl | $CHF_2$ | $OCH_2OCH_3$ |
| .519 | F | $CHF_2$ | $OCH_2OCH_3$ |
| .520 | H | COOH | $OCH_2OCH_3$ |
| .521 | Cl | COOH | $OCH_2OCH_3$ |
| .522 | F | COOH | $OCH_2OCH_3$ |
| .523 | H | $COOCH_2CH_3$ | $OCH_2OCH_3$ |
| .524 | Cl | $COOCH_2CH_3$ | $OCH_2OCH_3$ |
| .525 | F | $COOCH_2CH_3$ | $OCH_2OCH_3$ |
| .526 | H | CN | $OCH_2OCH_3$ |
| .527 | Cl | CN | $OCH_2OCH_3$ |
| .528 | F | CN | $OCH_2OCH_3$ |
| .529 | H | Cl | $OCH_2SCH_3$ |
| .530 | Cl | Cl | $OCH_2SCH_3$ |
| .531 | F | Cl | $OCH_2SCH_3$ |
| .532 | H | Br | $OCH_2SCH_3$ |
| .533 | Cl | Br | $OCH_2SCH_3$ |
| .534 | F | Br | $OCH_2SCH_3$ |
| .535 | H | I | $OCH_2SCH_3$ |
| .536 | Cl | I | $OCH_2SCH_3$ |
| .537 | F | I | $OCH_2SCH_3$ |
| .538 | H | $CH_3$ | $OCH_2SCH_3$ |
| .539 | Cl | $CH_3$ | $OCH_2SCH_3$ |
| .540 | F | $CH_3$ | $OCH_2SCH_3$ |
| .541 | H | OH | $OCH_2SCH_3$ |
| .542 | Cl | OH | $OCH_2SCH_3$ |
| .543 | F | OH | $OCH_2SCH_3$ |
| .544 | H | $OCF_3$ | $OCH_2SCH_3$ |
| .545 | Cl | $OCF_3$ | $OCH_2SCH_3$ |
| .546 | F | $OCF_3$ | $OCH_2SCH_3$ |
| .547 | H | CHO | $OCH_2SCH_3$ |
| .548 | Cl | CHO | $OCH_2SCH_3$ |
| .549 | F | CHO | $OCH_2SCH_3$ |
| .550 | H | $CHF_2$ | $OCH_2SCH_3$ |
| .551 | Cl | $CHF_2$ | $OCH_2SCH_3$ |
| .552 | F | $CHF_2$ | $OCH_2SCH_3$ |
| .553 | H | COOH | $OCH_2SCH_3$ |
| .554 | Cl | COOH | $OCH_2SCH_3$ |
| .555 | F | COOH | $OCH_2SCH_3$ |
| .556 | H | $COOCH_2CH_3$ | $OCH_2SCH_3$ |
| .557 | Cl | $COOCH_2CH_3$ | $OCH_2SCH_3$ |

TABLE C-continued

| Compd. No. | $R_{11}$ | $R_{12}$ | $R_{13}$ |
|---|---|---|---|
| .558 | F | COOCH$_2$CH$_3$ | OCH$_2$SCH$_3$ |
| .559 | H | CN | OCH$_2$SCH$_3$ |
| .560 | Cl | CN | OCH$_2$SCH$_3$ |
| .561 | F | CN | OCH$_2$SCH$_3$ |
| .562 | H | Cl | OCH$_2$CH$_2$CN |
| .563 | Cl | Cl | OCH$_2$CH$_2$CN |
| .564 | F | Cl | OCH$_2$CH$_2$CN |
| .565 | H | Br | OCH$_2$CH$_2$CN |
| .566 | Cl | Br | OCH$_2$CH$_2$CN |
| .567 | F | Br | OCH$_2$CH$_2$CN |
| .568 | H | I | OCH$_2$CH$_2$CN |
| .569 | Cl | I | OCH$_2$CH$_2$CN |
| .570 | F | I | OCH$_2$CH$_2$CN |
| .571 | H | CH$_3$ | OCH$_2$CH$_2$CN |
| .572 | Cl | CH$_3$ | OCH$_2$CH$_2$CN |
| .573 | F | CH$_3$ | OCH$_2$CH$_2$CN |
| .574 | H | OH | OCH$_2$CH$_2$CN |
| .575 | Cl | OH | OCH$_2$CH$_2$CN |
| .576 | F | OH | OCH$_2$CH$_2$CN |
| .577 | H | OCF$_3$ | OCH$_2$CH$_2$CN |
| .578 | Cl | OCF$_3$ | OCH$_2$CH$_2$CN |
| .579 | F | OCF$_3$ | OCH$_2$CH$_2$CN |
| .580 | H | CHO | OCH$_2$CH$_2$CN |
| .581 | Cl | CHO | OCH$_2$CH$_2$CN |
| .582 | F | CHO | OCH$_2$CH$_2$CN |
| .583 | H | CHF$_2$ | OCH$_2$CH$_2$CN |
| .584 | Cl | CHF$_2$ | OCH$_2$CH$_2$CN |
| .585 | F | CHF$_2$ | OCH$_2$CH$_2$CN |
| .586 | H | COOH | OCH$_2$CH$_2$CN |
| .587 | Cl | COOH | OCH$_2$CH$_2$CN |
| .588 | F | COOH | OCH$_2$CH$_2$CN |
| .589 | H | COOCH$_2$CH$_3$ | OCH$_2$CH$_2$CN |
| .590 | Cl | COOCH$_2$CH$_3$ | OCH$_2$CH$_2$CN |
| .591 | F | COOCH$_2$CH$_3$ | OCH$_2$CH$_2$CN |
| .592 | H | CN | OCH$_2$CH$_2$CN |
| .593 | Cl | CN | OCH$_2$CH$_2$CN |
| .594 | F | CN | OCH$_2$CH$_2$CN |
| .595 | H | Cl | CH$_2$CH$_2$CN |
| .596 | Cl | Cl | CH$_2$CH$_2$CN |
| .597 | F | Cl | CH$_2$CH$_2$CN |
| .598 | H | Br | CH$_2$CH$_2$CN |
| .599 | Cl | Br | CH$_2$CH$_2$CN |
| .600 | F | Br | CH$_2$CH$_2$CN |
| .601 | H | I | CH$_2$CH$_2$CN |
| .602 | Cl | I | CH$_2$CH$_2$CN |
| .603 | F | I | CH$_2$CH$_2$CN |
| .604 | H | CH$_3$ | CH$_2$CH$_2$CN |
| .605 | Cl | CH$_3$ | CH$_2$CH$_2$CN |
| .606 | F | CH$_3$ | CH$_2$CH$_2$CN |
| .607 | H | OH | CH$_2$CH$_2$CN |
| .608 | Cl | OH | CH$_2$CH$_2$CN |
| .609 | F | OH | CH$_2$CH$_2$CN |
| .610 | H | OCF$_3$ | CH$_2$CH$_2$CN |
| .611 | Cl | OCF$_3$ | CH$_2$CH$_2$CN |
| .612 | F | OCF$_3$ | CH$_2$CH$_2$CN |
| .613 | H | CHO | CH$_2$CH$_2$CN |
| .614 | Cl | CHO | CH$_2$CH$_2$CN |
| .615 | F | CHO | CH$_2$CH$_2$CN |
| .616 | H | CHF$_2$ | CH$_2$CH$_2$CN |
| .617 | Cl | CHF$_2$ | CH$_2$CH$_2$CN |
| .618 | F | CHF$_2$ | CH$_2$CH$_2$CN |
| .619 | H | COOH | CH$_2$CH$_2$CN |
| .620 | Cl | COOH | CH$_2$CH$_2$CN |
| .621 | F | COOH | CH$_2$CH$_2$CN |
| .622 | H | COOCH$_2$CH$_3$ | CH$_2$CH$_2$CN |
| .623 | Cl | COOCH$_2$CH$_3$ | CH$_2$CH$_2$CN |
| .624 | F | COOCH$_2$CH$_3$ | CH$_2$CH$_2$CN |
| .625 | H | CN | CH$_2$CH$_2$CN |
| .626 | Cl | CN | CH$_2$CH$_2$CN |
| .627 | F | CN | CH$_2$CH$_2$CN |

Table 143:

A preferred group of compounds of formula I corresponds to the general formula

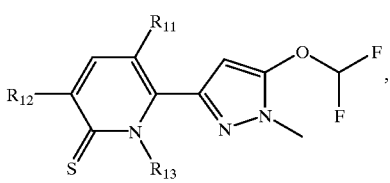

(I$_{143}$)

in which the sets of correlated substituents $R_{11}$, $R_{12}$ and $R_{13}$ are given in Table D, thus disclosing 627 specific compounds of formula I$_{143}$.

Table 144:

Another preferred group of compounds of formula I corresponds to the general formula

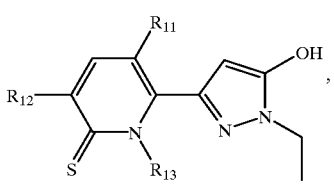

(I$_{144}$)

in which the sets of correlated substituents $R_{11}$, $R_{12}$ and $R_{13}$ are given in Table D, thus disclosing 627 specific compounds of formula I$_{144}$.

Table 145:

Another preferred group of compounds of formula I corresponds to the general formula (I$_{145}$)

in which the sets of correlated substituents $R_{11}$, $R_{12}$ and $R_{13}$ are given in Table D, thus disclosing 627 specific compounds of formula I$_{145}$.

Table 146:

Another preferred group of compounds of formula I corresponds to the general formula

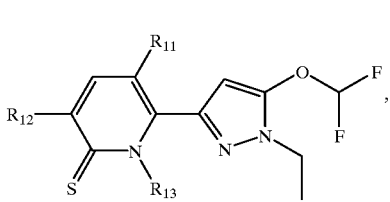

(I$_{146}$)

in which the sets of correlated substituents $R_{11}$, $R_{12}$ and $R_{13}$ are given in Table D, thus disclosing 627 specific compounds of formula I$_{146}$.

Table 147:

Another preferred group of compounds of formula I corresponds to the general formula

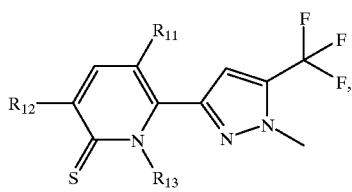

($I_{147}$)

in which the sets of correlated substituents $R_{11}$, $R_{12}$ and $R_{13}$ are given in Table D, thus disclosing 627 specific compounds of formula $I_{147}$.

Table 148:
Another preferred group of compounds of formula I corresponds to the general formula

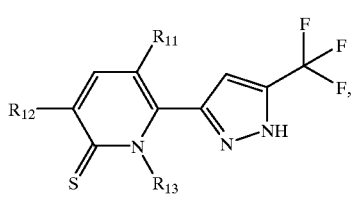

($I_{148}$)

in which the sets of correlated substituents $R_{11}$, $R_{12}$ and $R_{13}$ are given in Table D, thus disclosing 627 specific compounds of formula $I_{148}$.

Table 149:
Another preferred group of compounds of formula I corresponds to the general formula

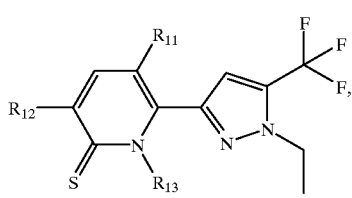

($I_{149}$)

in which the sets of correlated substituents $R_{11}$, $R_{12}$ and $R_{13}$ are given in Table D, thus disclosing 627 specific compounds of formula $I_{149}$.

Table 150:
Another preferred group of compounds of formula I corresponds to the general formula

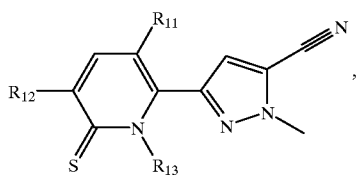

($I_{150}$)

in which the sets of correlated substituents $R_{11}$, $R_{12}$ and $R_{13}$ are given in Table D, thus disclosing 627 specific compounds of formula $I_{150}$.

Table 151:
Another preferred group of compounds of formula I corresponds to the general formula

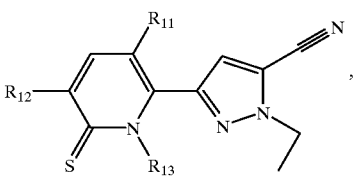

($I_{151}$)

in which the sets of correlated substituents $R_{11}$, $R_{12}$ and $R_{13}$ are given in Table D, thus disclosing 627 specific compounds of formula $I_{115}$.

Table 152:
Another preferred group of compounds of formula I corresponds to the general formula

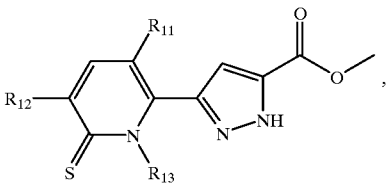

($I_{152}$)

in which the sets of correlated substituents $R_{11}$, $R_{12}$ and $R_{13}$ are given in Table D, thus disclosing 627 specific compounds of formula $I_{152}$.

Table 153:
Another preferred group of compounds of formula I corresponds to the general formula

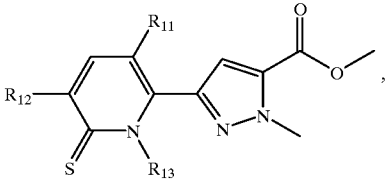

($I_{153}$)

in which the sets of correlated substituents $R_{11}$, $R_{12}$ and $R_{13}$ are given in Table D, thus disclosing 627 specific compounds of formula $I_{153}$.

Table 154:
Another preferred group of compounds of formula I corresponds to the general formula

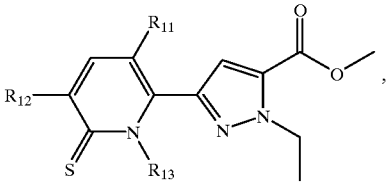

($I_{154}$)

in which the sets of correlated substituents $R_{11}$, $R_{12}$ and $R_{13}$ are given in Table D, thus disclosing 627 specific compounds of formula $I_{154}$.

Table 155:
Another preferred group of compounds of formula I corresponds to the general formula

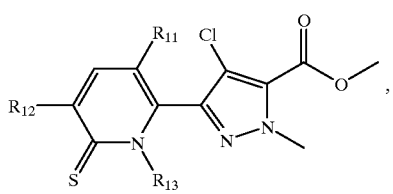
($I_{155}$)

in which the sets of correlated substituents $R_{11}$, $R_{12}$ and $R_{13}$ are given in Table D, thus disclosing 627 specific compounds of formula $I_{155}$.

Table 156:
Another preferred group of compounds of formula I corresponds to the general formula

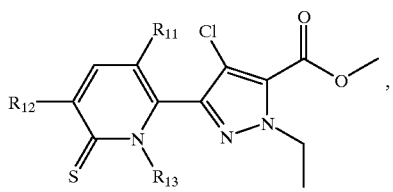
($I_{156}$)

in which the sets of correlated substituents $R_{11}$, $R_{12}$ and $R_{13}$ are given in Table D, thus disclosing 627 specific compounds of formula $I_{156}$.

Table 157:
Another preferred group of compounds of formula I corresponds to the general formula

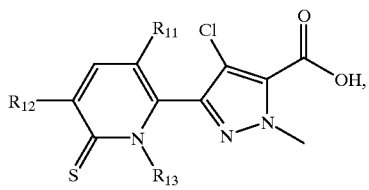
($I_{157}$)

in which the sets of correlated substituents $R_{11}$, $R_{12}$ and $R_{13}$ are given in Table D, thus disclosing 327 specific compounds of formula $I_{117}$.

Table 158:
Another preferred group of compounds of formula I corresponds to the general formula

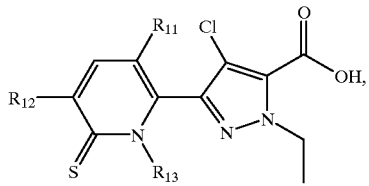
($I_{158}$)

in which the sets of correlated substituents $R_{11}$, $R_{12}$ and $R_{13}$ are given in Table D, thus disclosing 627 specific compounds of formula $I_{158}$.

Table 159:
Another preferred group of compounds of formula I corresponds to the general formula

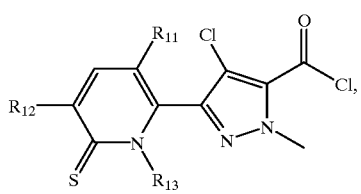
($I_{159}$)

in which the sets of correlated substituents $R_{11}$, $R_{12}$ and $R_{13}$ are given in Table D, thus disclosing 627 specific compounds of formula $I_{159}$.

Table 160:
Another preferred group of compounds of formula I corresponds to the general formula

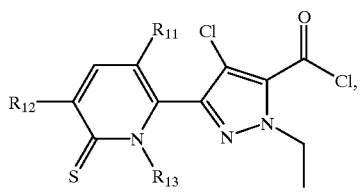
($I_{160}$)

in which the sets of correlated substituents $R_{11}$, $R_{12}$ and $R_{13}$ are given in Table D, thus disclosing 627 specific compounds of formula $I_{160}$.

Table 161:
Another preferred group of compounds of formula I corresponds to the general formula

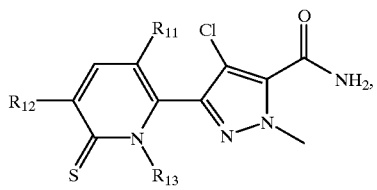
($I_{161}$)

in which the sets of correlated substituents $R_{11}$, $R_{12}$ and $R_{13}$ are given in Table D, thus disclosing 627 specific compounds of formula $I_{161}$.

Table 162:
Another preferred group of compounds of formula I corresponds to the general formula

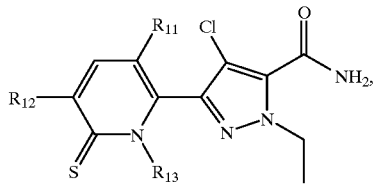
($I_{162}$)

in which the sets of correlated substituents $R_{11}$, $R_{12}$ and $R_{13}$ are given in Table D, thus disclosing 627 specific compounds of formula $I_{162}$.

Table 163:
Another preferred group of compounds of formula I corresponds to the general formula

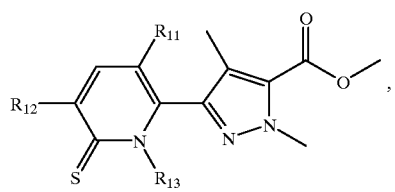

(I₁₆₃)

in which the sets of correlated substituents $R_{11}$, $R_{12}$ and $R_{13}$ are given in Table D, thus disclosing 627 specific compounds of formula $I_{163}$.

Table 164:

Another preferred group of compounds of formula I corresponds to the general formula

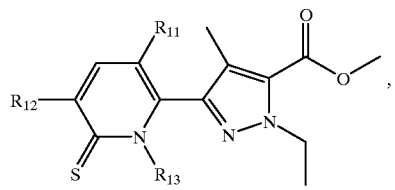

(I₁₆₄)

in which the sets of correlated substituents $R_{11}$, $R_{12}$ and $R_{13}$ are given in Table D, thus disclosing 627 specific compounds of formula $I_{164}$.

Table 165:

Another preferred group of compounds of formula I corresponds to the general formula

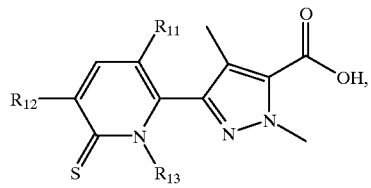

(I₁₆₅)

in which the sets of correlated substituents $R_{11}$, $R_{12}$ and $R_{13}$ are given in Table D, thus disclosing 627 specific compounds of formula $I_{165}$.

Table 166:

Another preferred group of compounds of formula I corresponds to the general formula

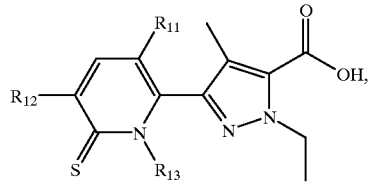

(I₁₆₆)

in which the sets of correlated substituents $R_{11}$, $R_{12}$ and $R_{13}$ are given in Table D, thus disclosing 627 specific compounds of formula $I_{166}$.

Table 167:

Another preferred group of compounds of formula I corresponds to the general formula

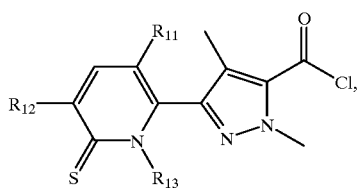

(I₁₆₇)

in which the sets of correlated substituents $R_{11}$, $R_{12}$ and $R_{13}$ are given in Table D, thus disclosing 627 specific compounds of formula $I_{167}$.

Table 168:

Another preferred group of compounds of formula I corresponds to the general formula

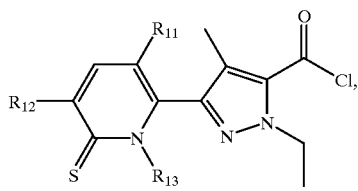

(I₁₆₈)

in which the sets of correlated substituents $R_{11}$, $R_{12}$ and $R_{13}$ are given in Table D, thus disclosing 627 specific compounds of formula $I_{168}$.

Table 169:

Another preferred group of compounds of formula I corresponds to the general formula

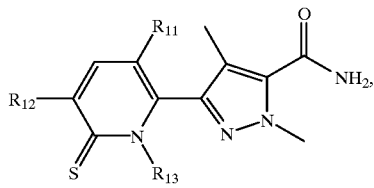

(I₁₆₉)

in which the sets of correlated substituents $R_{11}$, $R_{12}$ and $R_{13}$ are given in Table D, thus disclosing 627 specific compounds of formula $I_{169}$.

Table 170:

Another preferred group of compounds of formula I corresponds to the general formula

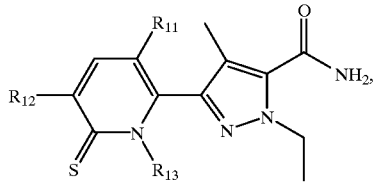

(I₁₇₀)

in which the sets of correlated substituents $R_{11}$, $R_{12}$ and $R_{13}$ are given in Table D, thus disclosing 627 specific compounds of formula $I_{170}$.

Table 171:

Another preferred group of compounds of formula I corresponds to the general formula

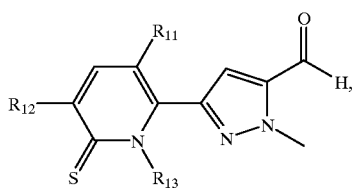
(I$_{171}$)

in which the sets of correlated substituents R$_{11}$, R$_{12}$ and R$_{13}$ are given in Table D, thus disclosing 627 specific compounds of formula I$_{171}$.

Table 172:

Another preferred group of compounds of formula I corresponds to the general formula

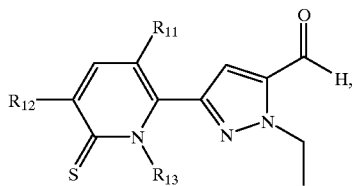
(I$_{172}$)

in which the sets of correlated substituents R$_{11}$, R$_{12}$ and R$_{13}$ are given in Table D, thus disclosing 627 specific compounds of formula I$_{172}$.

Table 173:

Another preferred group of compounds of formula I corresponds to the general formula

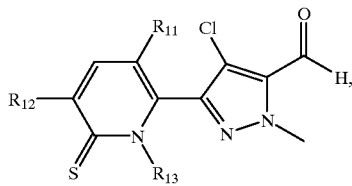
(I$_{173}$)

in which the sets of correlated substituents R$_{11}$, R$_{12}$ and R$_{13}$ are given in Table D, thus disclosing 627 specific compounds of formula I$_{173}$.

Table 174:

Another preferred group of compounds of formula I corresponds to the general formula

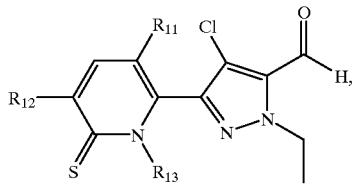
(I$_{174}$)

in which the sets of correlated substituents R$_{11}$, R$_{12}$ and R$_{13}$ are given in Table D, thus disclosing 627 specific compounds of formula I$_{174}$.

Table 175:

Another preferred group of compounds of formula I corresponds to the general formula

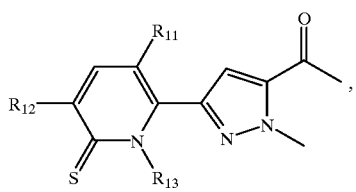
(I$_{175}$)

in which the sets of correlated substituents R$_{11}$, R$_{12}$ and R$_{13}$ are given in Table D, thus disclosing 627 specific compounds of formula I$_{175}$.

Table 176:

Another preferred group of compounds of formula I corresponds to the general formula

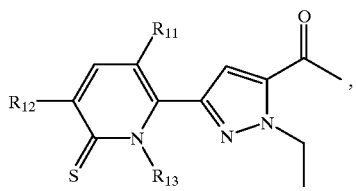
(I$_{176}$)

in which the sets of correlated substituents R$_{11}$, R$_{12}$ and R$_{13}$ are given in Table D, thus disclosing 627 specific compounds of formula I$_{176}$.

Table 177:

Another preferred group of compounds of formula I corresponds to the general formula

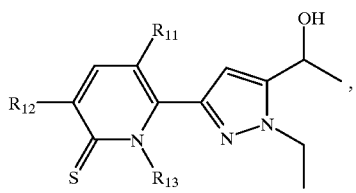
(I$_{177}$)

in which the sets of correlated substituents R$_{11}$, R$_{12}$ and R$_{13}$ are given in Table D, thus disclosing 627 specific compounds of formula I$_{177}$.

Table 178:

Another preferred group of compounds of formula I corresponds to the general formula

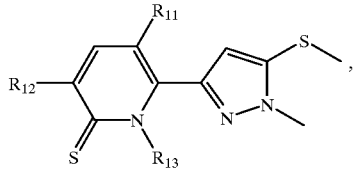
(I$_{178}$)

in which the rets of correlated substituents R$_{11}$, R$_{12}$ and R$_{13}$ are given in Table D, thus disclosing 627 specific compounds of formula I$_{178}$.

Table 179:

Another preferred group of compounds of formula I corresponds to the general formula

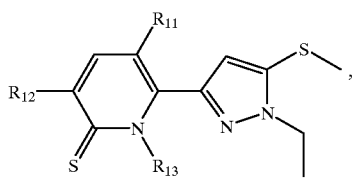

(I₁₇₉)

in which the sets of correlated substituents $R_{11}$, $R_{12}$ and $R_{13}$ are given in Table D, thus disclosing 627 specific compounds of formula $I_{179}$.

Table 180:

Another preferred group of compounds of formula I corresponds to the general formula

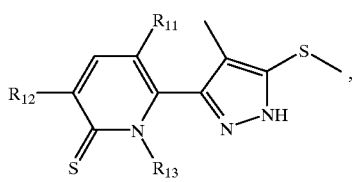

(I₁₈₀)

in which the sets of correlated substituents $R_{11}$, $R_{12}$ and $R_{13}$ are given in Table D, thus disclosing 627 specific compounds of formula $I_{180}$.

Table 181:

Another preferred group of compounds of formula I corresponds to the general formula

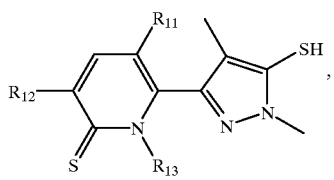

(I₁₈₁)

in which the sets of correlated substituents $R_{11}$, $R_{12}$ and $R_{13}$ ate given in Table D, thus disclosing 627 specific compounds of formula $I_{181}$.

Table 182:

Another preferred group of compounds of formula I corresponds to the general formula

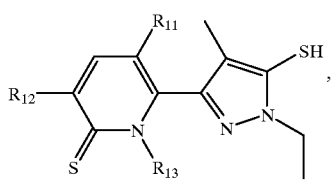

(I₁₈₂)

in which the sets of correlated substituents $R_{11}$, $R_{12}$ and $R_{13}$ are given in Table D, thus disclosing 627 specific compounds of formula $I_{182}$.

Table 183:

Another preferred group of compounds of formula I corresponds to the general formula

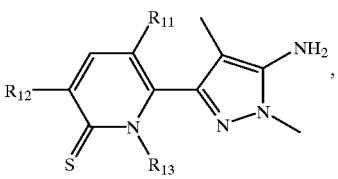

(I₁₈₃)

in which the sets of correlated substituents $R_{11}$, $R_{12}$ and $R_{13}$ are given in Table D, thus disclosing 627 specific compounds of formula $I_{183}$.

Table 184:

Another preferred group of compounds of formula I corresponds to the general formula

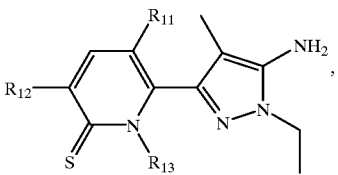

(I₁₈₄)

in which the sets of correlated substituents $R_{11}$, $R_{12}$ and $R_{13}$ are given in Table D, thus disclosing 627 specific compounds of formula $I_{184}$.

Table 185:

Another preferred group of compounds of formula I corresponds to the general formula

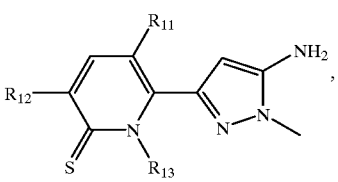

(I₁₈₅)

in which the sets of correlated substituents $R_{11}$, $R_{12}$ and $R_{13}$ are given in Table D, thus disclosing 627 specific compounds of formula $I_{185}$.

Table 186:

Another preferred group of compounds of formula I corresponds to the general formula

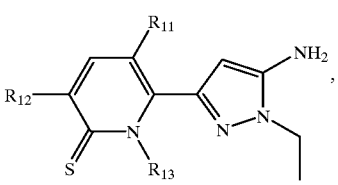

(I₁₈₆)

in which the sets of correlated substituents $R_{11}$, $R_{12}$ and $R_{13}$ are given in Table D, thus disclosing 627 specific compounds of formula $I_{186}$.

Table 187:

Another preferred group of compounds of formula I corresponds to the general formula

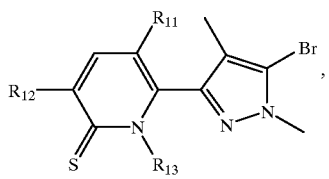
(I₁₈₇)

in which the sets of correlated substituents $R_{11}$, $R_{12}$ and $R_{13}$ are given in Table D, thus disclosing 627 specific compounds of formula $I_{187}$.

Table 188:

Another preferred group of compounds of formula I corresponds to the general formula

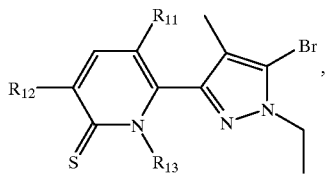
(I₁₈₈)

in which the sets of correlated substituents $R_{11}$, $R_{12}$ and $R_{13}$ are given in Table D, thus disclosing 627 specific compounds of formula $I_{188}$.

Table 189:

Another preferred group of compounds of formula I corresponds to the general formula

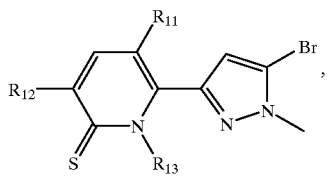
(I₁₈₉)

in which the sets of correlated substituents $R_{11}$, $R_{12}$ and $R_{13}$ are given in Table D, thus disclosing 627 specific compounds of formula $I_{189}$.

Table 190:

Another preferred group of compounds of formula I corresponds to the general formula

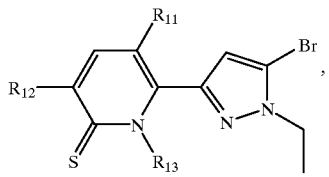
(I₁₉₀)

in which the sets of correlated substituents $R_{11}$, $R_{12}$ and $R_{13}$ are given in Table D, thus disclosing 627 specific compounds of formula $I_{190}$.

Table 191:

Another preferred group of compounds of formula I corresponds to the general formula

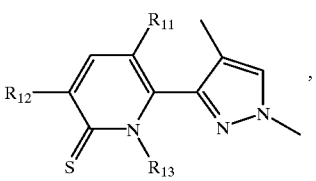
(I₁₉₁)

in which the sets of correlated substituents $R_{11}$, $R_{12}$ and $R_{13}$ are given in Table D, thus disclosing 627 specific compounds of formula $I_{191}$.

Table 192:

Another preferred group of compounds of formula I corresponds to the general formula

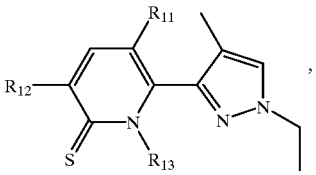
(I₁₉₂)

in which the sets of correlated substituents $R_{11}$, $R_{12}$ and $R_{13}$ are given in Table D, thus disclosing 627 specific compounds of formula $I_{192}$.

Table 193:

Another preferred group of compounds of formula I corresponds to the general formula

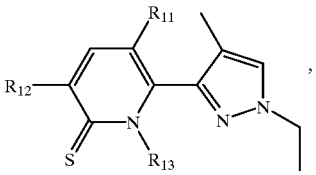
(I₁₉₃)

in which the sets of correlated substituents $R_{11}$, $R_{12}$ and $R_{13}$ are given in Table D, thus disclosing 627 specific compounds of formula $I_{193}$.

Table 194:

Another preferred group of compounds of formula I corresponds to the general formula

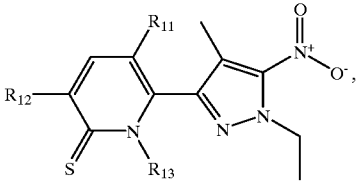
(I₁₉₄)

in which the sets of correlated substituents $R_{11}$, $R_{12}$ and $R_{13}$ are given in Table D, thus disclosing 627 specific compounds of formula $I_{194}$.

Table 195:

Another preferred group of compounds of formula I corresponds to the general formula

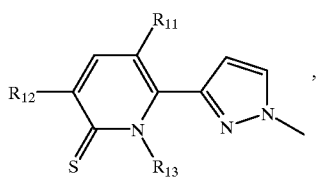

(I$_{195}$)

in which the sets of correlated substituents $R_{11}$, $R_{12}$ and $R_{13}$ are given in Table D, thus disclosing 627 specific compounds of formula I$_{195}$.

Table 196:

Another preferred group of compounds of formula I corresponds to the general formula

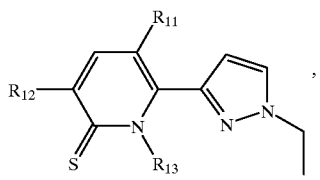

(I$_{196}$)

in which the sets of correlated substituents $R_{11}$, $R_{12}$ and $R_{13}$ are given in Table D, thus disclosing 627 specific compounds of formula I$_{196}$.

TABLE D

| Compd. No. | $R_{11}$ | $H_{12}$ | $R_{13}$ |
|---|---|---|---|
| .001 | H | Cl | CH$_2$CHCH$_2$ |
| .002 | Cl | Cl | CH$_2$CHCH$_2$ |
| .003 | F | Cl | CH$_2$CHCH$_2$ |
| .004 | H | Br | CH$_2$CHCH$_2$ |
| .005 | Cl | Br | CH$_2$CHCH$_2$ |
| .006 | F | Br | CH$_2$CHCH$_2$ |
| .007 | H | I | CH$_2$CHCH$_2$ |
| .008 | Cl | I | CH$_2$CHCH$_2$ |
| .009 | F | I | CH$_2$CHCH$_2$ |
| .010 | H | CH$_3$ | CH$_2$CHCH$_2$ |
| .011 | Cl | CH$_3$ | CH$_2$CHCH$_2$ |
| .012 | F | CH$_3$ | CH$_2$CHCH$_2$ |
| .013 | H | OH | CH$_2$CHCH$_2$ |
| .014 | Cl | OH | CH$_2$CHCH$_2$ |
| .015 | F | OH | CH$_2$CHCH$_2$ |
| .016 | H | OCF$_3$ | CH$_2$CHCH$_2$ |
| .017 | Cl | OCF$_3$ | CH$_2$CHCH$_2$ |
| .018 | F | OCF$_3$ | CH$_2$CHCH$_2$ |
| .019 | H | CHO | CH$_2$CHCH$_2$ |
| .020 | Cl | CHO | CH$_2$CHCH$_2$ |
| .021 | F | CHO | CH$_2$CHCH$_2$ |
| .022 | H | CHF$_2$ | CH$_2$CHCH$_2$ |
| .023 | Cl | CHF$_2$ | CH$_2$CHCH$_2$ |
| .024 | F | CHF$_2$ | CH$_2$CHCH$_2$ |
| .025 | H | COOH | CH$_2$CHCH$_2$ |
| .026 | Cl | COOH | CH$_2$CHCH$_2$ |
| .027 | F | COOH | CH$_2$CHCH$_2$ |
| .028 | H | COOCH$_2$CH$_3$ | CH$_2$CHCH$_2$ |
| .029 | Cl | COOCH$_2$CH$_3$ | CH$_2$CHCH$_2$ |
| .030 | F | COOCH$_2$CH$_3$ | CH$_2$CHCH$_2$ |
| .031 | H | CN | CH$_2$CHCH$_2$ |
| .032 | Cl | CN | CH$_2$CHCH$_2$ |
| .033 | F | CN | CH$_2$CHCH$_2$ |
| .034 | H | Cl | CH$_2$C$_6$H$_5$ |
| .035 | Cl | Cl | CH$_2$C$_6$H$_5$ |
| .036 | F | Cl | CH$_2$C$_6$H$_5$ |
| .037 | H | Br | CH$_2$C$_6$H$_5$ |
| .038 | Cl | Br | CH$_2$C$_6$H$_5$ |
| .039 | F | Br | CH$_2$C$_6$H$_5$ |
| .040 | H | I | CH$_2$C$_6$H$_5$ |
| .041 | Cl | I | CH$_2$C$_6$H$_5$ |
| .042 | F | I | CH$_2$C$_6$H$_5$ |
| .043 | H | CH$_3$ | CH$_2$C$_6$H$_5$ |
| .044 | Cl | CH$_3$ | CH$_2$C$_6$H$_5$ |
| .045 | F | CH$_3$ | CH$_2$C$_6$H$_5$ |
| .046 | H | OH | CH$_2$C$_6$H$_5$ |
| .047 | Cl | OH | CH$_2$C$_6$H$_5$ |
| .048 | F | OH | CH$_2$C$_6$H$_5$ |
| .049 | H | OCF$_3$ | CH$_2$C$_6$H$_5$ |
| .050 | Cl | OCF$_3$ | CH$_2$C$_6$H$_5$ |
| .051 | F | OCF$_3$ | CH$_2$C$_6$H$_5$ |
| .052 | H | CHO | CH$_2$C$_6$H$_5$ |
| .053 | Cl | CHO | CH$_2$C$_6$H$_5$ |
| .054 | F | CHO | CH$_2$C$_6$H$_5$ |
| .055 | H | CHF$_2$ | CH$_2$C$_6$H$_5$ |
| .056 | Cl | CHF$_2$ | CH$_2$C$_6$H$_5$ |
| .057 | F | CHF$_2$ | CH$_2$C$_6$H$_5$ |
| .058 | H | COOH | CH$_2$C$_6$H$_5$ |
| .059 | Cl | COOH | CH$_2$C$_6$H$_5$ |
| .060 | F | COOH | CH$_2$C$_6$H$_5$ |
| .061 | H | COOCH$_2$CH$_3$ | CH$_2$C$_6$H$_5$ |
| .062 | Cl | COOCH$_2$CH$_3$ | CH$_2$C$_6$H$_5$ |
| .063 | F | COOCH$_2$CH$_3$ | CH$_2$C$_6$H$_5$ |
| .064 | H | CN | CH$_2$C$_6$H$_5$ |
| .065 | Cl | CN | CH$_2$C$_6$H$_5$ |
| .066 | F | CN | CH$_2$C$_6$H$_5$ |
| .067 | H | Cl | CH$_2$CCH |
| .068 | Cl | Cl | CH$_2$CCH |
| .069 | F | Cl | CH$_2$CCH |
| .070 | H | Br | CH$_2$CCH |
| .071 | Cl | Br | CH$_2$CCH |
| .072 | F | Br | CH$_2$CCH |
| .073 | H | I | CH$_2$CCH |
| .074 | Cl | I | CH$_2$CCH |
| .075 | F | I | CH$_2$CCH |
| .076 | H | CH$_3$ | CH$_2$CCH |
| .077 | Cl | CH$_3$ | CH$_2$CCH |
| .078 | F | CH$_3$ | CH$_2$CCH |
| .079 | H | OH | CH$_2$CCH |
| .080 | Cl | OH | CH$_2$CCH |
| .081 | F | OH | CH$_2$CCH |
| .082 | H | OCF$_3$ | CH$_2$CCH |
| .083 | Cl | OCF$_3$ | CH$_2$CCH |
| .084 | F | OCF$_3$ | CH$_2$CCH |
| .085 | H | CHO | CH$_2$CCH |
| .086 | Cl | CHO | CH$_2$CCH |
| .087 | F | CHO | CH$_2$CCH |
| .088 | H | CHF$_2$ | CH$_2$CCH |
| .089 | Cl | CHF$_2$ | CH$_2$CCH |
| .090 | F | CHF$_2$ | CH$_2$CCH |
| .091 | H | COOH | CH$_2$CCH |
| .092 | Cl | COOH | CH$_2$CCH |
| .093 | F | COOH | CH$_2$CCH |
| .094 | H | COOCH$_2$CH$_3$ | CH$_2$CCH |
| .095 | Cl | COOCH$_2$CH$_3$ | CH$_2$CCH |
| .096 | F | COOCH$_2$CH$_3$ | CH$_2$CCH |
| .097 | H | CN | CH$_2$CCH |
| .098 | Cl | CN | CH$_2$CCH |
| .099 | F | CN | CH$_2$CCH |
| .100 | H | Cl | CH$_2$COOH |
| .101 | Cl | Cl | CH$_2$COOH |
| .102 | F | Cl | CH$_2$COOH |
| .103 | H | Br | CH$_2$COOH |
| .104 | Cl | Br | CH$_2$COOH |
| .105 | F | Br | CH$_2$COOH |
| .106 | H | I | CH$_2$COOH |
| .107 | Cl | I | CH$_2$COOH |
| .108 | F | I | CH$_2$COOH |
| .109 | H | CH$_3$ | CH$_2$COOH |
| .110 | Cl | CH$_3$ | CH$_2$COOH |
| .111 | F | CH$_3$ | CH$_2$COOH |
| .112 | H | OH | CH$_2$COOH |
| .113 | Cl | OH | CH$_2$COOH |
| .114 | F | OH | CH$_2$COOH |
| .115 | H | OCF$_3$ | CH$_2$COOH |
| .116 | Cl | OCF$_3$ | CH$_2$COOH |

TABLE D-continued

| Compd. No. | $R_{11}$ | $H_{12}$ | $R_{13}$ |
|---|---|---|---|
| .117 | F | $OCF_3$ | $CH_2COOH$ |
| .118 | H | CHO | $CH_2COOH$ |
| .119 | Cl | CHO | $CH_2COOH$ |
| .120 | F | CHO | $CH_2COOH$ |
| .121 | H | $CHF_2$ | $CH_2COOH$ |
| .122 | Cl | $CHF_2$ | $CH_2COOH$ |
| .123 | F | $CHF_2$ | $CH_2COOH$ |
| .124 | H | COOH | $CH_2COOH$ |
| .125 | Cl | COOH | $CH_2COOH$ |
| .126 | F | COOH | $CH_2COOH$ |
| .127 | H | $COOCH_2CH_3$ | $CH_2COOH$ |
| .128 | Cl | $COOCH_2CH_3$ | $CH_2COOH$ |
| .129 | F | $COOCH_2CH_3$ | $CH_2COOH$ |
| .130 | H | CN | $CH_2COOH$ |
| .131 | Cl | CN | $CH_2COOH$ |
| .132 | F | CN | $CH_2COOH$ |
| .133 | H | Cl | $CH_2COOCH_3$ |
| .134 | Cl | Cl | $CH_2COOCH_3$ |
| .135 | F | Cl | $CH_2COOCH_3$ |
| .136 | H | Br | $CH_2COOCH_3$ |
| .137 | Cl | Br | $CH_2COOCH_3$ |
| .138 | F | Br | $CH_2COOCH_3$ |
| .139 | H | I | $CH_2COOCH_3$ |
| .140 | Cl | I | $CH_2COOCH_3$ |
| .141 | F | I | $CH_2COOCH_3$ |
| .142 | H | $CH_3$ | $CH_2COOCH_3$ |
| .143 | Cl | $CH_3$ | $CH_2COOCH_3$ |
| .144 | F | $CH_3$ | $CH_2COOCH_3$ |
| .145 | H | OH | $CH_2COOCH_3$ |
| .146 | Cl | OH | $CH_2COOCH_3$ |
| .147 | F | OH | $CH_2COOCH_3$ |
| .148 | H | $OCF_3$ | $CH_2COOCH_3$ |
| .149 | Cl | $OCF_3$ | $CH_2COOCH_3$ |
| .150 | F | $OCF_3$ | $CH_2COOCH_3$ |
| .151 | H | CHO | $CH_2COOCH_3$ |
| .152 | Cl | CHO | $CH_2COOCH_3$ |
| .153 | F | CHO | $CH_2COOCH_3$ |
| .154 | H | $CHF_2$ | $CH_2COOCH_3$ |
| .155 | Cl | $CHF_2$ | $CH_2COOCH_3$ |
| .156 | F | $CHF_2$ | $CH_2COOCH_3$ |
| .157 | H | COOH | $CH_2COOCH_3$ |
| .158 | Cl | COOH | $CH_2COOCH_3$ |
| .159 | F | COOH | $CH_2COOCH_3$ |
| .160 | H | $COOCH_2CH_3$ | $CH_2COOCH_3$ |
| .161 | Cl | $COOCH_2CH_3$ | $CH_2COOCH_3$ |
| .162 | F | $COOCH_2CH_3$ | $CH_2COOCH_3$ |
| .163 | H | CN | $CH_2COOCH_3$ |
| .164 | Cl | CN | $CH_2COOCH_3$ |
| .165 | F | CN | $CH_2COOCH_3$ |
| .166 | H | Cl | OH |
| .167 | Cl | Cl | OH |
| .168 | F | Cl | OH |
| .169 | H | Br | OH |
| .170 | Cl | Br | OH |
| .171 | Br | Br | OH |
| .172 | H | I | OH |
| .173 | Cl | I | OH |
| .174 | F | I | OH |
| .175 | H | $CH_3$ | OH |
| .176 | Cl | $CH_3$ | OH |
| .177 | F | $CH_3$ | OH |
| .178 | H | OH | OH |
| .179 | Cl | OH | OH |
| .180 | F | OH | OH |
| .181 | H | $OCF_3$ | OH |
| .182 | Cl | $OCF_3$ | OH |
| .183 | F | $OCF_3$ | OH |
| .184 | H | CHO | OH |
| .185 | Cl | CHO | OH |
| .186 | F | CHO | OH |
| .187 | H | $CHF_2$ | OH |
| .188 | Cl | $CHF_2$ | OH |
| .189 | F | $CHF_2$ | OH |
| .190 | H | COOH | OH |
| .191 | Cl | COOH | OH |
| .192 | F | COOH | OH |
| .193 | H | $COOCH_2CH_3$ | OH |
| .194 | Cl | $COOCH_2CH_3$ | OH |
| .195 | F | $COOCH_2CH_3$ | OH |
| .196 | H | CN | OH |
| .197 | Cl | CN | OH |
| .198 | F | CN | OH |
| .199 | H | Cl | $OCH_2CHCH_2$ |
| .200 | Cl | Cl | $OCH_2CHCH_2$ |
| .201 | F | Cl | $OCH_2CHCH_2$ |
| .202 | H | Br | $OCH_2CHCH_2$ |
| .203 | Cl | Br | $OCH_2CHCH_2$ |
| .204 | F | Br | $OCH_2CHCH_2$ |
| .205 | H | I | $OCH_2CHCH_2$ |
| .206 | Cl | I | $OCH_2CHCH_2$ |
| .207 | F | I | $OCH_2CHCH_2$ |
| .208 | H | $CH_3$ | $OCH_2CHCH_2$ |
| .209 | Cl | $CH_3$ | $OCH_2CHCH_2$ |
| .210 | F | $CH_3$ | $OCH_2CHCH_2$ |
| .211 | H | OH | $OCH_2CHCH_2$ |
| .212 | Cl | OH | $OCH_2CHCH_2$ |
| .213 | F | OH | $OCH_2CHCH_2$ |
| .214 | H | $OCF_3$ | $OCH_2CHCH_2$ |
| .215 | Cl | $OCF_3$ | $OCH_2CHCH_2$ |
| .216 | F | $OCF_3$ | $OCH_2CHCH_2$ |
| .217 | H | CHO | $OCH_2CHCH_2$ |
| .218 | Cl | CHO | $OCH_2CHCH_2$ |
| .219 | F | CHO | $OCH_2CHCH_2$ |
| .220 | H | $CHF_2$ | $OCH_2CHCH_2$ |
| .221 | Cl | $CHF_2$ | $OCH_2CHCH_2$ |
| .222 | F | $CHF_2$ | $OCH_2CHCH_2$ |
| .223 | H | COOH | $OCH_2CHCH_2$ |
| .224 | Cl | COOH | $OCH_2CHCH_2$ |
| .225 | F | COOH | $OCH_2CHCH_2$ |
| .226 | H | $COOCH_2CH_3$ | $OCH_2CHCH_2$ |
| .227 | Cl | $COOCH_2CH_3$ | $OCH_2CHCH_2$ |
| .228 | F | $COOCH_2CH_3$ | $OCH_2CHCH_2$ |
| .229 | H | CN | $OCH_2CHCH_2$ |
| .230 | Cl | CN | $OCH_2CHCH_2$ |
| .231 | F | CN | $OCH_2CHCH_2$ |
| .232 | H | Cl | $OCH_2C_6H_5$ |
| .233 | Cl | Cl | $OCH_2C_6H_5$ |
| .234 | F | Cl | $OCH_2C_6H_5$ |
| .235 | H | Br | $OCH_2C_6H_5$ |
| .236 | Cl | Br | $OCH_2C_6H_5$ |
| .237 | F | Br | $OCH_2C_6H_5$ |
| .238 | H | I | $OCH_2C_6H_5$ |
| .239 | Cl | I | $OCH_2C_6H_5$ |
| .240 | F | I | $OCH_2C_6H_5$ |
| .241 | H | $CH_3$ | $OCH_2C_6H_5$ |
| .242 | Cl | $CH_3$ | $OCH_2C_6H_5$ |
| .243 | F | $CH_3$ | $OCH_2C_6H_5$ |
| .244 | H | OH | $OCH_2C_6H_5$ |
| .245 | Cl | OH | $OCH_2C_6H_5$ |
| .246 | F | OH | $OCH_2C_6H_5$ |
| .247 | H | $OCF_3$ | $OCH_2C_6H_5$ |
| .248 | Cl | $OCF_3$ | $OCH_2C_6H_5$ |
| .249 | F | $OCF_3$ | $OCH_2C_6H_5$ |
| .250 | H | CHO | $OCH_2C_6H_5$ |
| .251 | Cl | CHO | $OCH_2C_6H_5$ |
| .252 | F | CHO | $OCH_2C_6H_5$ |
| .253 | H | $CHF_2$ | $OCH_2C_6H_5$ |
| .254 | Cl | $CHF_2$ | $OCH_2C_6H_5$ |
| .255 | F | $CHF_2$ | $OCH_2C_6H_5$ |
| .256 | H | COOH | $OCH_2C_6H_5$ |
| .257 | Cl | COOH | $OCH_2C_6H_5$ |
| .258 | F | COOH | $OCH_2C_6H_5$ |
| .259 | H | $COOCH_2CH_3$ | $OCH_2C_6H_5$ |
| .260 | Cl | $COOCH_2CH_3$ | $OCH_2C_6H_5$ |
| .261 | F | $COOCH_2CH_3$ | $OCH_2C_6H_5$ |
| .262 | H | CN | $OCH_2C_6H_5$ |
| .263 | Cl | CN | $OCH_2C_6H_5$ |
| .264 | F | CN | $OCH_2C_6H_5$ |
| .265 | H | Cl | $OCH_2COOH$ |
| .266 | Cl | Cl | $OCH_2COOH$ |
| .267 | F | Cl | $OCH_2COOH$ |
| .268 | H | Br | $OCH_2COOH$ |
| .269 | Cl | Br | $OCH_2COOH$ |
| .270 | F | Br | $OCH_2COOH$ |

TABLE D-continued

| Compd. No. | $R_{11}$ | $H_{12}$ | $R_{13}$ |
|---|---|---|---|
| .271 | H | I | $OCH_2COOH$ |
| .272 | Cl | I | $OCH_2COOH$ |
| .273 | F | I | $OCH_2COOH$ |
| .274 | H | $CH_3$ | $OCH_2COOH$ |
| .275 | Cl | $CH_3$ | $OCH_2COOH$ |
| .276 | F | $CH_3$ | $OCH_2COOH$ |
| .277 | H | OH | $OCH_2COOH$ |
| .278 | Cl | OH | $OCH_2COOH$ |
| .279 | F | OH | $OCH_2COOH$ |
| .280 | H | $OCF_3$ | $OCH_2COOH$ |
| .281 | Cl | $OCF_3$ | $OCH_2COOH$ |
| .282 | F | $OCF_3$ | $OCH_2COOH$ |
| .283 | H | CHO | $OCH_2COOH$ |
| .284 | Cl | CHO | $OCH_2COOH$ |
| .285 | F | CHO | $OCH_2COOH$ |
| .286 | H | $CHF_2$ | $OCH_2COOH$ |
| .287 | Cl | $CHF_2$ | $OCH_2COOH$ |
| .288 | F | $CHF_2$ | $OCH_2COOH$ |
| .289 | H | COOH | $OCH_2COOH$ |
| .290 | Cl | COOH | $OCH_2COOH$ |
| .291 | F | COOH | $OCH_2COOH$ |
| .292 | H | $COOCH_2CH_3$ | $OCH_2COOH$ |
| .293 | Cl | $COOCH_2CH_3$ | $OCH_2COOH$ |
| .294 | F | $COOCH_2CH_3$ | $OCH_2COOH$ |
| .295 | H | CN | $OCH_2COOH$ |
| .296 | Cl | CN | $OCH_2COOH$ |
| .297 | F | CN | $OCH_2COOH$ |
| .298 | H | Cl | $OCH_2COOCH_3$ |
| .299 | Cl | Cl | $OCH_2COOCH_3$ |
| .300 | F | Cl | $OCH_2COOCH_3$ |
| .301 | H | Br | $OCH_2COOCH_3$ |
| .302 | Cl | Br | $OCH_2COOCH_3$ |
| .303 | F | Br | $OCH_2COOCH_3$ |
| .304 | H | I | $OCH_2COOCH_3$ |
| .305 | Cl | I | $OCH_2COOCH_3$ |
| .306 | F | I | $OCH_2COOCH_3$ |
| .307 | H | $CH_3$ | $OCH_2COOCH_3$ |
| .308 | Cl | $CH_3$ | $OCH_2COOCH_3$ |
| .309 | F | $CH_3$ | $OCH_2COOCH_3$ |
| .310 | H | OH | $OCH_2COOCH_3$ |
| .311 | Cl | OH | $OCH_2COOCH_3$ |
| .312 | F | OH | $OCH_2COOCH_3$ |
| .313 | H | $OCF_3$ | $OCH_2COOCH_3$ |
| .314 | Cl | $OCF_3$ | $OCH_2COOCH_3$ |
| .315 | F | $OCF_3$ | $OCH_2COOCH_3$ |
| .316 | H | CHO | $OCH_2COOCH_3$ |
| .317 | Cl | CHO | $OCH_2COOCH_3$ |
| .318 | F | CHO | $OCH_2COOCH_3$ |
| .319 | H | $CHF_2$ | $OCH_2COOCH_3$ |
| .320 | Cl | $CHF_2$ | $OCH_2COOCH_3$ |
| .321 | F | $CHF_2$ | $OCH_2COOCH_3$ |
| .322 | H | COOH | $OCH_2COOCH_3$ |
| .323 | Cl | COOH | $OCH_2COOCH_3$ |
| .324 | F | COOH | $OCH_2COOCH_3$ |
| .325 | H | $COOCH_2CH_3$ | $OCH_2COOCH_3$ |
| .326 | Cl | $COOCH_2CH_3$ | $OCH_2COOCH_3$ |
| .327 | F | $COOCH_2CH_3$ | $OCH_2COOCH_3$ |
| .328 | H | CN | $OCH_2COOCH_3$ |
| .329 | Cl | CN | $OCH_2COOCH_3$ |
| .330 | F | CN | $OCH_2COOCH_3$ |
| .331 | H | C | $CH_2CHO$ |
| .332 | Cl | Cl | $CH_2CHO$ |
| .333 | F | Cl | $CH_2CHO$ |
| .334 | H | Br | $CH_2CHO$ |
| .335 | Cl | Br | $CH_2CHO$ |
| .336 | F | Br | $CH_2CHO$ |
| .337 | H | I | $CH_2CHO$ |
| .338 | Cl | I | $CH_2CHO$ |
| .339 | F | I | $CH_2CHO$ |
| .340 | H | $CH_3$ | $CH_2CHO$ |
| .341 | Cl | $CH_3$ | $CH_2CHO$ |
| .342 | F | $CH_3$ | $CH_2CHO$ |
| .343 | H | OH | $CH_2CHO$ |
| .344 | Cl | OH | $CH_2CHO$ |
| .345 | F | OH | $CH_2CHO$ |
| .346 | H | $OCF_3$ | $CH_2CHO$ |
| .347 | Cl | $OCF_3$ | $CH_2CHO$ |
| .348 | F | $OCF_3$ | $CH_2CHO$ |
| .349 | H | CHO | $CH_2CHO$ |
| .350 | Cl | CHO | $CH_2CHO$ |
| .351 | F | CHO | $CH_2CHO$ |
| .352 | H | $CHF_2$ | $CH_2CHO$ |
| .353 | Cl | $CHF_2$ | $CH_2CHO$ |
| .354 | F | $CHF_2$ | $CH_2CHO$ |
| .355 | H | COOH | $CH_2CHO$ |
| .356 | Cl | COOH | $CH_2CHO$ |
| .357 | F | COOH | $CH_2CHO$ |
| .358 | H | $COOCH_2CH_3$ | $CH_2CHO$ |
| .359 | Cl | $COOCH_2CH_3$ | $CH_2CHO$ |
| .360 | F | $COOCH_2CH_3$ | $CH_2CHO$ |
| .361 | H | CN | $CH_2CHO$ |
| .362 | Cl | CN | $CH_2CHO$ |
| .363 | F | CN | $CH_2CHO$ |
| .364 | H | Cl | $OCH_2CHO$ |
| .365 | Cl | Cl | $OCH_2CHO$ |
| .366 | F | Cl | $OCH_2CHO$ |
| .367 | H | Br | $OCH_2CHO$ |
| .368 | Cl | Br | $OCH_2CHO$ |
| .369 | F | Br | $OCH_2CHO$ |
| .370 | H | I | $OCH_2CHO$ |
| .371 | Cl | I | $OCH_2CHO$ |
| .372 | F | I | $OCH_2CHO$ |
| .373 | H | $CH_3$ | $OCH_2CHO$ |
| .374 | Cl | $CH_3$ | $OCH_2CHO$ |
| .375 | F | $CH_3$ | $OCH_2CHO$ |
| .376 | H | OH | $OCH_2CHO$ |
| .377 | Cl | OH | $OCH_2CHO$ |
| .378 | F | OH | $OCH_2CHO$ |
| .379 | H | $OCF_3$ | $OCH_2CHO$ |
| .380 | Cl | $OCF_3$ | $OCH_2CHO$ |
| .381 | F | $OCF_3$ | $OCH_2CHO$ |
| .382 | H | CHO | $OCH_2CHO$ |
| .383 | Cl | CHO | $OCH_2CHO$ |
| .384 | F | CHO | $OCH_2CHO$ |
| .385 | H | $CHF_2$ | $OCH_2CHO$ |
| .386 | Cl | $CHF_2$ | $OCH_2CHO$ |
| .387 | F | $CHF_2$ | $OCH_2CHO$ |
| .388 | H | COOH | $OCH_2CHO$ |
| .389 | Cl | COOH | $OCH_2CHO$ |
| .390 | F | COOH | $OCH_2CHO$ |
| .391 | H | $COOCH_2CH_3$ | $OCH_2CHO$ |
| .392 | Cl | $COOCH_2CH_3$ | $OCH_2CHO$ |
| .393 | F | $COOCH_2CH_3$ | $OCH_2CHO$ |
| .394 | H | CN | $OCH_2CHO$ |
| .395 | Cl | CN | $OCH_2CHO$ |
| .396 | F | CN | $OCH_2CHO$ |
| .397 | H | Cl | $OCH_3$ |
| .398 | Cl | Cl | $OCH_3$ |
| .399 | F | Cl | $OCH_3$ |
| .400 | H | Br | $OCH_3$ |
| .401 | Cl | Br | $OCH_3$ |
| .402 | F | Br | $OCH_3$ |
| .403 | H | I | $OCH_3$ |
| .404 | Cl | I | $OCH_3$ |
| .405 | F | I | $OCH_3$ |
| .406 | H | $CH_3$ | $OCH_3$ |
| .407 | Cl | $CH_3$ | $OCH_3$ |
| .408 | F | $CH_3$ | $OCH_3$ |
| .409 | H | OH | $OCH_3$ |
| .410 | Cl | OH | $OCH_3$ |
| .411 | F | OH | $OCH_3$ |
| .412 | H | $OCF_3$ | $OCH_3$ |
| .413 | Cl | $OCF_3$ | $OCH_3$ |
| .414 | F | $OCF_3$ | $OCH_3$ |
| .415 | H | CHO | $OCH_3$ |
| .416 | Cl | CHO | $OCH_3$ |
| .417 | F | CHO | $OCH_3$ |
| .418 | H | $CHF_2$ | $OCH_3$ |
| .419 | Cl | $CHF_2$ | $OCH_3$ |
| .420 | F | $CHF_2$ | $OCH_3$ |
| .421 | H | COOH | $OCH_3$ |
| .422 | Cl | COOH | $OCH_3$ |
| .423 | F | COOH | $OCH_3$ |
| .424 | H | $COOCH_2CH_3$ | $OCH_3$ |

TABLE D-continued

| Compd. No. | $R_{11}$ | $H_{12}$ | $R_{13}$ |
|---|---|---|---|
| .425 | Cl | COOCH$_2$CH$_3$ | OCH$_3$ |
| .426 | F | COOCH$_2$CH$_3$ | OCH$_3$ |
| .427 | H | CN | OCH$_3$ |
| .428 | Cl | CN | OCH$_3$ |
| .429 | F | CN | OCH$_3$ |
| .430 | H | Cl | CH$_2$OCH$_3$ |
| .431 | Cl | Cl | CH$_2$OCH$_3$ |
| .432 | F | Cl | CH$_2$OCH$_3$ |
| .433 | H | Br | CH$_2$OCH$_3$ |
| .434 | Cl | Br | CH$_2$OCH$_3$ |
| .435 | F | Br | CH$_2$OCH$_3$ |
| .436 | H | I | CH$_2$OCH$_3$ |
| .437 | Cl | I | CH$_2$OCH$_3$ |
| .438 | F | I | CH$_2$OCH$_3$ |
| .439 | H | CH$_3$ | CH$_2$OCH$_3$ |
| .440 | Cl | CH$_3$ | CH$_2$OCH$_3$ |
| .441 | F | CH$_3$ | CH$_2$OCH$_3$ |
| .442 | H | OH | CH$_2$OCH$_3$ |
| .443 | Cl | OH | CH$_2$CCH$_3$ |
| .444 | F | OH | CH$_2$OCH$_3$ |
| .445 | H | OCF$_3$ | CH$_2$OCH$_3$ |
| .446 | Cl | OCF$_3$ | CH$_2$OCH$_3$ |
| .447 | F | OCF$_3$ | CH$_2$OCH$_3$ |
| .448 | H | CHO | CH$_2$OCH$_3$ |
| .449 | Cl | CHO | CH$_2$OCH$_3$ |
| .450 | F | CHO | CH$_2$OCH$_3$ |
| .451 | H | CHF$_2$ | CH$_2$OCH$_3$ |
| .452 | Cl | CHF$_2$ | CH$_2$OCH$_3$ |
| .453 | F | CHF$_2$ | CH$_2$OCH$_3$ |
| .454 | H | COOH | CH$_2$OCH$_3$ |
| .455 | Cl | COOH | CH$_2$OCH$_3$ |
| .456 | F | COOH | CH$_2$OCH$_3$ |
| .457 | H | COOCH$_2$CH$_3$ | CH$_2$OCH$_3$ |
| .458 | Cl | COOCH$_2$CH$_3$ | CH$_2$OCH$_3$ |
| .459 | F | COOCH$_2$CH$_3$ | CH$_2$OCH$_3$ |
| .460 | H | CN | CH$_2$OCH$_3$ |
| .461 | Cl | CN | CH$_2$OCH$_3$ |
| .462 | F | CN | CH$_2$OCH$_3$ |
| .463 | H | Cl | CH$_2$SCH$_3$ |
| .464 | Cl | Cl | CH$_2$SCH$_3$ |
| .465 | F | Cl | CH$_2$SCH$_3$ |
| .466 | H | Br | CH$_2$SCH$_3$ |
| .467 | Cl | Br | CH$_2$SCH$_3$ |
| .468 | F | Br | CH$_2$SCH$_3$ |
| .469 | H | I | CH$_2$SCH$_3$ |
| .470 | Cl | I | CH$_2$SCH$_3$ |
| .471 | F | I | CH$_2$SCH$_3$ |
| .472 | H | CH$_3$ | CH$_2$SCH$_3$ |
| .473 | Cl | CH$_3$ | CH$_2$SCH$_3$ |
| .474 | F | CH$_3$ | CH$_2$SCH$_3$ |
| .475 | H | OH | CH$_2$SCH$_3$ |
| .476 | Cl | OH | CH$_2$SCH$_3$ |
| .477 | F | OH | CH$_2$SCH$_3$ |
| .478 | H | OCF$_3$ | CH$_2$SCH$_3$ |
| .479 | Cl | OCF$_3$ | CH$_2$SCH$_3$ |
| .480 | F | OCF$_3$ | CH$_2$SCH$_3$ |
| .481 | H | CHO | CH$_2$SCH$_3$ |
| .482 | Cl | CHO | CH$_2$SCH$_3$ |
| .483 | F | CHO | CH$_2$SCH$_3$ |
| .484 | H | CHF$_2$ | CH$_2$SCH$_3$ |
| .485 | Cl | CHF$_2$ | CH$_2$SCH$_3$ |
| .486 | F | CHF$_2$ | CH$_2$SCH$_3$ |
| .487 | H | COOH | CH$_2$SCH$_3$ |
| .488 | Cl | COOH | CH$_2$SCH$_3$ |
| .489 | F | COOH | CH$_2$SCH$_3$ |
| .490 | H | COOCH$_2$CH$_3$ | CH$_2$SCH$_3$ |
| .491 | Cl | COOCH$_2$CH$_3$ | CH$_2$SCH$_3$ |
| .492 | F | COOCH$_2$CH$_3$ | CH$_2$SCH$_3$ |
| .493 | H | CN | CH$_2$SCH$_3$ |
| .494 | Cl | CN | CH$_2$SCH$_3$ |
| .495 | F | CN | CH$_2$SCH$_3$ |
| .496 | H | Cl | OCH$_2$OCH$_3$ |
| .497 | Cl | Cl | OCH$_2$OCH$_3$ |
| .498 | F | Cl | OCH$_2$OCH$_3$ |
| .499 | H | Br | OCH$_2$OCH$_3$ |
| .500 | Cl | Br | OCH$_2$OCH$_3$ |
| .501 | F | Br | OCH$_2$OCH$_3$ |
| .502 | H | I | OCH$_2$OCH$_3$ |
| .503 | Cl | 1 | OCH$_2$OCH$_3$ |
| .504 | F | I | OCH$_2$OCH$_3$ |
| .505 | H | CH$_3$ | OCH$_2$OCH$_3$ |
| .506 | Cl | CH$_3$ | OCH$_2$OCH$_3$ |
| .507 | F | CH$_3$ | OCH$_2$OCH$_3$ |
| .508 | H | OH | OCH$_2$OCH$_3$ |
| .509 | Cl | OH | OCH$_2$OCH$_3$ |
| .510 | F | OH | OCH$_2$OCH$_3$ |
| .511 | H | OCF$_3$ | OCH$_2$OCH$_3$ |
| .512 | Cl | OCF$_3$ | OCH$_2$OCH$_3$ |
| .513 | F | OCF$_3$ | OCH$_2$OCH$_3$ |
| .514 | H | CHO | OCH$_2$OCH$_3$ |
| .515 | Cl | CHO | OCH$_2$OCH$_3$ |
| .516 | F | CHO | OCH$_2$OCH$_3$ |
| .517 | H | CHF$_2$ | OCH$_2$OCH$_3$ |
| .518 | Cl | CHF$_2$ | OCH$_2$OCH$_3$ |
| .519 | F | CHF$_2$ | OCH$_2$OCH$_3$ |
| .520 | H | COOH | OCH$_2$OCH$_3$ |
| .521 | Cl | COOH | OCH$_2$OCH$_3$ |
| .522 | F | COOH | OCH$_2$OCH$_3$ |
| .523 | H | COOCH$_2$CH$_3$ | OCH$_2$OCH$_3$ |
| .524 | Cl | COOCH$_2$CH$_3$ | OCH$_2$OCH$_3$ |
| .525 | F | COOCH$_2$CH$_3$ | OCH$_2$OCH$_3$ |
| .526 | H | CN | OCH$_2$OCH$_3$ |
| .527 | Cl | CN | OCH$_2$OCH$_3$ |
| .528 | F | CN | OCH$_2$OCH$_3$ |
| .529 | H | Cl | OCH$_2$SCH$_3$ |
| .530 | Cl | Cl | OCH$_2$SCH$_3$ |
| .531 | F | Cl | OCH$_2$SCH$_3$ |
| .532 | H | Br | OCH$_2$SCH$_3$ |
| .533 | Cl | Br | OCH$_2$SCH$_3$ |
| .534 | F | Br | OCH$_2$SCH$_3$ |
| .535 | H | I | OCH$_2$SCH$_3$ |
| .536 | Cl | I | OCH$_2$SCH$_3$ |
| .537 | F | I | OCH$_2$SCH$_3$ |
| .538 | H | CH$_3$ | OCH$_2$SCH$_3$ |
| .539 | Cl | CH$_3$ | OCH$_2$SCH$_3$ |
| .540 | F | CH$_3$ | OCH$_2$SCH$_3$ |
| .541 | H | OH | OCH$_2$SCH$_3$ |
| .542 | Cl | OH | OCH$_2$SCH$_3$ |
| .543 | F | OH | OCH$_2$SCH$_3$ |
| .544 | H | OCF$_3$ | OCH$_2$SCH$_3$ |
| .545 | Cl | OCF$_3$ | OCH$_2$SCH$_3$ |
| .546 | F | OCF$_3$ | OCH$_2$SCH$_3$ |
| .547 | H | CHO | OCH$_2$SCH$_3$ |
| .548 | Cl | CHO | OCH$_2$SCH$_3$ |
| .549 | F | CHO | OCH$_2$SCH$_3$ |
| .550 | H | CHF$_2$ | OCH$_2$SCH$_3$ |
| .551 | Cl | CHF$_2$ | OCH$_2$SCH$_3$ |
| .552 | F | CHF$_2$ | OCH$_2$SCH$_3$ |
| .553 | H | COOH | OCH$_2$SCH$_3$ |
| .554 | Cl | COOH | OCH$_2$SCH$_3$ |
| .555 | F | COOH | OCH$_2$SCH$_3$ |
| .556 | H | COOCH$_2$CH$_3$ | OCH$_2$SCH$_3$ |
| .557 | Cl | COOCH$_2$CH$_3$ | OCH$_2$SCH$_3$ |
| .558 | F | COOCH$_2$CH$_3$ | OCH$_2$SCH$_3$ |
| .559 | H | CN | OCH$_2$SCH$_3$ |
| .560 | Cl | CN | OCH$_2$SCH$_3$ |
| .561 | F | CN | OCH$_2$SCH$_3$ |
| .562 | H | Cl | OCH$_2$CH$_2$CN |
| .563 | Cl | Cl | OCH$_2$CH$_2$CN |
| .564 | F | Cl | OCH$_2$CH$_2$CN |
| .565 | H | Br | OCH$_2$CH$_2$CN |
| .566 | Cl | Br | OCH$_2$CH$_2$CN |
| .567 | F | Br | OCH$_2$CH$_2$CN |
| .568 | H | I | OCH$_2$CH$_2$CN |
| .569 | Cl | I | OCH$_2$CH$_2$CN |
| .570 | F | I | OCH$_2$CH$_2$CN |
| .571 | H | CH$_3$ | OCH$_2$CH$_2$CN |
| .572 | Cl | CH$_3$ | OCH$_2$CH$_2$CN |
| .573 | F | CH$_3$ | OCH$_2$CH$_2$CN |
| .574 | H | OH | OCH$_2$CH$_2$CN |
| .575 | Cl | OH | OCH$_2$CH$_2$CN |
| .576 | F | OH | OCH$_2$CH$_2$CN |
| .577 | H | OCF$_3$ | OCH$_2$CH$_2$CN |
| .578 | Cl | OCF$_3$ | OCH$_2$CH$_2$CN |

TABLE D-continued

| Compd. No. | $R_{11}$ | $H_{12}$ | $R_{13}$ |
|---|---|---|---|
| .579 | F | $OCF_3$ | $OCH_2CH_2CN$ |
| .580 | H | CHO | $OCH_2CH_2CN$ |
| .581 | Cl | CHO | $OCH_2CH_2CN$ |
| .582 | F | CHO | $OCH_2CH_2CN$ |
| .583 | H | $CHF_2$ | $OCH_2CH_2CN$ |
| .584 | Cl | $CHF_2$ | $OCH_2CH_2CN$ |
| .585 | F | $CHF_2$ | $OCH_2CH_2CN$ |
| .586 | H | COOH | $OCH_2CH_2CN$ |
| .587 | Cl | COOH | $OCH_2CH_2CN$ |
| .588 | F | COOH | $OCH_2CH_2CN$ |
| .589 | H | $COOCH_2CH_3$ | $OCH_2CH_2CN$ |
| .590 | Cl | $COOCH_2CH_3$ | $OCH_2CH_2CN$ |
| .591 | F | $COOCH_2CH_3$ | $OCH_2CH_2CN$ |
| .592 | H | CN | $OCH_2CH_2CN$ |
| .593 | Cl | CN | $OCH_2CH_2CN$ |
| .594 | F | CN | $OCH_2CH_2CN$ |
| .595 | H | Cl | $CH_2CH_2CN$ |
| .596 | Cl | Cl | $CH_2CH_2CN$ |
| .597 | F | Cl | $CH_2CH_2CN$ |
| .598 | H | Br | $CH_2CH_2CN$ |
| .599 | Cl | Br | $CH_2CH_2CN$ |
| .600 | F | Br | $CH_2CH_2CN$ |
| .601 | H | I | $CH_2CH_2CN$ |
| .602 | Cl | I | $CH_2CH_2CN$ |
| .603 | F | I | $CH_2CH_2CN$ |
| .604 | H | $CH_3$ | $CH_2CH_2CN$ |
| .605 | Cl | $CH_3$ | $CH_2CH_2CN$ |
| .606 | F | $CH_3$ | $CH_2CH_2CN$ |
| .607 | H | OH | $CH_2CH_2CN$ |
| .608 | Cl | OH | $CH_2CH_2CN$ |
| .609 | F | OH | $CH_2CH_2CN$ |
| .610 | H | $OCF_3$ | $CH_2CH_2CN$ |
| .611 | Cl | $OCF_3$ | $CH_2CH_2CN$ |
| .612 | F | $OCF_3$ | $CH_2CH_2CN$ |
| .613 | H | CHO | $CH_2CH_2CN$ |
| .614 | Cl | CHO | $CH_2CH_2CN$ |
| .615 | F | CHO | $CH_2CH_2CN$ |
| .616 | H | $CHF_2$ | $CH_2CH_2CN$ |
| .617 | Cl | $CHF_2$ | $CH_2CH_2CN$ |
| .618 | F | $CHF_2$ | $CH_2CH_2CN$ |
| .619 | H | COOH | $CH_2CH_2CN$ |
| .620 | Cl | COOH | $CH_2CH_2CN$ |
| .621 | F | COOH | $CH_2CH_2CN$ |
| .622 | H | $COOCH_2CH_3$ | $CH_2CH_2CN$ |
| .623 | Cl | $COOCH_2CH_3$ | $CH_2CH_2CN$ |
| .624 | F | $COOCH_2CH_3$ | $CH_2CH_2CN$ |
| .625 | H | CN | $CH_2CH_2CN$ |
| .626 | Cl | CN | $CH_2CH_2CN$ |
| .627 | F | CN | $CH_2CH_2CN$ |

TABLE E

Prepared compounds from the above Tables with physicochemical data. The numbers in front of the point designates the number of the Table e.g. 1.150 signifies in Table 1 the compound No. 150 of Table A and 72.133 signifies in Table 72 the compound No. 133 of Table B.

| Compd. No. | Physicochemical data |
|---|---|
| 1.001 | m.p. 137–139° C. |
| 1.002 | m.p. 142–146° C. |
| 1.003 | m.p. 122–124° C. |
| 1.004 | amorphous (Example P45) |
| 1.007 | solid |
| 1.010 | resin |
| 1.015 | m.p. 76–78° C. |
| 1.031 | m.p. 88–90° C. |
| 1.045 | m.p. 85–86° C. |
| 1.080 | resin (Example P44) |
| 1.100 | m.p. 104–106° C. |
| 1.105 | m.p. 105–107° C. |
| 1.106 | resin |
| 1.111 | m.p. 93–94° C. |

TABLE E-continued

Prepared compounds from the above Tables with physicochemical data. The numbers in front of the point designates the number of the Table e.g. 1.150 signifies in Table 1 the compound No. 150 of Table A and 72.133 signifies in Table 72 the compound No. 133 of Table B.

| Compd. No. | Physicochemical data |
|---|---|
| 1.126 | m.p. 104–106° C. |
| 1.137 | m.p. 89–93° C. |
| 1.147 | resin. (Example P51) |
| 1.150 | m.p. 137–138° C. |
| 1.152 | m.p. 167–168° C. |
| 1.153 | m.p. 171–172° C. (Example P52) |
| 1.155 | m.p. 102–104° C. |
| 1.156 | m.p. 113–114° C. |
| 1.161 | m.p. 143–145° C. (Example P53) |
| 1.162 | m.p. 180–182° C. |
| 1.168 | m.p. 122–124° C. |
| 1.177 | solid (Example P47) |
| 1.181 | amorphous |
| 1.182 | m.p. 98–100° C. |
| 1.190 | oil |
| 1.195 | m.p. 83–85° C. (Example P46) |
| 1.205 | resin |
| 1.216 | m.p. 80–86° C. |
| 1.234 | amorphous (Example P49) |
| 1.244 | m.p. 146–148° C. (Example P50) |
| 1.294 | oil (Example P55) |
| 1.302 | m.p. 102–104° C. |
| 1.397 | resin (Example P32) |
| 1.400 | resin (Example P33) |
| 1.422 | m.p. 100–101° C. |
| 1.494 | m.p. 135–138° C. (Example P54) |
| 7.100 | m.p. 111–113° C. |
| 9.002 | resin |
| 9.100 | m.p. 110–112° C. |
| 10.100 | m.p. 126–127° C. |
| 22.002 | m.p. 131–133° C. |
| 22.100 | m.p. 190–191° C. (Example P43) |
| 28.100 | m.p. 189–192° C. (Example P42) |
| 72.083 | m.p. 152–153° C. (Example P60) |
| 72.113 | m.p. 250° C. (decomposition) (Example P59) |
| 72.133 | m.p. 140–143° C. (Example P58) |

Examples of specific formulations of the compounds of formula I, such as emulsifiable concentrates, solutions, wettable powders, coated, granules, extruder granules, dusts and suspension concentrates, are described in WO 97/34485, pages 9 to 13.

BIOLOGICAL EXAMPLES

Example B1:
Herbicidal Action Prior to Emergence of the Plants (Pre-Emergence Action)

Monocotyledonous and dicotyledonous test plants are sown in standard soil in plastics pots. Immediately after sowing, the test compounds, each in the form of an aqueous suspension or emulsion prepared from a 25% emulsifiable concentrate (Example F1, c) in WO 97/34485, pages 9 and 10), are applied by spraying at a rate of application of 2000. g of active ingredient/ha (500 liters water/ha). The test plants are then grown in a greenhouse under optimum conditions. After 3 weeks' test duration, the test is evaluated in accordance with a scale of nine ratings (1=total damage, 9=no action). Ratings of from 1 to 4 (especially from 1 to 3) indicate good to very good herbicidal action.

Test plants: Avena, Setaria, Sinapis, Stellaria

The compounds according to the invention exhibit a good herbicidal action.

Examples of the good herbicidal activity of the compounds of formula I are given in Table B1.

TABLE B1

Pre-emergence action:

| Test plant Compd. No. | Avena | Setaria | Sinapis | Stellaria | Concentration [g a.i./ha] |
|---|---|---|---|---|---|
| 1.001 | 1 | 1 | 1 | 1 | 2000 |
| 1.002 | 1 | 1 | 1 | 1 | 2000 |
| 1.003 | 1 | 1 | 1 | 1 | 2000 |
| 1.004 | 1 | 1 | 1 | 1 | 2000 |
| 1.010 | 1 | 1 | 1 | 1 | 2000 |
| 1.080 | 1 | 1 | 1 | 1 | 2000 |
| 1.100 | 1 | 1 | 1 | 1 | 2000 |
| 1.105 | 1 | 1 | 1 | 1 | 2000 |
| 1.106 | 2 | 1 | 1 | 1 | 2000 |
| 1.111 | 2 | 1 | 1 | 1 | 2000 |
| 1.126 | 1 | 1 | 1 | 1 | 2000 |
| 1.147 | 1 | 1 | 1 | 1 | 2000 |
| 1.150 | 1 | 1 | 1 | 1 | 2000 |
| 1.152 | 1 | 1 | 1 | 1 | 2000 |
| 1.153 | 1 | 1 | 1 | 1 | 2000 |
| 1.156 | 1 | 1 | 1 | 1 | 2000 |
| 1.168 | 1 | 1 | 1 | 1 | 2000 |
| 1.181 | 1 | 1 | 1 | 1 | 2000 |
| 1.190 | 2 | 1 | 1 | 1 | 2000 |
| 1.195 | 3 | 1 | 1 | 1 | 2000 |
| 1.205 | 1 | 1 | 1 | 1 | 2000 |
| 1.302 | 1 | 1 | 1 | 1 | 2000 |
| 1.400 | 1 | 1 | 1 | 1 | 2000 |
| 7.100 | 1 | 1 | 1 | 1 | 2000 |
| 9.002 | 1 | 3 | 1 | 1 | 2000 |
| 9.100 | 1 | 1 | 1 | 1 | 2000 |
| 10.100 | 1 | 1 | 1 | 1 | 2000 |
| 28.100 | 1 | 1 | 1 | 1 | 2000 |

The same results are obtained when compounds of formula I are formulated according to Examples F2 to F8 in WO 97/34485, pages 10 to 12.

Example B2:
Post-Emergence Herbicidal Action

Monocotyledonous and dicotyledonous test plants are grown in a greenhouse in plastics pots containing standard soil and at the 4- to 6-leaf stage are sprayed with an aqueous suspension or emulsion of the test substances of formula I, prepared from a 25% emulsifiable concentrate (Example F1, c) in WO 97/34485, pages 9 and 10), at a rate of application corresponding to 2000 g of active ingredient/ha (500 liters water/ha). The test plants are then grown on in the greenhouse under optimum conditions. After approximately 18 days' test duration, the test is evaluated in accordance with a scale of nine ratings (1=total damage, 9=no action). Ratings of from 1 to 4 (especially from 1 to 3) indicate good to very good herbicidal action.

Test plants: Avena, Setaria, Sinapis, Stellaria

In this test, too, the compounds of formula I exhibit a strong herbicidal action.

Examples of the good herbicidal activity of the compounds of formula I are given in Table B2.

TABLE B2

| Post-emergence action: | | | | | |
|---|---|---|---|---|---|
| Test plant Compd. No. | Avena | Setaria | Sinapis | Stellaria | Concentration [g a.i./ha] |
| 1.001 | 1 | 1 | 1 | 1 | 2000 |
| 1.002 | 1 | 1 | 1 | 1 | 2000 |
| 1.003 | 1 | 1 | 1 | 1 | 2000 |
| 1.004 | 1 | 2 | 1 | 1 | 2000 |
| 1.010 | 1 | 1 | 1 | 1 | 2000 |
| 1.080 | 1 | 1 | 1 | 1 | 2000 |
| 1.100 | 1 | 1 | 1 | 1 | 2000 |
| 1.105 | 1 | 2 | 1 | 1 | 2000 |
| 1.106 | 3 | 3 | 1 | 1 | 2000 |
| 1.111 | 2 | 1 | 1 | 2 | 2000 |
| 1.126 | 1 | 1 | 1 | 1 | 2000 |
| 1.147 | 1 | 1 | 1 | 1 | 2000 |
| 1.150 | 1 | 1 | 1 | 1 | 2000 |
| 1.152 | 1 | 1 | 1 | 1 | 2000 |
| 1.153 | 1 | 1 | 1 | 1 | 2000 |
| 1.156 | 1 | 1 | 1 | 1 | 2000 |
| 1.168 | 1 | 1 | 1 | 1 | 2000 |
| 1.181 | 1 | 1 | 1 | 1 | 2000 |
| 1.190 | 1 | 1 | 1 | 1 | 2000 |
| 1.195 | 1 | 1 | 1 | 1 | 2000 |
| 1.205 | 1 | 1 | 1 | 1 | 2000 |
| 1.302 | 1 | 1 | 1 | 1 | 2000 |
| 1.400 | 1 | 2 | 1 | 1 | 2000 |
| 7.100 | 1 | 1 | 1 | 1 | 2000 |
| 9.002 | 1 | 3 | 1 | 1 | 2000 |
| 9.100 | 2 | 2 | 1 | 1 | 2000 |
| 10.100 | 1 | 2 | 1 | 1 | 2000 |
| 28.100 | 1 | 1 | 1 | 1 | 2000 |

The same results are obtained when the compounds of formula I are formulated according to Examples F2 to F8 in WO 97/34485, pages 10 to 12.

What is claimed is:

1. A compound of formula I

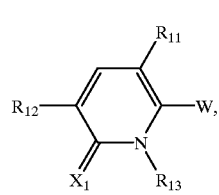

(I)

wherein

W is a group

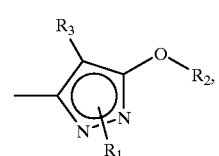

(W1)

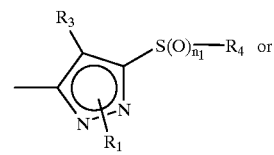

(W2)

or

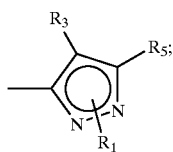

(W3)

$R_1$ is hydrogen, $C_1$–$C_4$alkyl, $C_1$–$C_4$haloalkyl, cyano-$C_1$–$C_4$alkyl, $C_3$- or $C_4$-alkenyl, $C_3$- or $C_4$-haloalkenyl, $C_3$- or $C_4$-alkynyl or $C_3$–$C_6$cycloalkyl;

$R_2$ is hydrogen, $C_1$–$C_4$alkyl, $C_1$–$C_4$haloalkyl, $C_3$–$C_6$alkenyl, $C_3$–$C_6$haloalkenyl, $C_3$–$C_6$alkynyl, $C_1$–$C_4$alkyl-S(O)$_2$— or $C_1$–$C_4$haloalkyl-S(O)$_2$—;

$R_3$ is hydrogen, $C_1$–$C_4$alkyl, $C_1$–$C_4$haloalkyl, $C_2$–$C_6$alkenyl, $C_2$–$C_6$haloalkenyl, $C_2$–$C_6$alkynyl, halogen, cyano, $NH_2C(S)$—, nitro or amino;

n, is 0, 1 or 2;

$R_4$ is hydrogen, $C_1$–$C_4$alkyl, $C_1$–$C_4$haloalkyl, $C_3$–$C_6$alkenyl, $C_3$–$C_6$haloalkenyl, $C_3$–$C_6$alkynyl or $C_3$–$C_6$cycloalkyl;

$R_5$ is hydrogen, halogen, $C_1$–$C_4$alkyl, $C_1$–$C_4$haloalkyl, cyano, nitro, amino, $NH_2C(O)$—, $NH_2C(S)$—, $C_1$–$C_4$alkylcarbonyl, $C_1$–$C_6$alkoxycarbonyl, $C_1$–$C_4$haloalkylcarbonyl, $C_2$–$C_4$allenylcarbonyl, $C_1$–$C_3$alkyl-CH(OH)—, OHC—, HOC(O)—, ClC(O)—, HON═CH—, $C_1$–$C_4$alkoxy-N═CH—, $C_2$–$C_4$haloalkenylcarbonyl or $C_2$–$C_4$alkynylcarbonyl;

$R_{11}$ is hydrogen, fluorine, chlorine, bromine or methyl;

$R_{12}$ is hydrogen, halogen, methyl, halomethyl, nitro, amino, hydroxy, OHC—, HOC(O)—, cyano, $C_1$–$C_4$alkoxycarbonyl or halomethoxy;

$X_1$ is O, S, $R_{20}$N═ or $R_{25}$ON═;

$R_{13}$ is hydroxy, $C_1$–$C_6$alkoxy, $C_3$–$C_6$alkenyloxy, $C_3$–$C_6$alkynyloxy, $C_1$–$C_6$haloalkoxy, $C_3$–$C_6$-haloalkenyloxy, $C_1$–$C_6$alkoxy-$C_1$–$C_6$alkyl, $C_3$–$C_6$alkenyloxy-$C_1$–$C_6$alkyl, $C_3$–$C_6$alkynyloxy-$C_1$–$C_6$alkyl, $C_1$–$C_6$alkoxy-$C_1$–$C_6$alkoxy-$C_1$–$C_6$alkyl, $B_1$—$C_1$–$C_6$alkoxy, $R_2,(R_{22})N$—, $C_1$–$C_6$alkyl, $C_3$–$C_6$alkenyl, $C_3$–$C_6$alkynyl, $C_2$–$C_6$haloalkyl, $C_3$–$C_6$haloalkenyl, $C_3$–$C_6$cycloalkyl, $C_3$–$C_6$halocycloalkyl, $B_1$—$C_1$–$C_6$alkyl, OHC—, $C_1$–$C_6$alkylcarbonyl, $C_1$–$C_6$alkylcarbonyloxy, $C_1$–$C_6$haloalkylcarbonyl, $C_2$–$C_6$alkenylcarbonyl, $C_1$–$C_6$alkoxycarbonyl, $C_1$–$C_6$alkyl-S(O)$_2$—, $C_1$–$C_6$haloalkyl-S(O)$_2$—, $(C_1$–$C_6$alkyl)$_2$N—N═CH—,

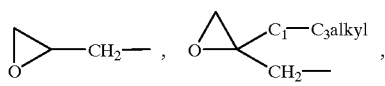

$B_1$—CH═N—, $(CH_3)_2$N—CH═N—, $(C_1$–$C_5$hydroxyalkyl)—CH$_2$—, $(B_1$—$C_1$–$C_5$hydroxyalkyl)—CH$_2$—, $(B_1$—$C_1$–$C_5$haloalkyl)—CH$_2$—, (hydroxy-$C_1$–$C_5$alkyl)—O— or $(B_1$—$C_1$–$C_5$hydroxyalkyl)—O—;

$B_1$ is cyano, OHC—, HOC(O)—, $C_1$–$C_6$alkylcarbonyl, $C_1$–$C_6$alkoxycarbonyl, $C_3$–$C_6$alkenyloxycarbonyl, $C_3$–$C_6$alkynyloxycarbonyl, benzyloxycarbonyl, benzyloxycarbonyl mono- to tri-substituted at the phenyl ring by halogen, $C_1$–$C_4$alkyl or by $C_1$–$C_4$haloalkyl, benzylthiocarbonyl, benzylthiocarbonyl mono- to tri-substituted at the phenyl ring by halogen, $C_1$–$C_4$-alkyl or by $C_1$–$C_4$haloalkyl, $C_1$–$C_6$haloalkoxycarbonyl, $C_1$–$C_6$alkylthio-C(O)—, $R_{26}(R_{27})NC(O)$—, phenyl, phenyl mono- to tri-substituted by halogen, $C_1$–$C_4$alkyl or by $C_1$–$C_4$haloalkyl, $C_1$–$C_6$-alkyl-S(O)$_2$—, $C_1$–$C_6$alkyl-S(O)—, $C_1$–$C_6$alkylthio, $C_3$–$C_6$cycloalkyl, $C_1$–$C_6$alkoxy, $C_3$–$C_6$alkenylthio or $C_3$–$C_6$alkynylthio;

$R_{20}$ is hydrogen, $C_1$–$C_6$alkyl, $C_3$–$C_6$alkenyl, $C_3$–$C_6$alkynyl, $C_2$–$C_6$haloalkyl, cyano, $R_{23}(R_{24})N$—, $C_1$–$C_6$alkoxycarbonyl, $C_3$–$C_6$alkenyloxycarbonyl, $C_3$–$C_6$alkynyloxycarbonyl, $C_2$–$C_6$haloalkoxycarbonyl, OHC—, $C_1$–$C_6$alkylcarbonyl, $C_1$–$C_6$haloalkylcarbonyl, $C_1$–$C_6$alkyl-S(O)$_2$—, $C_1$–$C_6$haloalkyl-S(O)$_2$—, phenyl, phenyl mono- to tri-substituted by halogen, $C_1$–$C_4$alkyl or by $C_1$–$C_4$haloalkyl, phenyl-$C_1$–$C_6$alkyl, or phenyl-$C_1$–$C_6$alkyl mono- to tri-substituted at the phenyl ring by halogen, $C_1$–$C_4$alkyl or by $C_1$–$C_4$haloalkyl;

$R_{21}$ and $R_{22}$ are each independently hydrogen, $C_1$–$C_6$alkyl, $C_3$–$C_6$alkenyl, $C_3$–$C_6$alkynyl, $C_1$–$C_6$-haloalkyl, $C_3$–$C_6$haloalkenyl, $C_3$–$C_6$cycloalkyl, $C_1$–$C_6$alkoxy-$C_1$–$C_6$alkyl, OHC—, $C_1$–$C_6$alkylcarbonyl, $C_1$–$C_6$haloalkylcarbonyl, $C_1$–$C_6$alkyl-S(O)$_2$— or $C_1$–$C_6$haloalkyl-S(O)$_2$—;

$R_{23}$ and $R_{24}$ are each independently as defined for $R_{21}$;

$R_{25}$ is hydrogen, $C_1$–$C_6$alkyl, $C_3$–$C_6$alkenyl, $C_3$–$C_6$alkynyl, $C_1$–$C_6$haloalkyl, $C_3$–$C_6$haloalkenyl, $C_1$–$C_6$alkoxy, $C_1$–$C_6$alkyl, benzyl, $C_1$–$C_6$alkyl-S(O)$_2$— or $C_1$–$C_6$haloalkyl-S(O)$_2$—;

$R_{26}$ and $R_{27}$ are each independently hydrogen, $C_1$–$C_6$alkyl, $C_3$–$C_6$alkenyl, $C_3$–$C_6$alkynyl, $C_1$–$C_6$haloalkyl, $C_3$–$C_8$haloalkenyl, phenyl, phenyl mono- to tri-substituted by halogen, $C_1$–$C_4$alkyl or by $C_1$–$C_4$haloalkyl, benzyl, or benzyl mono- to tri-substituted at the phenyl ring by halogen, $C_1$–$C_4$alkyl or by $C_1$–$C_4$haloalkyl;

or a pyrazole N-oxide, an agrochemically acceptable salt or a stereoisomer of that compound of formula I.

2. A compound of formula I according to claim 1 having the formula Ia

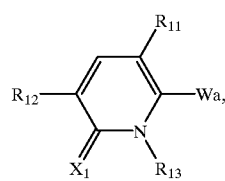

(Ia)

wherein

Wa is a group

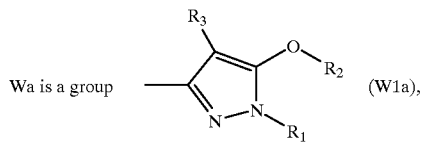

(W1a),

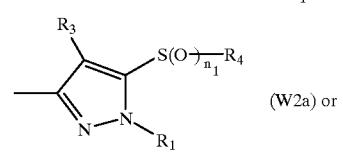

(W2a) or

-continued

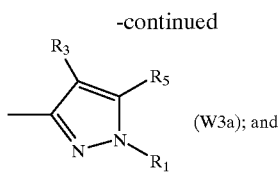

(W3a); and $R_1$, $R_2$, $R_3$, $R_4$, $R_5$, $R_{11}$, $R_{12}$, $R_{13}$, $X_1$ and $n_1$ are as defined in claim 1.

3. A process for the preparation of a compound of formula I according to claim 1

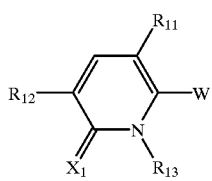
(I)

wherein $R_{11}$, $R_{12}$ and W are as defined in claim 1; $X_1$ is O or S; $R_{13}$ is $C_1$–$C_6$alkoxy-$C_1$–$C_6$-alkyl, $C_1$–$C_6$alkoxy-$C_1$–$C_6$alkoxy-$C_1$$C_6$alkyl, $C_1$–$C_6$alkyl, $C_3$–$C_6$alkenyl, $C_3$–$C_6$alkynyl, $C_2$–$C_6$-haloalkyl, $C_3$–$C_6$haloalkenyl, $C_3$–$C_6$cycloalkyl, $C_3$–$C_6$halocycloalkyl, $B_1$—$C_1$–$C_6$alkyl,

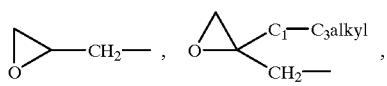

($C_1$–$C_5$hydroxyalkyl)—$CH_2$—, ($B_1$—$C_1$–$C_6$hydroxyalkyl)—$CH_2$— or ($B_1$—$C_1$–$C_6$haloalkyl)—$CH_2$—; and $B_1$ is as defined in claim 1, which comprises oxidising a compound of formula III

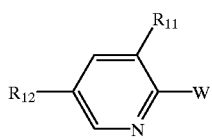
(III)

in a suitable solvent to form a compound of formula V

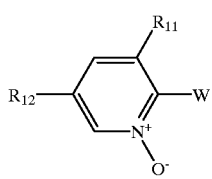
(V)

and subsequently rearranging that compound in an inert solvent in the presence of an anhydride or in the presence of antimony pentachloride to yield, after aqueous working up, a compound of formula II

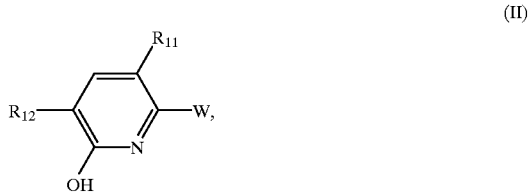
(II)

the radicals $R_{11}$, $R_{12}$ and W in the compounds of formulae II, III and V being as defined above, and then alkylating that compound in the presence of an inert solvent and a base with a compound of formula VI

(VI), wherein $R_{13}$ is as defined above and L is a leaving group, to form the compounds of formulae I and IV

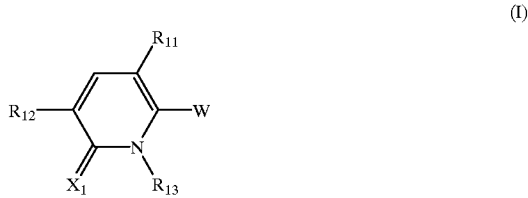
(I)

and

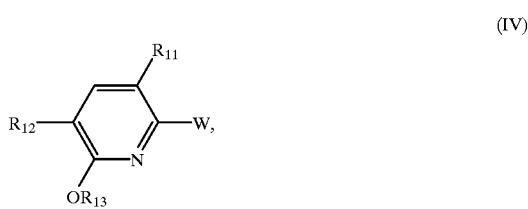
(IV)

wherein $R_{11}$, $R_{12}$, $R_{13}$ and W are as defined above and $X_1$ is O, and subsequently, where appropriate after separating off the compound of formula I, functionalising the pyridone group thereof according to the definition of $X_1$ and $R_{13}$.

4. A herbicidal and plant-growth-inhibiting composition having a herbicidally effective content of a compound of formula I according to claim 1 and comprising an inert carrier.

5. A composition according to claim 6 comprising from 0.1% to 95% of a compound of formula I.

6. A method of controlling undesired plant growth, which comprises applying a compound of formula I, or a composition comprising that compound, in a herbicidally effective amount to the crops of useful plants or to the locus thereof.

* * * * *